United States Patent [19]

Veltri et al.

[11] Patent Number: 5,989,811
[45] Date of Patent: Nov. 23, 1999

[54] SEXTANT CORE BIOPSY PREDICTIVE MECHANISM FOR NON-ORGAN CONFINED DISEASE STATUS

[75] Inventors: Robert W. Veltri, Oklahoma City; M. Craig Miller, Guthrie; Michael P. Bacus, Edmond; Kaveh Ashenayi, Tulsa, all of Okla.

[73] Assignee: Urocor, Inc., Oklahoma City, Okla.

[21] Appl. No.: 08/536,298

[22] Filed: Sep. 29, 1995

Related U.S. Application Data

[63] Continuation-in-part of application No. 08/315,210, Sep. 29, 1994.

[51] Int. Cl.$^6$ ............................. G01N 33/574; C12Q 1/68
[52] U.S. Cl. ............................. 435/6; 435/7.23; 435/7.21; 436/63; 436/64; 436/813
[58] Field of Search ............................. 435/6, 7.23, 7.21; 436/63, 64, 813

[56] References Cited

PUBLICATIONS

Ackerman et al., "Analysis of Risk Factors Associated with Prostate Cancer Extension to the Surgical Margin and Pelvic Node Metastasis at Radical Prostatectomy", *The Journal of Urology*, 150:1845–1850, 1993.

Bacus et al., "Prostate Adenocarcinoma—An Image–Analysis Technique for DNA Ploidy Determination", *Laboratory Medicine*, 24(4):225–231, 1993.

Badalament et al., "DNA Ploidy and Prostate–Specific Antigen as Prognostic Factors in Clinically Resectable Prostate Cancer", *Cancer*, 67:3014–3023, 1991.

Donald F. Gleason, MD, PhD, "Histologic Grading of Prostate Cancer: A Perspective", *Human Pathology*, 23(3):273–279, 1992.

Hammerer et al., "Digital Rectal Examination, Imaging, and Systematic–Sextant Biopsy in Identifying Operable Lymph Node–Negative Prostatic Carcinoma", *Eur Urol*, 22:281–287, 1992.

Katz et al., "Molecular Staging of Prostate Cancer with the Use of an Enhanced Reverse Transcriptase–PCR Assay", *Urology*, 43(6):765–775, 1994.

Miller et al., "A Multivariate Statistical Algorithm foir Predicting Organ–Confined Disease Status Based Upon the Sextant Biopsy Pathology, PSA and Quantitative Image Analysis", *UroCor*, Western Section AUA 71st Annual Meeting, Nov. 5–9, 1995, Scottsdale, AZ.

Ravery et al., "Systematic Biopsies Accurately Predict Extracapsular Extension of Prostate Cancer and Persistent/Recurrent Detectable PSA After Radical Prostatectomy", *Urology*, 44:371–376, 1994.

Terris et al., "Prediction of Prostate Cancer Volume Using Prostate–Specific Antigen Levels, Transrectal Ultrasound, and Systematic Sextant Biopsies", *Urology*, 45:75–80, 1995.

Ross et al., *Cancer*, vol. 72, pp. 3020–3028, Nov. 15, 1993.

Partin et al., *Cancer*, vol. 70, No. 1, pp. 161–168, 1992.

Dawson et al., *Anal. Quant. Cytol. Histol.*, vol. 15, No. 4, pp. 227–235, Aug. 1993.

Molnar, et al., Anal. Cell Pathol., vol. 5, No. 3, pp. 161–175, May 1993.

*Primary Examiner*—Toni R. Scheiner
*Attorney, Agent, or Firm*—Arnold White & Durkee

[57] ABSTRACT

A method for screening individuals at risk for the loss of organ confinement in prostate cancer is disclosed. The method is useful for evaluating cells from patients at risk for recurrence of prostate cancer following surgery for prostate cancer. Specifically, the method uses specific Markovian nuclear texture features, alone or in combination with other biomarkers, to determine whether the cancer will progress or lose organ confinement. In addition, methods of predicting the development of fatal metastatic disease by statistical analysis of selected biomarkers is also disclosed. The invention also contemplates a method that uses a neural network to analyze and interpret cell morphology data. Utilizing Markovian factors and other biomarkers as parameters, the network is first trained with a sets of cell data from known progressors and known non-progressors. The trained network is then used to predict the loss of organ confinement by evaluating patient samples.

33 Claims, 37 Drawing Sheets

PCNA Scoring:
Carrol et al. method; number of positive nuclei per 1000 nuclei scored in 40X fields within JHH pathologist confirmed cancerous areas
Cases without areas dotted for cancer: 3184-17109, 3184-22048, 3185-02004, 4182-18558, 3186-03135
PD-41 Scoring:
Positive staining ducts versus total number of ducts in JHH pathologist confirmed cancerous areas
Cases with part of dotted tumor area missing: 3185-20076A DNA1:
0 - Diploid
1 - ONR: Hypodiploid/*****
2 - ONR: >S+G2M/*****
3 - Ab: >S+G2M/*****
4 - Ab: Aneuploid/*****

DNA10:
0 - Hypodiploid, Diploid (0-1)
1 - ONR: >S+G2M(2)
2 - Ab: >S+G2M, Tetraploid, Aneuploid (3-5)

DNA10:
0 - Normal, ONR (0-2)   1 - Abnormal (3-5)

H2NInt:
0 - No definite staining of the cytoplasm in cancer area.
1 - Definite but faint staining of the cytoplasm in the cancer area.
2 - Moderate staining intensity of all cells within the cancer area with minor variations in staining intensity.
3 - Moderate to strong staining intensity of all cells within the cancer area with minor variations in staining intensity.
4 - Uniform strong staining of all cells in the cancer area.
Cases without areas dotted for cancer: 3184-17109, 3184-22048, H2NFDN:
0 = Negative   1 = Focal Staining (<30%)   2 = Diffuse Staining

FIG. 28B

SEXTANT CORE BIOPSY PREDICTIVE MECHANISM FOR NON-ORGAN CONFINED DISEASE STATUS

The present application is a continuation-in-part of co-pending U.S. patent application Ser. No. 08/315,210, filed Sep. 29, 1994. The entire text of the above-referenced disclosure is specifically incorporated by reference herein without disclaimer.

BACKGROUND OF THE INVENTION

1. Field of the Invention

The present invention relates to fields of computer-assisted quantitative image analysis and methods to classify cells related to cancer progression. More specifically, it concerns methods of multivariate statistical analysis as applied to prediction of organ-confined disease status based upon the sextant biopsy pathology, PSA and quantitative image analysis. Also set forth is a method of predicting non-organ-confined disease status in patients based upon results of tests performed prior to election of any treatment or following such treatment.

2. Description of the Related Art

Prostate cancer is diagnosed in 100/100,000 white males and in 70.1/100,000 black males in the United States. It is the second leading cause of male cancer deaths and the most commonly diagnosed cancer in men in the United States representing 21% of all newly diagnosed cancers. In 1993 an estimated 165,000 men in the United States were diagnosed with clinically apparent prostate cancer and 35,000 will succumb to the disease. The age-specific increase in incidence achieves a maximum of 1000/100,000 in men >75 years of age. The lifetime risk of developing clinical prostate cancer in the U.S. is 8.7% for white and 9.4% for black Americans with a lifetime risk of dying being 2.6% and 4.3% respectively. The risk of developing prostate cancer has risen 42.6% since 1975 as compared to an increase of only 26% in risk of developing lung cancer for that same time period. Approximately 65% of prostate cancers are clinically localized at the time of diagnosis and potentially curable with standard surgical techniques, yet only 50% of men are found to have disease confined to the prostate at the time of surgery. Pack and Spitz (Pack R. and Spitz M. A. The Cancer Bulletin, 45:384–388, 1993), reviewing the epidemiology of prostate cancer, indicated several definable risk factors such as age, race, dietary fat consumption, vasectomy, and familial aggregation with at least a two-fold increased risk for first generation relatives of men with prostate cancer (rare autosomal dominant inheritance). These causal correlations, though impressive, can not yet explain the complex etiology, biologic heterogeneity, and rapidly increasing incidence of this disease, and await further investigations of genetic, epigenetic and environmental factors.

The mortality rate for prostate cancer has been steadily increasing over the past 40 years and will continue to do so as our population ages. This clinically evident disease represents only the tip of the iceberg in that nearly 30 percent of all men over age 50 harbor a silent microscopic form of latent prostate cancer. Current early detection methods are increasing the numbers of this latent form of cancer identified, which now represent more than 11 million cases within the male population in the United States, and growth rate studies indicate that these tumors appear to grow very slowly and the great majority should remain clinically silent. Recent advancements in transrectal ultrasonography and the development of a serum based assay (prostate specific antigen, PSA) for early detection has caused the diagnosis of premalignant neoplasias as well as prostate cancer to increase at an alarming rate. Many of these newly diagnosed neoplasias could represent the non-aggressive, potentially latent form of the disease that may never have become clinically evident if followed without therapy. Unfortunately, no accurate and specific methods presently exist to distinguish the more potentially aggressive form of prostate cancer from the latent form of the disease; thus most patients diagnosed are presently treated as though they had the aggressive form of the disease. At present, the factors to be considered in assessing cancer progression are estimates and significance of tumor volume, pre- and post-operative histological grading of cancer and high grade intraepithelial neoplasia, clinical and pathological stage, and serum prostate specific antigen (PSA) to predict biological aggressiveness of prostate cancer. These techniques Generally have only marginal predictive value.

It is well accepted that the epigenetic and genetic transformation of a normal prostatic epithelial cell to a cancer cell with progression to a metastatic phenotype requires multiple steps. The development of methods to quantify accurately these changes in order to better predict tumor aggressiveness has been the subject of much experimental work in prostate cancer. The use of chromatin texture feature data extracted from either H&E or Feulgen stained sections correlate well to classification of malignant cells. However, the sensitivity of Markovian texture measurements is complicated by the level of pixel gray level resolution (grain). Dawson et al. used a CAS-100 Image Analysis System and software to measure 22 Markovian texture features at 20 levels of pixel resolution (grain) and found ten features that discriminated chromatin patterns in breast cancer images captured by the CAS-100. Markovian analysis is a method based on determining gray-level transition probabilities and it allows discrimination among different nuclear texture features; the value for each feature depending on the level of grain resolution for each measurement.

Christen et al. applied a linear discriminant statistical model analysis of shape, size and texture features of H&E stained prostate nuclei to a high efficiency, 93% correct classification of normal and abnormal cells. Also, Irinopoulou et al. employed Feulgen stained nuclei and a computer-assisted image analysis system to characterize digitized images (512×512 pixels, with 256 possible gray tone levels) from twenty-three patients with Stage B carcinoma of the prostate followed for at least three years. Using five chromatin texture features and discriminant analysis methodology, these patients could be divided into those with a good and poor prognosis.

In spite of the progress made in predicting the organ confinement of prostate cancer cells, it is evident that improvements are needed in the accuracy of such determinations. A particular advantage would be realized by the development of methods that provide for accurate and reproducible statistical analysis of prognostic variables to maximize the aggregate positive predictive value while simultaneously reducing false negatives and false positives.

SUMMARY OF INVENTION

The present invention provides new and improved methods for determining the potential for prostate cancers to spread beyond the confines of the organ. The methods involve assessing treatable, localized prostate cancers using core biopsies, fine needle aspirates in order to: (1) better evaluate which patients have tumors that need any treatment, (2) determine the prognosis of patients with prostate cancer pathologically localized to the gland, after surgery, so that adjuvant treatment of those patients with a high probability of disease progression might begin earlier in the natural course of the disease, and finally, (3) provide more objective means to select patients for chemoprevention trials using dietary modifications, retinoids, and hormonal manipulation (i.e. 5-alpha reductase inhibitors).

For the purposes of this invention, progression is defined as recurrence of disease post-treatment (surgery or irradiation), for example in the case of prostate cancer, as determined by PSA elevation, clinical evidence of local or regional tumor recurrence, distant metastasis, or death. Organ confined disease status is defined as prostate cancer that is still contained within the prostate gland and has not invaded the prostatic capsule.

The invention provides a series of pre-treatment methods applied to sextant core biopsies to determine the status of disease confinement to the prostate. In certain embodiments, a statistically analyzed combination that includes quantitative nuclear image features selected from pathologically important tissue sections and appropriately selected biomarkers provides an aggregate positive predictive value with negligible false negatives and false positives that exceeds current conventional pathological methods for predicting non-organ confinement, or tumor extension beyond the prostate gland. The aggregate positive predictive power of the model, all parameters (i.e. quantitative nuclear image features and biomarkers), was achieved using clinically and pathologically well defined patient samples. The ultimate goal of this invention is to apply these predictive capabilities to prostate biopsies for determination of non-organ confined disease status.

This invention provides a method to collect nuclear images and extract all relevant nuclear morphometric descriptors (NMD's ), including size, shape, texture (Markovian analysis), and DNA content features. Additionally, other biomarkers were used in combination with nuclear morphometric descriptors. Select biomarkers within the scope of the instant invention include, but are not limited to, PSA values (both total PSA and the free PSA to total PSA ratio), the number of positive sextant core biopsies, tumor location (whether base, mid, or apex involvement), the sum percent area of tumor involvement, Gleason score, DNA ploidy, and RT-PCR analysis of prostate marker mRNA. The NMD's combined with the biomarkers can then be analyzed to construct a non-parametric, non-linear mathematical model (e.g. Applying statistical methods such as logistic regression; discriminate analysis (Bayesian classifier or Fischer analysis); recursive partitioning methods (Classification and Regression Trees, or CART); or neural networks (both standard and proprietary)), that can yield a single predictive probability for prostate cancer organ confinement, with or without conventional pathological grading. The pathologically significant areas are identified by an expert trained in the identification of abnormal cells and tissue architecture associated with malignancies of the prostate. Such abnormalities may be present in core biopsies, or fine needle aspirates that have been fixed using methods that preserve the antigenicity of the biomolecules of diagnostic significance, cellular architecture, and integrity of the deoxyribonucleic acid (DNA) or chromatin.

According to the present invention, a method of predicting organ confined disease status is provided, comprising the steps of first obtaining a clinical sample from a subject, then analyzing cell nuclei from areas selected by pathology experts and collecting the NMD's as well as phenotypic cellular biomarker information, and thirdly, predicting organ confinement or nonconfinement status using non-parametric statistical analysis of the data or the use of trained neural networks. Cell sampling for image analysis involves the selection of intact cell nuclei representative of the worst state of differentiation as well as, when present, well to moderately differentiated cancer cells. This provides a measure of tumor heterogeneity often present in prostate cancer. It is suggested that at least 50% of the cells analyzed be of the worst state of cellular differentiation present in the clinical sample, and that the remainder of the cancer cells analyzed represent the well to moderately differentiated cell population, if present, in the clinical sample.

It is an object of the present invention that the more accurate staging of prostate cancer may spare many patients enormous morbidity and high costs of ineffectual traditional therapies for localized disease such as in radical prostatectomy that are inappropriately applied to non-organ confined disease due to inaccurate staging. Alternatively, more recent attempts at pre-treatment downstaging therapy may be monitored using the procedures set forth in the instant invention in combination with other repeat sextant biopsies. It is a further object of the invention that in addition to these protocols being used as a tool for monitoring patients during the course of their disease, the invention also provides more accurate disease staging combined with current conventional technology, which will lead to more appropriate early selection of patient management options, including, but not limited to surgery, radiation therapy, chemotherapy, and gene therapy.

In certain embodiments, the resulting data includes biomarker results (e.g. including but not limited to PSA values, the number of positive sextant core biopsies, tumor location (whether base, mid, or apex involvement), the sum percent area of tumor involvement, Gleason score, DNA ploidy, and RT-PCR analysis of prostate marker mRNA) and NMD's, calculated based on nuclear size, shape, and DNA content, as well as texture features derived by nearest neighbor relational analysis of individual pixel gray levels to mathematically determine several features (e.g. including, but not limited to, object sum, optical density. object size, object shape, picograms of DNA, angular second moment, contrast, correlation difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, and configurable run length). For the purposes of this invention, these parameters are collectively referred to as prognostic parameters.

Clinical samples obtained from patients at risk for occurrence or recurrence of prostate cancer are analyzed and values generated for various prognostic parameters, including the nuclear morphometric descriptors (NMD's). The univariant or multivariant NMD's are then used to calculate a Quantitative Nuclear Grade (QNG) for the case, using a formula derived from a logistic regression model. Summary statistics from the NMD's (e.g. standard deviation and variance) and raw data from the biomarkers are analyzed using logistic regression. The logistic regression may be applied in a univariate or multivariate mode. As used herein, multivariate analysis means that several univariately significant independent variables are jointly regressed on the same dependent variable. A dependent variable refers to a clinical outcome (e.g. regional tumor recurrence, distant metastasis, or death), or a pathological disease state (e.g. organ confinement status). Based upon significance levels, the statistical program selects only those univariately significant independent variables that contribute to the correct prediction of the dependent variable (e.g. progression or organ confined disease status). Notable is the fact that future changes in the model, such as measurement of NMD's (e.g. different magnifications for collection, improved camera resolution, etc.) and\or additional biomarkers, may change the parameters needed and only improve upon the predictive power of the models by small percentages so it may approach 100%.

It is therefore an object of the present invention to provide a method for predicting the loss of organ confinement that comprises first providing prostate cells from a subject, then analyzing various prognostic parameters in the prostate cells, the prognostic parameters including nuclear morphometric descriptors and selected biomarkers, and predicting the loss of organ confinement by statistical analysis of the predictive parameters. The predictive parameters include nuclear morphometric descriptors that are univariate or multivariate significant, and wherein the nuclear morphometric descriptors may be selected from the group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.

In other embodiments, the nuclear morphometric descriptors may also be selected from the group consisting of object sum, optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, and configurable run length. The nuclear morphometric descriptors may also be Markovian nuclear texture factors.

Biomarkers that are contemplated within the scope of the instant invention include, but are not limited to Gleason score, number of positive sextant core biopsies, sum % area tumor involvement, and tumor location. Moreover, it is also contemplated that PSA antigenicity and RT-PCR mRNA levels of selected markers is within the scope of the invention.

The invention also provides a method of predicting the loss of organ confinement before radical prostatectomy that comprises the steps of first, obtaining cells from a subject, then analyzing selected predictive parameters in the cells, followed by predicting the recurrence of prostate cancer in the cell samples by statistical analysis of the predictive parameters. These predictive parameters include nuclear morphometric descriptors or selected biomarkers, and the statistical analysis may be univariate or multivariate statistical analysis.

The predictive parameters are selected from the group consisting of Gleason score, nuclear morphometric descriptors, serum PSA, number of positive sextant core biopsies, tumor location DNA ploidy, sum % area of tumor involvement, or RT-PCR mRNA levels. As in previous embodiments, the nuclear morphometric descriptors are selected from the group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.

In other embodiments, the nuclear morphometric descriptors are selected from the group consisting of object sum, optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, or configurable run length.

It is contemplated that the statistical analysis used in the present invention may be univariate or multivariate analysis, and further the statistical analysis may be performed by a neural network.

In an exemplary embodiment, the instant invention is a method of predicting the loss of organ confinement in which cells are provided from a subject, the prognostic parameters include nuclear morphometric descriptors (including object sum, optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, or configurable run length), PSA values, the number of positive sextant core biopsies, tumor location (whether base, mid, or apex involvement), the sum percent area of tumor involvement, Gleason score, and DNA ploidy. From statistical analysis of these parameters (such as multivariate analysis or neural networks) the loss of organ confinement may be predicted. In a further embodiment, the predictive parameter RT-PCR analysis of mRNA is included with the other parameters.

As used herein, a receiver operating characteristic (ROC) curve plots an independent variable's sensitivity (true positive fraction) on the y-axis against 1-specificity (the false positive fraction) on the x-axis as the cutoff value for a predicted positive observation is varied. A positive observation means that the predicted probability is greater than or equal to an investigator selected cutoff value. The ROC curve or plot is useful for determining the sensitivity, specificity, and negative and positive predictive values of a single test or a multiparameter test. In addition, the ROC curve can be used to establish the optimum threshold cutoff for a continuous variable. When quantitating the area under a ROC curve, an area of 1.0 means a perfect predictive value, while an area of 0.5 means no predictive value and is due to random chance alone.

For the purposes of the invention, sensitivity is the fraction of observed positive cases that are correctly classified and equals: true positives÷{true positives+false negatives}. The positive predictive value equals: true positives÷{true positives+false positives}.

Specificity is the fraction of observed negative cases that are correctly classified and equals: true negatives÷{true negatives+false positives}. The negative predictive value equals: true negatives÷{true negatives+false negatives}.

As used herein, Markovian analysis means a process by which an image (pattern space) is transformed into a transitional-probability space. The Markovian approach to texture measurement treats images as stochastic processes in the form of discrete Markovian fields, yielding matrices of gray-level transition probabilities. These probabilities are arrays of numbers that describe digital images in terms of the probability of occurrence of different gray levels and sequences of gray levels. One embodiment of the invention utilizes 13 Markovian factors, 4 DNA content factors, and 5 shape factors.

Texture is an important visual feature for many pattern recognition tasks. As used herein, texture describes the interdependent characteristics of pixels within a neighboring area. Regular texture has more or less periodic patterns, while random texture is best described by its "coarseness". A texture parameter is a local statistic, meaning that the statistic is computable from a set of neighboring picture points in a neighborhood that is small compared to the number of picture points in the entire region.

A Markovian matrix of the present invention is constructed using a cell nucleus image using QDA v3.0 software on a CAS-200 Image Analysis System. Using the QDA Morphology mode of CMP v3.0 and Cellsheet® v.1.0d software allows the measurement and calculation of the features listed in Table I. Moreover, CMP v3.0 and Cellsheet® v.1.0d calculate 22 different Markovian nuclear descriptors based upon the gray-level transition probabilities of Feulgen stained nuclei. The Cellsheet® software may be sued to calculate the features listed in Tables I and II, respectively. It is further recognized that any program, in addition to CMP and Celisheet® that calculates texture features may; be used within the scope of the present invention.

The step size selected may range from 1 pixel to 256 pixels. The step size defines the size of the "grain" or picture point in number of pixels that is to be compared to the neighboring picture points. Each cell nucleus image is normalized by partitioning the image into eight equally frequent gray level ranges, each range consisting of an equal number of pixels. In other embodiments, the normalization may be done by partitioning the image into 16, 32, 64, or any number of gray levels. This normalization process is done by first plotting each individual pixel optical density (gray level) that is above an operator set threshold against the number of pixels. This plot is divided into eight equally frequent gray-level ranges (optical density ranges); each range containing an equal number of pixels (FIG. 1A and FIG. 2B). This yields a normalized cell nucleus image consisting of pixels with gray-level values ranging from 0–7.

TABLE I

Nuclear Morphometric Descriptors Measured Using CMP v3.0 in the QDA Morphology Mode.

1. (OBSD) Object Sum OD
2. (OBSZ) Object Size
3. (OBSH) Object Shape
4. Picograms of DNA
5. (TXA001) Angular Second Moment
6. (TXB001) Contrast
7. (TXC001) Correlation
8. (TXD001) Difference Moment
9. (TXE001) Inverse Difference Moment
10. (TXF001) Sum Average
11. (TXG001) Sum Variance
12. (TXH001) Sum Entropy
13. (TXI001) Entropy
14. (TXJ001) Difference Variance
15. (TXK001) Difference Entropy
16. (TXL001) Information Measure A
17. (TXM001) Information Measure B
18. (TXN001) Maximal Correlation Coeff.
19. (TXO001) Coefficient of Variation
20. (TXP001) Peak Transition Probability
21. (TXQ001) Diagonal Variance
22. (TXR001) Diagonal Moment
23. (TXS001) Second Diagonal Moment
24. (TXT001) Product Moment
25. (TXU001) Triangular Symmetry
26. (TXV001) Blobness
27. (TXW) Standard Deviation
28. Cell Classification (1 = Hypodiploid, 2 = Diploid, 3 = S-Phase, 5 = Tetraploid, 6 = Hyperploid)

NOTE:
Values 5–26 are grain dependent Markovian texture features. Grain may be looked at as a measurement in pixels of the width of an average sized object. The grain values for all of these measurements were set to 1.

As a further step, an 8×8 gray-level transition matrix is constructed from the normalized cell nucleus image by comparing the gray-levels of neighboring picture points (e.g. if a given picture point has a normalized value of 4, and its neighboring picture point has a normalized value of 3, an entry is made in the matrix at location Row-4 and Column-3, and all of the entries at this location are summed). This matrix is then transformed into an 8×8 conditional gray-level transition probability matrix by dividing every matrix entry by the total number of pixels in the cell nucleus image. This "Markovian" probability matrix (Equation 1) is then used to compute the 22 Markovian texture features (Table I).

Equation 1

8×8 Conditional Grey-Level Transition Probability Matrix (Markovian)

$$M = \begin{bmatrix} P_L(0/0) & P_L(0/1) & \cdots & P_L(0/7) \\ P_L(1/0) & P_L(1/1) & \cdots & P_L(1/7) \\ \vdots & \vdots & \vdots & \vdots \\ P_L(7/0) & P_L(7/1) & \cdots & P_L(7/7) \end{bmatrix}$$

where each matrix element $P_L(i/j)$ is defined as the conditional probability of gray-level i occurring L picture points after gray-level j occurs, where L is defined as the step size (or size in pixels of the picture point).

More recently, JVB Imaging (Elmhurst, Ill.) has written a software application called ILM Morphometry v1.0 that can be applied to listmode files (*.ILM) generated using a CAS-200 Image Analysis System. This program therefore allows the measurement and calculation of the same features as the CMP v3.0 software (Markovian and DNA Content features) as well as eight additional features (listed in Table II). The inventors have tested this new software on the patient sample reported in this invention and obtained similar statistical model performance as with the CMP v3.0 software. A newer version of this program, titled Cellsheet® v1.0d, has been used in later studies.

TABLE II

Nuclear Morphometric Descriptors Measured
Using ILM Morphometry v1.0

1. Object Sum Optical Density
2. Object Size
3. Object Shape
4. Picograms of DNA
5. Angular Second Moment
6. Contrast
7. Correlation
8. Difference Moment
9. Inverse Difference Moment
10. Sum Average
11. Sum Variance
12. Sum Entropy
13. Entropy
14. Difference Variance
15. Difference Entropy
16. Information Measure A
17. Information Measure B
18. Maximal Correlation Coefficient
19. Coefficient of Variation
20. Peak Transition Probability
21. Diagonal Variance
22. Diagonal Moment
23. Second Diagonal Moment
24. Product Moment
25. Triangular Symmetry
26. Standard Deviation
27. Cell Classification
    (1 = Hypodiploid, 2 = Diploid, 3 = S-
    Phase, 5 = Tetraploid,
    6 = Hyperploid)
28. Perimeter
29. DNA Index
30. Density
31. Average Optical Density
32. Feret X
33. Feret Y
34. Maximum Diameter
35. Minimum Diameter
36. Elongation NOTE:
Values 5–26 are grain dependent Markovian texture features. Grain may be looked at as a measurement in pixels of the width of an average sized object. The grain values for all of these measurements were set to 1.

In exemplary embodiments of the invention, consideration must be given to several parameters, such as cell selection, magnification, pixel shape and size, camera resolution (number of pixels in the x and y dimension, e.g. number of pixels per $\mu m^2$), and Markovian step size, which can significantly alter nuclear morphometric descriptor outputs (FIG. 2). The NMD's have been demonstrated in this invention to be significant independent variables in the prediction of tumor progression and organ confined disease status. As previously indicated, the method for cell selection is critical because of the need to sample biologic tumor heterogeneity. Additionally, the total number of NMD's required to predict an outcome is decreased as the magnification increases (Table III; also see FIGS. 3–6), as well as significant changes in the individual NMD's required. The latter is due to an increase in the number of pixels per $\mu m^2$ that would enhance the resolution of calculations for the NMD's. Also notable, the predictive power for all outcomes using the NMD component of the model increases as the magnification increases.

TABLE III

Magnification Effects (40× vs. 63×) upon Number of Nuclear
Morphometric Descriptors needed to Accurately Predict
Progression in a Subset of 10 Progressors and 10 Non-Progressors

|  | 40X | | 63X | |
| --- | --- | --- | --- | --- |
|  | CMP v3.0* | JVB v1.0** | CMP v3.0* | JVB v1.0** |
| P Value Cutoff | 0.45 | 0.50 | 0.25 | 0.70 |
| Sensitivity | 90.00% | 90.00% | 100.00% | 90.00% |
| Positive Pred. Value | 90.00% | 100.00% | 76.92% | 100.00% |
| Specificity | 90.00% | 100.00% | 70.00% | 100.00% |
| Negative Pred. Value | 90.00% | 90.91% | 100.00% | 90.91% |
| # False Positives | 1 | 0 | 3 | 0 |
| # False Negatives | 1 | 1 | 0 | 1 |
| Area Under ROC Curve | 0.9400 | 0.9500 | 0.9400 | 0.9600 |
| NMD's in Model | 6 Markovian & Area | 5 Markovian & Sum O.D, Area, Perimeter | 5 Markovian & Area | 4 Markovian & Sum O.D. |
| # Concordant NMD's | 3 | | 3 | |
| # Discordant NMD's | 4 | 5 | 3 | 2 |

*Number of CMP Nuclear Morphometric Descriptors (NMD's) = 28
**Number of JVB Nuclear Morphometric Descriptors (NMD's) = 36

In other embodiments, either non-parametric statistical methods, or standard or proprietary neural networks were used to validate the utility of NMD's and biomarkers for the prediction of two possible outcomes, progression and organ confined disease status. Using a clinically and pathologically well-defined retrospective patient sample diagnosed with localized prostate cancer, logistic regression methods were applied on a well defined patient sample (n=124) (Table IV) to determine which NMD's and biomarkers were capable (e.g. statistically significant) of predicting either progression or organ confined disease status.

LOGISTIC REGRESSION PROGRESSION MODEL:

The invention applies logistic regression to select the univariately significant variables for progression (Table V) using the STATA™ statistical software package (STATA™ command: logistic). Next, these univariately significant variables are multivariately assessed using backwards stepwise logistic regression (STATA™ command: swlogis) to determine which independent variables (e.g. NMD's (CMP or JVB), Gleason Score, and biomarkers) are retained to predict progression (Tables VI, Via, VII, and VIIa).

TABLE IV

JHH-1 PATIENT SAMPLE

| | | | |
| --- | --- | --- | --- |
| Average Age: | 59.6 ± 6.4 years [40–87 yrs] | Non-progressors: | 74(60%) |
| First operation: | Jun-'75 | Progressors: | 50(40%) |
| Last Operation: | Jun-'91 | Avg. Time to Prog: | 3.62 ± 2.1 years |

TABLE IV-continued

| | | | | | |
|---|---|---|---|---|---|
| Time to assess: | 6.6 ± 3.1 years [1–15 yrs] | | Local Recurrence: | 11(9%) | |
| Clin. Stage A1, A2 | 6% | | Distant Mets: | 5(4%) | |
| Clin. Stage B1, B2 | 94% | | | | |

| | | | | | GLEASON GRADING | |
|---|---|---|---|---|---|---|
| PATHOLOGY DIAGNOSIS | | | | SCORE | PRE-OP | POST-OP |
| STAGE T1b | 2(2%) | FCP + | = 89 (72%) | 2 | 0% | 1% |
| STAGE T1c | 1(1%) | FCP − | = 35 (28%) | 3 | 1% | 0% |
| STAGE T2a | 72(58%) | ECP + | = 52 (42%) | 4 | 11% | 1% |
| STAGE T2b | 45(36%) | ECP − | = 72 (58%) | 5 | 25% | 27% |
| STAGE T2c | 4(3%) | OC NO | = 95 (77%) | 6 | 41% | 28% |
| | | OC Yes | = 29 (23%) | 7 | 19% | 36% |
| | | SM + | = 52 (42%) | 8 | 2% | 6% |
| | | SM − | = 72 (58%) | 9 | 0% | 1% |
| | | SV+ | = 0 | | | |
| | | LN+ | = 0 | | | |

TABLE V

Univariate Analysis for
Progression Prediction using STATA ™ Logistic Regression

| Independent Variable | Statistical Significance (p Value) |
|---|---|
| Post Operative Gleason Score | p ≤ 0.00001 |
| Nuclear Roundness Variance* | p ≤ 0.00001 |
| Best CAS-200 CMP v3.0 Nuclear Morphometric Descriptors | p ≤ 0.00001 |
| Best CAS-200 JVB v1.0 Nuclear Morphometric Descriptors | p ≤ 0.00001 |
| CAS-200 DNA Ploidy - 1 (C-DNA1) | p = 0.0080 |
| CAS-200 DNA Ploidy - 10 (C-DNA10) | p = 0.0274 |
| CAS-200 DNA Ploidy - JIE (JHHDNA10) | p = 0.0109 |
| Her-2/neu Antigenicity: Focal, Diffuse, Negative (H2NFDN) | p = 0.0147 |
| PCNA Antigenicity | p = 0.1600** |
| PD-41 Antigenicity above a 5% cutoff | p = 0.3045** |

*Measured using DynaCell ™ system at Johns Hopkins Hospital
**Not Statistically Significant. Must be less than 0.0500 to be statistically significant.

TABLE VI

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for
CMP Textrue Features, Biomarkers, Post Gleason, & JHH-NRV in Progression Prediction

| | A | B | C | D2 | H | I |
|---|---|---|---|---|---|---|
| | PostGL | JHH-NRV | Biomarkers (n = 3)** | CMP Nuclear Descriptors (n = 12)* | CMP Nuclear Descriptors (n = 13)* PostGL | CMP Nuclear Descriptors (n = 10)* JHH-NRV |
| Positive Cutoff (p >=#) | 0.50 | 0.35 | 0.40 | 0.35 | 0.40 | 0.40 |
| SENSITIVITY | 78.00% | 86.00% | 62.00% | 86.00% | 84.00% | 86.00% |
| Pos Predictive Value | 73.58% | 78.18% | 54.39% | 65.15% | 85.71% | 84.31% |
| SPECIFICITY | 81.08% | 83.56% | 64.86% | 68.92% | 90.54% | 89.04% |
| Neg Predictive Value | 84.51% | 89.71% | 71.64% | 87.93% | 89.33% | 90.28% |
| % False Positives | 26.42% | 21.82% | 45.61% | 34.85% | 14.29% | 15.69% |
| % False Negatives | 15.49% | 10.29% | 28.36% | 12.07% | 10.67% | 9.72% |
| Area Under ROC Curve | 0.8262 | 0.8975 | 0.7108 | 0.8557 | 0.9154 | 0.9556 |
| Significance | <0.00001 | <0.00001 | 0.0009 | <0.00001 | <0.00001 | <0.00001 |

| | J | K | L | M | N |
|---|---|---|---|---|---|
| | CMP Nuclear Descriptors (n = 13)* JHH-NRV PostGL | CMP Nuclear Descriptors (n = 12)* Biomarkers (n = 2)**** | CMP Nuclear Descriptors (n = 12)* Biomarkers (n = 2)*** PostGL | CMP Nuclear Descriptors (n = 10)* Biomarkers (n = 2)**** JHH-NRV | CMP Nuclear Descriptors (n = 13)* Biomarkers (H2NFDN) JHH-NRV PostGL |
| Positive Cutoff (p >=#) | 0.50 | 0.45 | 0.45 | 0.45 | 0.50 |
| SENSITIVITY | 94.00% | 78.00% | 86.00% | 92.00% | 96.00% |

TABLE VI-continued

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for
CMP Textrue Features, Biomarkers, Post Gleason, & JHH-NRV in Progression Prediction

| | | | | | |
|---|---|---|---|---|---|
| Pos Predictive Value | 97.92% | 73.58% | 84.31% | 88.46% | 100.00% |
| SPECIFICITY | 98.63% | 81.08% | 89.19% | 91.78% | 100.00% |
| Neg Predictive Value | 96.00% | 84.51% | 90.41% | 94.37% | 97.33% |
| % False Positives | 2.08% | 26.42% | 15.69% | 11.54% | 0.00% |
| % False Negatives | 4.00% | 15.49% | 9.59% | 5.63% | 2.67% |
| Area Under ROC Curve | 0.9885 | 0.8857 | 0.9368 | 0.9726 | 0.9915 |
| Significance | <0.00001 | <0.00001 | <0.00001 | <0.00001 | <0.00001 |

*NOTE: n = number of CMP Nuclear Descriptors which survived the model, either Sid. Deviation or Variance or both statistics.
**NOTE: Surviving Biomarkers are C-DNA1, H2NFDN, and PD41-5
***NOTE: Surviving Biomarkers are C-DNAI and H2NFDN
****NOTE: Surviving Biomarkers are H2NFDN and PD41-5

TABLE VIa

| Feature | D1 | D2 | H | I | J | K | L | M | N |
|---|---|---|---|---|---|---|---|---|---|
| 1 | X | X | X | | X | | | X | X |
| 2 | X | | X | X | X | X | | X | X |
| 3 | X | X | X | X | X | X | X | | X |
| 4 | X | X | X | | X | X | X | | X |
| 5 | | | | | | | | | |
| 6 | X | X | | X | X | X | X | X | X |
| 7 | X | X | X | X | X | X | X | X | X |
| 8 | X | | X | | | | | X | |
| 9 | | | | | | | | | |
| 10 | X | X | X | X | X | X | X | X | X |
| 11 | X | X | X | | X | X | X | | X |
| 12 | | | | | | | | | |
| 13 | | | | | | | | | |
| 14 | X | X | X | X | X | X | X | X | X |
| 15 | X | X | X | X | X | X | X | X | X |
| 16 | | | | | | | | | |
| 17 | X | X | X | X | X | X | X | X | X |
| 18 | | | | | | | | | |
| 19 | | | | | | | | | |
| 20 | | | | | | | | | |
| 21 | | | | | | | | | |
| 22 | X | X | X | X | X | X | X | X | X |
| 23 | X | | | | | | | | |
| 24 | | | | | | | | | |
| 25 | | | | | | | | | |
| 26 | | | | | | | | | |
| 27 | X | X | X | X | X | X | X | X | X |
| 28 | | | | | | | | | |

TABLE VII

Univariate/Multivariate Analysis for Prostate Cancer Progression
{N = 124 Radical Prostatectomy Specimens)
Progressors/Non-Progressors: 50/74
Statistical Analysis of JHH-1 Database using Univariately Significant STDEV & VAR Statistics for
JVB Texture Features, Biomarkers, Post Gleason, & JHH-NRV in Progression Prediction

| | A | B | C | D2 | H | I |
|---|---|---|---|---|---|---|
| | PostGL | JHH-NRV | Biomarkers (n = 3)** | JVB Nuclear Descriptors (n = 19)* | JVB Nuclear Descriptors (n = 16)* PostGL | JVB Nuclear Descriptors (n = 17)* JHH-NRV |
| Positive Cutoff (p >=#) | 0.50 | 0.35 | 0.40 | 0.40 | 0.50 | 0.40 |
| SENSITIVITY | 78.00% | 86.00% | 62.00% | 86.00% | 86.00% | 96.00% |
| Pos Predictive Value | 73.58% | 78.18% | 54.39% | 76.79% | 86.00% | 94.12% |
| SPECIFICITY | 81.08% | 83.56% | 64.86% | 82.43% | 90.54% | 95.89% |
| Neg Predictive Value | 84.51% | 89.71% | 71.64% | 89.71% | 90.54% | 97.22% |
| % False Positives | 26.42% | 21.82% | 45.61% | 23.21% | 14.00% | 5.88% |
| % False Negatives | 15.49% | 10.29% | 28.36% | 10.29% | 9.46% | 2.78% |
| Area Under ROC Curve | 0.8262 | 0.8975 | 0.7108 | 0.9300 | 0.9462 | 0.9866 |
| Significance | <0.00001 | <0.00001 | 0.0009 | <0.00001 | <0.00001 | <0.00001 |

| | J | K | L | M | N |
|---|---|---|---|---|---|
| | JVB Nuclear Descriptors (n = 15)* JHH-NRV | JVB Nuclear Descriptors (n = 17)* Biomarkers (n = 2)**** | JVB Nuclear Descriptors (n = 17)* Biomarkers (n = 3)** PostGL | JVB Nuclear Descriptors (n = 17)* Biomarkers (n = 3)** JHH-NRV | JVB Nuclear Descriptors (n = 14)* Biomarkers (n = 2)*** JHH-NRV PostGL |
| Positive Cutoff (p >=#) | 0.50 | 0.45 | 0.50 | 0.50 | 0.50 |
| SENSITIVITY | 98.00% | 88.00% | 88.00% | 92.00% | 98.00% |

TABLE VII-continued

Univariate/Multivariate Analysis for Prostate Cancer Progression
{N = 124 Radical Prostatectomy Specimens}
Progressors/Non-Progressors: 50/74
Statistical Analysis of JHH-1 Database using Univariately Significant STDEV & VAR Statistics for
JVB Texture Features, Biomarkers, Post Gleason, & JHH-NRV in Progression Prediction

| | | | | | |
|---|---|---|---|---|---|
| Pos Predictive Value | 98.00% | 81.48% | 88.00% | 95.83% | 98.00% |
| SPECIFICITY | 98.63% | 86.49% | 91.89% | 97.26% | 98.63% |
| Neg Predictive Value | 98.63% | 91.43% | 91.89% | 94.67% | 98.63% |
| % False Positives | 2.00% | 18.52% | 12.00% | 4.17% | 2.00% |
| % False Negatives | 1.37% | 8.57% | 8.11% | 5.33% | 1.37% |
| Area Under ROC Curve | 0.9934 | 0.9503 | 0.9589 | 0.9885 | 0.9948 |
| Significance | <0.00001 | <0.00001 | <0.00001 | <0.00001 | <0.00001 |

*NOTE: n = number of JVB Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are C-DNA1 and H2NFDN
****NOTE: Surviving Biomarkers are H2NFDN and PD41-5

TABLE VIIa

| Feature | D1 | D2 | H | I | J | K | L | M | N |
|---|---|---|---|---|---|---|---|---|---|
| 1 | X | X | | X | X | X | X | X | X |
| 2 | X | X | X | X | X | X | X | X | X |
| 3 | X | X | X | X | X | X | X | X | X |
| 4 | X | X | X | X | X | X | X | X | |
| 5 | | | | | | | | | |
| 6 | | | | | | | | | |
| 7 | X | X | X | X | | X | X | | X |
| 8 | X | X | | X | X | | | X | X |
| 9 | | | | | | | | | |
| 10 | X | X | X | X | X | X | X | X | X |
| 11 | X | X | X | X | X | X | X | X | X |
| 12 | | | | | | | | | |
| 13 | | | | | | | | | |
| 14 | X | X | X | | X | X | X | X | |
| 15 | X | X | X | X | | X | X | X | X |
| 16 | | | | | | | | | |
| 17 | X | X | | X | X | X | X | X | |
| 18 | | | | | | | | | |
| 19 | | | | | | | | | |
| 20 | | | | | | | | | |
| 21 | | | | | | | | | |
| 22 | X | X | | X | X | | | X | X |
| 23 | X | | | | | | | | |
| 24 | X | X | X | X | X | X | X | X | X |
| 25 | | | | | | | | | |
| 26 | X | X | X | | | X | X | X | |
| 27 | | | | | | | | | |
| 28 | X | X | X | X | | X | X | X | |
| 29 | X | X | X | | | X | X | | X |
| 30 | X | | X | X | X | X | | X | X |
| 31 | X | X | X | X | X | | X | X | |
| 32 | | | | | | | | | |
| 33 | | | | | | | | | |
| 34 | X | X | X | X | X | X | X | X | X |
| 35 | X | X | X | X | X | X | X | | X |
| 36 | | | | | | | | | |

In another embodiment, the ability of Her-2/neu antigenic expression to identify high risk sub-populations of well to moderately differentiated Gleason grades (2–6) as well as high Gleason grades (>7) is clearly demonstrated in FIG. 19.

Additionally, it was demonstrated that non-diploid DNA ploidy status selected out a subset of well to moderately differentiated Gleason grades (2–6) that were at risk for progression (FIG. 20).

LOGISTIC REGRESSION ORGAN CONFINEMENT MODEL:

This invention also applies logistic regression to select the univariately significant variables for organ confinement (Table VIII) using the STATA™ statistical software package (STATA™ command: logistic). Next, these univariately significant variables are multivariately assessed using backwards stepwise logistic regression (STATA™ command: swlogis) to determine which independent variables (e.g. NMD's (CMP or JVB), Gleason Score, and biomarkers) are retained to predict organ confinement (Tables IX, Ixa, X, and Xa).

TABLE VIII

Univariate Analysis for Organ Confined Disease Status Prediction
using STATA ™ Logistic Regression

| Independent Variable | Statistical Significance (p Value) |
|---|---|
| Post Operative Gleason Score | $p \leq 0.00001$ |
| Nuclear Roundness Variance* | p = 0.0073 |
| Best CAS-200 CMP v3.0 Nuclear Morphometric Descriptors | p = 0.0005 |
| Best CAS-200 JVB v1.0 Nuclear Morphometric Descriptors | p = 0.0003 |
| CAS-200 DNA Ploidy - 1 (C-DNA1) | p = 0.0703** |
| CAS-200 DNA Ploidy - 10 (C-DNA10) | p = 0.0546** |
| CAS-200 DNA Ploidy - JIE (JHHDNA10) | p = 0.0499 |
| Her-2/neu Antigenicity: Focal, Diffuse, Negative (H2NFDN) | p = 0.0023 |
| PCNA Antigenicity | p = 0.1330** |
| PD-41 Antigenicity | p = 0.0198 |

*Measured using DynaCell ™ system at Johns Hopkins Hospital
**Not Statistically Significant. Must be less than 0.0500 to be statistically significant.

TABLE IX

Univariate/Multivariate Analysis for Prostate Cancer Organ Confinment
{N = 124 Radical Prostatectomy Specimens}
Organ Confined/Non-Organ Confined: 29/95
Statistical Analysis of JHH-1 Database using Univariately Significant STDEV & VAR Statistics for
CMP Texture Features, Biomarkers, Post Gleason, & JHH-NRV in Organ Confinment Prediction

|  | A<br>PostGL | B<br>JHH-NRV | C<br>Biomarkers<br>(n = 3)** | D2<br>CMP Nuclear<br>Descriptors<br>(n = 10)* | H<br>CMP Nuclear<br>Descriptors<br>(n = 11)*<br>PostGL | I<br>CMP Nuclear<br>Descriptors<br>(n = 13)*<br>JHH-NRV |
|---|---|---|---|---|---|---|
| Positive Cutoff (p >=#) | 0.20 | 0.30 | 0.25 | 0.30 | 0.25 | 0.25 |
| SENSITIVITY | 86.21% | 58.62% | 55.17% | 72.41% | 82.76% | 82.76% |
| Pos Predictive Value | 35.21% | 39.53% | 34.04% | 52.50% | 54.55% | 57.14% |
| SPECIFICITY | 51.58% | 72.34% | 67.37% | 80.00% | 78.95% | 80.85% |
| Neg Predictive Value | 92.45% | 85.00% | 83.12% | 90.48% | 93.75% | 93.83% |
| % False Positives | 64.79% | 60.47% | 65.96% | 47.50% | 45.45% | 42.86% |
| % False Negatives | 7.55% | 15.00% | 16.88% | 9.52% | 6.25% | 6.17% |
| Area Under ROC Curve | 0.733 | 0.6618 | 0.6973 | 0.8635 | 0.9180 | 0.8833 |
| Significance | <0.00001 | 0.0073 | 0.0026 | 0.0005 | <0.00001 | 0.0017 |

|  | J<br>CMP Nuclear<br>Descriptors<br>(n = 14)*<br>JHH-NRV<br>PostGL | K<br>CMP Nuclear<br>Descriptors<br>(n = 12)*<br>Biomarkers<br>(n = 2)**** | L<br>CMP Nuclear<br>Descriptors<br>(n = 14)*<br>Biomarkers<br>(PD41-5)<br>PostGL | M<br>CMP Nuclear<br>Descriptors<br>(n = 12)*<br>Biomarkers<br>(n = 3)**<br>JHH-NRV | N<br>CMP Nuclear<br>Descriptors<br>(n = 14)*<br>Biomarkers<br>(n = 2)****<br>JHH-NRV<br>PostGL |
|---|---|---|---|---|---|
| Positive Cutoff (p >=#) | 0.50 | 0.40 | 0.50 | 0.35 | 0.50 |
| SENSITIVITY | 68.97% | 68.97% | 75.86% | 75.86% | 72.41% |
| Pos Predictive Value | 83.33% | 66.67% | 78.57% | 62.86% | 75.00% |
| SPECIFICITY | 95.74% | 89.47% | 93.68% | 86.17% | 92.55% |
| Neg Predictive Value | 90.91% | 90.43% | 92.71% | 92.05% | 91.58% |
| % False Positives | 16.67% | 33.33% | 21.43% | 37.14% | 25.00% |
| % False Negatives | 9.09% | 9.57% | 7.29% | 7.95% | 8.42% |
| Area Under ROC Curve | 0.9219 | 0.8831 | 0.9397 | 0.9028 | 0.9413 |
| Significance | <0.00001 | 0.0015 | <0.00001 | 0.0006 | <0.00001 |

*NOTE: n = number of CMP Nuclear Descriptors which survived the model either Std. Deviation or Variance or both statistics.
**NOTE: Surviving Biomarkers are C-DNA1, H2NFDN and PD41-5
***NOTE: Surviving Biomarkers are H2NFDN and PD41-5
****NOTE: Surviving Biomarkers are C-DNA1 and PD41-5

TABLE IXa

| Feature | D1 | D2 | H | I | J | K | L | M | N |
|---|---|---|---|---|---|---|---|---|---|
| 1 | X | X | X | X | X | X | X | X | X |
| 2 |  |  |  |  |  |  |  |  |  |
| 3 |  |  |  |  |  |  |  |  |  |
| 4 | X | X | X | X | X | X | X | X | X |
| 5 |  |  |  |  |  |  |  |  |  |
| 6 | X | X | X | X | X | X | X | X | X |
| 7 |  |  |  |  |  |  |  |  |  |
| 8 | X | X | X |  | X |  | X |  | X |
| 9 |  |  |  |  |  |  |  |  |  |
| 10 | X | X | X | X | X | X | X | X | X |
| 11 | X | X | X | X | X | X | X | X | X |
| 12 |  |  |  |  |  |  |  |  |  |
| 13 | X |  |  | X | X | X | X | X | X |
| 14 | X |  | X | X | X | X | X |  | X |
| 15 | X | X | X | X | X | X | X | X | X |
| 16 | X | X | X | X | X | X | X | X | X |
| 17 | X |  |  | X | X | X | X | X | X |
| 18 |  |  |  |  |  |  |  |  |  |
| 19 |  |  |  |  |  |  |  |  |  |
| 20 |  |  |  |  |  |  |  |  |  |
| 21 |  |  |  |  |  |  |  |  |  |
| 22 | X |  |  | X | X | X | X | X | X |
| 23 | X |  |  |  |  |  |  |  |  |
| 24 | X | X | X | X | X | X | X | X | X |
| 25 |  |  |  |  |  |  |  |  |  |
| 26 | X | X | X | X | X |  | X | X | X |
| 27 | X |  |  |  |  |  |  |  |  |
| 28 |  |  |  |  |  |  |  |  |  |

TABLE X

Univariate/Multivariate Analysis for Prostate Cancer Organ Confinement
{N = 124 Radical Prostatectomy Specimens}
Organ Confined/Non-Organ Confined: 29/95
Statistical Analysis of JHH-1 Database using Univariately Significant STDEV & VAR Statistics for
JVB Texture Features, Biomarkers, Post Gleason, & JHH-NRV in Organ Confinement Prediction

|  | A | B | C | D2 | H | I |
|---|---|---|---|---|---|---|
|  |  |  | Biomarkers | JVB Nuclear Descriptors | JVB Nuclear Descriptors (n = 15)* | JVB Nuclear Descriptors (n = 16)* |
|  | PostGL | JHH-NRV | (n = 3)** | (n = 15)* | PostGL | JHH-NRV |
| Positive Cutoff (p >=#) | 0.20 | 0.30 | 0.25 | 0.35 | 0.40 | 0.40 |
| SENSITIVITY | 86.21% | 58.62% | 55.17% | 86.21% | 79.31% | 79.31% |
| Pos Predictive Value | 35.21% | 39.53% | 34.04% | 64.10% | 71.88% | 65.71% |
| SPECIFICITY | 51.58% | 72.34% | 67.37% | 85.26% | 90.53% | 87.23% |
| Neg Predictive Value | 92.45% | 85.00% | 83.12% | 95.29% | 93.48% | 93.18% |
| % False Positives | 64.79% | 60.47% | 65.96% | 35.90% | 28.13% | 34.29% |
| % False Negatives | 7.55% | 15.00% | 16.88% | 4.71% | 6.52% | 6.82% |
| Area Under ROC Curve | 0.7330 | 0.6618 | 0.6973 | 0.9143 | 0.9470 | 0.9156 |
| Significance | <0.00001 | 0.0073 | 0.0026 | 0.0003 | <0.00001 | 0.0003 |

|  | J | K | L | M | N |
|---|---|---|---|---|---|
|  | JVB Nuclear Descriptors (n = 15)* (dropped) PostGL | JVB Nuclear Descriptors (n = 16)* Biomarkers (n = 2)*** | JVB Nuclear Descriptors (n = 15)* Biomarkers (n = 2)*** PostGL | JVB Nuclear Descriptors (n = 16)* Biomarkers (n = 2)*** JHH-NRV | JVB Nuclear Descriptors (n = 16)* Biomarkers (n = 3)** (dropped) PostGL |
| Positive Cutoff (p >=#) | 0.40 | 0.40 | 0.40 | 0.40 | 0.40 |
| SENSITIVITY | 79.31% | 82.76% | 93.10% | 82.76% | 93.10% |
| Pos Predictive Value | 71.88% | 75.00% | 81.82% | 72.73% | 81.82% |
| SPECIFICITY | 90.53% | 91.58% | 93.68% | 90.43% | 93.68% |
| Neg Predictive Value | 93.48% | 94.57% | 97.80% | 94.44% | 97.80% |
| % False Positives | 28.13% | 25.00% | 18.18% | 27.27% | 18.18% |
| % False Negatives | 6.52% | 5.43% | 2.20% | 5.56% | 2.20% |
| Area Under ROC Curve | 0.9470 | 0.9336 | 0.9670 | 0.9384 | 0.9655 |
| Significance | <0.00001 | <0.00001 | <0.00001 | <0.00001 | <0.00001 |

*NOTE: n = number of JVB Nuclear Descriptors which survived the model, either Std. Deviation or Variance or both statistics.
**NOTE: Surviving Biomarkers are C-DNA1, H2NFDN, and PD41-5
***NOTE: Surviving Biomarkers are H2NFDN and PD41-5

TABLE Xa

| Feature | D1 | D2 | H | I | J | K | L | M | N |
|---|---|---|---|---|---|---|---|---|---|
| 1 | X | X | X | X | X | X | X | X | X |
| 2 |  |  |  |  |  |  |  |  |  |
| 3 |  |  |  |  |  |  |  |  |  |
| 4 | X | X | X | X | X | X | X | X | X |
| 5 |  |  |  |  |  |  |  |  |  |
| 6 | X | X | X | X | X | X | X | X | X |
| 7 |  |  |  |  |  |  |  |  |  |
| 8 | X | X | X | X | X | X | X | X | X |
| 9 |  |  |  |  |  |  |  |  |  |
| 10 | X | X | X | X | X | X | X | X | X |
| 11 | X | X | X | X | X | X | X | X | X |
| 12 |  |  |  |  |  |  |  |  |  |
| 13 | X | X | X | X | X | X |  | X | X |
| 14 | X | X | X | X | X | X | X | X | X |
| 15 | X | X | X | X | X | X | X | X | X |
| 16 | X | X | X | X | X | X | X | X | X |
| 17 | X | X | X | X | X | X | X | X | X |
| 18 |  |  |  |  |  |  |  |  |  |
| 19 |  |  |  |  |  |  |  |  |  |
| 20 |  |  |  |  |  |  |  |  |  |
| 21 |  |  |  |  |  |  |  |  |  |
| 22 | X | X | X | X | X | X | X | X | X |
| 23 | X |  |  |  |  |  |  |  |  |
| 24 | X | X | X | X | X | X | X | X | X |
| 25 |  |  |  |  |  |  |  |  |  |
| 26 | X |  |  | X |  | X | X | X | X |
| 27 |  |  |  |  |  |  |  |  |  |
| 28 |  |  |  |  |  |  |  |  |  |
| 29 | X |  |  |  |  |  |  |  |  |
| 30 | X | X | X | X | X | X | X | X | X |
| 31 | X | X | X | X | X | X | X | X | X |
| 32 |  |  |  |  |  |  |  |  |  |
| 33 |  |  |  |  |  |  |  |  |  |
| 34 |  |  |  |  |  |  |  |  |  |
| 35 |  |  |  |  |  |  |  |  |  |
| 36 |  |  |  |  |  |  |  |  |  |

TABLE Xb

JHH1 METASTATIC SUBSET
n = 13

| PCode | OC | PROG | PostGL | Exposure | Local | Distant | PD41 | DNA Ploidy | Her-2/neu | JVB NMD Predicted Progression Probatility | JVB NMD Predicted Progression Outcome (Cutoff = 0.40) | Total Model (Model L) Predicted Probabilities | Total Model (JVB Progression Model L) Predicted Outcome (Cutoff = 0.50) |
|---|---|---|---|---|---|---|---|---|---|---|---|---|---|
| 45  | 0 | 1 | 9 | 7 | 0 | 1 | + | Aneuploid | + | 0.9988 | 1 | 0.9645 | 1 |
| 100 | 0 | 1 | 6 | 7 | 1 | 1 | + | Aneuploid | + | 0.3499 | 0 | 0.1498 | 0 |
| 101 | 0 | 1 | 6 | 1 | 1 | 0 | + | Aneuploid | + | 0.0917 | 0 | 0.4268 | 0 |
| 105 | 0 | 1 | 8 | 8 | 1 | 0 | + | Aneuploid | + | 0.7284 | 1 | 0.9763 | 1 |
| 149 | 1 | 1 | 6 | 1 | 1 | 0 | − | Aneuploid | + | 0.9767 | 1 | 0.5812 | 1 |
| 200 | 0 | 1 | 7 | 5 | 1 | 0 | + | Aneuploid | − | 0.7355 | 1 | 0.8157 | 1 |
| 210 | 0 | 1 | 8 | 6 | 1 | 0 | + | Diploid | + | 0.9997 | 1 | 0.9999 | 1 |
| 260 | 0 | 1 | 7 | 1 | 1 | 1 | − | Aneuploid | + | 0.8009 | 1 | 0.8254 | 1 |
| 359 | 0 | 1 | 7 | 2 | 1 | 0 | − | Diploid | + | 1.0000 | 1 | 0.9906 | 1 |
| 410 | 0 | 1 | 7 | 4 | 0 | 1 | + | Diploid | + | 0.6481 | 1 | 0.6127 | 1 |
| 498 | 0 | 1 | 7 | 3 | 1 | 0 | + | Diploid | + | 0.7657 | 1 | 0.9685 | 1 |
| 699 | 0 | 1 | 8 | 3 | 1 | 0 | + | Aneuploid | + | 0.8843 | 1 | 0.9999 | 1 |
| 753 | 0 | 1 | 7 | 2 | 0 | 1 | − | Aneuploid | + | 1.0000 | 1 | 1.0000 | 1 |

OC: 1 = Organ Confined Disease, 0 = Non-Organ Confined Disease
PROG: 1 = Disease Progression, 0 = Non-Progression of Disease
PostGL: Combined Post-Operative Gleason Score
Exposure: The time in years that it took for disease progression.
Local: 1 = Metastasis to surrounding tissue (i.e. lymph nodes and seminal vesicles), 0 = No local metastasis.
Distant: 1 = Metastasis to distant site (i.e. bone marrow), 0 = No distant metastasis.
Predicted Outcomes: 1 = Prostate cancer predicted to progress, 0 = Prostate cancer predicted not to progress.

METHODS TO OBTAIN PATIENT-SPECIFIC RESULTS:

Logistic Regression Method—STATA™ provides a command (logit, an estimated maximum-likelihood logit model) that provides the weighted coefficients for the statistically significant independent variables used in the multivariate model and the model constant. The general formulas for calculating the predictive index and predictive probability are as follows:

The final calculation of the predictive probability provides a patient-specific value, between 0 and 1, for the probability of a specific outcome (e.g. progression or organ confined disease status). The threshold value (cutoff) for the predicted probability is selected based upon the results of the ROC curves. Table XI illustrates patient specific NMD and multi-parameter (combined) predictive probabilities calculated using this method.

TABLE XI

Use of Logistic Regression (logit) to Predict Patient-Specific Outcomes

| Case I.D. | PD41-5 | C-DNA1 | H2NFDN | PostGL | Morphometry Predictive Probability | Combined Parameters Predictive Probabilities | Predicted Outcome (Cutoff: 0.50) |
|---|---|---|---|---|---|---|---|
| 33   | + | Diploid      | Focal   | 5 | 0.14 | 0.02 | 0 |
| 34   | − | Ab: >S + G2M | Diffuse | 7 | 0.92 | 0.93 | 1 |
| 149  | − | Aneuploid    | Focal   | 6 | 0.98 | 0.58 | 1 |
| 9952 | − | Hypodiploid  | Diffuse | 4 | 0.09 | 0.00 | 0 |

Predictive Index $(xb) = (\beta_0 + \beta_1 \text{var}(1) + \beta_2 \text{var}(2) + \cdots + \beta_n \text{var}(n))$ Predictive Probability $(p) = e^{xb}/(1 + e^{xb})$ Where:

$\beta_0$ = Formula Constant $\beta_1$ through $\beta_n$ = Weight factors for variables 1 through $n$ var(1) through var($n$) = Independent variables being used in logistic regression model.

Neural Networks—The first network configuration to be considered was a standard multilayer sigmoidal network with a single hidden layer. The neural network input layer consisted of either 15, 28, or 30 input nodes to accommodate the input data set of either 15, 28, or 30 measurements (NMD's and Gleason Score). The activation function in each hidden layer and output layer neuron is sigmoid. Different network configurations (number of hidden layer neurons) with various training termination conditions were tested. FIG. 29 illustrates the neural network configuration used in this study. It was found, for the given training set, that the neural network classifier works best with 20 hidden layer neurons and when the training is terminated at approximately 1000 iterations.

The second network configuration tested consisted of a single hidden layer as well. However, the non-linearity function used was the sinusoidal function (proprietary Hybrid network). The output layer neurons still used the sigmoidal transfer function. It had the same structure as the first network (see FIG. 29). A number of different frequencies were tested to find the best combination. The best frequency was found to be F=0.2.

All networks (standard and hybrid with 15, 28, or 30 inputs) were tested using the ten different combinations of randomly selected test (18) and training (106) cases. The threshold value (cutoff) used in all cases was 0.5. Table XII summarizes the results using the standard sigmoidal neural networks applied to the n=124 patient sample described in this invention (Tables XIIa, b, & c). Notable is the fact that this network degrades as the number of input features is increased from 15 to 28 to 30. Please note that the 28 and 30 feature networks did not undergo pre-selection using logistic regression methods. The best performing network was the one labeled "15 Input Features", where the features were pre-selected based upon statistical significance using logistic regression methods. Therefore, the use of statistical methods to pre-select statically significant features improves network performance.

Also it is evident from the variation in the predictive rates among the ten trained networks that if the number of patients is increased, the performance of the network should be significantly improved.

TABLE XII

Sigmoidal Neural Network Comparisons: JHH-1 (n = 124)

| Network # | Progression Predictive Rates | | |
|---|---|---|---|
| | 15 Feature NN | 28 Feature NN | 30 Feature NN |
| 1 | 78% | 61% | 67% |
| 2 | 83% | 61% | 61% |
| 3 | 89% | 50% | 50% |
| 4 | 67% | 83% | 67% |
| 5 | 67% | 72% | 72% |
| 6 | 83% | 78% | 67% |
| 7 | 89% | 78% | 72% |
| 8 | 78% | 78% | 72% |
| 9 | 72% | 78% | 78% |
| 10 | 89% | 72% | 72% |
| Mean | 79% | 71% | 68% |
| Standard Error | 3% | 3% | 2% |
| Median | 81% | 75% | 70% |
| Mode | 78% | 78% | 72% |
| Standard Deviation | 9% | 10% | 8% |
| Variance | 1% | 1% | 1% |

TABLE XIIa

Sigmoidal Neural Network: 15 Input Features

| Network # | Predictive Rate | Total Error | % Error Progressors | % Error Non-Progressors |
|---|---|---|---|---|
| 1 | 78% | 22% | 33% | 11% |
| 2 | 83% | 17% | 33% | 0% |
| 3 | 89% | 11% | 22% | 0% |
| 4 | 67% | 33% | 55% | 11% |
| 5 | 67% | 33% | 55% | 11% |
| 6 | 83% | 17% | 22% | 11% |
| 7 | 89% | 11% | 22% | 0% |
| 8 | 78% | 22% | 33% | 11% |
| 9 | 72% | 28% | 33% | 22% |
| 10 | 89% | 11% | 11% | 11% |
| Mean | 80% | 21% | 32% | 9% |
| Standard Error | 3% | 3% | 4% | 2% |
| Median | 81% | 20% | 33% | 11% |
| Mode | 89% | 11% | 33% | 11% |
| Standard Deviation | 9% | 9% | 14% | 7% |
| Variance | 1% | 1% | 2% | 0% |

TABLE XIIb

Sigmoidal Neural Network: 28 Input Features

| Network # | Predictive Rate | Total Error | % Error Progressors | % Error Non-Progressors |
|---|---|---|---|---|
| 1 | 61% | 39% | 55% | 22% |
| 2 | 61% | 39% | 55% | 22% |
| 3 | 50% | 50% | 67% | 33% |
| 4 | 83% | 17% | 33% | 0% |
| 5 | 72% | 28% | 44% | 11% |
| 6 | 78% | 22% | 33% | 11% |
| 7 | 78% | 22% | 33% | 11% |
| 8 | 78% | 22% | 33% | 11% |
| 9 | 78% | 22% | 44% | 0% |
| 10 | 72% | 28% | 44% | 11% |
| Mean | 71% | 29% | 44% | 13% |
| Standard Error | 3% | 3% | 4% | 3% |
| Median | 75% | 25% | 44% | 11% |
| Mode | 78% | 22% | 33% | 11% |
| Standard Deviation | 10% | 10% | 12% | 10% |
| Variance | 1% | 1% | 1% | 1% |

TABLE XIIc

Sigmoidal Neural Network: 30 Input Features

| Network # | Predictive Rate | Total Error | % Error Progressors | % Error Non-Progressors |
|---|---|---|---|---|
| 1 | 67% | 33% | 44% | 22% |
| 2 | 61% | 39% | 67% | 11% |
| 3 | 50% | 50% | 67% | 33% |
| 4 | 67% | 33% | 67% | 0% |
| 5 | 72% | 28% | 44% | 11% |
| 6 | 67% | 33% | 44% | 22% |
| 7 | 72% | 28% | 44% | 11% |
| 8 | 72% | 28% | 33% | 22% |
| 9 | 78% | 22% | 44% | 0% |
| 10 | 72% | 28% | 44% | 11% |
| Mean | 68% | 32% | 50% | 14% |
| Standard Error | 2% | 2% | 4% | 3% |
| Median | 70% | 31% | 0% | 11% |
| Mode | 72% | 28% | 0% | 11% |
| Standard Deviation | 8% | 8% | 12% | 10% |
| Variance | 1% | 1% | 2% | 1% |

Table XIII illustrates the results for the Hybrid neural network using the n=124 patient sample described in this invention (Tables XIIIa, b, & c). The same observations as made for the standard sigmoidal network above apply to the Hybrid neural network. In conclusion, the use of appropriately trained standard or Hybrid neural networks can be used to predict patient specific outcomes (e.g. progression or organ confined disease status).

When predicting organ confined disease, one would first provide a neural network; then train the neural network using a first set of prognostic parameters obtained from cells known to lose organ confinement and a second set of prognostic parameters obtained from cells known not to lose organ confinement, followed by analyzing prognostic parameters in tumor cells of an individual having an unknown state of organ confinement and predicting the loss of organ confinement in cells of the individual having an unknown state of organ confinement using the prognostic parameters and the trained neural network. The prognostic parameters may be the number of positive sextant core biopsies, sum area of tumor involvement, and quantitative nuclear grade. In other embodiments, the prognostic parameters may be serum PSA, tumor location, number of positive sextant core biopsies, sum area of tumor involvement, quantitative nuclear grade, DNA ploidy, and post operative Gleason score.

The neural network may employ the prognostic parameters that include the quantitative nuclear grade group comprising difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation. In still further embodiments, the quantitative nuclear grade parameters are object sum, optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, and configurable run length.

The neural network of the instant invention may also include additional biomarkers, such as the determination of RT-PCR mRNA levels. The network may be of the back propagation type, or it may be of the hybrid type.

Classification and Regression Trees (CART)—Application of recursive partitioning methods using the SYSTAT CART™ for DOS v1.02 (Evanston, Ill.) software program was performed. This method is another example of a non-parametric statistical classifier. The use of this method yields similar classification results using the well defined patient sample (n=124), and can generate a patient specific outcome using a trained CART. Those experienced in the art of non-parametric statistical classifiers realize that several other such methods exist and can be applied to achieve this same end.

TABLE XIII

Hybrid Neural Network Comparisons: JHH-1 (n = 124)

| | Progression Predictive Rates | | |
|---|---|---|---|
| Network # | 15 Feature NN | 28 Feature NN | 30 Feature NN |
| 1 | 67% | 72% | 67% |
| 2 | 67% | 56% | 67% |
| 3 | 83% | 56% | 56% |
| 4 | 67% | 56% | 67% |
| 5 | 72% | 67% | 78% |
| 6 | 89% | 72% | 72% |
| 7 | 89% | 67% | 78% |
| 8 | 78% | 72% | 67% |
| 9 | 72% | 72% | 67% |
| 10 | 78% | 67% | 78% |

TABLE XIII-continued

Hybrid Neural Network Comparisons: JHH-1 (n = 124)

| | Progression Predictive Rates | | |
|---|---|---|---|
| Network # | 15 Feature NN | 28 Feature NN | 30 Feature NN |
| Mean | 76% | 68% | 70% |
| Standard Error | 3% | 1% | 2% |
| Median | 75% | 67% | 67% |
| Mode | 67% | 67% | 67% |
| Standard Deviation | 9% | 4% | 7% |
| Variance | 1% | 0% | 0% |

TABLE XIIIa

Hybrid Neural Network: 15 Input Features

| Network # | Predictive Rate | Total Error | % Error Progressors | % Error Non-Progressors |
|---|---|---|---|---|
| 1 | 67% | 33% | 44% | 22% |
| 2 | 67% | 33% | 55% | 11% |
| 3 | 83% | 17% | 22% | 11% |
| 4 | 67% | 33% | 44% | 22% |
| 5 | 72% | 28% | 44% | 11% |
| 6 | 89% | 11% | 22% | 0% |
| 7 | 90% | 11% | 22% | 0% |
| 8 | 78% | 22% | 33% | 11% |
| 9 | 72% | 28% | 33% | 22% |
| 10 | 78% | 22% | 22% | 22% |
| Mean | 76% | 24% | 34% | 13% |
| Standard Error | 3% | 3% | 4% | 3% |
| Median | 75% | 25% | 33% | 11% |
| Mode | 67% | 33% | 22% | 22% |
| Standard Deviation | 9% | 9% | 12% | 9% |
| Variance | 1% | 1% | 1% | 1% |

TABLE XIIIb

Hybrid Neural Network: 28 Input Features

| Network # | Predictive Rate | Total Error | % Error Progressors | % Error Non-Progressors |
|---|---|---|---|---|
| 1 | 72% | 28% | 33% | 22% |
| 2 | 56% | 44% | 55% | 33% |
| 3 | 56% | 44% | 67% | 22% |
| 4 | 56% | 44% | 67% | 22% |
| 5 | 67% | 33% | 44% | 22% |
| 6 | 72% | 28% | 44% | 11% |
| 7 | 67% | 33% | 55% | 11% |
| 8 | 72% | 28% | 33% | 22% |
| 9 | 72% | 28% | 44% | 11% |
| 10 | 67% | 33% | 55% | 11% |
| Mean | 66% | 34% | 50% | 19% |
| Standard Error | 2% | 2% | 4% | 2% |
| Median | 67% | 33% | 50% | 22% |
| Mode | 67% | 28% | 55% | 11% |
| Standard Deviation | 7% | 7% | 12% | 7% |
| Variance | 1% | 1% | 1% | 1% |

TABLE XIIIc

Hybrid Neural Network: 30 Input Features

| Network # | Predictive Rate | Total Error | % Error Progressors | % Error Non-Progressors |
|---|---|---|---|---|
| 1 | 67% | 33% | 44% | 22% |
| 2 | 67% | 33% | 44% | 22% |
| 3 | 56% | 44% | 78% | 11% |
| 4 | 67% | 33% | 55% | 11% |

TABLE XIIIc-continued

Hybrid Neural Network: 30 Input Features

| Network # | Predictive Rate | Total Error | % Error Progressors | % Error Non-Progressors |
|---|---|---|---|---|
| 5 | 78% | 22% | 33% | 11% |
| 6 | 72% | 28% | 33% | 22% |
| 7 | 78% | 22% | 22% | 22% |
| 8 | 67% | 33% | 44% | 22% |
| 9 | 67% | 33% | 55% | 11% |
| 10 | 78% | 22% | 33% | 11% |
| Mean | 70% | 30% | 44% | 17% |
| Standard Error | 2% | 2% | 5% | 2% |
| Median | 67% | 33% | 44% | 17% |
| Mode | 67% | 33% | 44% | 22% |
| Standard Deviation | 7% | 7% | 16% | 6% |
| Variance | 0% | 0% | 2% | 0% |

BRIEF DESCRIPTION OF THE DRAWINGS

The following drawings form part of the present specification and are included to following demonstrate certain aspects of the present invention. The invention may be better understood by reference to one or more of these drawings in combination with the detailed description of specific embodiments presented herein.

FIG. 28A and FIG. 28B. DNA Classification scheme for prostate image analysis Normal range: Diploid: S-Phase+G2M<10% of cells studied; Out of normal range: Hypodiploid: DNA Index<0.70>S+G2M: 11–21% of cells studied (includes hyperploidy); Abnormal range: >S+G2M: >22% of cells studied; aneuploid: >10% of cells studied; tetraploid: >16% of cells studied.

DETAILED DESCRIPTION

Figure 1A:
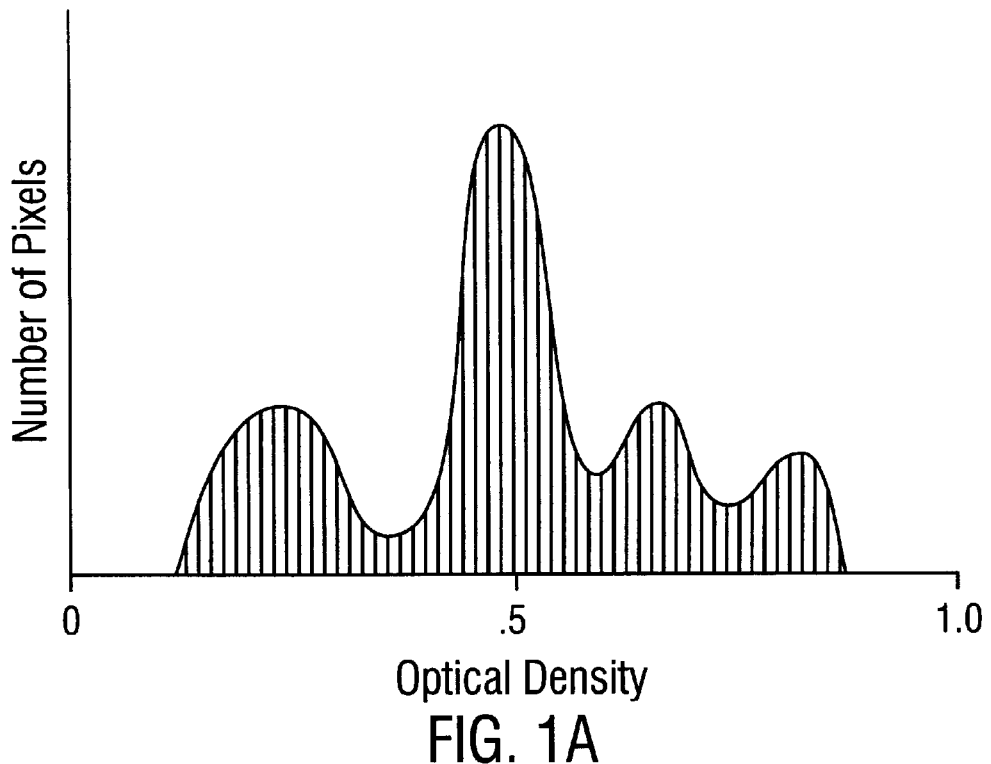
FIG. 1A and FIG. 1B. Normalization plot of each individual pixel optical density (gray level), divided into eight equally frequent gray-level ranges (optical density ranges); each range containing an equal number of pixels.
Figure 1B:
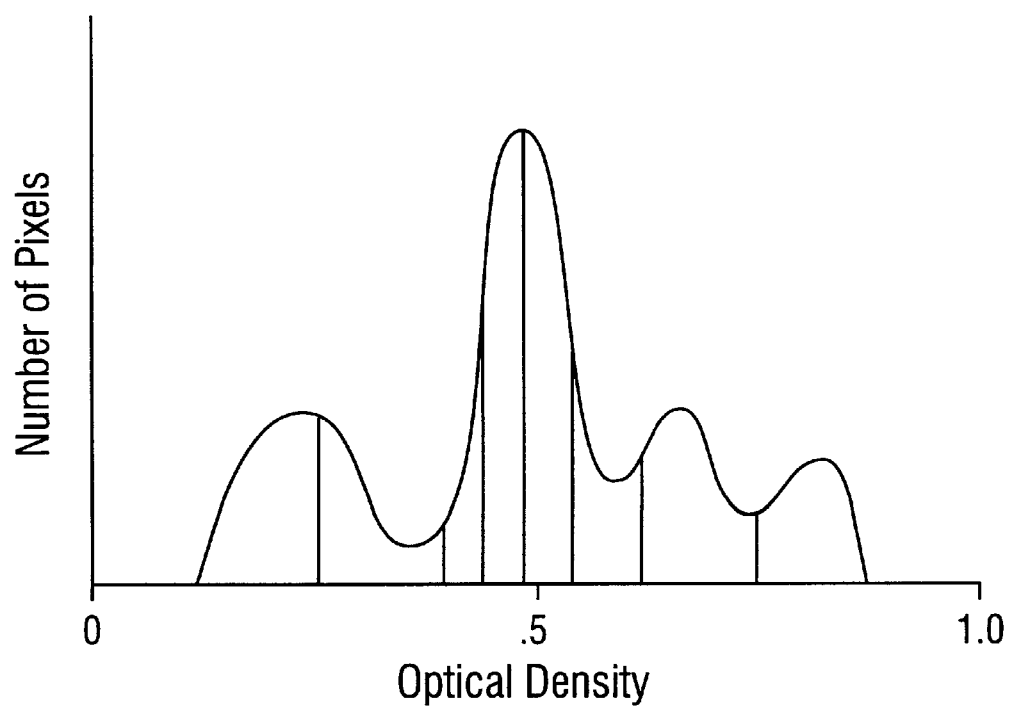
Figure 2:
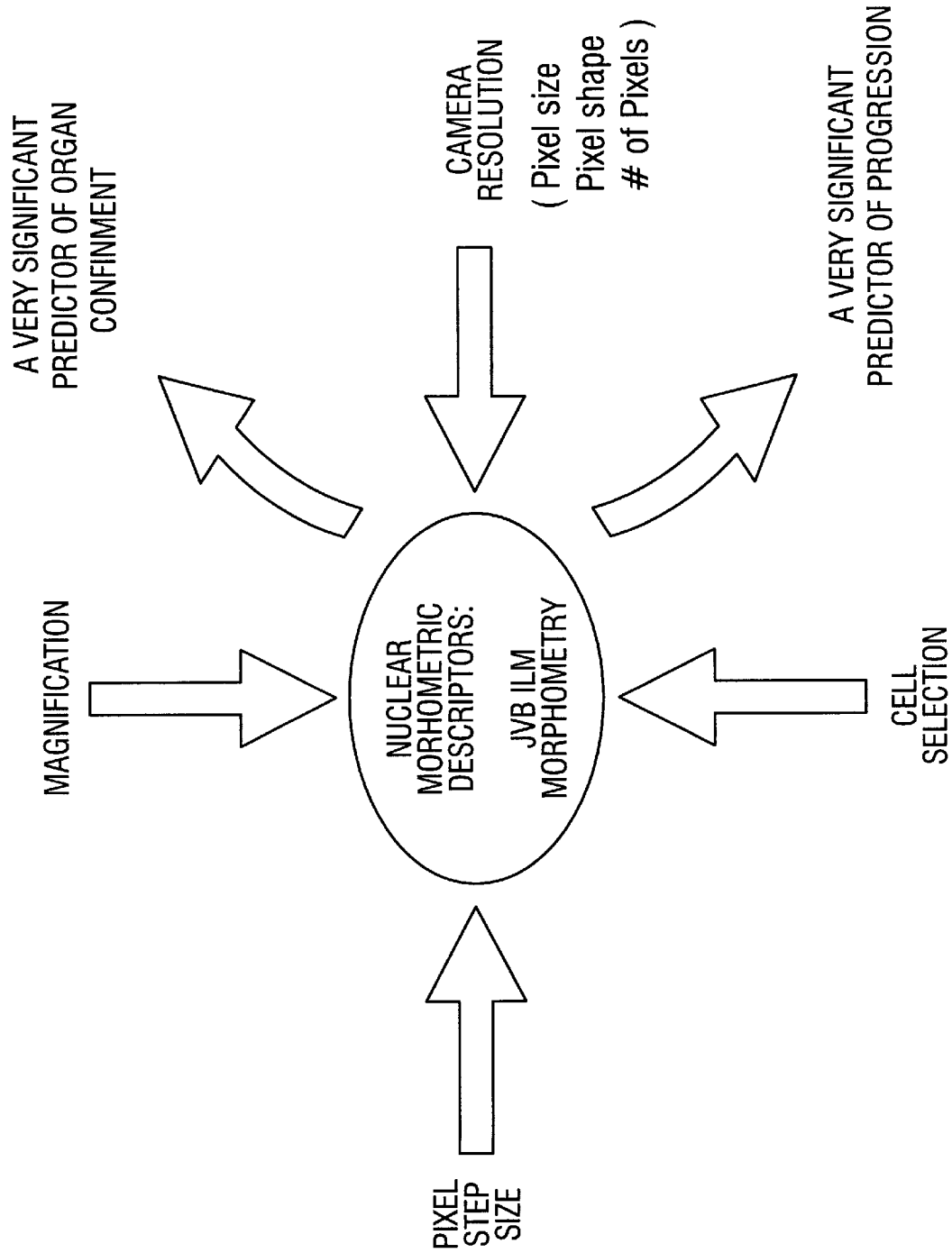
FIG. 2. Parameters including cell selection, magnification, camera resolution, (pixel size, pixel shape and number of pixels) and Markovian step size that can significantly alter nuclear morphometric descriptor outputs.
Figure 3:
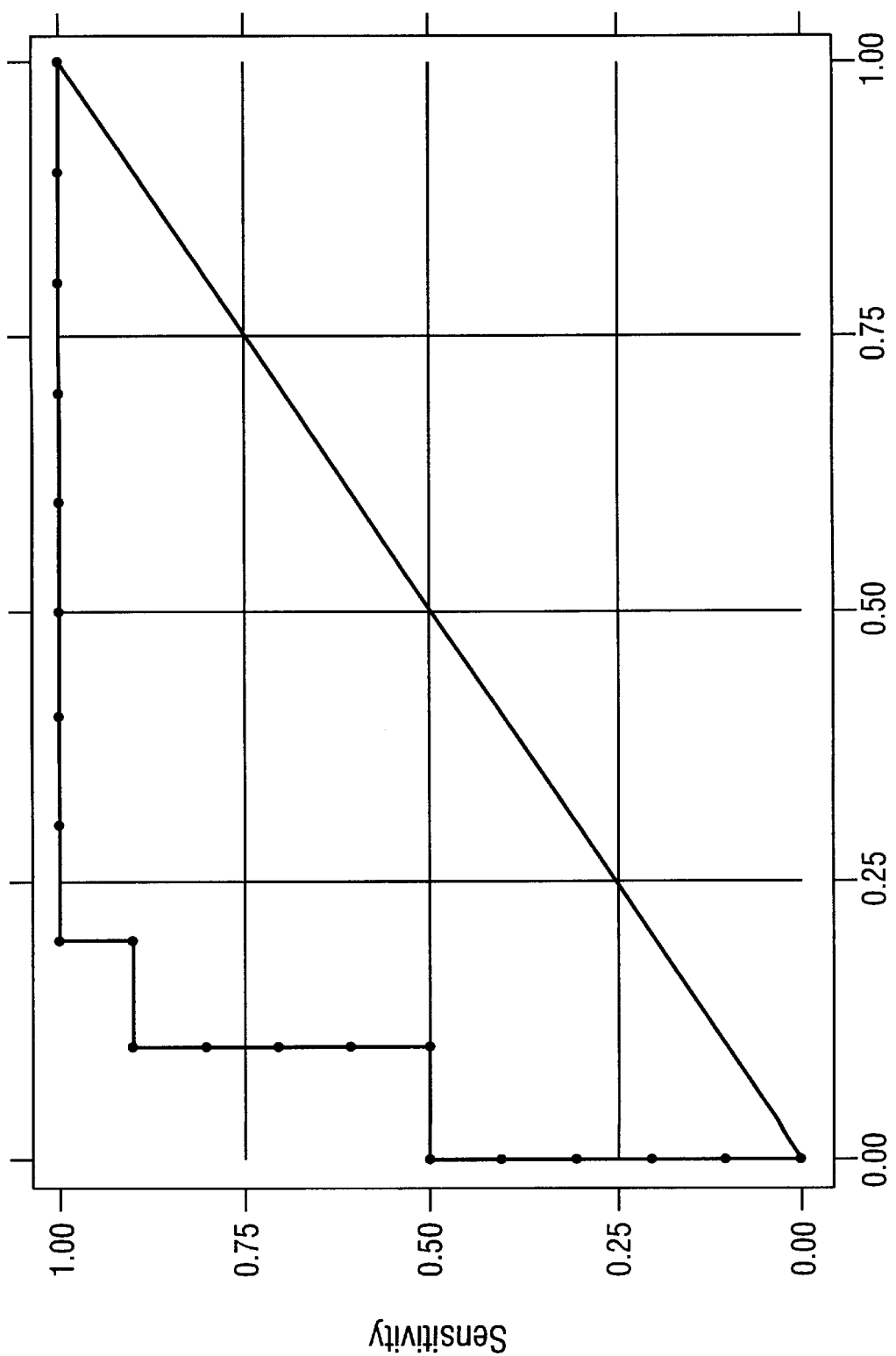
FIG. 3. Identification of progressors (subset of 20 cases using standard deviation and variance of best CMP 40× nuclear morphometric descriptors. This figure shows the predictive power using the combined CMP NMD's measured with a 40× objective. Using 7 different CMP NMD's, a ROC curve was produced with an area under the curve of 94%.
Figure 4:
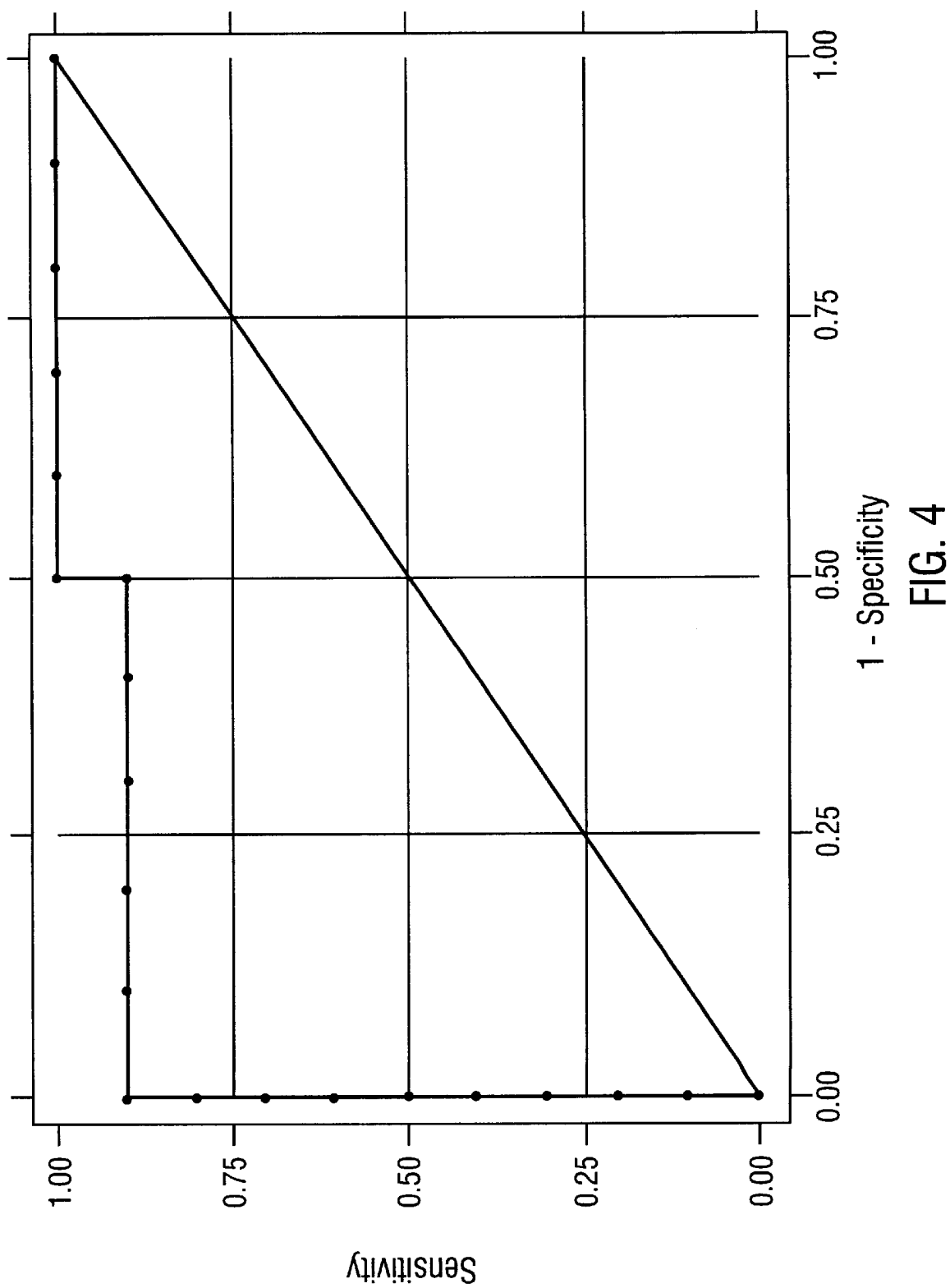
FIG. 4. Identification of progressors (subset of 20 cases) using standard deviation and variance of best JVB 40× nuclear morphometric descriptors. This figure shows the predictive power using the combined JVB NMD's measured with a 40× objective. Using 8 different JVB NMD's, a ROC curve was produced with an area under the curve of 95%.
Figure 5:
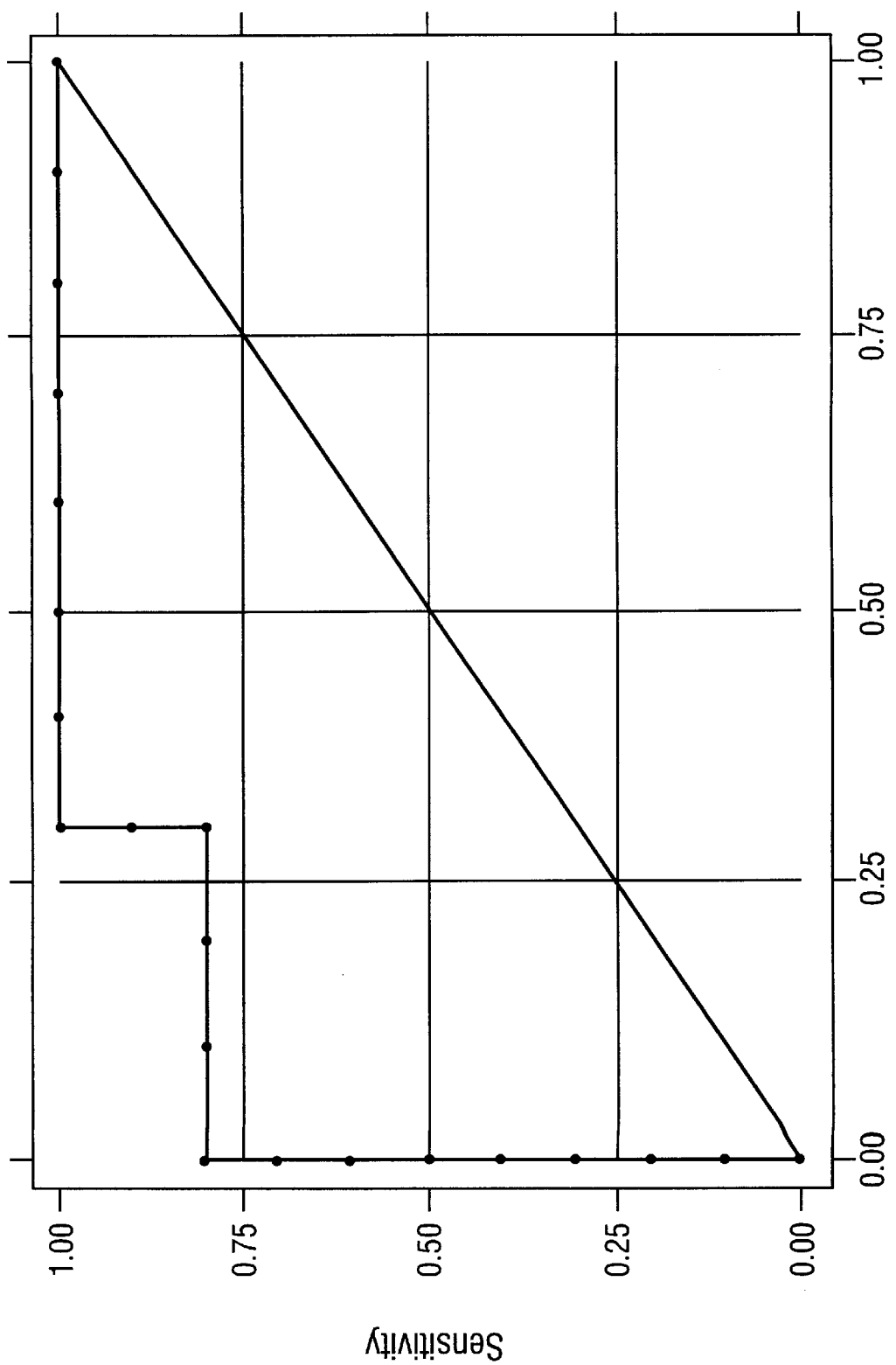
FIG. 5. Identification of progressors (subset of 20 cases) using standard deviation and variance of best CMP 63× nuclear morphometric descriptors. This figure shows the predictive power using the combined CMP NMD's measured with a 63× objective. Using 6 different CMP NMD's, a ROC curve was produced with an area under the curve of 94%.
Figure 6:
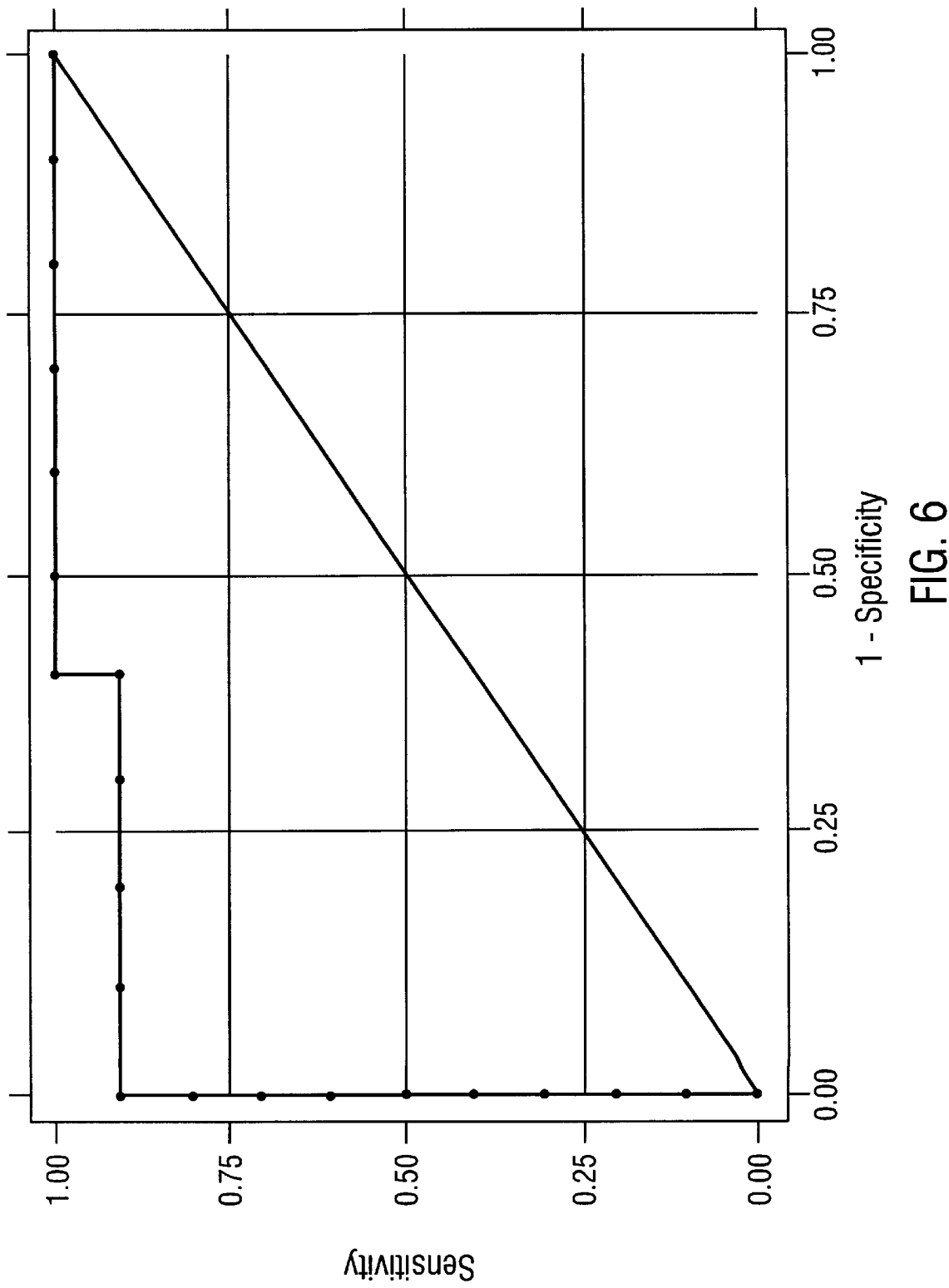
FIG. 6. Identification of progressors (subset of 20 cases) using standard deviation and variance of best JVB 63× nuclear morphometric descriptors. This figure shows the predictive power using the combined JVB NMD's measured with a 63× objective. Using 5 different JVB NMD's, a ROC curve was produced with an area under the curve of 96%.
Figure 7:
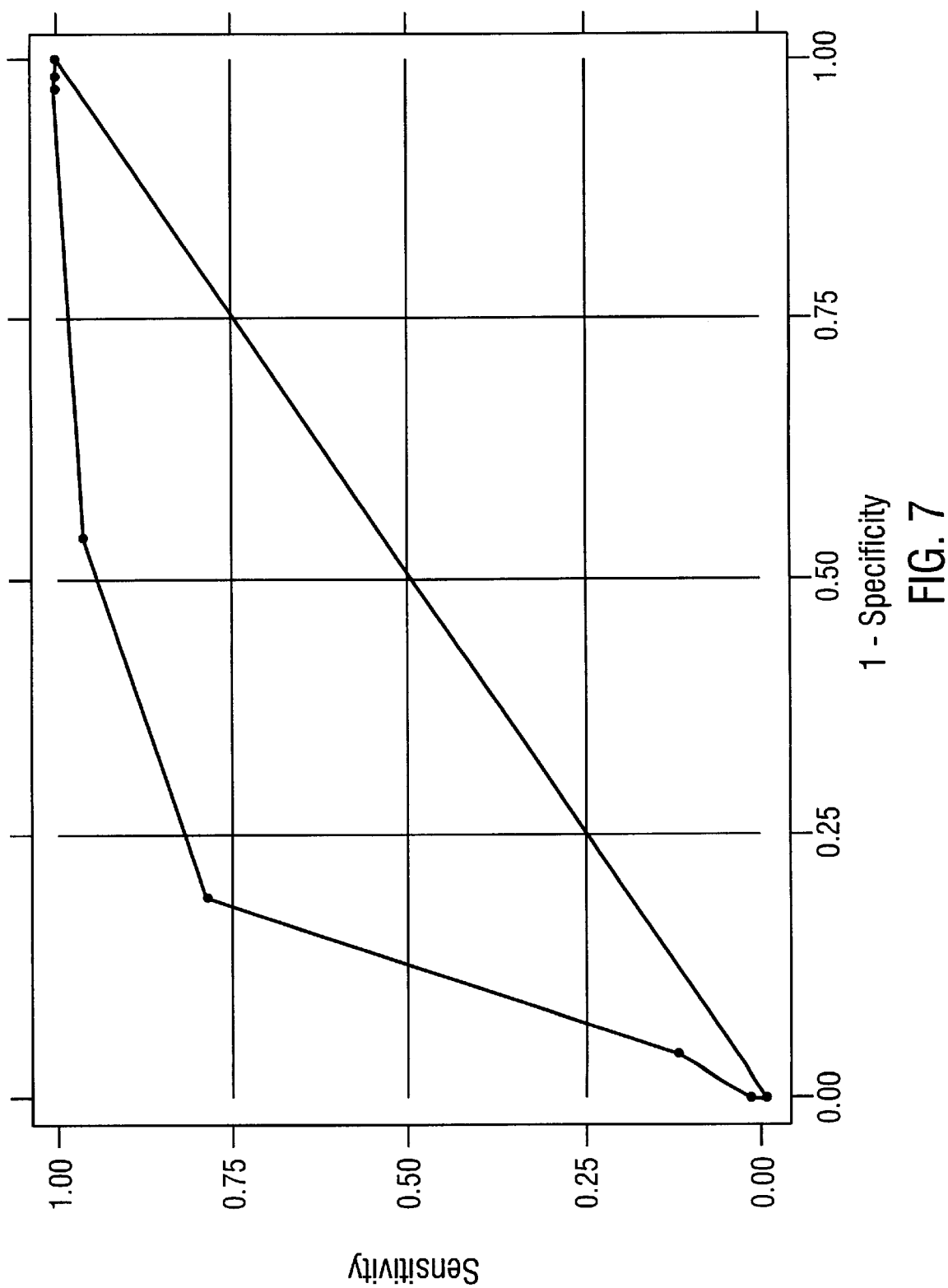
FIG. 7. Post-operative Gleason score significance in the prediction of prostate cancer progression. A ROC curve was produced with an area under the curve of 82.62%. This figure illustrates the predictive power of Post Operative Gleason Score as a single independent variable to predict progression. Please refer to Column A of Table VI.
Figure 8:
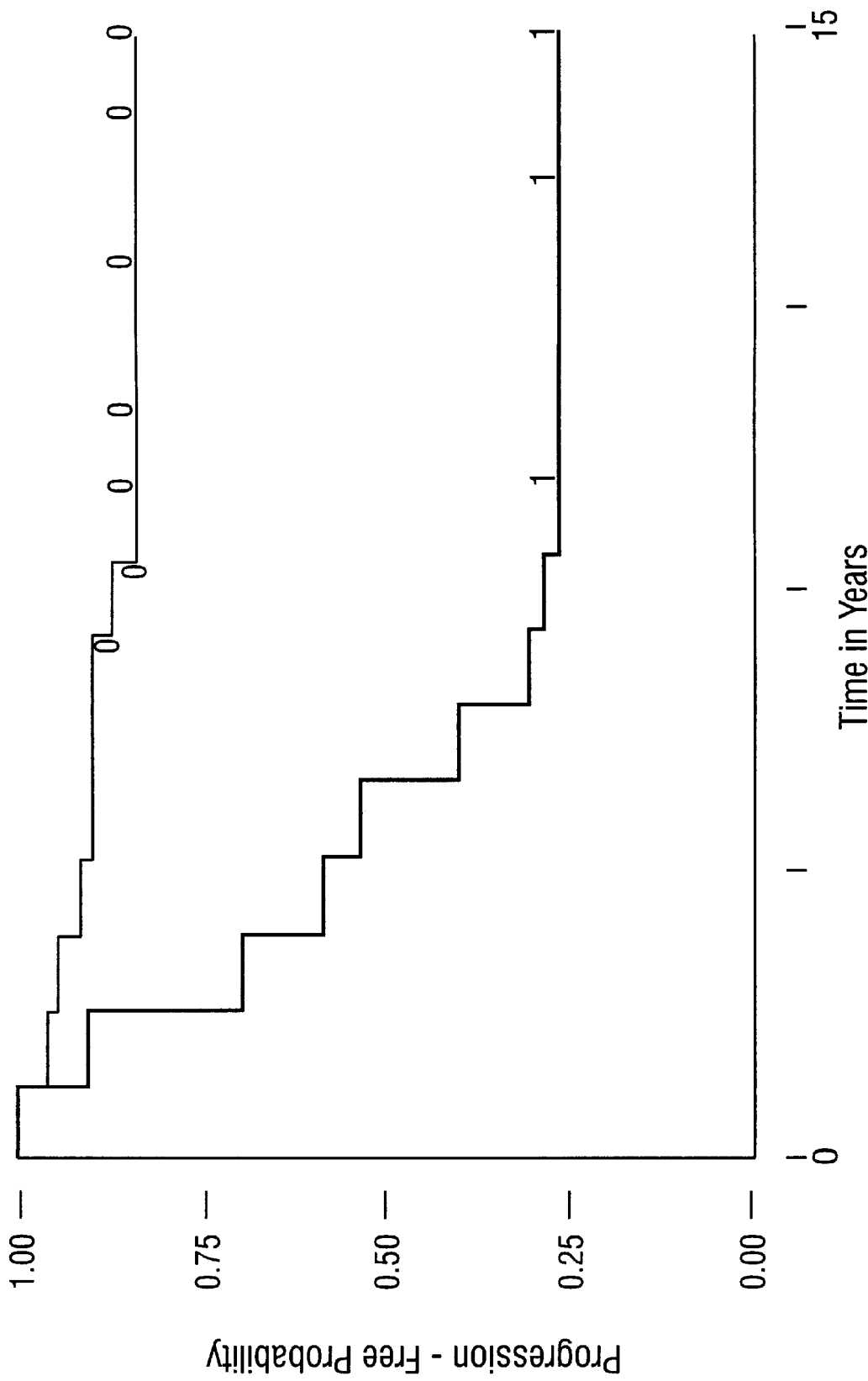
FIG. 8. Post-operative Gleason score significance in the prediction of prostate cancer progression (0=predicted not to progress; 1=predicted to progress). This figure demonstrates the ability of the Post Operative Gleason Score alone to stratify progressors and non-progressors using a Kaplan-Meier Survival (Recurrence) Curve. This is the pathologic standard against which all models are tested.
Figure 9:
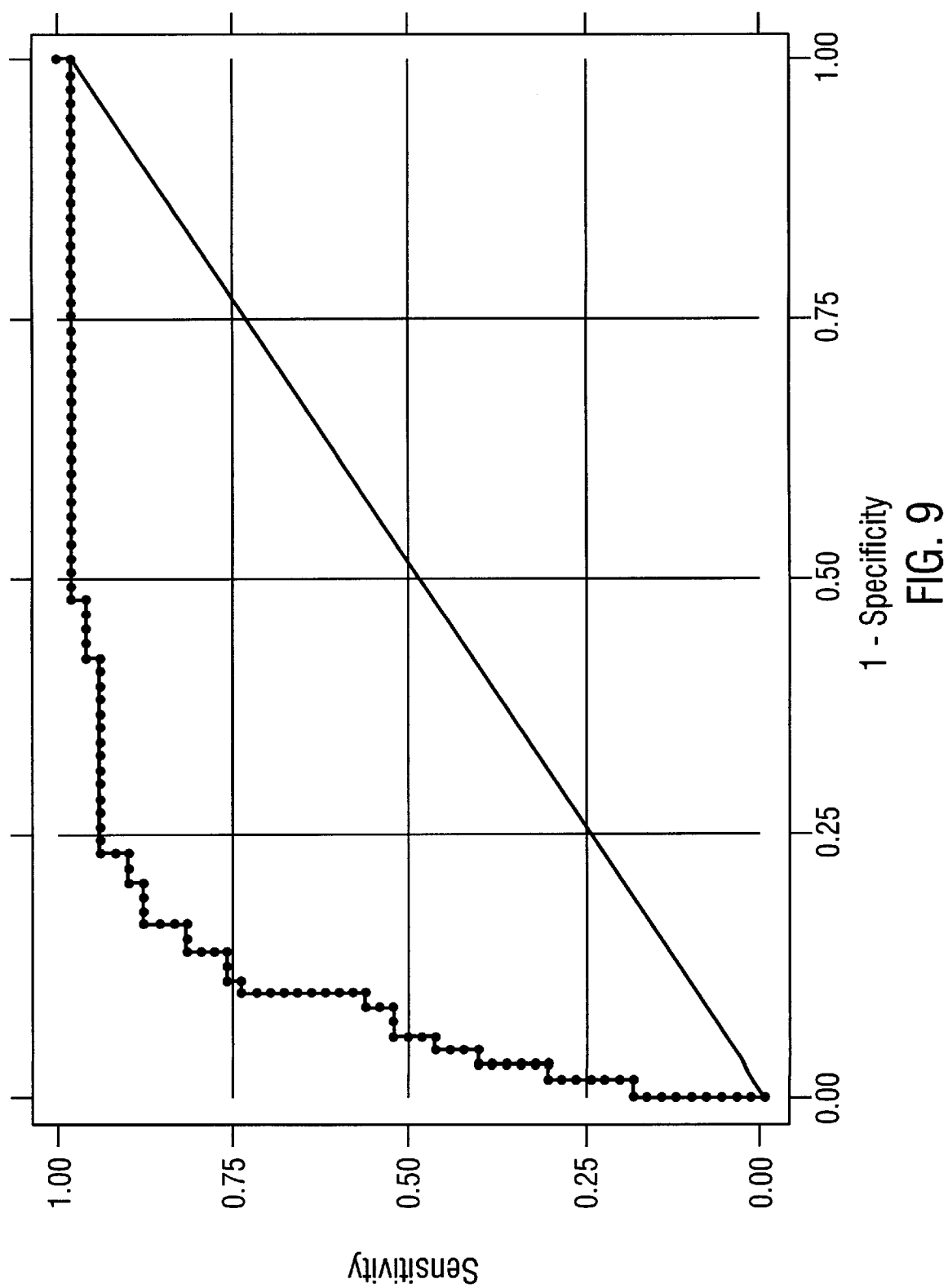
FIG. 9. Nuclear roundness variance significance in the prediction of prostate cancer progression. This figure illustrates the predictive power of Nuclear Roundness Variance (as measured by the DynaCell System at 100×) to predict progression. A ROC curve was produced with an area under the curve of 89.75%. Please refer to Column B of Table VI.
Figure 10:
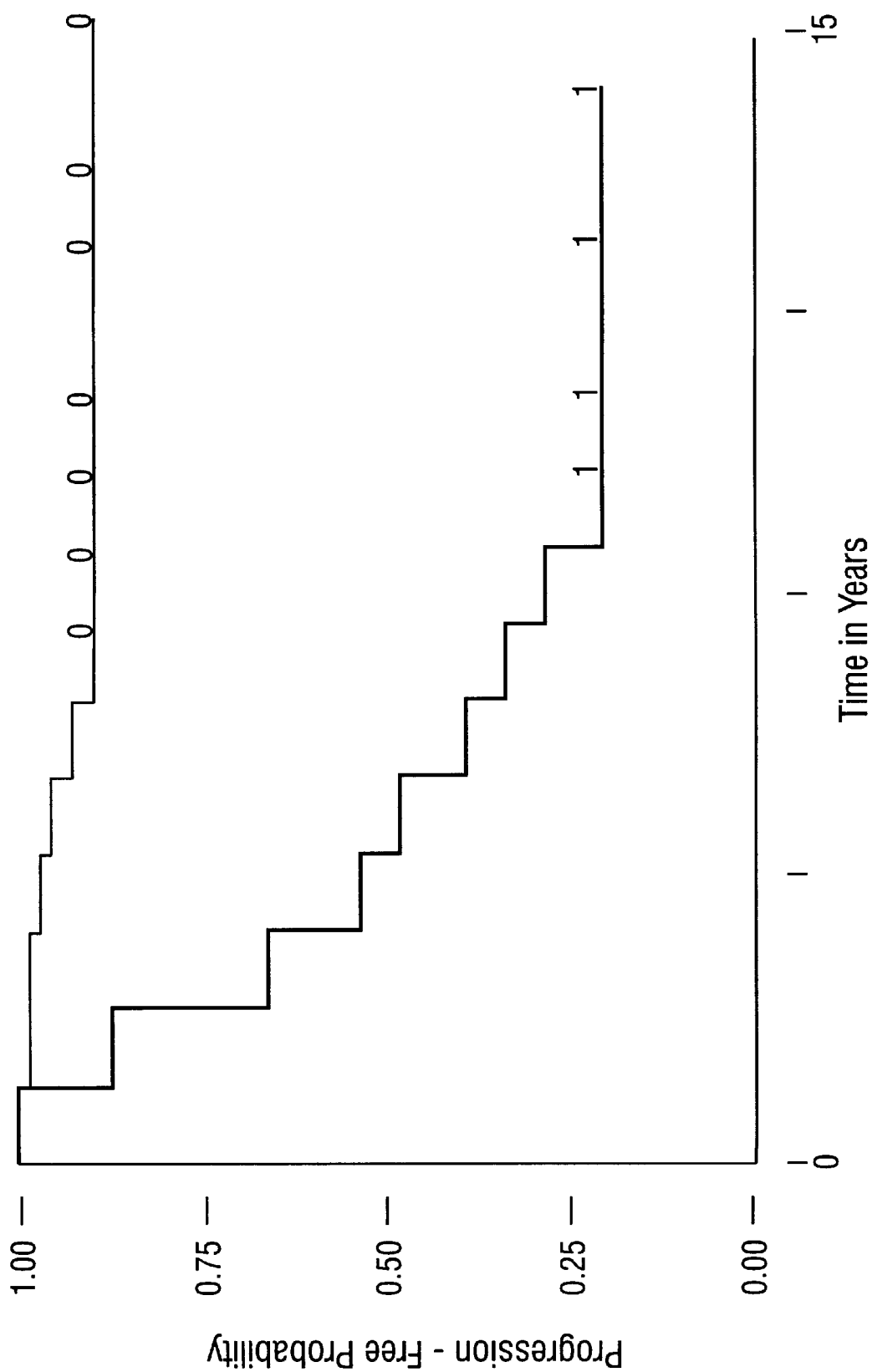
FIG. 10. Nuclear roundness variance significance in the prediction of prostate cancer progression (0=predicted not to progress; 1=predicted to progress). This figure demonstrates the ability of Nuclear Roundness Variance alone to stratify progressors and non-progressors using a Kaplan-Meier Survival (Recurrence) Curve FIG. 11. 12 CMP nuclear descriptors found to be significant in the prediction of prostate cancer progression. This figure illustrates the predictive power of the 12 CMP NMD's to predict progression. A ROC curve was produced with an area under the curve of 85.57%. Please refer to Column D2 of Table VI.
Figure 11:
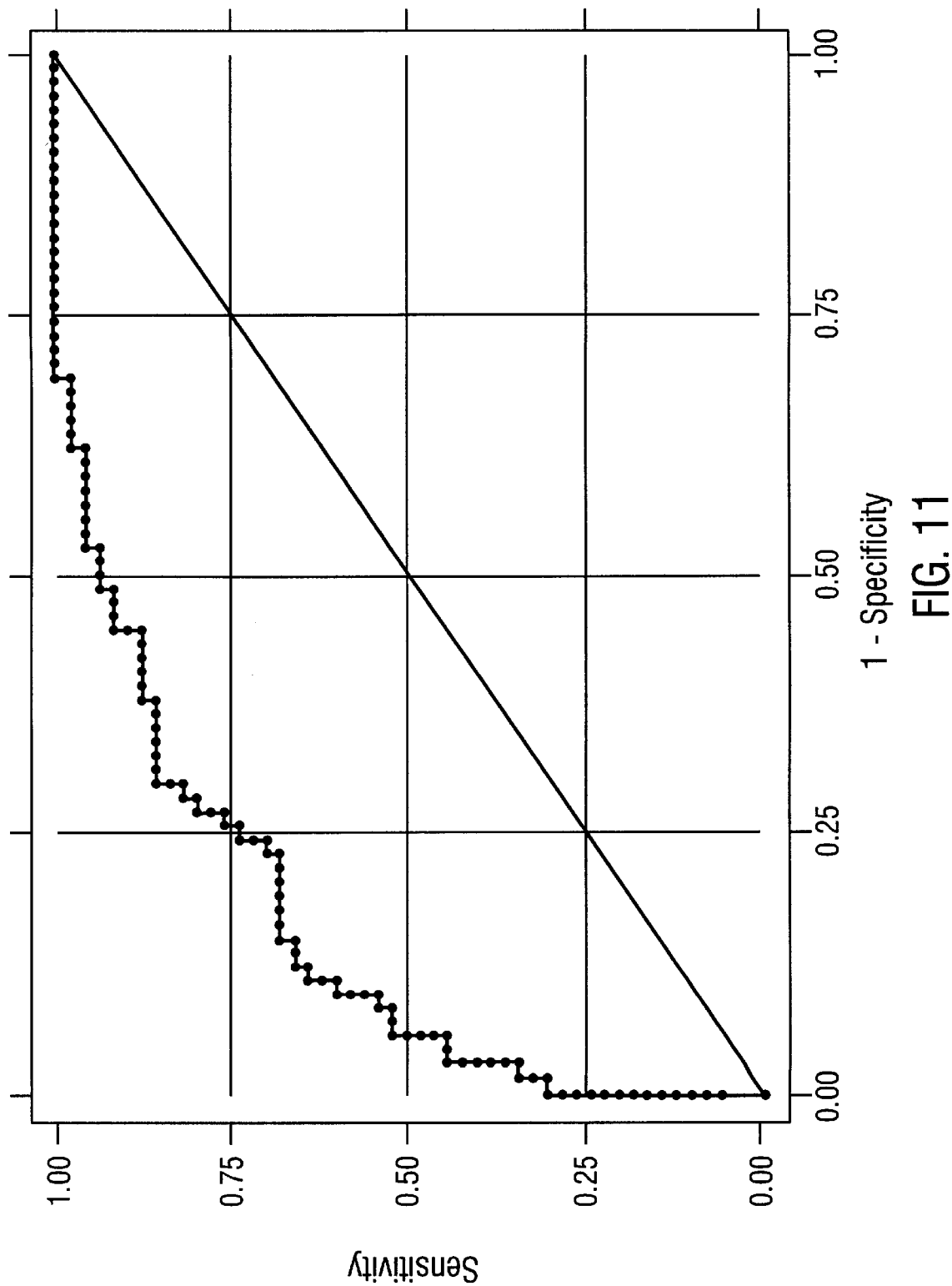
Figure 12:
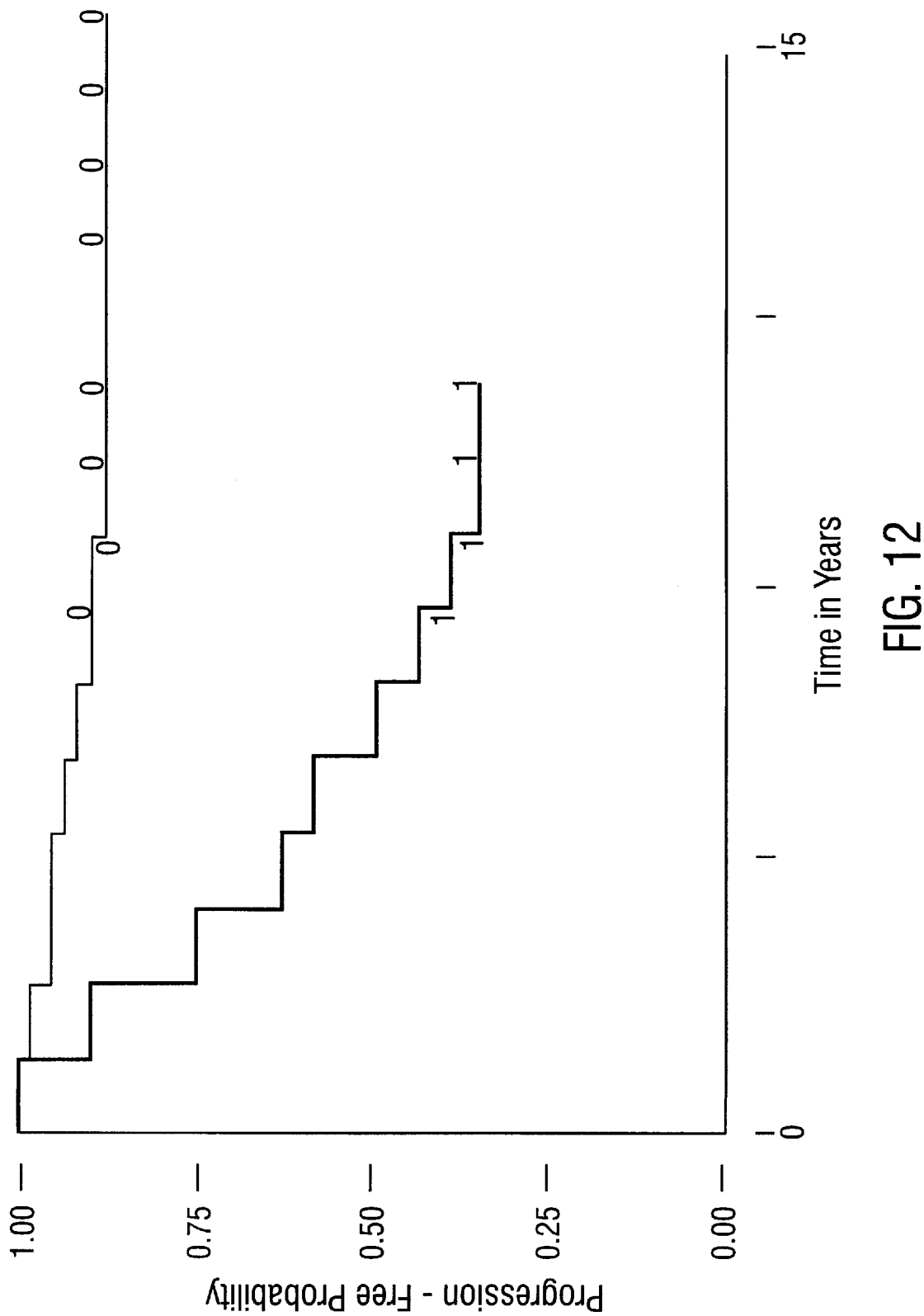
FIG. 12. CMP nuclear descriptors found to be significant in the prediction of prostate cancer progression (0=predicted not to progress; 1=predicted to progress). This figure demonstrates the ability of the 12 CMP NMD's to stratify progressors and non-progressors using a Kaplan-Meier Survival (Recurrence) Curve.
Figure 13:
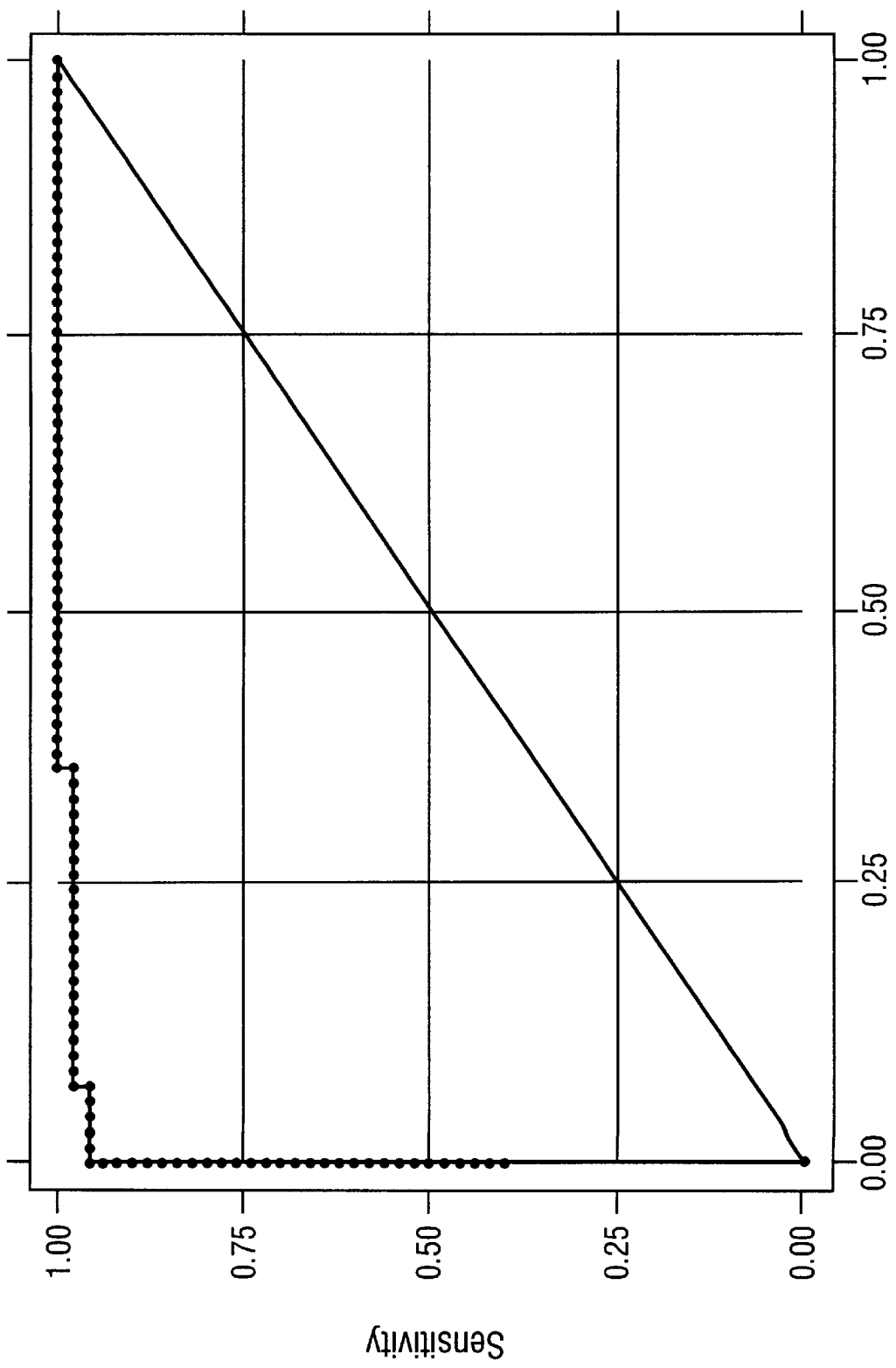
FIG. 13. 13 CMP nuclear descriptors, Her-2/neu staining, nuclear roundness variance, and post op Gleason found to be significant in the prediction of prostate cancer progression. This figure illustrates the predictive power of the 13 CMP NMD's, 1 biomarker, NRV, and Gleason Score combined to predict progression. A ROC curve was produced with an area under the curve of 99.15%. Please refer to Column N of Table VI.
Figure 14:
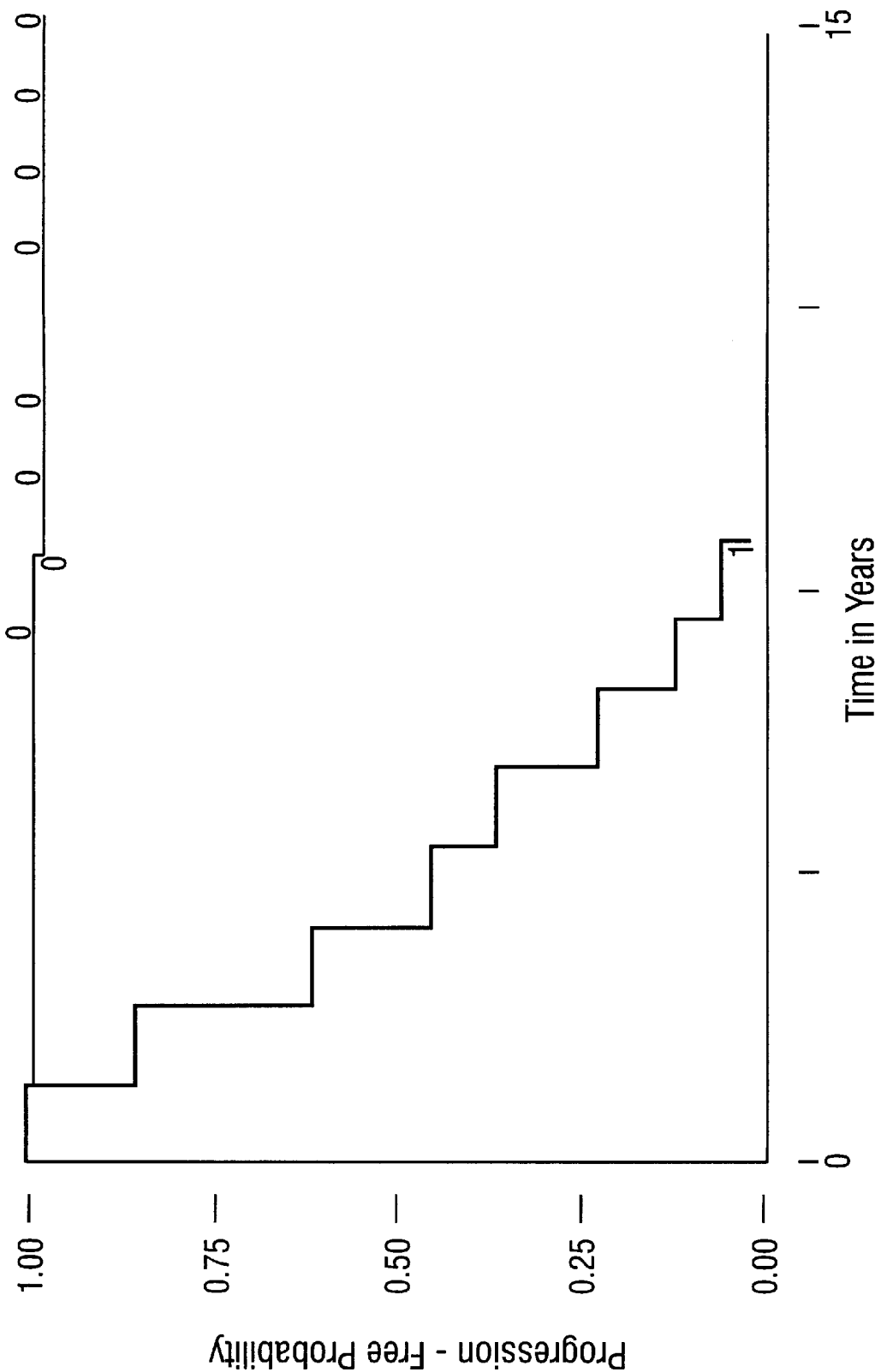
FIG. 14. 13 CMP nuclear descriptors, Her-2/neu staining, nuclear roundness variance, and post-op Gleason found to be significant in the prediction of prostate cancer progression (0=predicted not to progress; 1=predicted to progress). This figure demonstrates the ability of the 13 CMP NMD's, 1 biomarker, NRV, and Gleason Score combined to stratify progressors and non-progressors using a Kaplan-Meier Survival (Recurrence) Curve.
Figure 15:
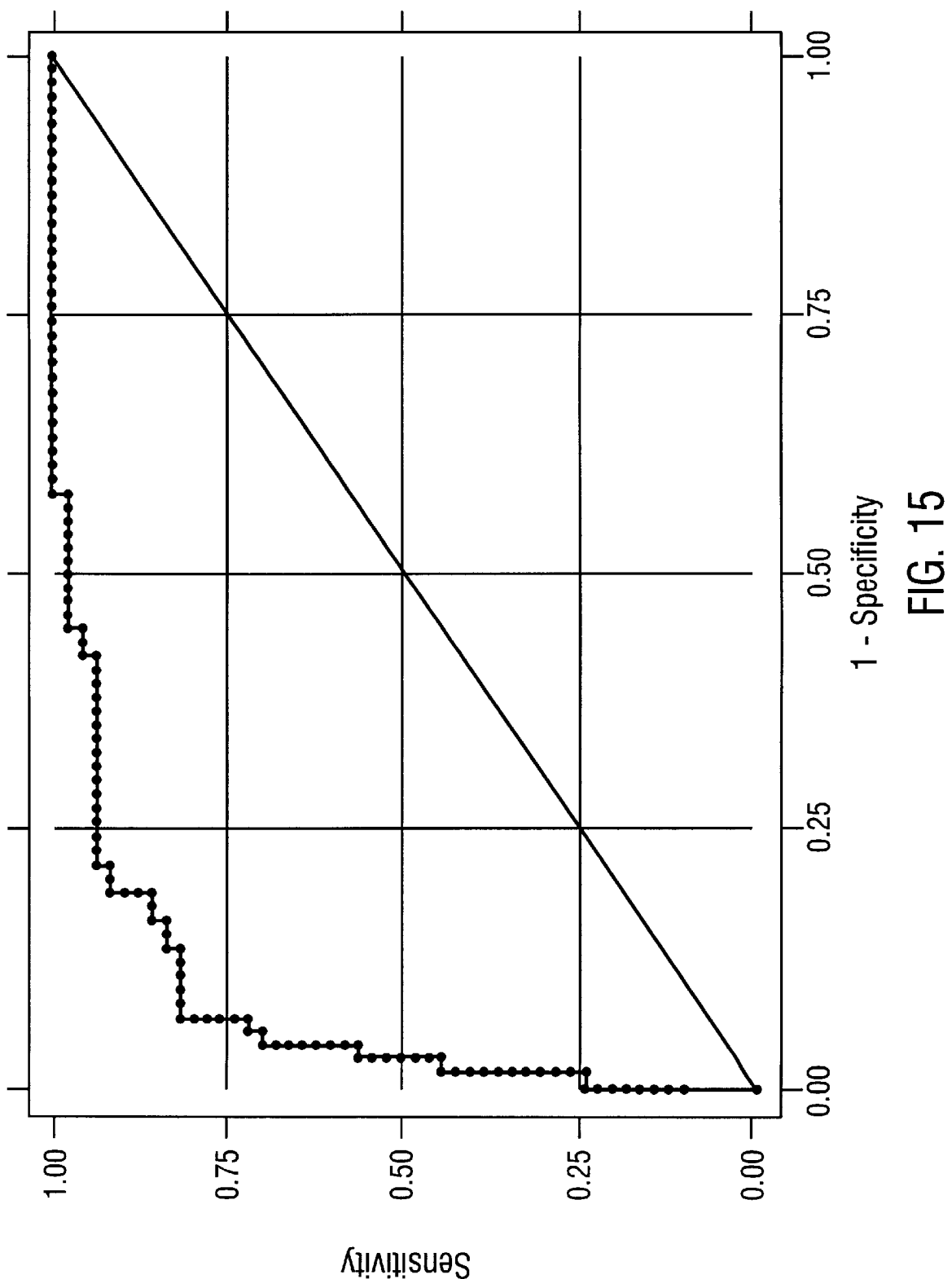
FIG. 15. 19 JVB nuclear descriptors found to be significant in the prediction of prostate cancer progression. This figure illustrates the predictive power of the 19 JVB NMD 's to predict progression. A ROC curve was produced with an area under the curve of 93%. Please refer to Column D2 of Table VII. Also, please note the difference in the number of features required for JVB NMD's as well as an increase the predictive power of the model as compared to CMP NMD's in FIG. 10.
Figure 16:
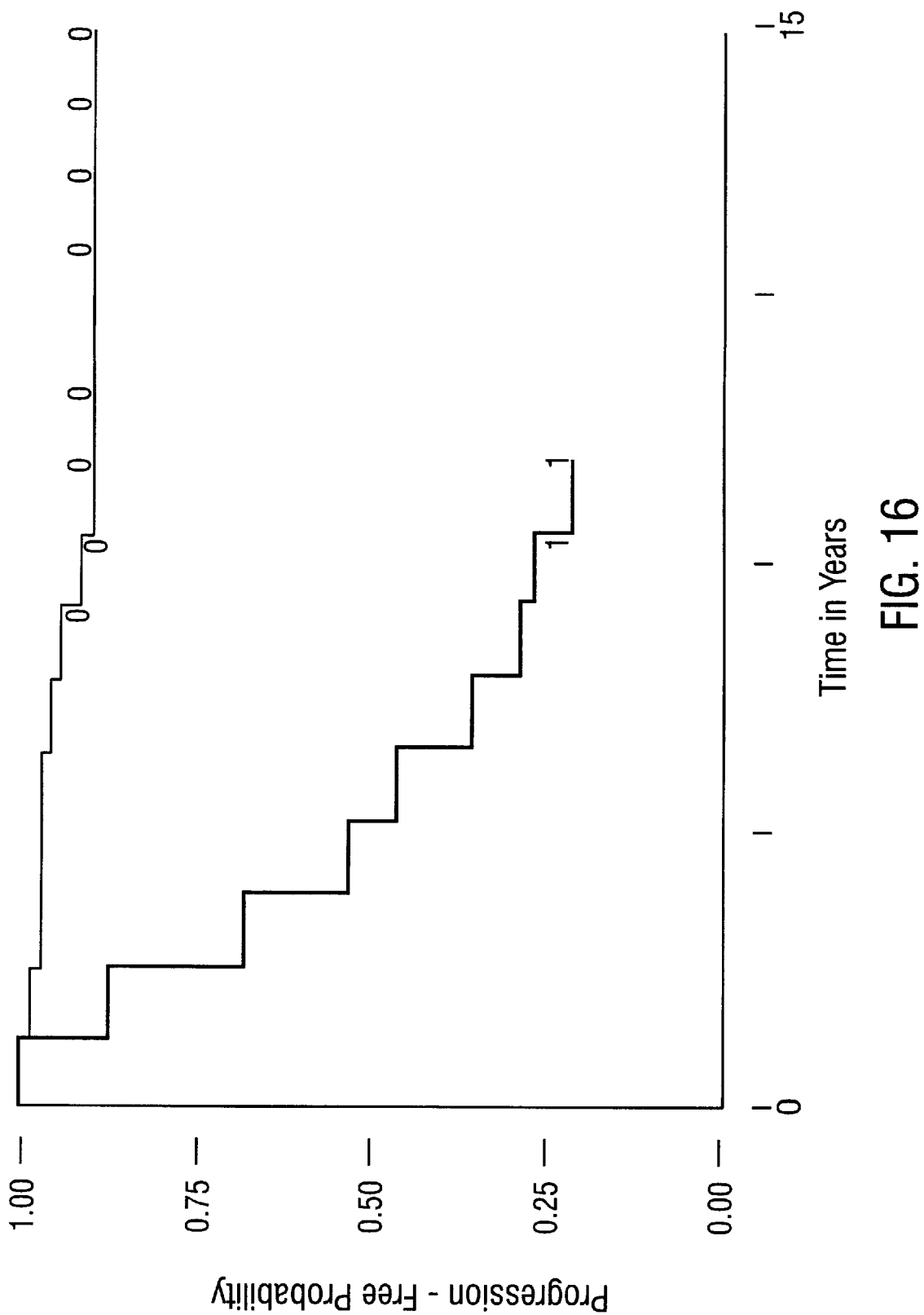
FIG. 16. 19 JVB nuclear descriptors found to be significant in the prediction of prostate cancer progression (0=predicted not to progress; 1=predicted to progress). This figure demonstrates the ability of the 19 JVB NMD's to stratify progressors and non-progressors using a Kaplan-Meier Survival (Recurrence) Curve. Please note the difference in the ability of JVB NMD's to stratify progressors and non-progressors as compared to CMP NMD's in FIG. 11.
Figure 17:
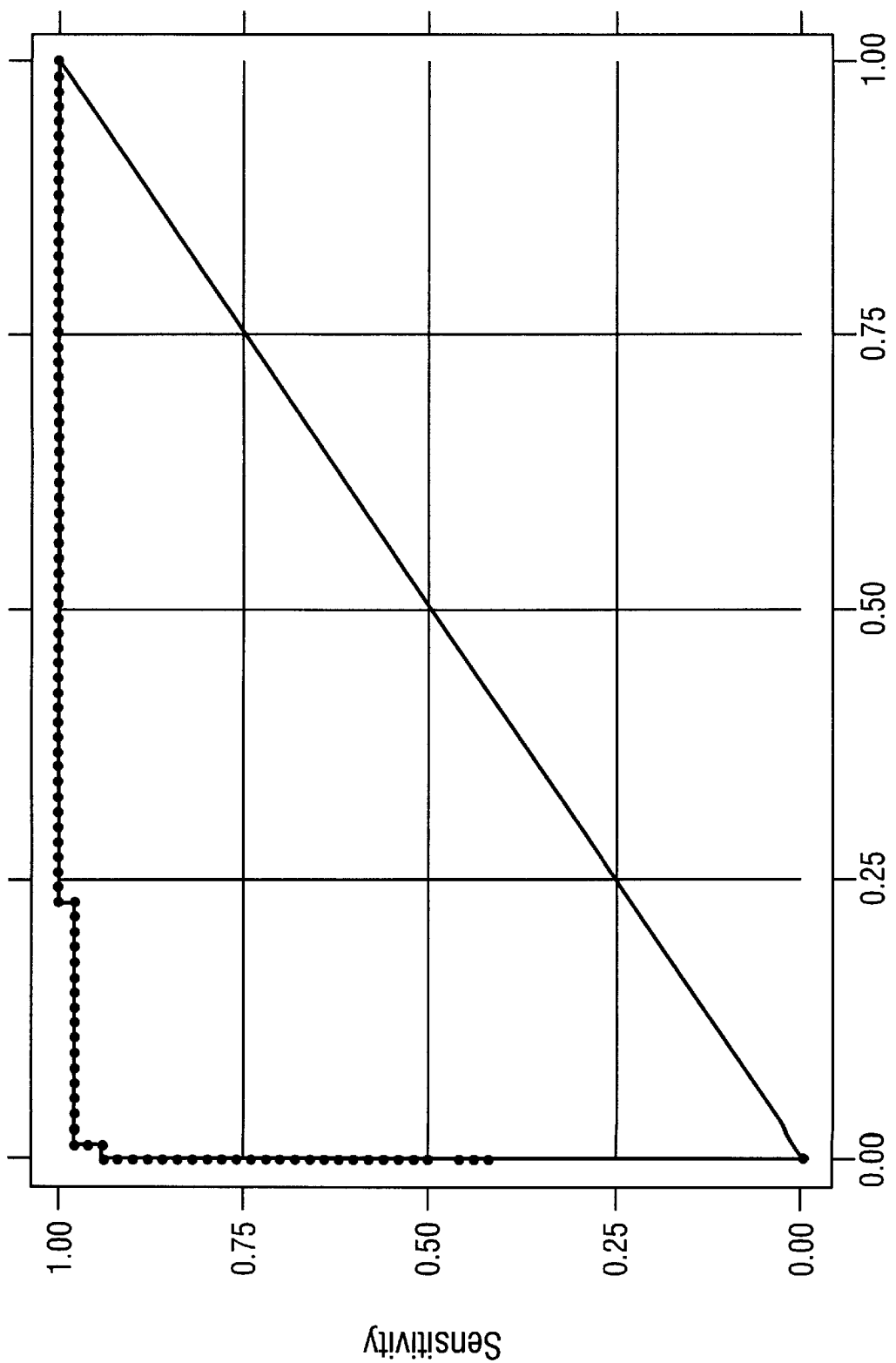
FIG. 17. 14 JVB nuclear descriptors, 2 biomarkers, nuclear roundness variance, and post-op Gleason found to be significant in the prediction of prostate cancer progression. This figure illustrates the predictive power of the 14 JVB NMD's, 2 biomarkers, NRV, and Gleason Score combined to predict progression. A ROC curve was produced with an area under the curve of 99.48%. Please refer to Column N of Table VII.
Figure 18:
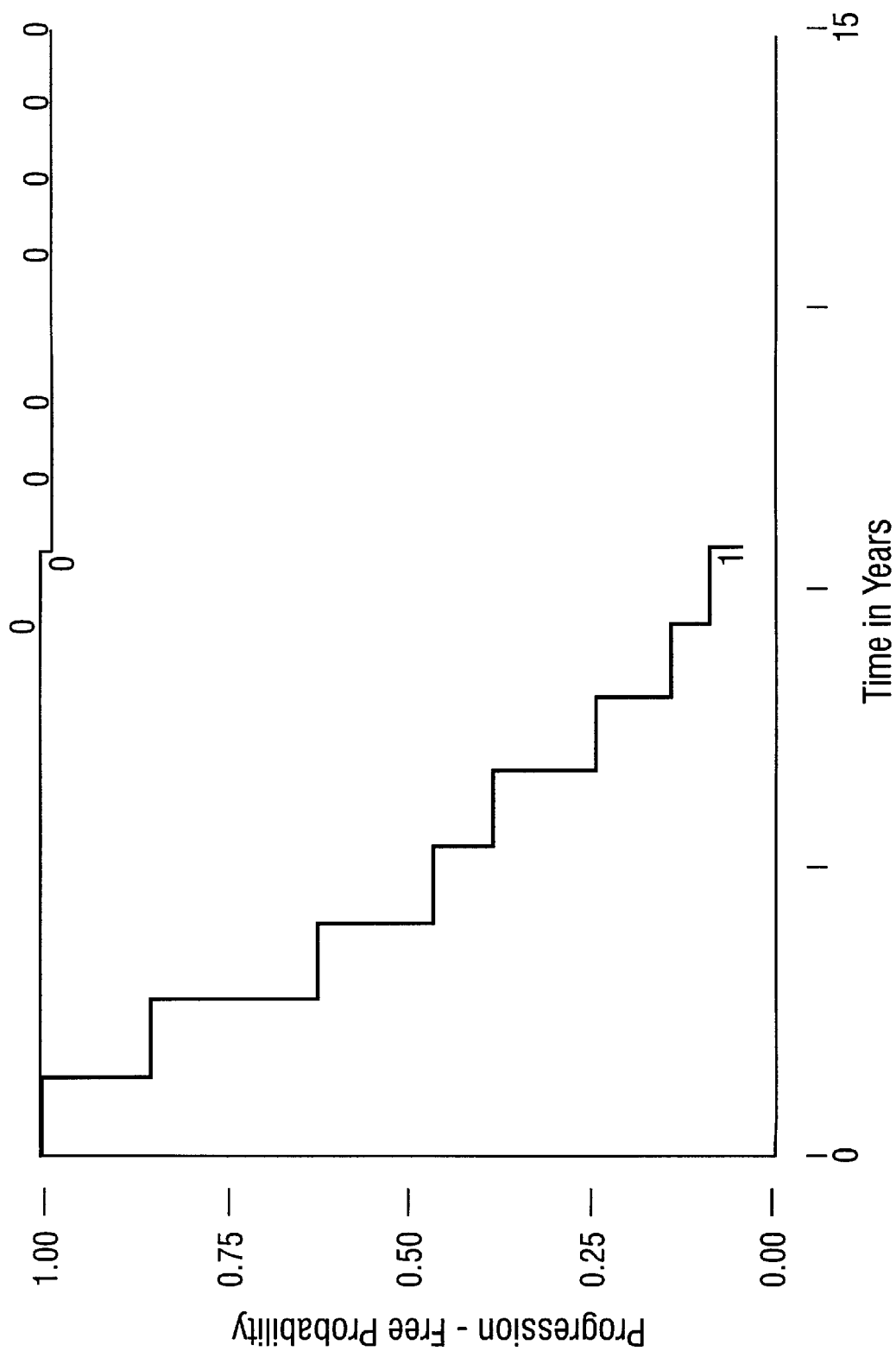
FIG. 18. 14 JVB nuclear descriptors, 2 biomarkers, nuclear roundness variance, and post-op Gleason found to be significant in the prediction of prostate cancer progression (0=predicted not to progress; 1=predicted to progress). This figure demonstrates the ability of the 14 JVB NMD's, 2 biomarkers, NRV, and Gleason Score combined to stratify progressors and non-progressors using a Kaplan-Meier Survival (Recurrence) Curve.
Figure 19:
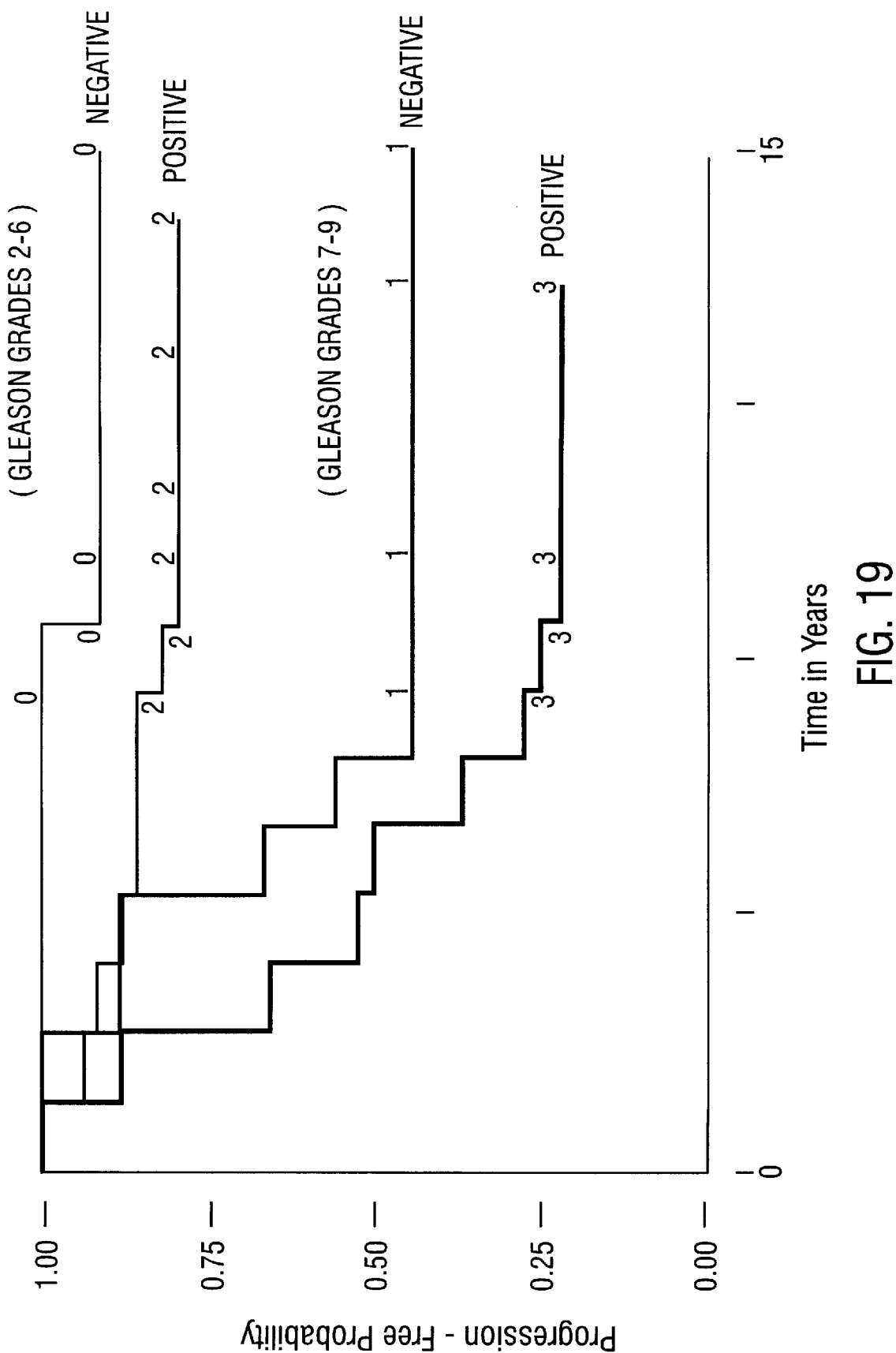
FIG. 19. Stratification of progressors among well co moderately differentiated prostate cancers using Her-2/neu antigenic expression (Kaplan-Meier Survival (Recurrence) Curve).
Figure 20:
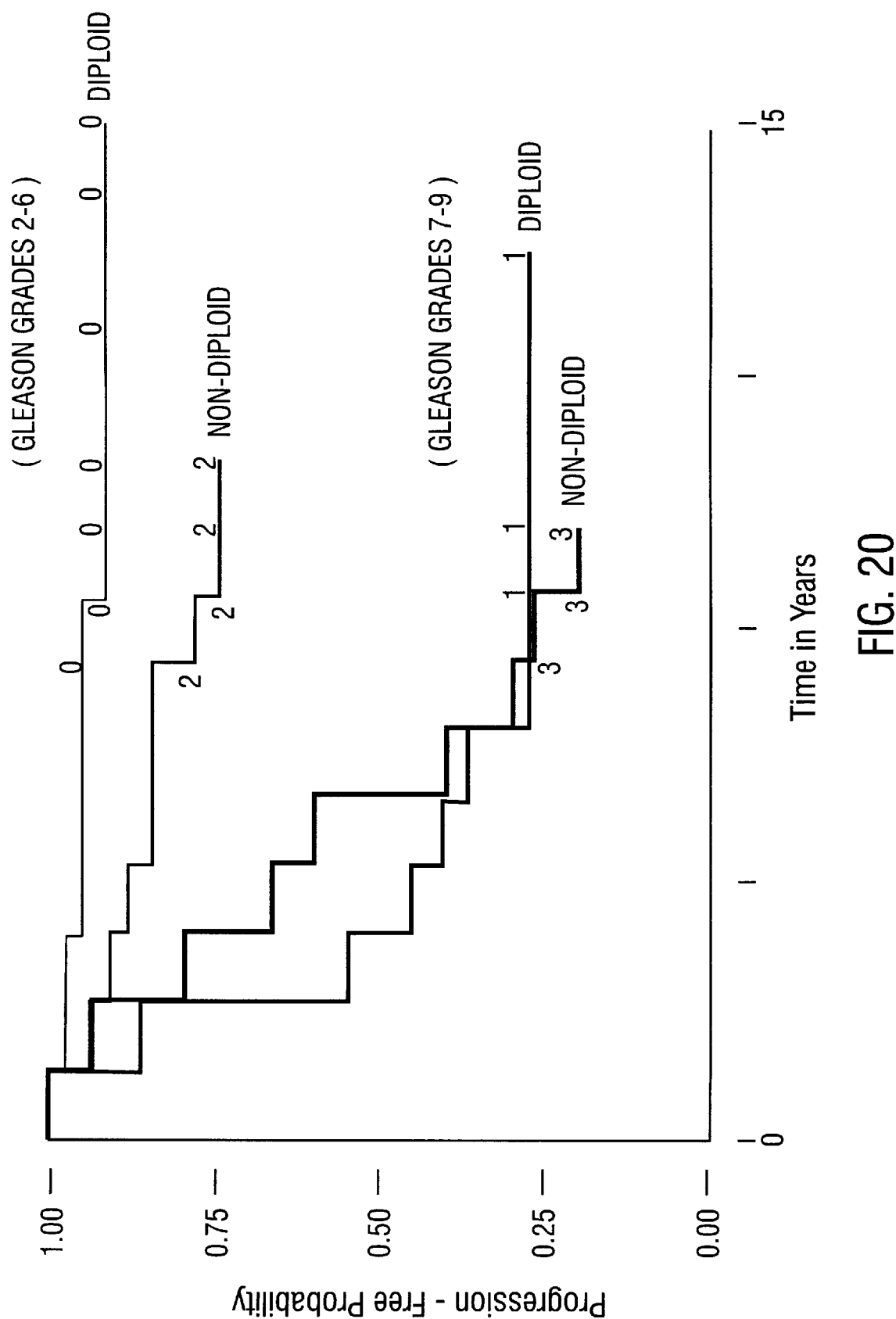
FIG. 20. Stratification of progressors among well to moderately differentiated prostate cancers using DNA ploidy cytometry (Kaplan-Meier Survival (Recurrence) Curve).
Figure 21:
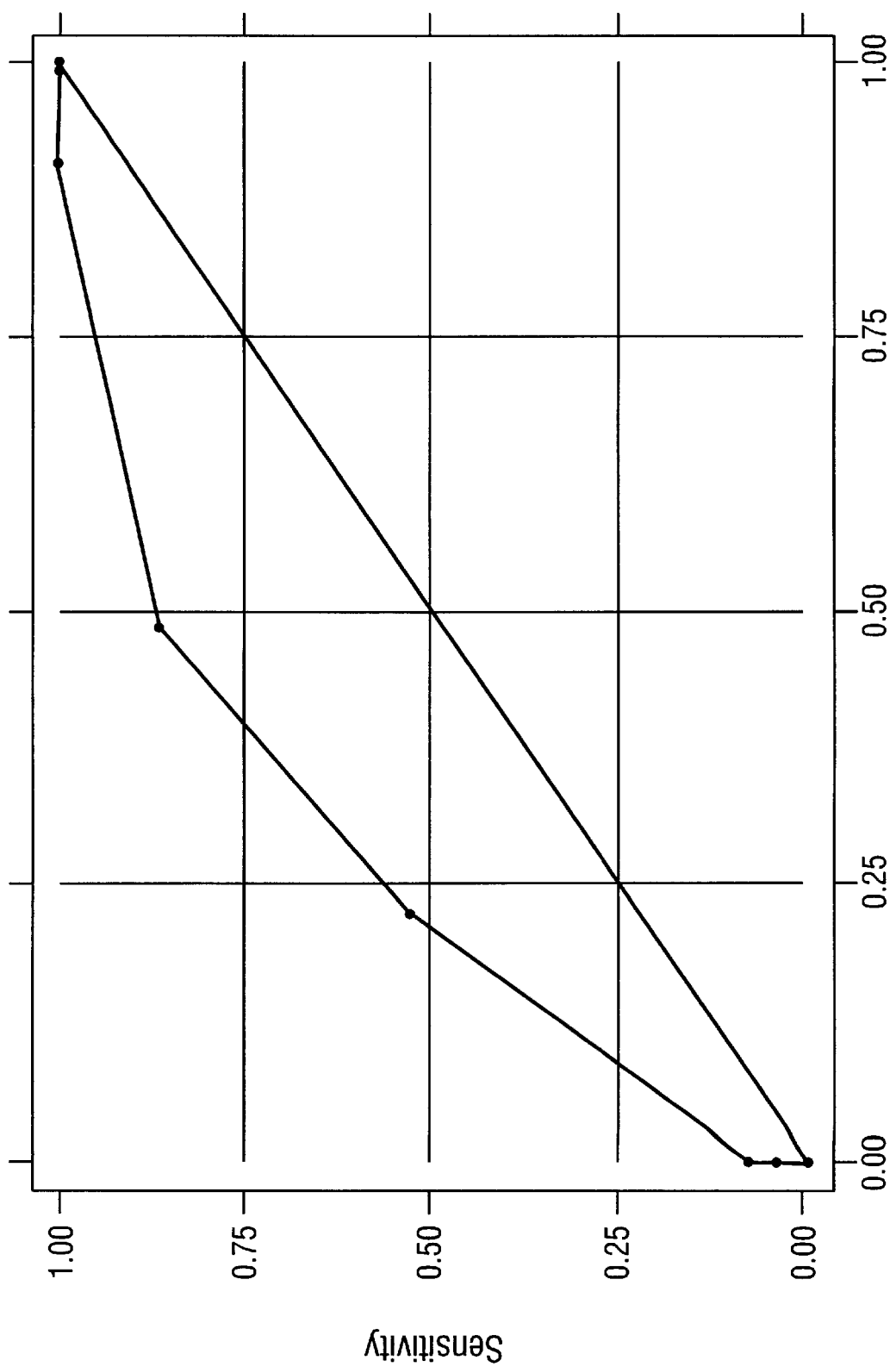
FIG. 21. Post-operative Gleason score significance significance in the prediction of organ confinement status. This figure illustrates the predictive power of Post Operative Gleason Score to predict organ confined disease status. A ROC curve was produced with an area under the curve of 73.3%. Please refer to Column A of. Table IX. Note the lower predictive value of this independent variable as compared to the same variable used to predict progression (see FIG. 6).
Figure 22:
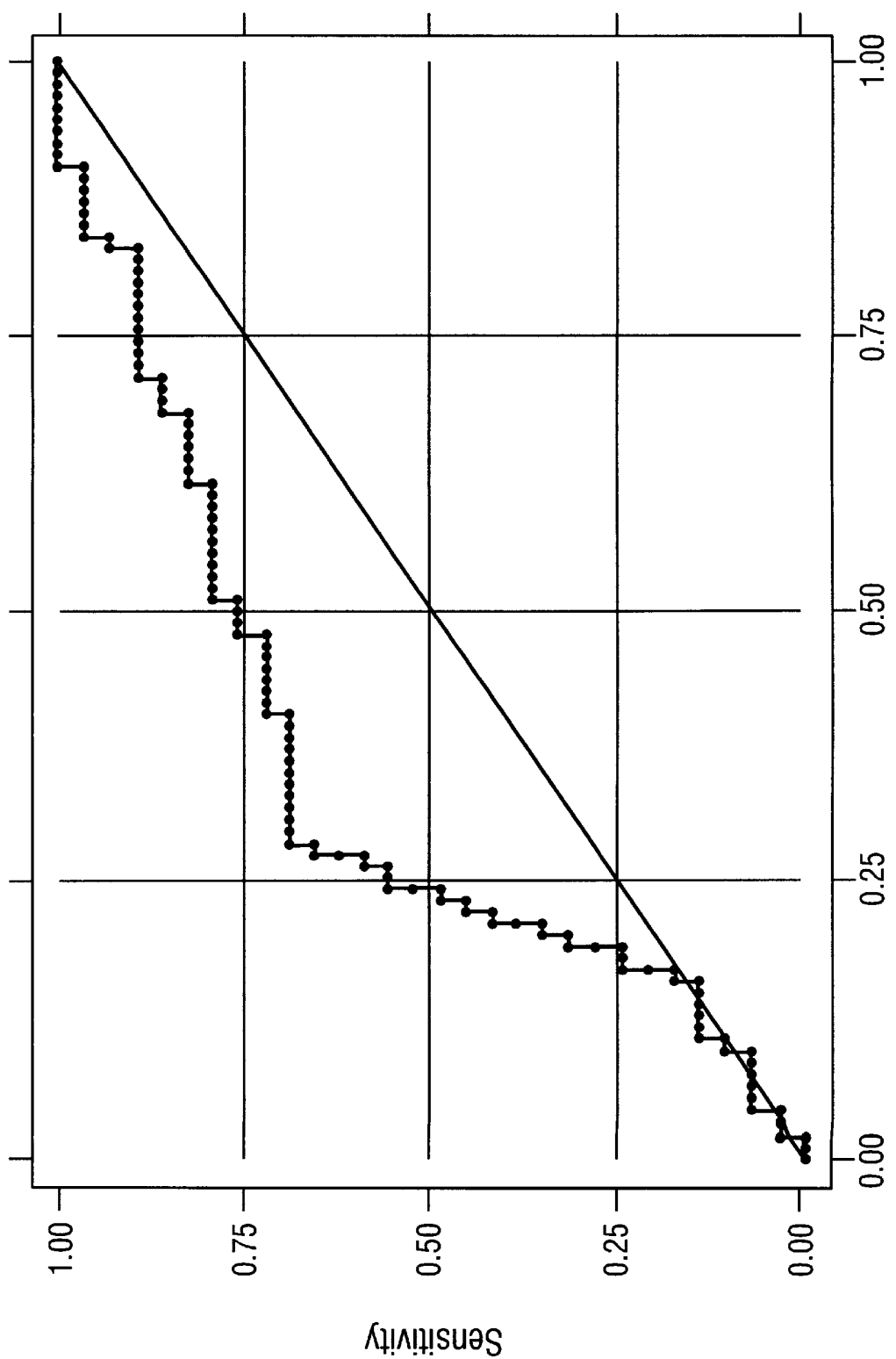
FIG. 22. Nuclear roundness variance significance in the prediction of organ confinement status. This figure illustrates the predictive power of Nuclear Roundness Variance to predict organ confined disease status. A ROC curve was produced with an area under the curve of 66.18%. Please refer to Column B of Table IX. Once again note the much lower predictive value of this independent variable compared to its contribution in prediction progression (see FIG. 9).
Figure 23:
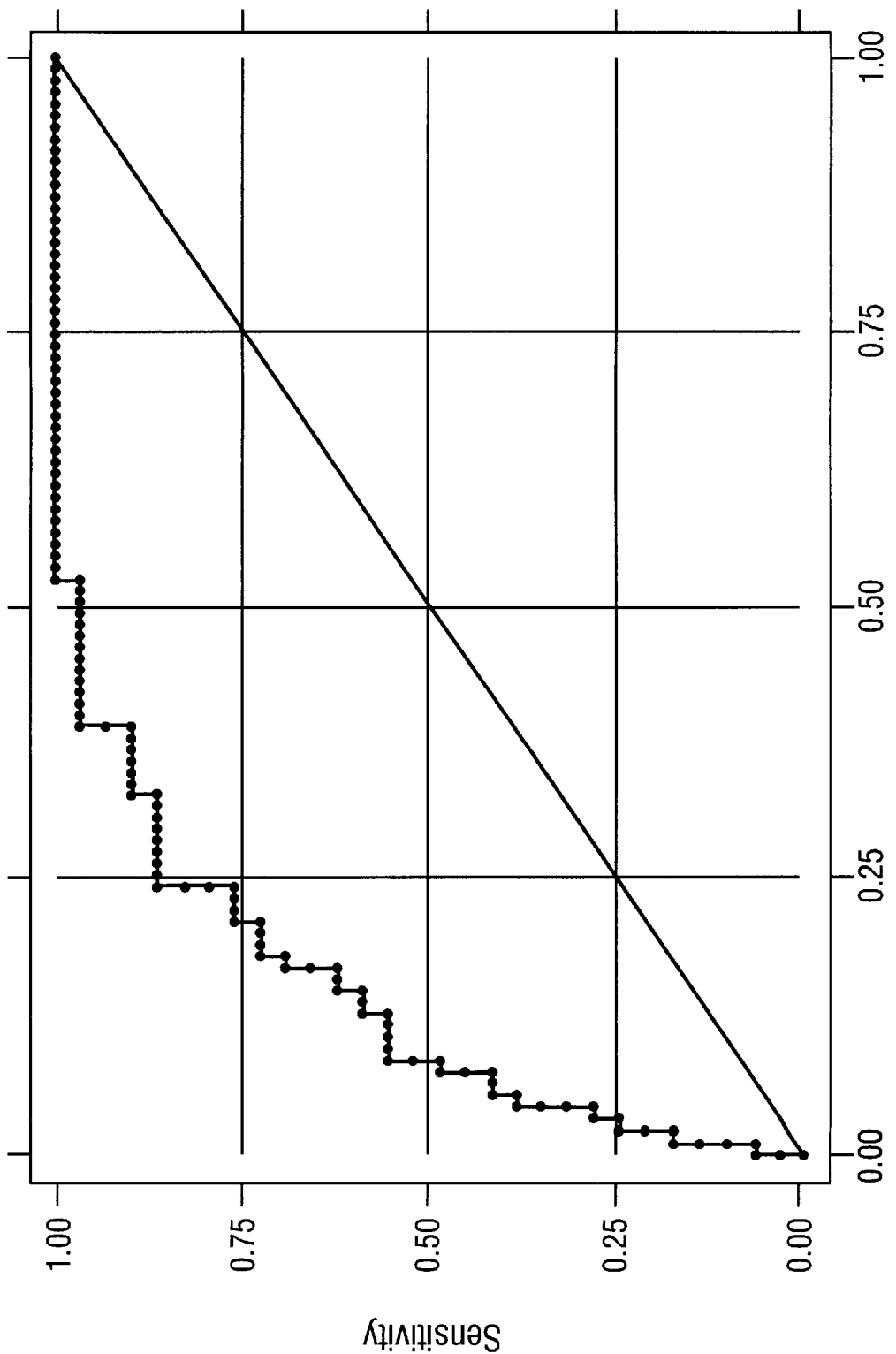
FIG. 23. 10 CMP nuclear descriptors found to be significant in the prediction of organ confinement status. This figure illustrates the predictive power of the 10 CMP NMD's to predict organ confined disease status. A ROC curve was produced with an area under the curve of 86.35%. Please refer to Column D2 of Table IX. Note he significant improvement of the CMP NMD's alone as compared to NRV alone (FIG. 22) in the prediction of organ confined disease status.
Figure 24:
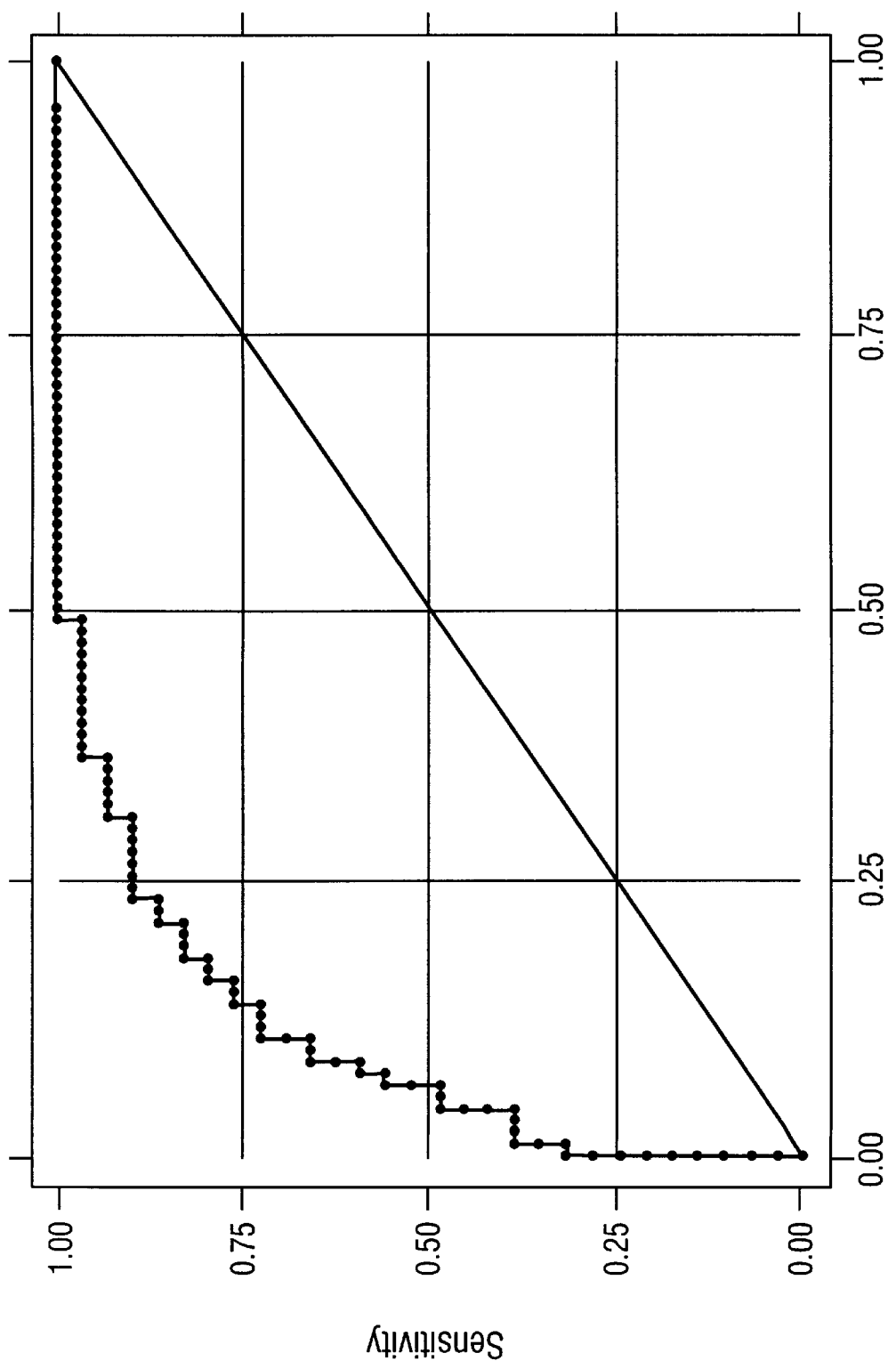
FIG. 24. 12 CMP nuclear descriptors, 3 biomarkers, and nuclear roundness variance found to be significant in the prediction of organ confinement status. This figure illustrates the predictive power of the 12 CMP NMD's, 3 biomarkers, and NRV to predict organ confined disease status. A ROC curve was produced with an area under the curve of 90.28%. Please refer to Column M of Table IX.
Figure 25:
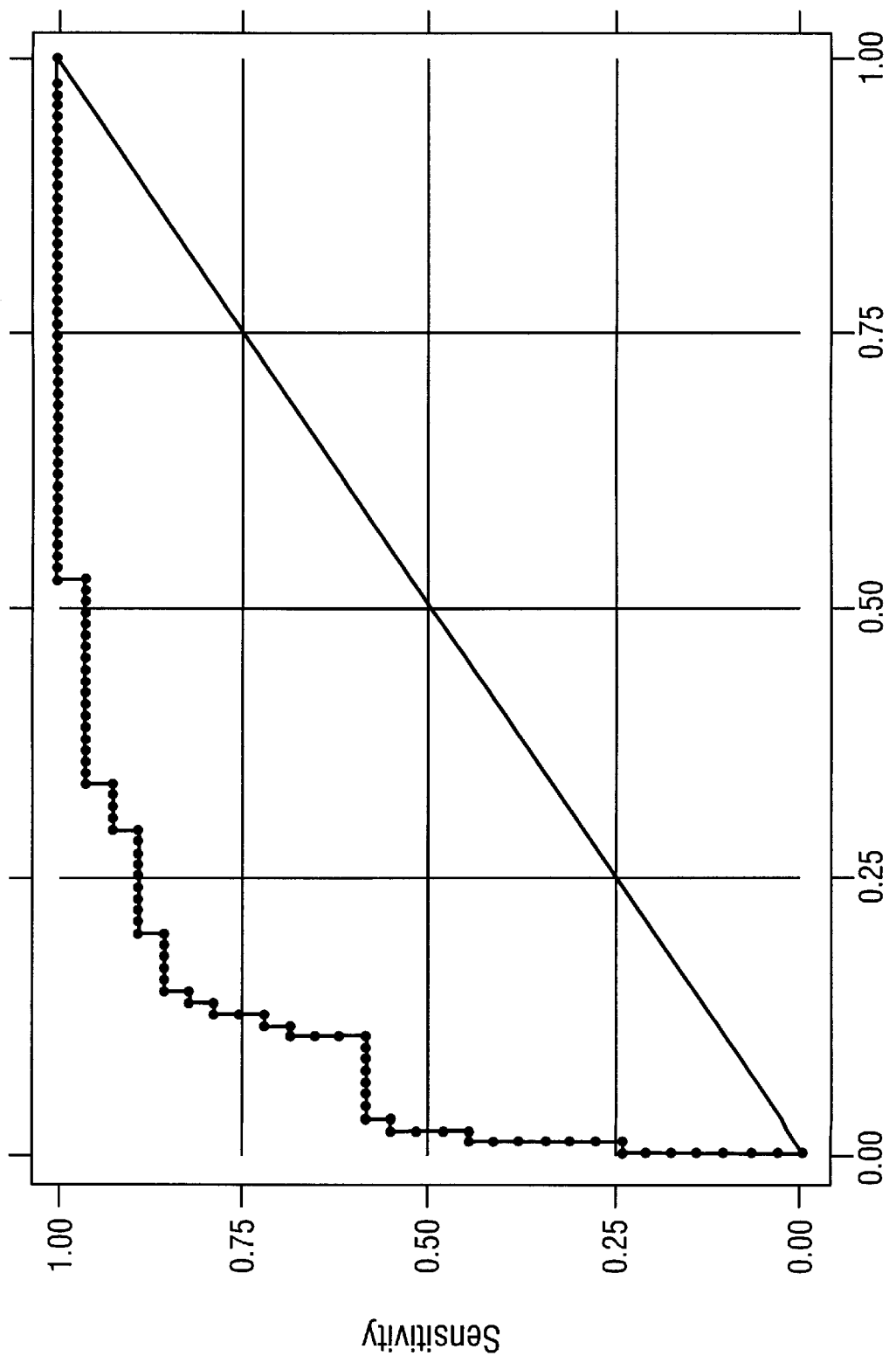
FIG. 25. 15 JVB nuclear descriptors found to be significant in the prediction of organ confinement status. This figure illustrates the predictive power of the 15 JVB NMD's to predict organ confined disease status. A ROC curve was produced with an area under the curve of 91.43%. Please refer to Column D2 of Table X. Note the improvement of predictive power when using JVB NMD's alone as compared to CMP NMD's alone (FIG. 22) in the prediction of organ confined disease status.
Figure 26:
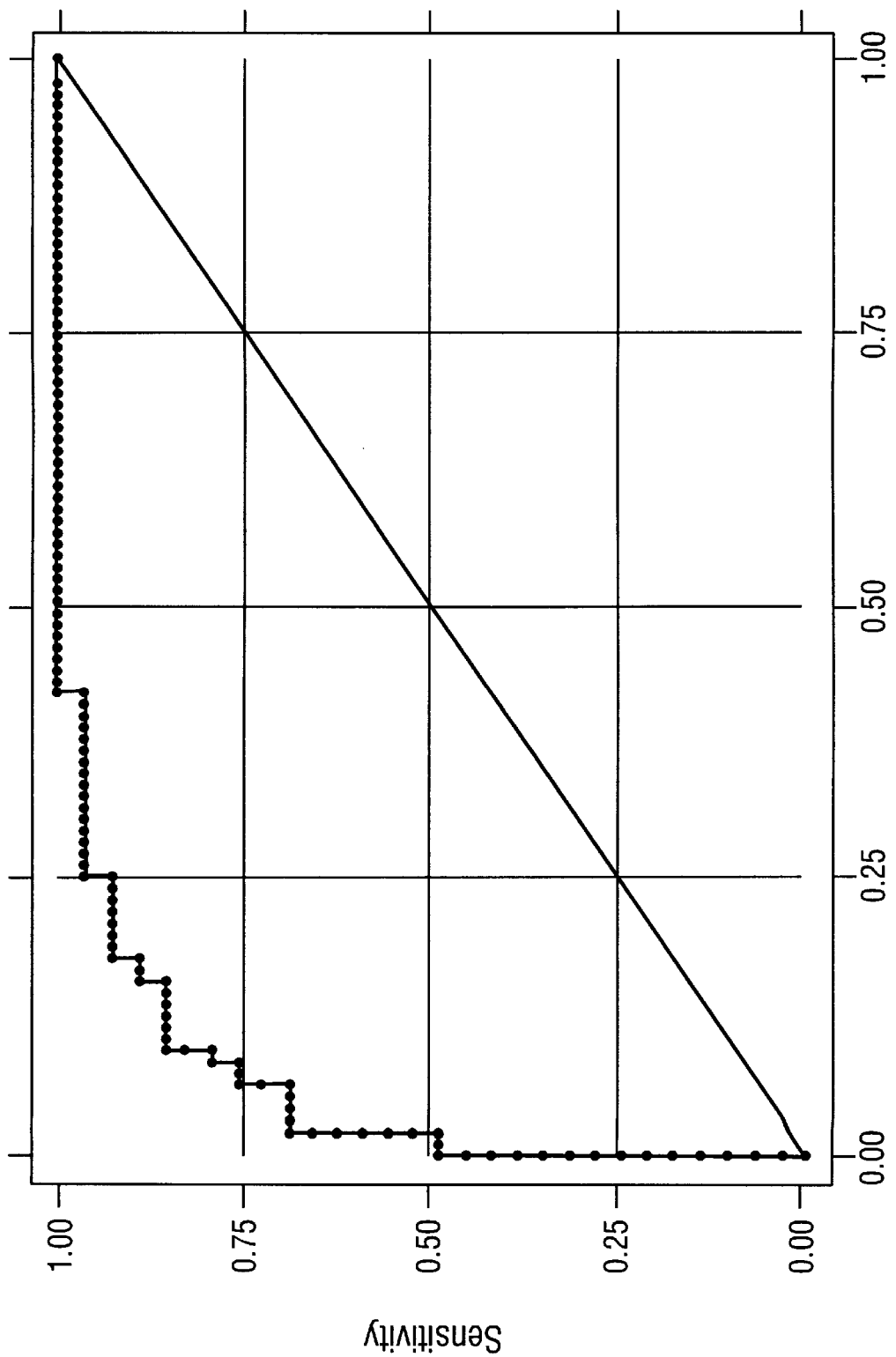
FIG. 26. 15 JVB nuclear descriptors and post-op Gleason found to be significant in the prediction of organ confinement status. This figure illustrates the predictive power of the 15 JVB NMD's and Post Operative Gleason score to predict organ confined disease status. A ROC curve was produced with an area under the curve of 94.7%. Please refer to Column H of Table X.
Figure 27:
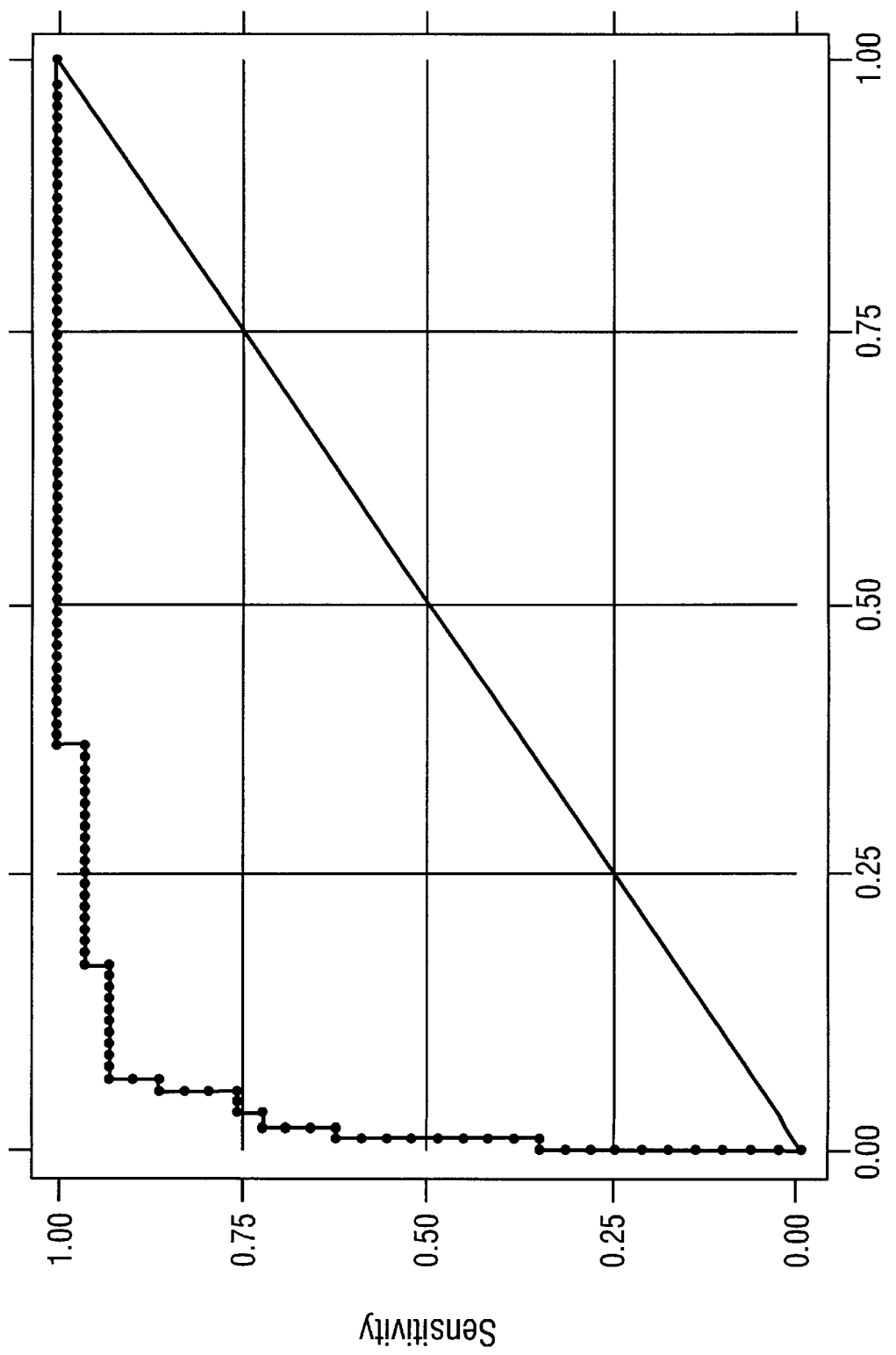
FIG. 27. 16 JVB nuclear descriptors, 3 biomarkers, nuclear roundness variance (DROPPED), and post-op Gleason found to be significant in the prediction of organ confinement status. This figure illustrates the predictive power of the 16 JVB NMD's, 3 biomarkers, and Post Operative Gleason score to predict organ confined disease status. A ROC curve was produced with an area under the curve of 96.55%. Please refer to Column N of Table X. Note that NRV was dropped as a significant independent variable in this model.

The invention, in its broadest sense, is a method for predicting organ confined disease status or the potential for progression of prostate cancer following radical surgery using either non-parametric statistical analysis methods or neural networks. The parameters assessed by these methods include, but are not limited to, cellular biomarkers and nuclear morphometric descriptors. The invention provides a method to collect nuclear images and extract all relevant shape, size, Markovian texture, and DNA content features important to construction of a mathematical method that gives a single predictive probability for prostate cancer progression or organ localization, with or without pathological grading. The texture features utilized in the present invention are set forth in Table XV (CellSheet™ v.1.0d). It is recognized that in predicting the probability of prostate cancer progression and organ localization, prognostic variable factors other than those listed may be used within the scope and spirit of the present invention.

Also embodied in the present invention is the use of a trained neural network to provide a single predictive probability for prostate cancer progression or organ localization given any number of inputs. The multi-layer perceptron network of the present invention is a feed-forward network with one or more hidden layers of neurons between the input and output layers. Using this architecture, many shortcomings of the single layer perceptron are avoided. However, because of the added complexity, the convergence theorem and weight adjustment procedure suggested by Rosenblatt is not applicable. An alternate procedure called "back propagation" has been independently developed by Werbos (Werbos, Ph.D. Thesis, Harvard University, 1974), Parker (Parker, Innovation Report, 581–664, File 1, Office of Technology Licensing, Stanford University, October, 1982), and Rumelhart (see Rumelhart et al., Parallel Distributed Processing Explorations in the Microstructures of Cognition Vol. 1, Foundations, MIT Press, Cambridge, Mass., 1988). This procedure is effective and allows for efficient use of multi-layer perceptrons. But the procedure does not guarantee convergence to the global minima at all times. Also, it requires a large number of training iterations in order to learn a given set of transformations.

Because of the problems associated with back propagation, it is of interest to modify the weight adjustment procedure and/or the model developed by Rosenblatt to enable single-layer perceptrons to solve problems such as XOR problems. In this work, a modified perceptron is utilized. The modified perceptron used is a multiple threshold perceptron that is capable of solving XOR problems. This modified perceptron is obtained by changing the non-linearity function. Unlike previous efforts in developing multiple threshold perceptrons the perceptron of the present invention is capable of handling both binary and analog inputs. The procedure requires fewer number of iterations to develop appropriate input to output transformations when compared to back propagation.

For the purposes of this invention, the following clinical and pathological staging criteria is used. The use of other criteria does not depart from the scope and spirit of the invention.

T0—No evidence of Prostatic tumor.

T1—Clinically inapparent tumor, non-palpable nor visible by imaging.

T1a—Tumor is incidental histologic finding with three or fewer microscopic foci. Non-palpable, with 5% or less of TURP chips (trans-urethral resected prostate tissue) positive for cancer.

T1b—Tumor is incidental histologic finding with more than three microscopic foci. Non-palpable, with greater then 5% of TURP chips (trans-urethral resected prostate tissue) positive for cancer.

T1c—Tumor is non-palpable, and is found in one or both lobes by needle biopsy diagnosis.

T2—Tumor is confined within the prostate.

T2a—Tumor present clinically or grossly, limited to the prostate, tumor 1.5 cm or less in greatest dimension, with normal tissue on at least three sides. Palpable, half of 1 lobe or less.

T2b—Tumor present clinically or grossly, limited to the prostate, tumor more than 1.5 cm in greatest dimension, or in only one lobe. Palpable, greater than half of 1 lobe but not both lobes.

T2c—Tumor present clinically or grossly, limited to the prostate, tumor more than 1.5 cm in greatest dimension, and in both lobes. Palpable, involves both lobes.

T3—Tumor extends through the prostatic capsule.

T3a—Palpable tumor extends unilaterally into or beyond the prostatic capsule, but with no seminal vesicle or lymph node involvement. Palpable, unilateral capsular penetration.

T3b—Palpable tumor extends bilaterally into or beyond the prostatic capsule, but with no seminal vesicle or lymph node involvement. Palpable, bilateral capsular penetration.

T3c—Palpable tumor extends unilaterally and or bilaterally beyond the prostatic capsule, with seminal vesicle and/or lymph node involvement. Palpable, seminal vesicle or lymph node involvement.

T4—Tumor is fixed or invades adjacent structures other than the seminal vesicles or lymph nodes.

T4a—Tumor invades any of: bladder neck, external sphincter, rectum.

T4b—Tumor invades levator muscles and/or is fixed to pelvic wall.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

DNA Staining Procedure Using CAS Quantitative DNA Staining Kit (Elmhurst, Ill.; Catalog #102300-01)

Preparation of Feulgen Stain Solution:

Place 90 ml of Type I $H_2O$ in a volumetric flask and add 10 ml of 1N HCL. Place a stir bar in a 125 ml Erlenmeyer flask and add the above solution. Add 1 vial of DNA stain reagent to the flask while stirring the solution. Place a rubber stopper in the flask, and stir the contents for at least 1 hour. This Feulgen stain solution should be filtered through a Whatman No. 1 filter immediately before staining of the specimen.

Preparation of Feulgen Rinse Solution:

Place 285 ml of Type I $H_2O$ in a 500 ml graduated cylinder and add 15 ml of 1N HCL. Pour this solution into a 500 ml bottle. Immediately before rinsing, place 1 vial of DNA rinse reagent into the bottle and mix the contents by swirling. This solution is stable for 2–3 hours.

Preparation of Calibration Slides:

To prepare the control cells, place two (2) CAS calibration slides (Elmhurst, Ill.; Catalog #102202-00) in 10% neutral buffered formalin for 30 minutes at room temperature. The calibration slides are touch-prep rat hepatocytes that have a known shape, size, and DNA amount. Next, rinse the CAS calibration slides in running deionized $H_2O$ for 5 minutes.

Preparation of Tissue Samples:

The 5 $\mu$m formalin fixed, paraffin embedded, tissue sections are first placed on Probe-On™ Plus microscope slides.

Place the slides in Hemo-De for 1 minute at 45° C., and then drain the Hemo-De from the slides with the aid of absorbent paper. This step is repeated three (3) more times.

Next, place the specimen slides in absolute ethanol for 1 minute at room temperature, and then drain the alcohol from the slides with the aid of absorbent paper. Repeat this step one (1) more time.

Finally, place the specimen slides in PBS (Ph 7.6) with 0.1% Triton X-100 for 10 seconds at room temperature, and then drain the PBS from the slides with the aid of absorbent paper. Repeat this step one (1) more time.

Feulgen Staining Procedure:

Place the slides (CAS calibration slides and specimen slides) in 5N HCL for 1 hour at room temperature. Next, place all of the slides in the Feulgen stain solution for 1 hour at room temperature (stir while staining). Drain the Feulgen stain solution and rinse the slides in the Feulgen rinse solution for 30 seconds at room temperature, followed by rinsing the slides in Feulgen rinse solution for 5 minutes at room temperature, followed by rinsing the slides in Feulgen rinse solution for 10 minutes at room temperature. The slides are then rinsed in running deionized $H_2O$ for 5 minutes. Destaining is done in 1% acid alcohol for 5 minutes at room temperature. This is followed by dipping the slides in 95% ethanol 10 times, followed by dipping the slides in absolute ethanol 10 times, followed by finally dipping the slides in xylene 10 times. Place a cover slip on the slides using a toluene or xylene based mounting media.

EXAMPLE II

Collection and Processing of CAS-200 CMP v3.0 Nuclear Morphometric Descriptors (40× Objective)

The morphometry data from the radical prostatectomy specimens is captured using the Cell Measurement Program v3.0 (CMP v3.0) software from a CAS-200 Image Analysis System. First, a study is set up in CMP v3.0 using the QDA Morphology Mode. The QDA Morphology Mode of CMP v3.0 allows the measurement of the Sum O.D., size, shape, cell class, and the 22 Markovian texture features (a step size of 1 was used in this invention) for each cell (see Table I), as well as the generation of a DNA histogram through the use of the QDA v3.0 software program on the CAS-200 Image Analysis System. Once the study is set up, the CMP v3.0 program (under the QDA Morphology Mode) activates the QDA v3.0 program, and the optical system is calibrated using the CAS calibration slides that were stained with the specimen slides. At least 20 calibration cells are measured, with a calibration peak percent coefficient of variation (% C.V.) of less than 2.0%. (NOTE: If the % C.V. is greater than 2.0%, a problem has occurred in the staining process.) Next, at least 125 cancer cells are analyzed using the method described in Example IV, and the cell nuclear images captured from each 5 µm Feulgen stained tissue section, with all of the sum O.D., size, shape, and Markovian texture measurements being saved to a CMP v3.0 vector (*.VEC) file. The nuclear cell images and DNA content information are saved to a QDA v3.0 listmode (*.ILM) file. The CMP vector file (*.VEC) is then converted to a Lotus 1-2-3 file (*.WK1) using the CMP Exporting Utility (a feature of the CMP v3.0 software). The DNA content information contained in the listmode file is extracted with specially written software and saved to a comma delimited text file. The Lotus 1-2-3 file (*.WK1) is then transferred to a 486 PC equipped with Windows v3.1 and Excel v5.0 for Windows, and an Excel v5.0 macro file is used to convert the Lotus 1-2-3 file (*.WK1) into separate Excel v5.0 files (*.XLS) for each case, each file containing the following information for every cell captured from that particular specimen: the sum O.D, size, shape, cell class, 22 Markovian texture features, and DNA content; (referred to collectively as CMP Nuclear Morphometric Descriptors, or CMP NMD's ). Each Excel v5.0 file (*.XLS) also contains the means, standard deviations, variances, minima, and maxima for each CMP NMD. In addition, the macro creates a summary file containing the above statistics for each CMP NMD from every case.

EXAMPLE III

Collection and Processing of JVB ILM Morphometry v1.0 Nuclear Morphometric Descriptors The morphometry data from radical prostatectomy specimens is captured from the saved listmode files (*.ILM) using the JVB ILM Morphometry v.1.0 software program, which allows the measurement and calculation of up to 36 different features. The listmode files (*.ILM) are created using the QDA v3.0 software from a CAS-200 Image Analysis System. The optical system is calibrated using the CAS calibration slides that were stained with the specimen slides by measuring at least 20 calibration cells, with a calibration peak percent coefficient of variation (% C.V.) of less than 2.0%. (NOTE: If the % C.V. is greater than 2.0%, a problem has occurred in the staining process.) Next, at least 125 cancer cells are analyzed using the method described in Example IV, and the cell nuclear images captured from each 5 µm Feulgen stained tissue section. The DNA content information and cell nuclear images are saved to a listmode (.ILM) file. The listmode files (*.ILM) are then transferred to a 486 PC equipped with Windows v3.1 and Excel v5.0 for Windows, and converted using the JVB ILM Morphometry v1.0 program into 36 measurements (collectively referred to as JVB Nuclear Morphometric Descriptors, or JVB NMD's ), which are contained in a Microsoft Access Database file (*.MDB). These 36 measurements include the sum O.D., size, shape, DNA content, 22 Markovian texture features, and nuclear shape features (see Table II). The Microsoft Access Database file (*.MDB) is then converted to an ASCII comma delimited file (*.CSV) using a conversion feature of the JVB ILM Morphometry v1.0 program. Finally, using Excel v5.0, an Excel v5.0 macro file is used to convert the ASCII comma delimited file (*.CSV) into separate Excel v5.0 files (*.XLS) for each case, each file containing the JVB NMD's for every cell captured from that particular specimen. Each Excel v5.0 file (*.XLS) also contains the means, standard deviations, variances, minima, and maxima for each JVB NMD. In addition, the macro creates a summary file containing the above statistics for each JVB NMD from every case.

EXAMPLE IV

Cancer Cell Selection Method

The inventors used a cell selection process for the radical prostatectomy specimens that seemed to introduce the least amount of bias and took into account the heterogeneity of prostate cancer tumors. The tumor area must first be identified by an expert pathologist. Once the tumor area(s) have been identified, a minimum of 25 image fields and a maximum of 5–6 cells per image field must then be analyzed and the cell nuclear images captured. The cells selected may not be overlapping, and they may not contain any "holes", which is the result of an improper background threshold setting. Sample the entire circled tumor area. The best way to do this is to mentally partition the circled tumor area into four separate quadrants, and then measure a minimum of 6–7 image fields per quadrant. In each quadrant, select image fields from the "worst" (e.g. Highest grade) cancer areas. (NOTE: The "worst" area in each quadrant may vary from low grade, well differentiated cancer to high grade, poorly differentiated cancer. Just be sure to measure from the "worst" area in each of the four quadrants.) Once you have collected the required number of cells, save the DNA information and nuclear images to a listmode file.

EXAMPLE V

Analysis of CAS-200 DNA Histograms

The DNA histograms were interpreted and classified by three different methods by the consensus of five individuals.

Figure 28A:
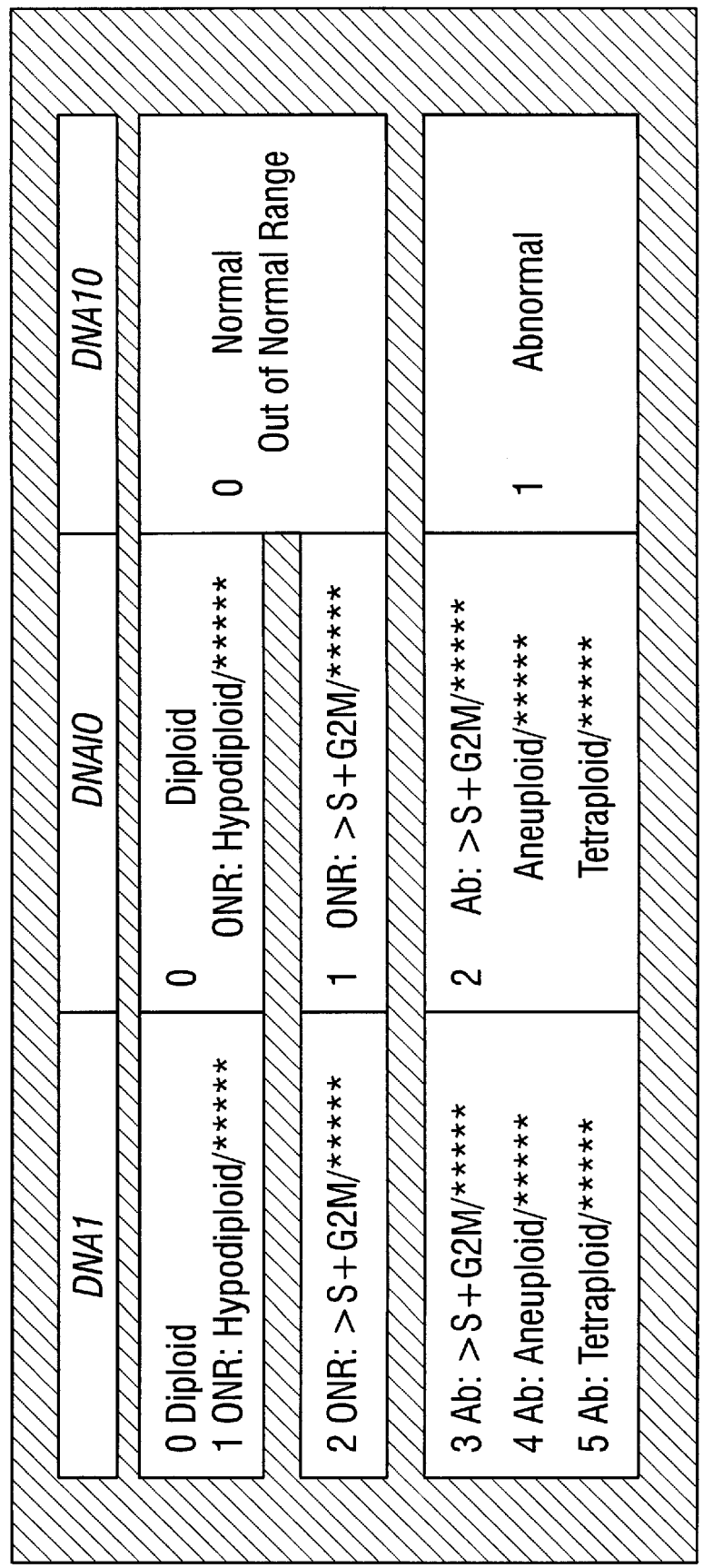
Figure 29:
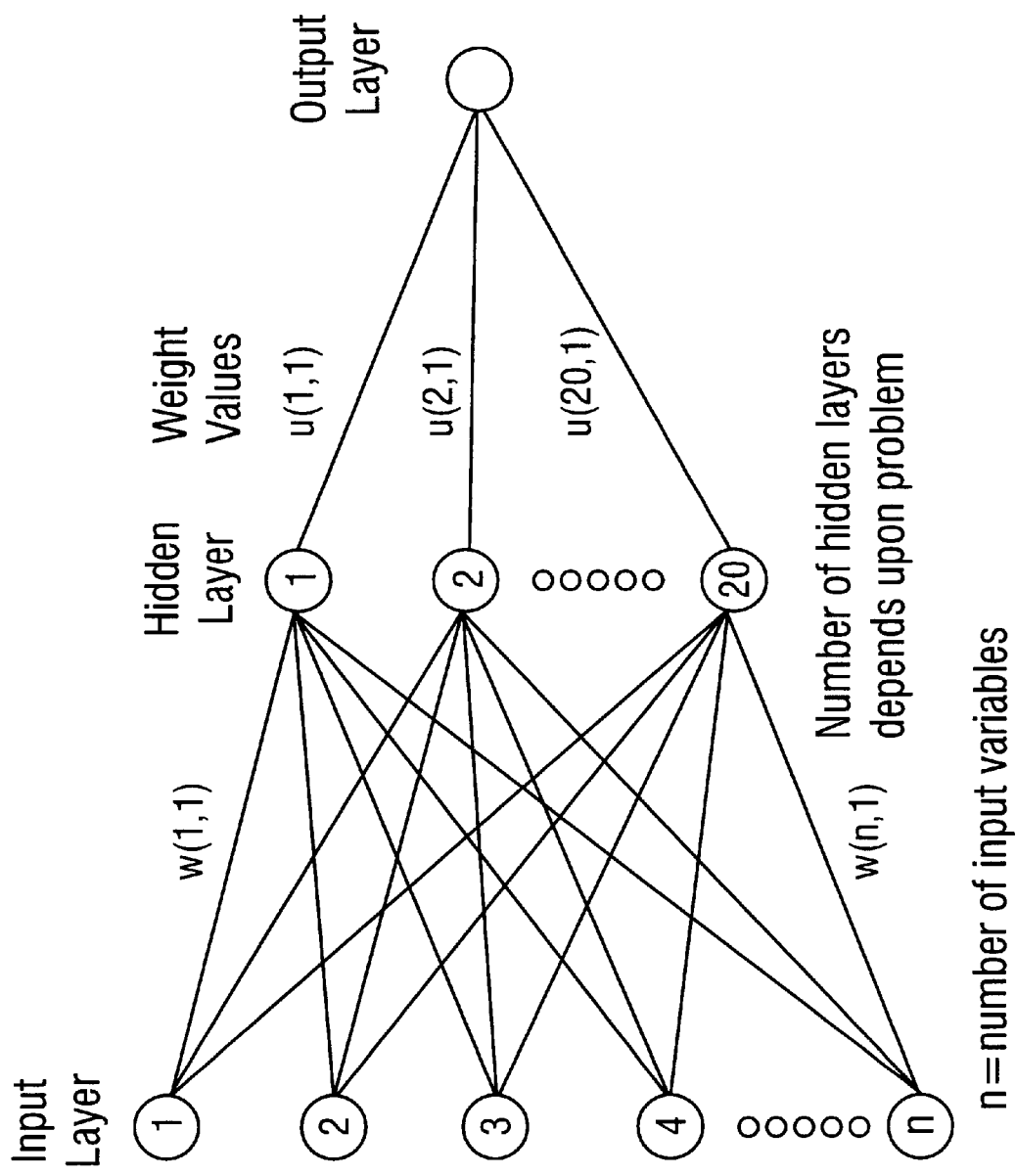
FIG. 29. Neural network configuration.

The three different methods employed cut-offs based upon the results of a DNA Consensus meeting held at Prautz Neck, ME in 1992 (Shankey, T. V. et al. Cytometry 14:497–500, 1993). The histograms were interpreted by four different individuals, and a consensus DNA ploidy classification agreed upon. The classification methods are as follows: (See FIG. 28A and FIG. 28B)

DNA-1=(0) Diploid; (1) ONR: Hypodiploid; (2) ONR: >S+G2M (11–21%); (3) Abnormal: >S+G2M ($\geq$21%); (4) Abnormal: Aneuploid; and (5) Abnormal: Tetraploid DNA-IO=(0) Diploid and ONR: Hypodiploid; (1) ONR: >S+G2M (11-21%); (2) Abnormal: >S+G2M ($\geq$21%). Aneuploid, and Tetraploid DNA-10=(0) Normal and Out of Normal Range; (1) Abnormal The three different methods employed cut-offs determined by the inventors. The histograms were interpreted, and the classification methods are as follows:

JHHDNA=(0) Diploid; (1) Tetraploid; (2) Aneuploid

JHHDNA10=(0) Diploid; (1) Non-Diploid (i.e. Tetraploid and Aneuploid)

JHH %>2N=Percentages of S-Phase and Tetraploid fractions combined from ploidy determinations.

For statistical analysis, each classification scheme coded every subclass as a result for each patient (i.e. CDI DNA Ploidy: Diploid=0, Hypodiploid=1, ONR: >S+G2M=2, Tetraploid=5, Normal=0, Abnormal=1; JHH DNA Ploidy: Diploid=0, Tetraploid=1, Non-Diploid=1, etc.). The JHH %>2N classification method used the percentage as a result for each patient. These coded results were used for statistical analysis.

EXAMPLE VI

Nuclear Roundness Factor Measurement and Calculation of Variance

Definition of Nuclear Roundness Factor

The nuclear roundness factor represents a dimensionless, size-invariant shape descriptor that is based on the ratio of the calculated radius for the measured perimeter divided by the calculated radius for the measured area of the nucleus. This descriptor yields a low value of 1.00 for a perfect circle and increases as the shape of the nucleus deviates from circularity. In mathematical terms:

Perimeter $(P)=2\pi r_p$ and Area $(A)=\pi r_a^2$

Solve Equations for the Radius $(r_p)=(P)/(2\pi)$ and $(r_a)=\sqrt{A/\pi}$

Substitute Radius Equations into Nuclear Roundness Factor Equation

Nuclear Roundness Factor $(NRF)=r_p/r_a=((P)/(2\pi))/(\sqrt{A/\pi})$

The variance in the nuclear roundness (NRV) was calculated using the following formula:

$$(NRV) \text{ Variance} = \sum_{j=1}^{j=n}(Y_j - Y)^2/n$$

n=Number of cells measured j=The $j^{th}$ cell $Y_j$=The nuclear roundness factor of the $j^{th}$ cell Y=The average or mean nuclear roundness factor for all of the cells

Measurement of Nuclear Roundness using the DynaCELL™ System

Histologic tissue sections (5–6 $\mu$m) were cut from re-embedded paraffin blocks of radical prostatectomy specimens. Multiple sections were cut (thirty sections per specimen), and one set of slides from each specimen were stained with Hematoxylin and Eosin (Sakura Diversified Stainer, Model DRS-601) and Feulgen stain (Cell Analysis Systems, Elmhurst, Ill.). The H&E staining procedure was performed on sections #1, 10, 20, and 30 for purposes of pathology review to confirm the presence of cancer for additional biomarker studies. All pathologic radical prostatectomy specimens were assigned Gleason scores (sum). The nuclear roundness factor measurements were performed using the H&E sections. A total of 150 cancerous nuclei from the primary tumor were analyzed with a Zeiss inverted IM microscope (Carl Zeiss, Inc. Thornwood, N.Y.) equipped with a Zeiss Planochromatic 100X oil emersion objective, giving a total magnification of 2440x. The nuclear images were digitized and analyzed with the DynaCELL™ Motility Morphometry Measurement workstation (JAW Associates, Inc., Annapolis, Md.). In this invention, the nuclear roundness variance measurement is the only calculation used from the DynaCELL™ Motility Morphometry Measurement software.

EXAMPLE VII

Utilization of Increased Magnification (63x) to Reduce the Number of NMD's Required to Predict Progression Using a subset of the original patient sample (10 progressors and 10 non-progressors), measurements were conducted as in Examples II & III, except that instead of using the normal 40x objective, a 63x objective lens was used. The data and statistics obtained using the 63x objective were analyzed and compared to the data and statistics obtained using the 40x objective. Table III summarizes the results of the statistical analysis using the 40x and 63x data to predict prostate cancer progression in the subset of 20 patients. Please note that the total number of NMD's required to predict an outcome is decreased as the magnification increases (Table III; also see FIGS. 3–6), as well as significant changes in the actual individual NMD's utilized in the model.

EXAMPLE VIII

Immunochemical Staining for Her-2/neu (c-erbB2)

Her-2-neu (c-erbB2) monoclonal antibody (Ab-3, OP-15) was provided by Oncogene Sciences Inc. (Uniondale, N.Y.) as a gift. The SuperSensitive MultiLink™ kit (BioGenex Inc., Calif.), which employs the strep-avidin biotin complex (ABC) alkaline phosphatase (AP) labelling method, was used for monoclonal antibody detection. All staining was performed with the MicroProbe™ manual staining system (Fisher Scientific, Pittsburgh, Pa.) that utilizes capillary action vertical staining principles. Incubation for the monoclonal antibody was 4° centigrade overnight. Briefly, the staining procedure includes first preparing the immunostaining reagents as follows:

Immunostaining Reagent Preparation

PBS pH 7.6 with 0.1% Triton X-100

Place 450 ml of Type I $H_2O$ into a 500 ml graduated cylinder. Then add one envelope of Coulter PBS Buffer Reagent (Coulter Source, Marietta, Ga.) to the type I water while stirring. Adjust the pH to 7.6 with approximately 20 drops of 1 N NaOH (a plastic transfer pipet is useful in adding the NaOH). Pipette 500 µl of Triton X-100 to the solution. Next, Adjust the volume of the solution to 500 ml with Type I $H_2O$.

PBS pH 7.6 with 0.5% Triton X-100

Place 450 ml of Type I $H_2O$ into a 500 ml graduated cylinder. Then add one envelope of Coulter PBS Buffer Reagent to the type I water while stirring. Adjust the pH to 7.6 with approximately 20 drops of 1 N NaOH (a plastic transfer pipet is useful in adding the NaOH). Pipette 2.5 ml of Triton X-100 to the solution. Adjust the volume of the solution to 500 ml with Type I $H_2O$.

1M Levamisole Stock Solution

Measure 241 mg (0.241 g) of levamisole (Sigma) using an analytic balance. Place the levamisole into a 1.5 ml microcentrifuge tube containing 1 ml of Type I $H_2O$. Mix the contents with the aid of a vortex mixer. Store the solution at 4° C. until it is used.

5% Nonfat dry milk with PBS pH 7.6 0.1% Triton X-100, 0.05% thimerosal

Place 5 grams of nonfat dry milk in a Erlenmeyer flask containing 100 ml PBS pH 7.6 with 0.1% Triton™ X-100. Then, add 0.05 g of thimerosal and mix the solution by stirring. Store 5 ml aliquots of the solution at −80° C. Upon thawing, the solution should be stored at 4° C. Do not use this solution if it has been stored at 4° C. for longer than 5 days.

0.5% Nonfat dry milk with PBS pH 7.6 0.1% Triton X-100

Pipette 100 µl 5.0% nonfat dry milk with PBS pH 7.6 0.1% Triton X-100, 0.05% thimerosal into a 1.5 ml microcentrifuge tube or 10 ml test tube containing 900 µl of PBS pH 7.6 with 0.1% Triton X-100. Mix the solution with the aid of a vortex. The solution should be stored at 4° C. Do not use this solution if it has been stored at 4° C. for longer than 5 days.

C-Neu, Her-2/Neu (1:40)

Pipette 875 µl of PBS pH 7.6 with 0.1% Triton X-100 into a 1.5 ml microcentrifuge tube or 10 ml test tube. Pipette 100 µl 5.0% nonfat dry milk with PBS pH 7.6 with 0.1% Triton X-100 to the tube and mix the solution with the aid of a vortex. Then, pipette 25 µl of C-Neu (ab-3) to the tube and mix with the aid of a vortex. The antibody should be added last to the solution.

Normal Mouse Serum Control (1:1000)

Pipette 899 µl of PBS pH 7.6 with 0.1% Triton X-100 into a 1.5 ml microcentrifuge tube or 10 ml test tube. Pipette 100 µl 5.0% nonfat dry milk with PBS ph 7.6 with 0.1% Triton X-100 to the tube and mix the solution with the aid of a vortex. Pipette 1 µl Normal Mouse Serum (Dako) to the solution and mix with the vortex. The normal mouse serum should be added last to the solution.

Mouse IgGi Isotypic Control (1:200)

Pipette 895 µl of PBS pH 7.6 with 0.1% Triton X-100 into a 1.5 ml microcentrifuge tube or 10 ml test tube. Pipette 100 µl 5.0% nonfat dry milk with PBS ph 7.6 with 0.1% Triton X-100 to the tube and mix the solution with the aid of a vortex. Pipette 5 µl Mouse IgG1 Isotypic Control (Coulter) to the solution and mix with the vortex. The Mouse IgG1 Isotypic Control should be added last to the solution.

2Ab (Biotinylated anti-mouse IgG, Multilink)

Comes premixed in the BioGenex Large Volume Multi-Link Kit

Label (Streptavidin/Alkaline Phosphatase)

Comes premixed in the BioGenex Large Volume Multi-Link Kit

Fast Red Chromogen Solution

Pipette 5 µl of 1.0 M Levamisole to the 5 ml vial of Naphthol Phosphate in Tris Buffer. Add one Fast Red Tablet to the solution and vortex until the tablet is completely dissolved. This solution must be used immediately after preparation.

*Levamisole is added to the Fast Red Solution to block endogenous alkaline phosphatase activity.

The Her-2/neu antigenicity was then scored. The scoring method assessed the amount of staining area within the "dotted cancer zone" as either negative (0), focal (1), or diffuse (2), and the intensity of the staining was scored as 0–4+, ranging from negative (0) to strong red color (4+) resulting from the AP red substrate reaction (see FIG. 28A and FIG. 28B).

EXAMPLE IX

Immunochemical Staining for PD-41

The PD-41 (Prostate Mucin Antigen) monoclonal antibody was provided by Dr. George Wright at Eastern Virginia Medical School under a materials transfer agreement. The SuperSensitive MultiLink™ kit (BioGenex Inc., Calif.), which employs the strep-avidin biotin complex (ABC) alkaline phosphatase (AP) labelling method, was used for monoclonal antibody detection. All staining was performed with the MicroProbe™ manual staining system (Fisher Scientific, Pittsburgh, Pa.) that utilizes capillary action vertical staining principles. Incubation for the monoclonal antibody was 37° centigrade for 15 minutes. Briefly, the staining procedure includes first preparing the immunostaining reagents as in Example X, except with the following changes:

Inmunostaining Reagent Preparation

PD-41 (15 µg/ml)

Place 800 µl of PBS pH 7.6 with 0.1% Triton X-100 in a 1.5 ml microcentrifuge tube. Add 100 µl 5% milk to the tube and mix the contents with the aid of a vortex mixer. Then, add 100 µl of PD-41 to the tube and mix the contents with the aid of a vortex mixer.

CAS Red Chromogen Solution

Add 900 µl of Type I $H_2O$ to a 1.5 ml microcentrifuge tube. Add the 1 µl of 1 M levamisole to the tube. Then, add 100 µl of CAS red substrate concentrate and mix the contents with the aid of a vortex mixer. Add 45 µl of CAS red chromogen concentrate (always add this ingredient last) to the solution and mix the contents with the aid of a vortex mixer. This solution must be used immediately after preparation.

The PD-41 antigenicity was then scored. The scoring method employed the number of positive staining ducts divided by the total number of ducts in the "dotted cancerous zone". The percentages of positively staining ducts was used as a patient result.

PD-41 Background

Monoclonal antibody PD-41, a mouse $IgG_{1k}$, was first described by Beckett et al. (Beckett, M L, Lipford, G B, Haley, C l, Schellhammer, P F and Wright, G L. Monoclonal Antibody PD41 Recognizes an Antigen Restricted to Prostate Adenocarcinomas. Cancer Res. 51:1326–1333, 1991) by its reactivity to an prostate adenocarcinoma-restricted mucoprotein known as prostate mucin antigen (PMA). The target PMA, an O-linked oligosaccharide-associated protein with a molecular weight of >400 kd in prostate cancer patient seminal plasma, has not been demonstrated to recognize mucins at other organ sites. Wright et al. (Wright, G L, Beckett, M L et al. Mucins as biomarkers of prostate carcinoma. J. Urol. 149:450A, 1993) demonstrated immunoperoxidase immunoreactivity of PD-41 with in 100% of primary, 71% of metastatic carcinomas and under 1% of normal and benign prostatic tissues, including BPH.

An independent study of 95 prostate needle core biopsy paraffin-embedded sections showed PD-41 reactivity in ductal epithelia and/or prostatic glandular secretions within 56% (53/95) of prostate tumor specimens (Marley, G M, Veltri, R W, Patton, K P and Wright. G L. Histochemical Expression of a Unique Prostate Mucin Antigen from Core Biopsies. Proc. Amer. Assoc. Cancer Res. 34:28, 1993). When Gleason score or DNA ploidy were employed as stratification parameters, PD-41 proved to be an independent factor of prognostic value. Clinical follow-ups of 61% of this cohort confirmed that PD-41 expression acted as an independent marker of tumor aggressiveness (Veltri, R W et al., recent CDI unpublished data).

EXAMPLE X

The Patient Sample

A group of one hundred and twenty-four (124) patients with localized prostate cancer were used in this study. The sample was optimized for the evaluation of tumor progression. The patients had clinically localized prostate cancer and were followed for evidence of progression based upon one or more of the following events: a detectable post-operative prostate specific antigen (PSA) level, local recurrence, evidence of metastasis following radical prostatectomy, or death. The patient sample had been clearly defined for preoperative Gleason grades, post-operative Gleason grades, clinical and pathological stage, organ disease confinement, focal or established capsular penetration, and surgical margin status. None of these patients had any seminal vesicle or lymph node invasion. As used herein, pre-operative Gleason sore is the highest Gleason score from all positive sextant biopsies for a single case. The demographics of the patient sample is illustrated in Table IV.

EXAMPLE XI

Statistical Analysis—Logistic Regression

The logistic regression statistical analysis of the data was performed using the STATA™ v3.1 (Stata Corporation, College Station, Tex.) statistical analysis software program. This invention applied logistic regression to every independent parameter (e.g. NMD's, biomarkers, Gleason scores, etc.) first to select the univariately significant variables for progression or organ confined disease status (Table V & VIII) using the STATA™ statistical software package (STATA™ command: logistic). Statistical significance consisted of p values $\leq 0.05$. Next, the univariately significant independent variables were multivariately assessed using backwards stepwise logistic regression (STATA™ command: swlogis) to determine which independent variables (e.g. NMD's (CMP or JVB), Gleason Score, and biomarkers) were aggregately significant in the prediction of progression or organ confined disease status (Tables VI, VIa, VII, VIIa, IX, IXa, X, & Xa). The software program generated Receiver Operator Characteristic (ROC) curves with investigator selected cutoff, resulting in optimized sensitivity, specificity, positive predictive values, and negative predictive values (see above listed tables and FIGS. 7–27). Kaplan-Meier actuary plots were also generated for the progression analysis.

STATA™ also provides a command (logit, an estimated maximum-likelihood logit model) that provides the weighted coefficients for the statistically significant independent variables used in the multivariate model as well as the model constant. The general formulas for calculating the predictive index and predictive probability are as follows:

Predictive Index $(xb)=(\beta_0+\beta_1 \text{var}(1)+\beta_2 \text{var}(2)+ \text{- - -} +\beta_n \text{var}(n))$ Predictive Probability $(p)=e^{xb}/(1+e^{xb})$ Where:
$\beta_2$=Formula Constant;
$\beta_1$ through $\beta_0$=Weight factors for variables 1 through n;
var(1) through
var(s)=Independent variables being used in logistic regression model.

The final calculation of the predictive probability provides a patient-specific value, between 0 and 1, for the probability of a specific outcome (e.g. progression or organ confined disease status). The threshold value (cutoff) for the predicted probability is selected based upon the results of the ROC curves. Equation 2 gives an example using the weighted formula.

EQUATION 2

Formula for Progression Predicted Probability of JVB Morphometry Features Alone

Predictive Index:
Morphometry $x_j b=(-61.2378)+(-0.7827881)(\text{stdev1})+(3.209138)(\text{stdev2})+(13.90239)(\text{stdev4})+(-1381.354)(\text{stdev7})+(11.52351)(\text{stdev8})+(-1.18553)(\text{stdev10})+(-0.603529)(\text{stdev11})+(0.6900095)(\text{stdev14})+(1254.563)(\text{stdev15})+(2964.96)(\text{stdev17})+(2.370112)(\text{stdev24})+(505.4493)(\text{stdev26})+(-7.731191)(\text{stdev28})+(84.19147)(\text{stdev31})+(-28.88644)(\text{stdev34})+(0.01796)(\text{var1})+(-0.0390615)(\text{var2})+(7.529075)(\text{var3})+(-45.39564)(\text{var4})+(12174.49)(\text{var7})+(-18176.55)(\text{var15})+(-26895.28)(\text{var17})+(-2.079085)(\text{var22})+(1.093606)(\text{var28})+(2180.479)(\text{var29})+(1.959982)(\text{var34})+(-7.559859)(\text{var35})$ Predictive Probability:
Morphometry $P_j=\exp(x_j b)/(1+\exp(x_j b))$,
where $x_j$=The (row) vector of independent variables of the $j_{th}$ observation, (i.e., the independent variable value).
b=The corresponding estimated parameter (column) vector, (i.e., the weight factor associated with that particular independent variable).

$P_j$=Predicted probability of a positive outcome for the $j_{th}$ observation.

EXAMPLE XII

Application of Neural Networks

The multilayer feed forward perceptron with error back propagation training method is chosen for this work. The back propagation method is a gradient based learning procedure, but has the drawback of local optimum. Studies show sigmoid activation function, which is often used with neural network, is not necessarily the optimal choice. It has been suggested in certain classes of problems that the use of sinusoidal or gaussian activation functions reduce the training time substantially. In this work, both sigmoid and sinusoidal activation functions are studied.

In a multilayer neural network, hidden layers are of particular importance. How well the network approximates the discriminate surface to a large degree depends on the number of hidden neurons. Allowing too few or too many parameters to be used in the training will lead to under or over fitting. Therefore, efforts have been made to identify the optimal number of hidden neurons.

The neural network (NN) software program of the present invention has a single hidden layer. Morphometry data from the radical prostatectomy samples was analyzed, and a total of 28 NMD's were extracted. Backwards stepwise logistic regression analysis of the data utilizing the STATA™ software showed that only 14 of the NMD's were multivariately significant. The 30 feature network used all 28 NMD's, post operative Gleason score, as well as the perimeter and nuclear roundness variance calculated using the CAS-200). Using the data sets of 15, 28, and 30 measurements, two different network types were trained, a standard multilayer sigmoidal type with a single hidden layer, and a hybrid network previously described. Further utilization of the data used for training these networks within the scope of the invention will result in networks with greater accuracy.

EXAMPLE XIII

Organ Confinement Model

The following example describes the procedures for multivariate statistical analysis as applied to the prediction of organ-confined disease status that is based on sextant biopsy pathology, PSA and quantitative image analysis.

The parameters utilized for the model include patient PSA, number of positive sextant core biopsies, tumor location (base and/or apex involvement), Sum % area of tumor involvement, Gleason Score, DNA ploidy, and quantitative nuclear grade (a combination of size, shape, and DNA content descriptors, and Markovian texture as determined using a CAS-200 Image Analysis System).

A total of two-hundred and twenty-seven (227) sextant biopsy specimens provided, (n=150) including from collaborators at Ohio State University (n=77) that were used to prepare the trained algorithm (Table XIV). One hundred and eighteen (118 or 52%) patients were non-organ confined (NOC) with 13 (6%) of these NOC patients having positive lymph nodes and 43 (19%) having seminal vesicle involvement. Five micron sections were prepared from paraffin-embedded specimens and placed on Probe-On™ slides, the first section was stained from paraffin-embedded specimens and placed on Probe-On™ slides, the first section was stained with H&E and the next with the Feulgen stain (B-D Cellular Imaging Systems, San Jose, Calif.). The sequential H&E and Feulgen stained slides were screened and "dotted" by uropathologists. From the "dotted" areas of the Feulgen stained slides, 125 intact cancer cell nuclei were analyzed using the CAS-200 Image Analysis Systems (B-D Cellular Imaging Systems, San Jose, Calif.). Cellsheet™ v1.0d, a new listmode file conversion software package (JVB Imaging, Elmhurst, Ill.) which calculates 38 NMD's, including shape, size, and DNA content descriptors, and Markovian texture features (Pressman, 1976) (Table XV), was employed to process the nuclear image data. All data were analyzed using STATA™ (Stata Corp., College Station, Tex.), CART (CART v1.02, Salford Systems, San Diego, Calif.), and the p values were calculated using the non-parametric logistic regression analysis method.

TABLE XIV

Sextant Core Predictive Algorithm for Non-Organ Confined Disease Status Patient Sample (n = 227)*

| Average Age: | 64.8 ± 5.9 years [47–78 yrs] |
|---|---|

Post Operative Pathology

Organ Confined: 109/227 (48%)
Non-Organ Confined: 118/227 (52%)
+Seminal Vesicles: 43/220 (19%)
+Lymph Nodes: 13/223 (6%)
+Capsular Penetration: 77/212 (34%)
+Surgical Margins: 77/217 (34%)

Pre-Operative Pathology

| Number of Positive Cores: | Tumor Location | (% Positive) | Pre-Op Gleason Score: | |
|---|---|---|---|---|
| 1  67 (30%) | Apex | 136 (60%) | 2 | 0 (0%) |
| 2  60 (26%) | Mid | 125 (55%) | 3 | 0 (0%) |
| 3  63 (28%) | Base | 108 (48%) | 4 | 1 (1%) |
| 4  21 (9%) |  |  | 5 | 15 (7%) |
| 5  6 (3%) | Apex and/or Base | 183 (81%) | 6 | 94 (41%) |
| 6  7 (4%) |  |  | 7 | 87 (38%) |
|  |  |  | 8 | 21 (9%) |
|  |  |  | 9 | 9 (4%) |

*150 UroCor, Inc. Sextant Biopsy Cases [1994–1995] 77 Ohio State University (Dr. Badalament) Sextant Biopsy Cases

TABLE XV

CellSheet ™ v1.0d Nuclear Morphometric Descriptors

| | |
|---|---|
| 1. Object Sum Optical Density | 22. Diagonal Moment* |
| 2. Object Size | 23. Second Diagonal Moment* |
| 3. Object Shape | 24. Product Moment* |
| 4. Picograms of DNA | 25. Triangular Symmetry* |
| 5. Angular Second Moment* | 26. Standard Deviation |
| 6. Contrast* | 27. Cell Classification |
| 7. Correlation* | (1=Hypodiploid, 2=Diploid, |
| 8. Difference Moment* | 3=S-Phase, 5=Tetraploid, |
| 9. Inverse Difference Moment* | 6=Hyperploid) |
| 10. Sum Average* | 28. Perimeter |
| 11. Sum Variance* | 29. DNA Index |
| 12. Sum Entropy* | 30. Density |
| 13. Entropy* | 31. Average Optical Density |
| 14. Difference Variance* | 32. Feret X |
| 15. Difference Entropy* | 33. Feret Y |
| 16. Information Measure A* | 34. Maximum Diameter |
| 17. Information Measure B* | 35. Minimum Diameter |
| 18. Maximal Correlation Coefficient* | 36. Elongation |
| 19. Coefficient of Variation* | 37. Run Length |
| 20. Peak Transition Probability* | 38. Configurable Run Length |
| 21. Diagonal Variance* | |

*NOTE: Values 5–25 are grain dependent Markovian texture features. Grain may be looked at as a measurement in pixels of the width of an averaged sized object. The grain values for all of these measurements were set to 1.

A. Specimen Collection and Processing

Each patient had their prostate biopsied in six different areas (left apex, left mid, left base, right apex, right mid, and right apex) using an 18-gauge "tru-cut" type needle and a spring driven biopsy gun. Each biopsy was placed in a properly labeled vial containing 10% neutral buffered formalin. The specimens were then processed and embedded in separate paraffin blocks using Tissue-Tec processing and embedding stations. Each block is labelled, and then multiple 5 µm tissue sections are cut, placed on glass slides, air dried, and heat fixed. The first and third slides (Levels I & III) are H&E stained. The second slide (Level II) is Feulgen stained, and the fourth slide (Level IV) is stored.

Each of the H&E slides was reviewed by a pathologist to determine which of the slides contains tumor cells. The number of positive cores is determined by adding up the number of areas which contain tumor (i.e. left base, left mid, left apex, right base, right mid, or right apex).

The pathologist determines from each positive slide a Gleason score, and then calculates the percent of tumor involvement for that biopsy. This is done by measuring first the total length of the tissue in the 5 µm section, and then the total length of the tissue which is involved in the tumor. The percentage of tumor involvement is then calculated by dividing the tumor length by the overall biopsy length. Once these determinations have been done for each slide, the total % involvement is calculated by adding up the percentages of tumor involvement from each positive biopsy.

The tumor location variable is then determined. If there is tumor involvement in the base and/or apex biopsies $\geq 5\%$ total, a value of 1 is entered for the variable. If the involvement of tumor in the base and/or apex biopsies is <5% total, a value of 0 is entered for the variable.

The highest Gleason score is determined by simply using the highest Gleason score from the positive biopsies for that particular case. The pathologist then determines the positive core biopsy that best represents the "worst" area of tumor for the case, and that biopsy is used for the DNA ploidy and quantitative nuclear grade calculations.

B. Collection and Processing of Feulgen Stained Cancer Nuclei and Calculation of Quantitative Nuclear Grade The Feulgen stained cancer cell nuclei from the 5 µm sextant biopsy specimens are analyzed and the images captured using the QDA v3.0 software program on a CAS-200 Image Analysis System. The optical system is calibrated using the CAS calibration slides that were stained with the specimen slides by measuring at least 20 calibration cells, with a resulting calibration peak percent coefficient of variation (% CV) of less than 2.0%. Next, using the biopsy which is the most representative of the cancer (selected by the pathologist), a minimum of 125 cancer cell nuclei are analyzed using the method described below at the specified magnification. The QDA v3.0 software program generates a DNA histogram and saves the nuclear images as well as the DNA content information to a listmode file (*.ILM). The listmode file is then uploaded into a network system using a Cortex program, and the nuclear images are converted into 38 different nuclear morphometric descriptors (NMD's ) (8 nuclear shape descriptors, 8 DNA content descriptors, and 22 Markovian texture descriptors) using a customized version of the Cell Sheet v1.0d program. A C-language program is then used to calculate the variance of each of the 38 different NMD's for the population of cells measured from a particular case (i.e. 125 cells). The variances of 22 of the 38 NMD's are then used to calculate a Quantitative Nuclear Grade (QNG) for the case, using a formula derived from a logistic regression model (Table XVI).

TABLE XVI

| Quantitative Nuclear Grade Formula | |
|---|---|
| N227QNG PI = | (1.519492) + (−1.167831)(Var3) + (−24.77048)(Var4) + (102580)(Var5) + (−0.0010737)(Var6) + (1667.514)(Var7) + (1.33661)(Var8) + (−662.9786)(Var9) + (0.00000248)(Var11) + (−45668.71(Var12) + (0.0019424)(Var14) + (−2541.086)(Var17) + (1154.989)(Var19) + (−6269.475)(Var20) + (14700000)(Var21) + (−1751.078)(Var26) + (1.042041)(Var27) + (0.2199372)(Var28) + (1276.338)(Var29) + (−1.377949)(Var34) + (−1.394814)(Var35) + (22.47551)(Var36) + (−16.41575)(Var38) |
| N227QNG = | exp(N227Txt PI)/(1 + exp(N227Txt PI)) |
| Var3: | Population Variance (n-1) of Object Shape |
| Var4: | Population Variance (n-1) of Pg. DNA |
| Var5: | Population Variance (n-1) of Angular Second Moment (Pixel Step Size = 1) |
| Var6: | Population Variance (n-1) of Contrast (Pixel Step Size = 1) |
| Var7: | Population Variance (n-1) of Correlation (Pixel Step Size = 1) |
| Var8: | Population Variance (n-1) of Difference Moment (Pixel Step Size = 1) |
| Var9: | Population Variance (n-1) of Inverse Difference Moment (Pixel Step Size = 1) |
| Var11: | Population Variance (n-1) of Sum Variance (Pixel Step Size = 1) |
| Var12: | Population Variance (n-1) of Sum Entropy (Pixel Step Size = 1) |
| Var14: | Population Variance (n-1) of Difference Variance (Pixel Step Size = 1) |
| Var17: | Population Variance (n-1) of Information Measure B (Pixel Step Size = 1) |
| Var19: | Population Variance (n-1) of Coefficient of Variation (Pixel Step Size = 1) |
| Var20: | Population Variance (n-1) of Peak Transition Probability (Pixel Step Size = 1) |
| Var21: | Population Variance (n-1) of Diagonal Variance (Pixel Step Size = 1) |
| Var26: | Population Variance (n-1) of Standard Deviation |
| Var27: | Population Variance (n-1) of Cell Classification |
| Var28: | Population Variance (n-1) of Perimeter |
| Var29: | Population Variance (n-1) of DNA Index |
| Var34: | Population Variance (n-1) of Maximum Diameter |
| Var35: | Population Variance (n-1) of Minimum Diameter |
| Var36: | Population Variance (n-1) of Elongation |
| Var38: | Population Variance (n-1) of Configurable Run Length (Pixel Sample Size = 1, Pixel Difference Threshold = 0.1, Projection Configuration: All four possibilities, Normalized to Cell Area) |

C. Cancer Cell Selection Method

The biopsy to be analyzed for DNA and QNG is selected by an expert pathologist. The biopsy chosen is the one which the pathologist thinks is the most representative of the cancer present in the sextant biopsy specimen. The cancer area on the biopsy is identified and marked by the pathologist. Once the tumor area(s) have been identified, a minimum of 125 Feulgen stained nuclei representing the "worst" cells present are analyzed and the images captured. The cells selected may not be overlapping, and they may not contain any "holes". which is the result of an improper background threshold setting in the QDA software. The "worst" cells are the highest grade cancer cells present in the tumor area(s), which may vary from low grade, well differentiated cancer to high grade, poorly differentiated cancer. Once the required number of cells are collected, the DNA content information and nuclear images are saved to a listmode file.

D. Analysis of CAS-200 DNA Histograms

Three different methods employing cut-offs based upon the results of a DNA consensus meeting held a Prautz Neck, Me. in 1992 (Shankey TV, et al. Cytometry 14:397–500, 1992) were used to interpret and classify the DNA histograms. The histograms were interpreted by the pathologists, and a DNA ploidy classification assigned to the case. The classification methods are as follows:

DNA1: (0) Diploid; (1) Out of Normal Range (ONR: Hypodiploid,m (2) ONR: >S+G2M [11–21%]; (3) Abnormal: >S+G2M [>21%]; (4) Abnormal: Aneuploid [>10% cells in aneuploid peak]; and (5) Abnormal: Tetraploid [>16% cells in tetraploid peak]

DNAIO: (0) Diploid; (1) ONR: Hypodiploid and ONR: >S+G2M [11–21%]; (2) Abnormal: >S+G2M [>21%], Aneuploid [>10% cells in aneuploid peak], and Tetraploid [>16% cells in tetraploid peak]

DNA10: (0) Diploid and ONR, (2) Abnormal

E. Pathological Assessment of Sextant Core Biopsies

An expert pathologist reviews the H&E and Feulgen stained 5 μm sections and identifies the biopsies which contain cancer for each case, as well as determining the Gleason score and the % linear involvement of the tumor for every positive sextant biopsy involved in a single case. The pre-biopsy PSA value for each case is provided by the physician, when available.

F. Quantitative Nuclear Grade

The Quantitative Nuclear Grade (QNG) utilizes quantitative micro-spectrophotometric image analysis with a CAS-200 image analysis system (Becton-Dickinson-Cell Analysis Systems, San Jose, Calif.) to capture uropathologist selected cancer cell nuclear images stated by the Feulgen method. A unique software package (CellSheet™, Elmhurst, Ill.) is used to transform listmode data files into nuclear features which mathematically characterize shape, size, DNA content, and chromatin complexity. There are 38 nuclear descriptors, and they include eight DNA content descriptors, eight size and shape descriptors, and twenty-two Markovian texture (chromatin complexity) descriptors. The inventors have studied the application of this software closely with the developer and determined important features that are useful for urologic malignancies, and in particular prostate cancer. The present studies required testing several hundred pathologically defined specimens with well characterized clinical follow-up in order to assess the correlation of the QNG variables to specific outcomes such as progression and pathological stage (non-organ-confined disease status). The Quantitative Nuclear Grade (QNG) is calculated using non-parametric logistic regression statistical methods that determine the univariately and multivariately significant subset of the 38 available Cell Sheet™ descriptors that are useful for the prediction of the outcome of interest. The QNG technology has been applied to both sextant core biopsies and pathologically diagnostic radical prostatectomy blocks successfully.

G. Statistical Analysis of N227SXNT Database

Figure 30:
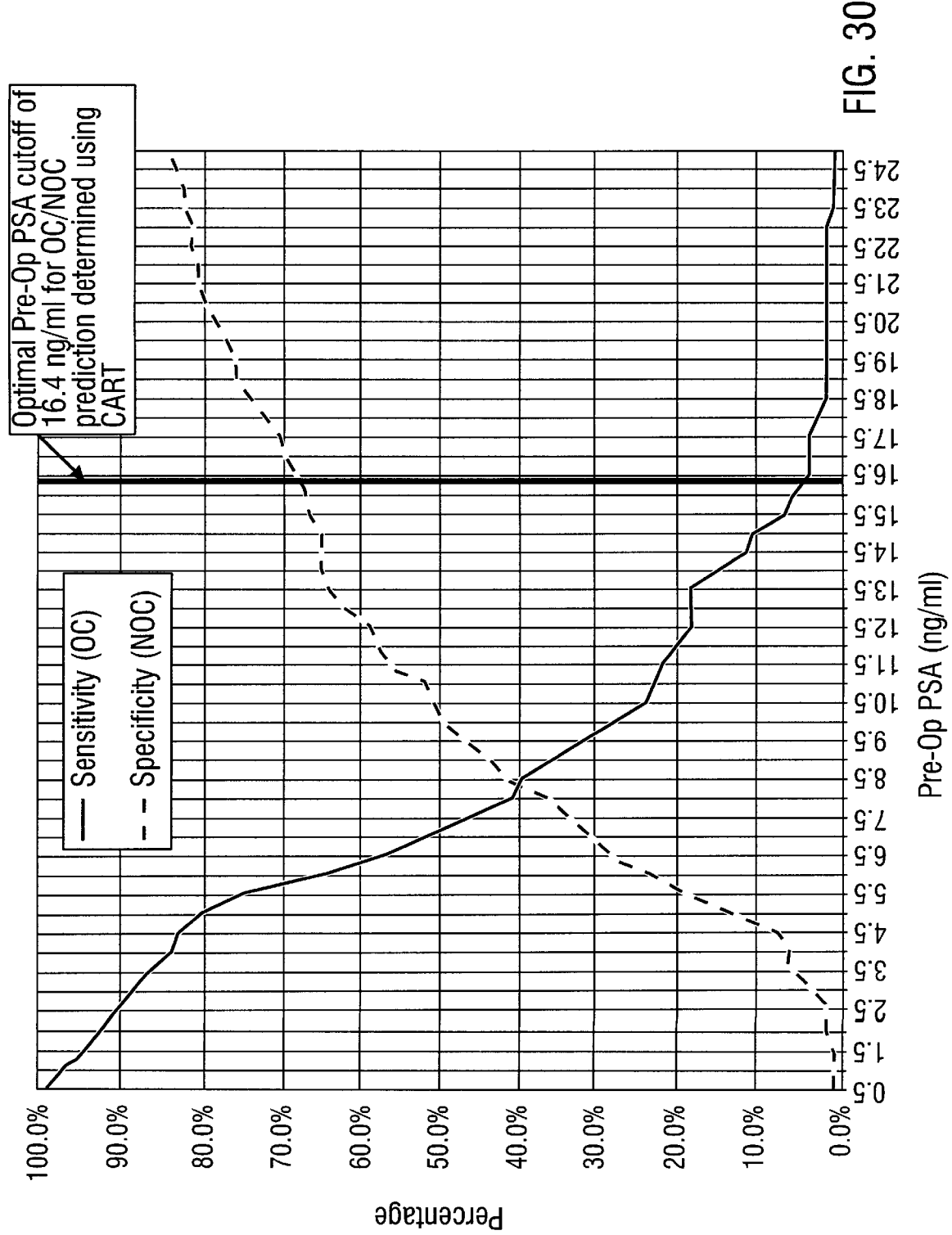
FIG. 30. Pre-operative PSA sensitivities and specificities for sextant biopsy cases with n=227.
Figure 31:
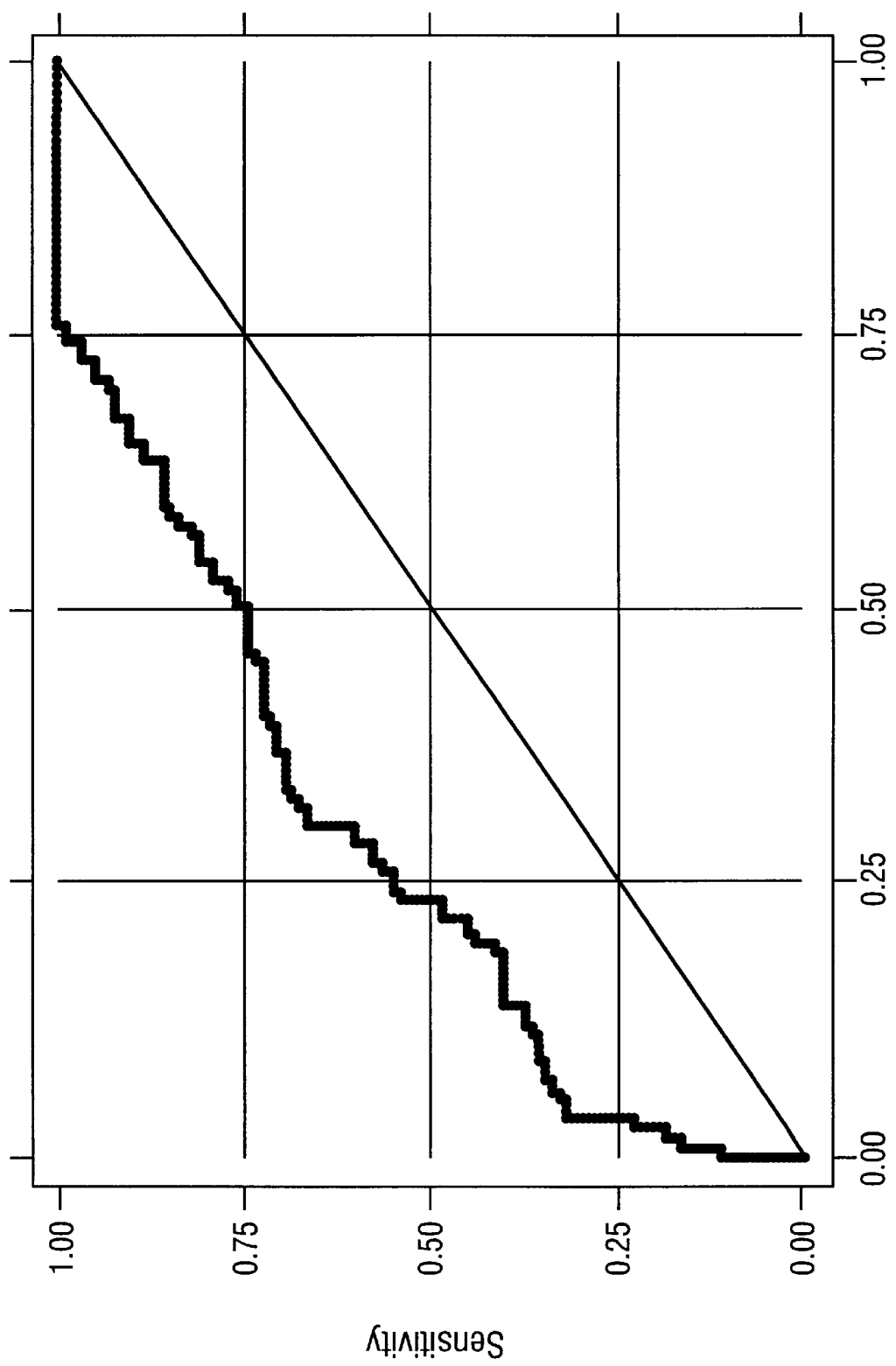
FIG. 31. Shows the predictive power using the quantitative nuclear grade with variance of 22 texture features, a ROC curve was produced with an area under the curve of 73%.
Figure 32:
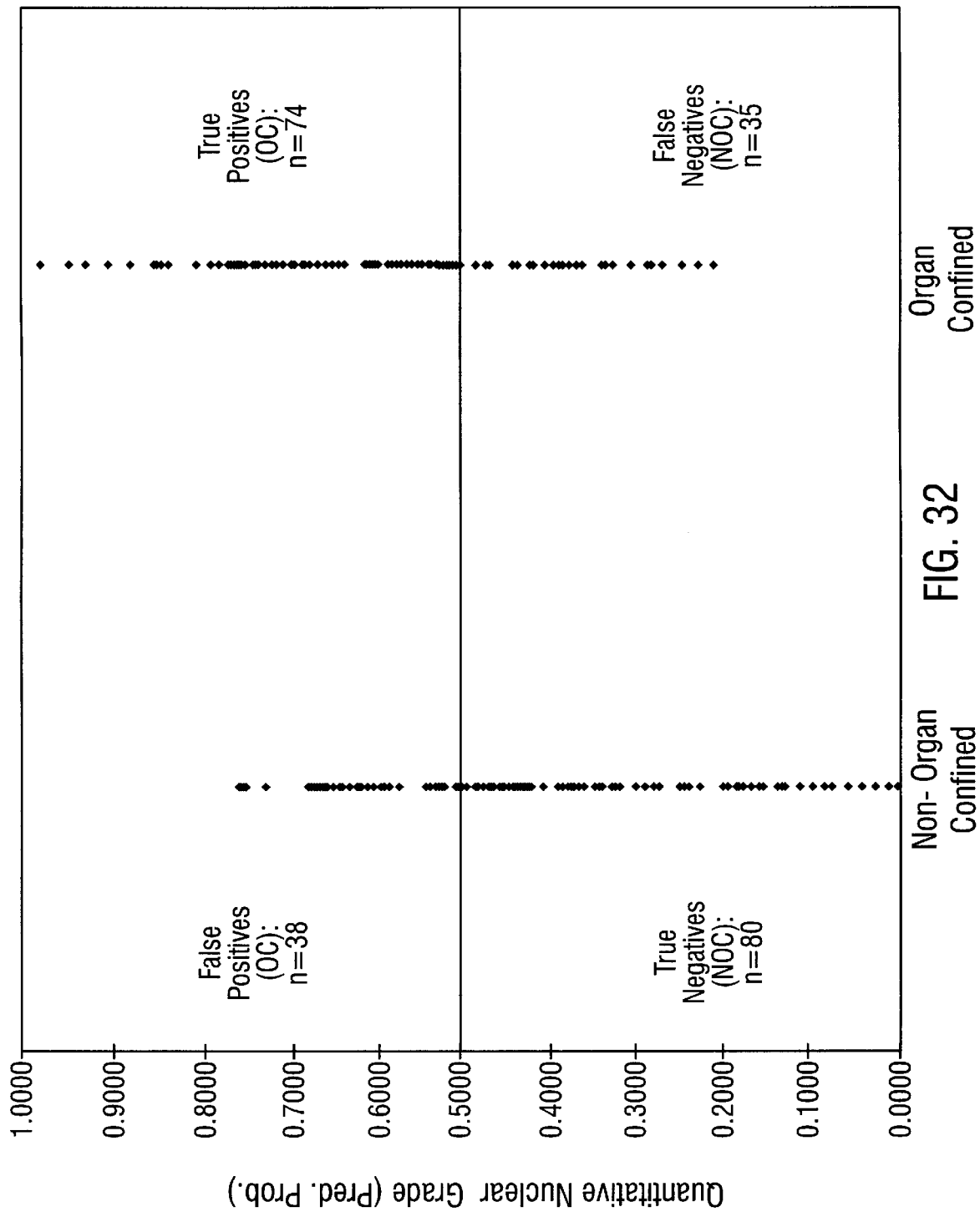
FIG. 32. Organ confinement as related to Quantitative Nuclear Grade, varying 22 textual features.

CART analysis (CART v1.02, Salford Systems, San Diego, Calif.) was used to determine optimal cutoff (i.e. maximum sensitivity) for Pre-Op PSA by limiting the tree growth to two result nodes (FIG. 30). Pre-Op PSA is the pre-sextant biopsy PSA value, and the optimal cutoff value was found to be $\leq 16.3$ ng/ml. A binary variable was created for the PSA values; 0=PSA$\leq$16.3 ng/ml, 1=PSA>16.3 ng/ml. Next, the variances of all 38 NMD's obtained from the CellSheet™ v1.0d Beta4 program (JVB Imaging, Elmhurst, Ill.) were multivariately assessed for their significance in the prediction of organ confinement using backwards stepwise logistic regression (STATA™, College Station, Texas). The variances of twenty-two NMD's were retained in a multivariate model. The model constant and weighting factors for the twenty-two multivariately significant NMD's were obtained by estimating the maximum-likelihood logit model, and the predictive probabilities were then calculated and used as the QNG variable (FIG. 31). CART was tried to determine an optimal cutoff, but the use of the continuous QNG variable proved to be the most univariately significant in the prediction of organ confinement (FIG. 32). The formulas utilized in determining organ confinement are set forth in Table XVII.

TABLE XVII

Formulas for Determining Organ Confinement

| | |
|---|---|
| PosCores: | Number of cores positive for cancer. |
| HiPreGI: | Highest Gleason score from all positive cores for a single case. |
| TotInv: | Sum of the % Involvement from all positive cores for a single case. |
| DNAIO: | DNA Ploidy from single diagnostic core (Diploid = 0, ONR = 1, or Abnormal = 2) |
| BsApx10-5: | Involvement in the Base or Apex cores $\geq$5%. ($\geq$5% Involvement = 1, <5% Involvement = 0) |
| PrePSA16: | Pre-Biopsy PSA Score ($\geq$16.3 ng/ml = 1, <16.3 ng/ml = 0) |
| N227QNG: | Quantitative Nuclear Grade - Predictive Probability calculated using Variance of 22 Cell Sheet v1.0d Beta2 features |

Formula for cases with PSA Values:

(SxtPSA-PI)
Predictive Index = (1.978019) + (0.1267477)(PosCores) + (−0.5226136)(HiPreGI) + (−0.0064845)(TotInv) + (0.2130566)(DNAIO) + (−0.7773022)(BsAPX10-5) + (−2.203646)(PrePSA16) + (5.08648)(N227QNG)
Predictive Probability = exp(SXtPSA-PI)/(1 + exp(SxtPSA-PI))
Organ Confinement Prediction: 0 = Predicted to be Non-Organ Confined (any Predictive Probability $\leq$ 0.500)

TABLE XVII-continued

Formulas for Determining Organ Confinement

1 = Predicted to be Organ Confined (any Predictive Probability > 0.500)

Formula for cases without PSA Values:

(SxtNoPSA-PI)
Predictive Index = (1.026344) + (0.1539648)(PosCores) + (−0.4467591)(HiPreGI) + (−0.007922)(TotInv) + (0.3137451)(DNAIO) + (−06676012)(BsApx10-5) + (5.07514)(N227QNG)
Predictive Probability = exp(SxtNoPSA-PI)/(1 + exp(SxtNoPSA-PI))
Organ Confinement Prediction: 0 = Predicted to be Non-Organ Confined (any Predictive Probability ≦ 0.500)
1 = Predicted to be Organ Confined (any Predictive Probability > 0.500)

A number of tumor location (i.e., Base, Apex, Mid) variables were analyzed using logistic regression to determine their univariate significance in the prediction of organ confinement. The most significant univariate variable was determined to be involvement of ≧5% in the base and/or apex biopsies. A number of Gleason scoring variables (i.e. Age, DNA ploidy, Quantitative Nuclear Grade, Number of Positive Cores, Sum Total % Involvement, ect.) were analyzed using logistic regression to determine their univariate significance in the prediction of organ confinement. Note: DNA ploidy (DNA10) was retained in the multivariate model even though it was not univariately significant. The univariately significant variables (i.e. Number of Positive Cores, Total % Involvement, Highest Gleason Score, PSA at a cutoff of ≦16.3 ng/ml, Base and/or Apex Involvement ≧5%, and the Quantitative Nuclear Grade) and DNA ploidy (DNA10) were multivariately assessed for their significance in predicting organ confinement using logistic regression.

Results

Figure 33:
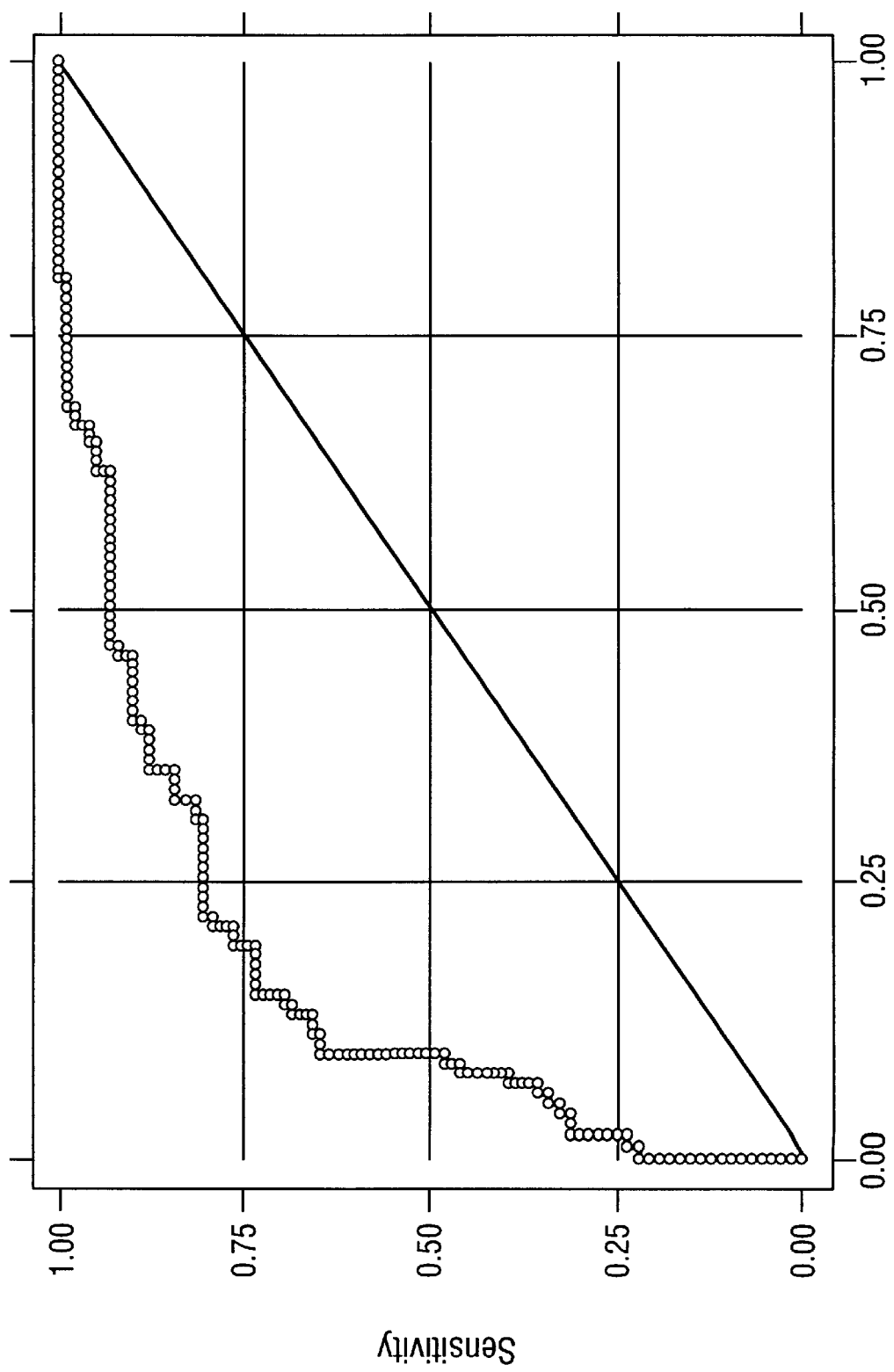
FIG. 33. UroScore plus PSA: Prediction or organ confined disease status. This figure shows the predictive power of the system with PSA, predicting organ confined disease status. A ROC curve was produced with an area under the curve of 85.55%. (Sensitivity=81%; Specificity=78%; PPV=78% and NPV=81%.
Figure 34:
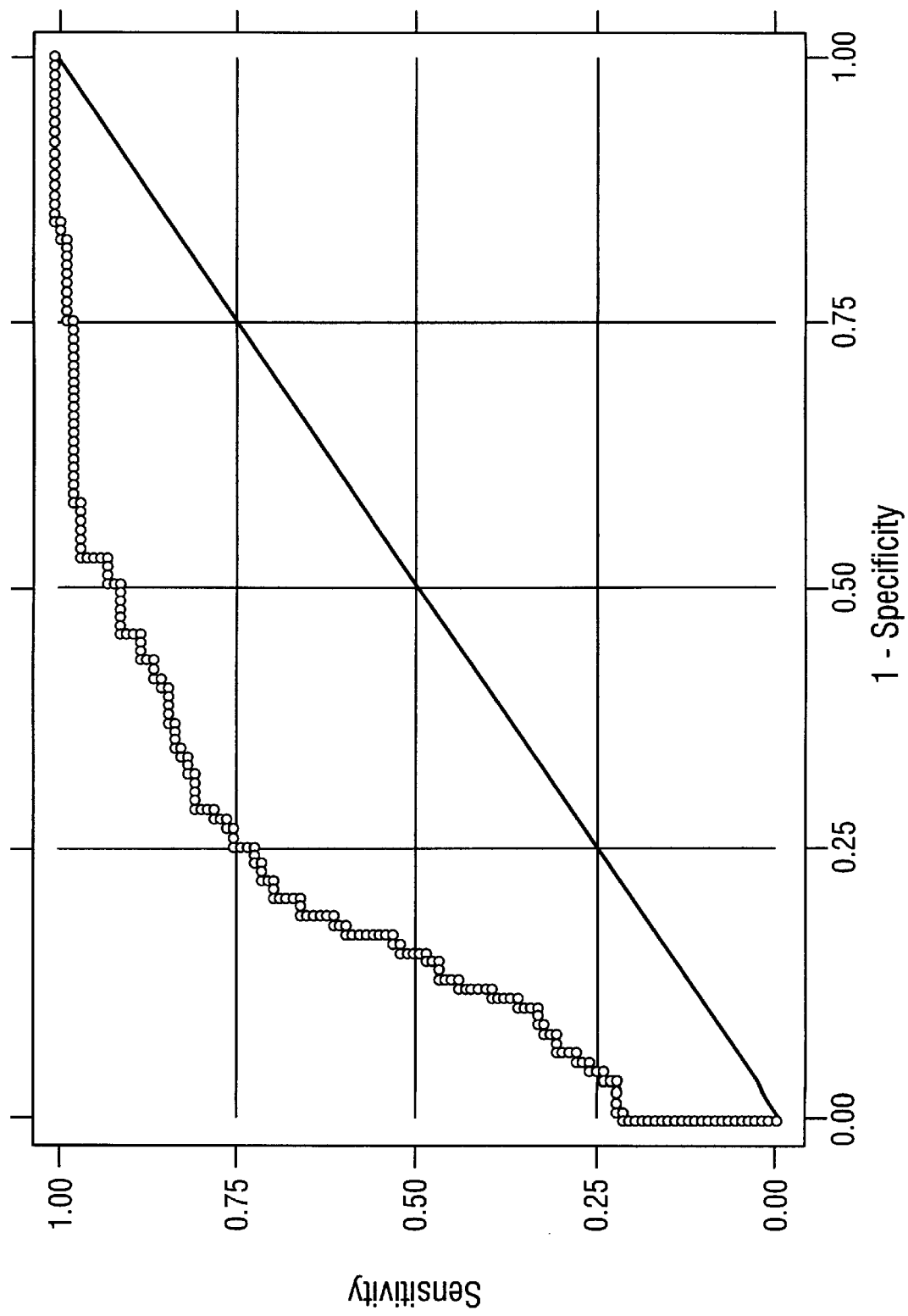
FIG. 34. UroScore minus PSA: Prediction of organ confined disease status. This figure shows the predictive power of the system without PSA, predicting organ confined disease status. A ROC curve was produced with an area under the curve of 81.18%. (Sensitivity=75%; Specificity=74%; PPV=73% and NPV=76%.
Figure 35:
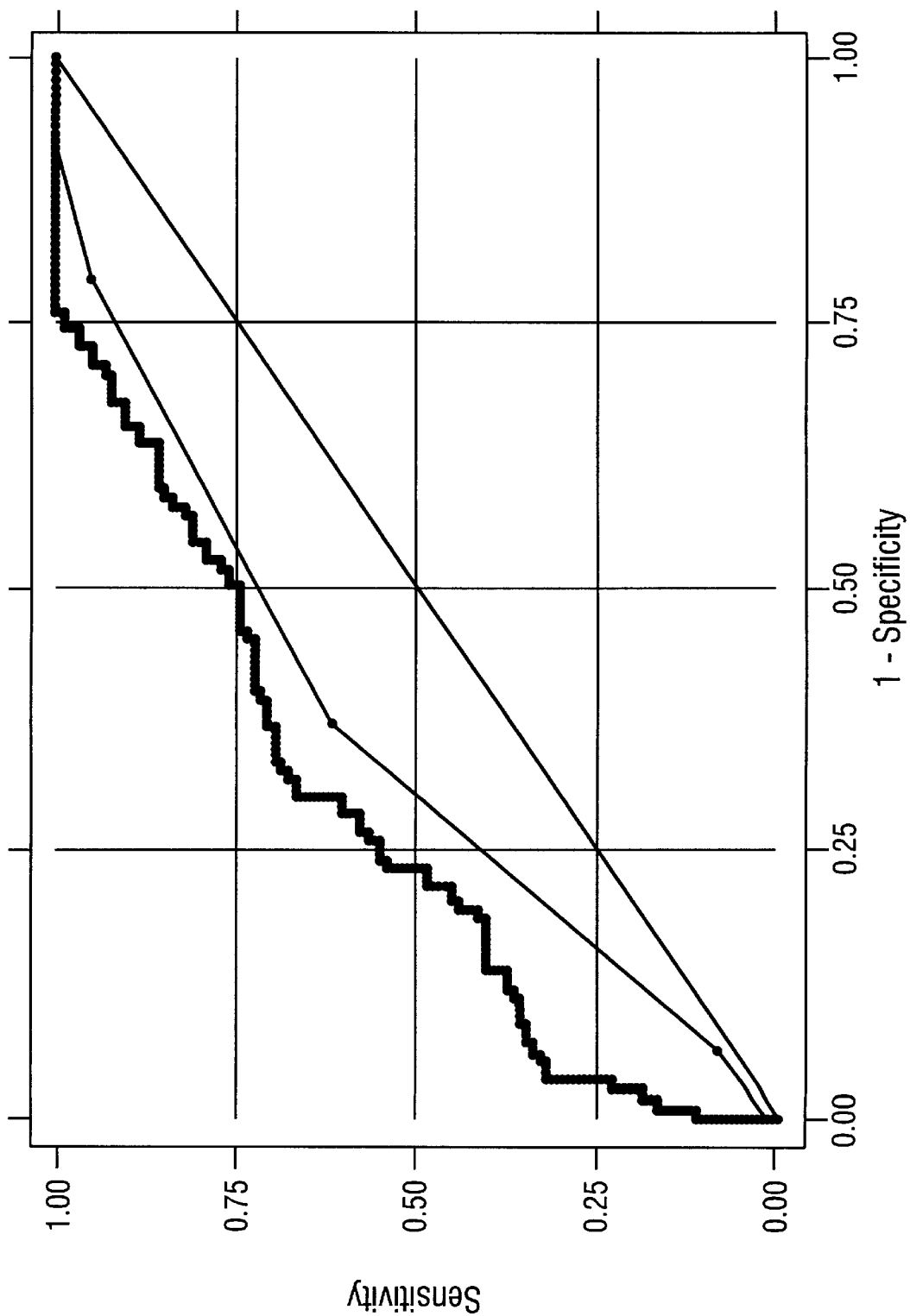
FIG. 35. Quantitative nuclear grade and Gleason score: Prediction of organ confined disease status. This figure shows the predictive power of quantitative nuclear grade and Gleason score (Quantitative nuclear grad AUC=0.7292; Highest pre-op Gleason score AUC=0.6460).

The univariately significant independent variables included # of positive cores (p<0.00001), biopsy Gleason score (p<0.00001), quantitative nuclear grade (p<0.00001), sum % tumor involvement (p<0.00001), pre-operative PSA at 16.3 ng/mL cutoff (p<0.00001), and tumor location (base and/or apex involvement) (p=0.00008) (Table XVIII). Using a multivariate backward stepwise variant of logistic regression, the above independent variables, including DNA ploidy, were retained in a model to identify the non-organ confined prostate cancer cases. The complete model (n=217) had a sensitivity=81.1%, specificity=77.5%, positive predictive value (PPV)=77.5%, negative predictive value (NPV)= 81.1%, and the area under the Receiver Operator Curve (AUC) was 0.8555 (FIG. 34). When PSA values were dropped from the algorithm, the model (n=227) had a sensitivity of 75.2%, specificity of 73.7%, PPV of 72.6%, NPC of 76.3%, and an AUC of 0.8118 (FIG. 33). In FIG. 35, illustrated is quantitative nuclear grade alone as a much greater predictor of organ confined disease status that the highest pre-op Gleason score. While QNG has an AUC of 0.7292, the highest pre-op Gleason score only reached an AUC of 0.6460 (Table XVIII).

Figure 36:
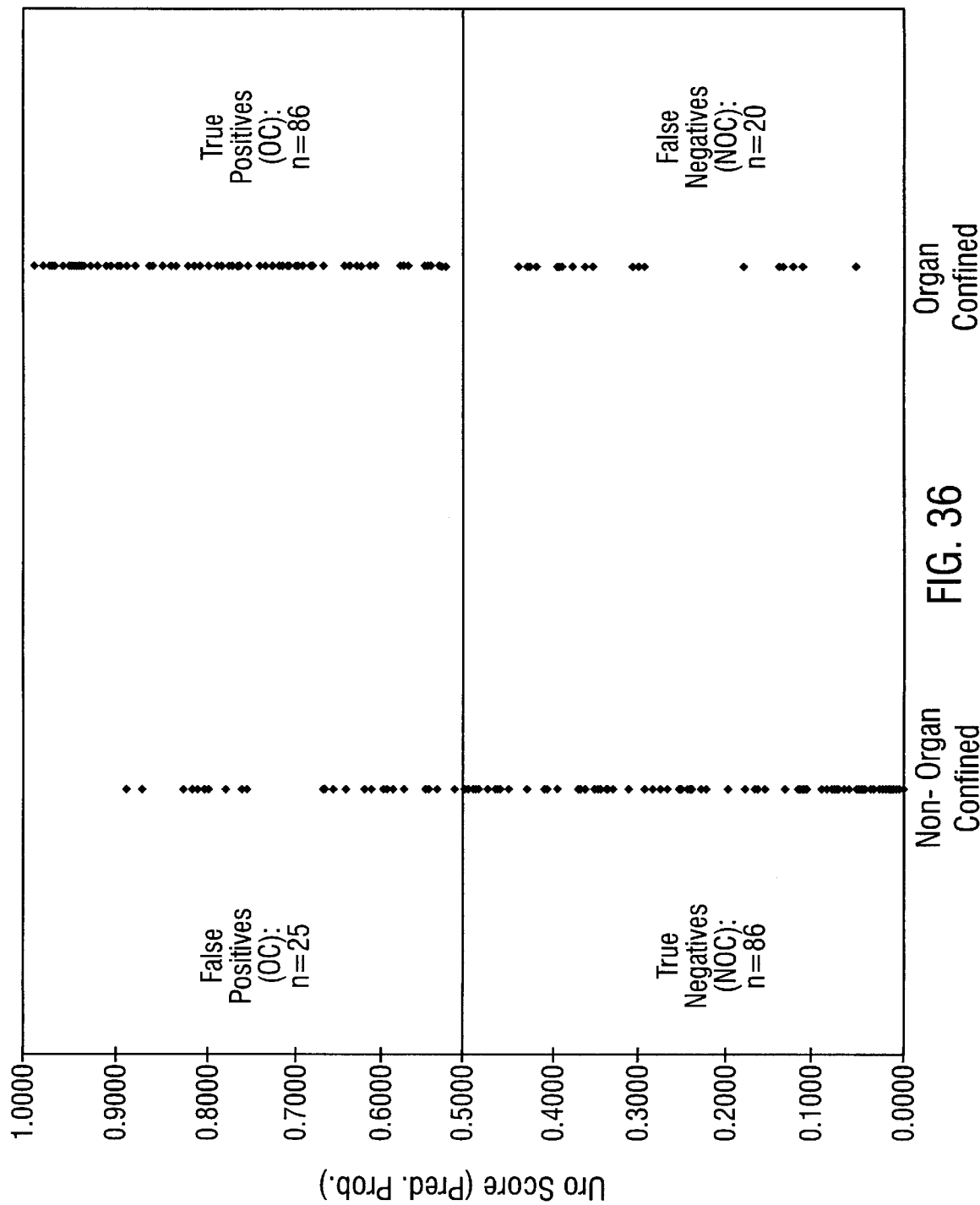
FIG. 36. Shows the power of the system with PSA to predict true positives, false positives, true negatives, and false negatives.

To identify a patient as "OC" or "NOC", the threshold value of 0.5 was used. If the output was greater than 0.5, it was considered "1", otherwise it was classified as "0". Thus. a "1" is considered "OC", and a "0" is considered "NOC'. As seen in FIG. 36, the addition of PSA to the system yielded true positives for organ confinement of 86, versus false positives for non organ confinement of 25. True non organ confined negatives were 86, while false negatives for organ confinement were 20 (n=217).

TABLE XVIII

Sextant Core Predictive Algorithm for Non-Organ Confined Disease Status

| INDEPENDENT VARIABLE | Sensitivity | Specificity | PPV | NPV | AUC |
|---|---|---|---|---|---|
| Highest Pre-Op Gleason Score* | 61.5% | 63.6% | 60.9% | 64.1% | 0.6460 |
| Number of Positive Cores* | 67.0% | 54.2% | 57.5% | 64.0% | 0.6452 |
| Total % Involvement | 74.3% | 57.6% | 61.8% | 70.8% | 0.7006 |
| DNA Ploidy (Diploid, ONR, Abnormal) | 56.0% | 49.2% | 50.4% | 54.7% | 0.5353 |
| Pre-Op PSA (<=16.3)* | 96.2% | 31.5% | 57.3% | 89.7% | 0.6433 |
| Tumor Location (Base/Apex >= 5%)* | 28.4% | 89.0% | 70.5% | 57.4% | 0.5871 |
| Quantitative Nuclear Grade* | 67.9% | 67.8% | 66.1% | 69.6% | 0.7292 |

*p < 0.0025 (Logistic Regression Method)

In summary, the instant methodology has the ability to predict non-organ confined disease status using a combination of laboratory and pathology data obtained from serum and sextant biopsy specimens collected at diagnosis. The method significantly enhances the ability of a practitioner to maximize the cumulative contribution of the data collected to the benefit of patient.

EXAMPLE XIV

Use of RT-PCR in Prediction of Organ Confinement

A additional predictive parameter that may be used in the organ confinement procedure is RT-PCR. Reverse transcription (RT) of RNA to cDNA followed by relative quantitative PCR may be used to determine the relative concentrations of specific mRNA species isolated from normal, benign and cancerous prostate tissues. By determining that the concentration of a specific RNA species varies, it is shown that the gene encoding the specific mRNA species is differentially expressed. This technique may be used to confirm that mRNA transcripts shown to be differentially regulated are differentially expressed in organs that have lost confinement versus those in which the disease remains confined. As such, the RT-PCR test will be incorporated as an additional parameter in the instant invention, applied to both pre- and post-treatment monitoring.

In PCR, the number of molecules of the amplified target DNA increase by a factor approaching two with every cycle of the reaction until some reagent becomes limiting. Thereafter, the rate of amplification becomes increasingly diminished until there is not an increase in the amplified target between cycles. If one plots a graph on which the cycle number is on the X axis and the log of the concentration of the amplified target DNA is on the Y axis, one observes that a curved line of characteristic shape is formed by connecting the plotted points. Beginning with the first cycle, the slope of the line is positive and constant. This is said to be the linear portion of the curve. After some reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR is directly proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range portion of the PCR reaction.

The final concentration of the target DNA in the plateau portion of the curve is determined by the availability of reagents in the reaction mix and is independent the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR study to successfully determine the relative abundances of a particular mRNA species is that relative concentrations of the amplifiable cDNAs must be normalized to some independent standard. The goal of an RT-PCR study is to determine the abundance of a particular mRNA species relative to the average abundance of all mRNA species in the sample.

Most protocols for competitive PCR utilize internal PCR internal standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The discussion above describes the theoretical considerations for an RT-PCR assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This is very important since this assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR with an internal standard.

The presence of amplification products corresponding to prostate cancer-marker nucleic acids can be detected by several alternative means. In one embodiment, the amplification product can be detected by gel electrophoresis and ethidium bromide staining. Alternatively, following the gel electrophoresis step the amplification product can be detected by standard Southern blotting techniques, using an hybridization probe selected to bind specifically to a prostate cancer-marker nucleic acid sequence. Probe hybridization may in turn be detected by a standard labelling means, for example, by incorporation of [$^{32}$P] nucleotides followed by autoradiography. The amplification products may alternatively be detected using a solid phase detection system as described above, utilizing a prostate cancer-marker specific hybridization probe and an appropriate labelling means. The presence of prostate cancer-marker nucleic acids in blood or lymph node samples can be taken as indicative of a patient with metastatic prostate cancer.

One embodiment of the instant invention comprises a method for identification of prostate cancer cells in a biological sample by amplifying and detecting nucleic acids corresponding to prostate cancer cell markers. The biological sample can be any tissue or fluid in which prostate cancer cells might be present. Various embodiments include bone marrow aspirate, bone marrow biopsy, lymph node aspirate, lymph node biopsy, spleen tissue, fine needle aspirate, skin biopsy or organ tissue biopsy. Other embodiments include samples where the body fluid is peripheral blood, lymph fluid, ascites, serous fluid, pleural effusion, sputum, cerebrospinal fluid, lacrimal fluid, stool or urine.

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification.

Pairs of primers that selectively hybridize to nucleic acids corresponding to prostate cancer-specific markers are contacted with the isolated nucleic acid under conditions that permit selective hybridization. Once hybridized, the nucleic acid: primer complex is contacted with one or more enzymes that facilitate template-dependent nucleic acid synthesis. Multiple rounds of amplification, also referred to an "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology; Bellus, 1994).

Following detection, one may compare the results seen in a given patient with a statistically significant reference group of normal patients and prostate cancer patients. In this way, it is possible to correlate the amount of marker detected with various clinical states.

1. Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form although the single-stranded form is preferred.

2. Template Dependent Amplification Methods

A number of template dependent processes are available to amplify the marker sequences present in a given template sample. One of the best known amplification methods is the polymerase chain reaction (referred to as PCR) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared which are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described ib Sambrook et al., 1989. Alternative methods for reverse transcription utilize thermostable DNA polymerases. These methods are described in WO 90/07641 filed Dec. 21, 1990; Polymerase chain reaction methodologies are well known in the art.

Another method for amplification is the ligase chain reaction ("LCR"), disclosed in EPA No. 320 308, incorporated herein by reference in its entirety. in LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'[alpha-thio]-triphosphates in one strand of restriction site may also be useful in the amplification of nucleic acids in the present invention. Walker et al., *Proc. Natl. Acad. Sci. USA* 89:392–396 (1992), incorporated herein by reference in its entirety.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added a biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling prove and the reaction is repeated.

Still another amplification methods described in GB Application No. 2 202 328. and in PCT Application No. PCT/US89/01025, each of which is incorporated herein by reference in its entirety, may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR. Kwoh et al., *Proc. Natl. Acad. Sci. USA* 86:1173 (1989); Gingeras et al., PCT Application WO 88/10315, incorporated herein by reference in their entirety. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman, M. A., In: PCR PROTOCOLS. A GUIDE TO METHODS AND APPLICATIONS, Academic Press, N.Y. (1990) and Ohara et al., *Proc. natl. Acad. Sci. USA*, 86:5673–5677 (1989), each herein incorporated by reference in their entirety.

Methods based on ligation of two (or more) oligonucleotides in the presence of nucleic acid having the sequence of the resulting "di-oligonucleotide," thereby amplifying the di-oligonucleotide, may also be used in the amplification step of the present invention. Wu et al., *Genomics* 4:560 (1989), incorporated herein by reference in its entirety.

3. Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

4. Identification Methods

Amplification products must be visualized in order to confirm amplification of the marker sequences. One typical visualization method involves staining of a gel with ethidium bromide and visualization under UV light. Alternatively, if the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, where the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

The basic technique of differential display has been described in detail (Liang and Pardee, 1992). Total cell RNA is primed for first strand reverse transcription with an anchoring primer composed of oligo dT. The oligo dT primer is extended using a reverse transcriptase, for example, Moloney Murine Leukemia Virus (MMLV) reverse transcriptase. The synthesis of the second strand is primed with an arbitrarily chosen oligonucleotide, using reduced stringency conditions. Once the double-stranded cDNA has been synthesized, amplification proceeds by standard PCR techniques, utilizing the same primers. The resulting DNA fingerprint is analyzed by gel electrophoresis and ethidium bromide staining or autoradiography. A side by side comparison of fingerprints obtained from tumor versus normal tissue samples using the same oligonucleotide primers identifies mRNAs that are differentially expressed.

RNA fingerprinting technology has been demonstrated as being effective in identifying genes that are differentially expressed in cancer (Liang et al., 1992; Wong et al., 1992; Sager et al. 1993; Mok et al., 1994; Watson et al., 1994; Chen et al., 1995; An et al., 1995). The present invention utilizes the RNA fingerprinting technique to identify genes that are differentially expressed in human prostate cancer.

RT-PCR Protocols for Confirmation of Differential Expression of mRNA

A. Reverse transcription

Five µg of total cell RNA from each tissue sample was reverse transcribed into cDNA. Reverse transcription was performed with 400 units of MMLV reverse transcriptase (GIBCO/BRL) in the presence of 50 mM Tris-HCl (pH 8.3), 75 mM KCl, 3 mM $MgCl_2$, 10 mM DTT, 500 µM dNTP, 50 ng random hexamers per microgram of RNA, and 1 U/µl RNase inhibitor. The reaction volume was 60 µl. The reaction mixture was incubated at room temperature for 10 minutes, then at 37° C. for 50 minutes. After reverse transcription the enzyme was denatured by heating to 65° C. for 10 minutes. After heat denaturation the samples were diluted with water to a final volume of 300 µl.

Studies may be performed utilizing RT-PCR to examine mRNAs for differential expression, employing various oligonucleotides primers directed to nucleotide sequences of marker proteins of interest. These primers are used to direct the amplification of the cDNA fragments.

B. Relative Quantitative RT-PCR With an Internal Standard

The concentrations of the original total cell RNAs were determined by measurement of $OD_{260/280}$ (Sambrook et al., 1989) and confirmed by examination of ribosomal RNAs on ethidium bromide stained agarose gels. It is required that all quantitative PCR reactions be normalized for equal amounts of amplifiable cDNA after the reverse transcription is completed. One solution to this is to terminate the reactions by driving the PCR reactions into plateau phase. This approach was utilized in some studies because it is quick and efficient. Lipocortin II was used as the internal standard or competitor. These PCRs were set up as:

Reagents: 200 µM each dNTP, 200 nM each oligonucleotide primer, 1× PCR buffer (Boehringer Mannheim including 1.5 mM $MgCl_2$), 3 µl diluted cDNA, and 2.5 units of Taq DNA polymerase/100 µl of reaction volume.

Cycling parameters: 30 cycles of 94° C. for 1 min; 55° C. for 1min; and 72° C. for two min. Thermocyclers were either the MJ research thermocycler or the Stratagene Robocycler.

C. Relative Quantitative RT-PCR with an External Standard

There are three problems with the relative quantitative RT-PCR strategy described above. First, the internal standard must be roughly 4–10 times more abundant that the target for this strategy to normalize the samples. Second, because most of the PCR products are templated from the more abundant internal standard, the assay is less than optimally sensitive. Third, the internal standard must be truly unvarying. The result is that while the strategy described above is fast, convenient and applicable to samples of varying quality, it lacks sensitivity to modest changes in abundances.

To address these issues, a normalization may be performed using both the β-actin and asparagine synthetase mRNAs as external standards. These PCR reactions are performed with sufficient cycles to observe the products in the linear range of their amplification curves. Photographic negatives of gels of ethidium bromide stained PCR products are produced for each experiment. These negatives may be scanned and quantified using a BioRad densitometer. The quantified data may then normalized for variations in the starting concentrations of amplifiable cDNA by comparing the quantified data from each experiment with that derived from a similar experiment which amplified a cDNA fragment copied from the β-actin mRNA.

EXAMPLE XV

Results of Neural Networks Tools for Organ Confined Study

These studies show the feasibility of using artificial neural networks (ANN) with noise factor for diagnosis of a cancer patient as organ confined (OC) or non-organ confined (NOC). The data set used by the inventors consisted of pathology and texture variables for 227 cases, and was used to generate the formula for the study. Ten cases did not have complete data, and were eliminated from the data set before any training and/or test sets were created. Thus, 197 cases were used for training, with 20 cases saved for testing.

In order to find and extract all available information form the data set, ten different combinations of training sets and test sets were created. The training sets (197 data points) were randomly chosen from the pool of 217 data points and the remaining 20 points were used for testing. This was done to compensate for the fact that the inventors had a small data set and to make sure the inventors have identified all useful information. Output value of <0.5 indicates the patient is OC, and output value of >0.5 indicates the patient is NOC.

The network configuration considered was a standard multilayer sigmoidal network with a single hidden layer. The learning rate used was 0.7 and the noise factor was 0.2. The neural network input layer consisted of 7 or 8 neurons to accommodate the input data set of 7 or 8 measurements. The activation function in each hidden layer and output layer neuron is sigmoid. Different network configurations (number of hidden layer neurons) with various training termination conditions were tested. For a given training data set, the neural network classifier tends to work best with 4 hidden layer neurons, and when the training is terminated at or below 10,000 iterations. Most cases, however, required around 1,000 iterations. The output layer consists of two neurons, used to eliminate any chance of confusing the network during the training phase.

A total of three different studies were conducted, with two separate networks utilizing a standard backpropagation algorithm for training in each study. The results from these studies are set forth in Tables XIX-XX. The first network was trained using the data from the inventors' database (UroCor, Inc., Tulsa, Okla.). The second network was trained after the training data was corrupted by adding noise, to force the network to identify useful information and discard the unwanted noise.

In the first study, shown in Table XIX, the inventors used total of 7 inputs consisting of the seven variables used for model and the threshold PSA value. Each of the networks were tested using the ten different test sets described above, and the table shows the total number of correct classifications in each test set of 20. The first column presents results of the tests where no noise was added. The second column presents results of the test cases where noise was added. Therefore, each table identifies the 20 test patterns used as well as the combined percent accuracy for both OC output and NOC output.

For example, in Table XIX, comparing Test Set 2 and Test Set 10 (column 1) shows that it is possible to construct a network to classify a patient's status as OC or NOC very accurately, about 95% and 100% respectively. Additional manipulations of the data used for training these networks, within the scope of the skilled artisan, may result in determining the parameters required to make the network more accurate. It should be noted that repeatability at this point is directly a function of quality of data used for training.

Further analysis of the individual responses in each test set that is set forth in Table XIX points out the fact that many misclassified cases are very close to being correct. The inventors believe this problem may be resolved by adding noise to the data. To test this hypothesis the inventors created a new data set by adding random noise to the training set. As is evident from the results in Test Sets 1–10, the system performance was improved significantly. While some borderline cases which were initially classified correctly were misclassified because of the additional noise, modification of their noise input may be accomplished in such a way that such misclassification could be reduced as network learns more about the data during the training.

For the second group of studies, set forth in Table XX, the inventors used the exact same variables used for the model, but the threshold PSA was replaced with its actual normalized value. Two networks were trained; one used noisy input while the other was trained with the input that had no added noise. Both networks had similar performance, about the same as the network with threshold PSA.

TABLE XIX

| | Number Correct for 7 Inputs (no PrePSA) | |
|---|---|---|
| | No Noise | With Noise |
| Test Set 1 | 17 | 17 |
| Test Set 2 | 19 | 19 |
| Test Set 3 | 19 | 18 |
| Test Set 4 | 14 | 15 |
| Test Set 5 | 11 | 12 |
| Test Set 6 | 16 | 14 |
| Test Set 7 | 15 | 16 |
| Test Set 8 | 16 | 15 |
| Test Set 9 | 13 | 14 |
| Test Set 10 | 19 | 20 |
| Overall Accuracy | 79.50% | 80.00% |

TABLE XX

| | Number Correct for 7 Inputs (no PrePSA-16) | |
|---|---|---|
| | No Noise | With Noise |
| Test Set 1 | 17 | 17 |
| Test Set 2 | 19 | 19 |
| Test Set 3 | 18 | 18 |
| Test Set 4 | 12 | 12 |
| Test Set 5 | 14 | 14 |
| Test Set 6 | 14 | 14 |
| Test Set 7 | 17 | 17 |
| Test Set 8 | 12 | 13 |
| Test Set 9 | 15 | 15 |
| Test Set 10 | 19 | 19 |
| Overall Accuracy | 78.50% | 79.00% |

All of the methods disclosed and claimed herein can be made and executed with undue experimentation in light of the present disclosure. While the methods of this invention have been described in terms of preferred embodiments, it will be apparent to those of skill in the art that variations may be applied to the methods, and in the steps or in the sequence of steps of the method described herein without departing from the concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The following is the Microsoft Excel v5.0 source code for the macro program used to convert the CMP v3.0 vector files as set forth in Example II.

```
' CMP Macro
' Macro recorded 6/16/94 by Craig Miller
'
' Keyboard Shortcut: Ctrl+c
'
Sub CMP()
    MsgBox "To run this macro, you must first convert the listmode files using the CDI.BP IMPOR
T.40X program in CORTEX.  If you have not done this, please select the file named END.XLS"
OpenLine:
    MsgBox "Open the *.WK1 Vector file which you wish to separate, or end the macro by selectin
g the END.WK1 file"
    ChDrive "F"
    ChDir "F:\USERS\MCM\40X"
    OpenFile = Application.GetOpenFilename("Lotus 1-2-3 (*.wk1), *.wk1")
    Workbooks.Open Filename:=OpenFile
    FileLength = Len(OpenFile)
    SearchStr = "X\"
    Period = InStr(OpenFile, SearchStr)
    OpenFile1 = Mid(OpenFile, Period + 2)
    FileLength1 = Len(OpenFile1)
    SearchStr1 = "."
    Period1 = InStr(OpenFile1, SearchStr1)
    OpenFile2 = Left(OpenFile1, Period1 - 1)
    CASENUM = Range("A2").Value
' If there are no values in the file, end the macro.  If data is present, proceed
    If CASENUM = "" Then GoTo LastLine Else GoTo FormatLine
FormatLine:
    Application.ScreenUpdating = False
    Cells.Select
    With Selection
        .HorizontalAlignment = xlCenter
        .VerticalAlignment = xlBottom
        .WrapText = False
        .Orientation = xlHorizontal
    End With
    With Selection.Font
        .Name = "Times New Roman"
        .FontStyle = "Regular"
        .Size = 10
        .Strikethrough = False
        .Superscript = False
        .Subscript = False
        .OutlineFont = False
        .Shadow = False
        .Underline = xlNone
        .ColorIndex = xlAutomatic
    End With
    Columns("B:C").Select
    Selection.Delete Shift:=xlToLeft
    Columns("E:G").Select
    Selection.Insert Shift:=xlToRight
    Columns("A:AE").Select
    Selection.Cut
    Workbooks.Open Filename:="C:\CRAIG\MACROS\WK1CNVRT.BLK"
    ActiveSheet.Paste
    Range("B:D,H:AD").Select
    Selection.NumberFormat = "0.000000"
    Range("E:G").Select
    Selection.NumberFormat = "0.00"
    Columns("A:AE").Select
    Selection.EntireColumn.AutoFit
    With Selection.Borders(xlLeft)
        .Weight = xlThin
        .ColorIndex = xlAutomatic
    End With
    With Selection.Borders(xlRight)
        .Weight = xlThin
        .ColorIndex = xlAutomatic
    End With
```

```
    With Selection.Borders(xlTop,
        .Weight = xlThin
        .ColorIndex = xlAutomatic
    End With
    With Selection.Borders(xlBottom)
        .Weight = xlThin
        .ColorIndex = xlAutomatic
    End With
    Selection.BorderAround LineStyle:=xlNone
    Range("A2").Select
    Application.ScreenUpdating = True
    ChDrive "F"
    ChDir "F:\USERS\MCM\40X\CMP"
        With ActiveWorkbook
            .Title = ""
            .Subject = ""
            .Author = "Craig Miller"
            .Keywords = ""
            .Comments = ""
        End With
    ActiveWorkbook.SaveAs Filename:=OpenFile2, FileFormat:=xlNormal, _
        Password:="", WriteResPassword:="", ReadOnlyRecommended:= _
        False, CreateBackup:=False
    Application.ScreenUpdating = False
    CASENUM = Range("A2").Value
    While CASENUM <> ""
' Select all cells pertaining to this particular case
    Application.ScreenUpdating = False
        y = 3
            While Cells(y, 1) = CASENUM
                y = y + 1
            Wend
' Select the cells for one case, copy them to a blank CMP template, _
    and delete the first and last row (blank rows from template).
        Range(Cells(2, 1), Cells(y - 1, 31)).Select
        Selection.Copy
        Workbooks.Open Filename:="C:\CRAIG\MACROS\CASCMP.BLK"
        Selection.Insert Shift:=xlDown
        Rows("3:3").Select
        Application.CutCopyMode = False
        Selection.Delete Shift:=xlUp
        y = 3
            While Cells(y, 1) = CASENUM
                y = y + 1
            Wend
        Range(Cells(y, 1), Cells(y, 31)).Select
        Selection.Delete Shift:=xlUp
' Make the first column the cell number
        Range("A1").Select
        ActiveCell.FormulaR1C1 = "Cell"
        Range("A3").Select
        ActiveCell.FormulaR1C1 = "1"
        Range("A4").Select
        ActiveCell.FormulaR1C1 = "2"
        Set Source = Range(Cells(3, 1), Cells(4, 1))
        Set FILL = Range(Cells(3, 1), Cells(y - 1, 1))
        Source.AutoFill destination:=FILL
' Sort all of the cells according to first the Area and second the Shape
        Set CELLDATA = Range(Cells(3, 1), Cells(y - 1, 31))
        CELLDATA.Sort Key1:=Range("C3"), Order1:=xlAscending, Key2:=Range _
            ("D3"), Order2:=xlAscending, Header:=xlGuess, OrderCustom:=1, _
            MatchCase:=False, Orientation:=xlTopToBottom
        Columns("E:E").Select
        Selection.Delete Shift:=xlToLeft
' Select the position where the DNA and perimeter information will be _
    pasted, and open the DNA file created in CORTEX having the same name _
    as the *.ILM file.
        Range("E3").Select
        CASENUM = Trim(CASENUM)
        ChDrive "F"
```

Macro Source Code

```
        ChDir "F:\USERS\MCM\PFS"
        Workbooks.OpenText Filename:=CASENUM, Origin:= _
            xlWindows, StartRow:=2, DataType:=xlDelimited, TextQualifier _
            :=xlDoubleQuote, ConsecutiveDelimiter:=False, Tab:=False, _
            Semicolon:=False, Comma:=True, Space:=False, Other:=False, _
            FieldInfo:=Array(Array(1, 1), Array(2, 1), Array(3, 1), Array(4, 1))
' Determine the number of cells present and calculate the perimeter for _
    each cell
        I = 1
            While Cells(I, 1) > 0
                I = I + 1
            Wend
        Set Source = Cells(1, 5)
        Set FILL = Range(Cells(1, 5), Cells(I - 1, 5))
        Range("E1").Select
        ActiveCell.FormulaR1C1 = "=SQRT(RC[-4]*RC[-3])"
        Source.AutoFill destination:=FILL
        Range(Cells(1, 5), Cells(I - 1, 5)).Select
        Selection.Copy
        Selection.PasteSpecial Paste:=xlValues, Operation:=xlNone, _
            SkipBlanks:=False, Transpose:=False
        Application.CutCopyMode = False
' Sort the cells according to first the Area and second the Shape
        Rows("1:1").Select
        Selection.Sort Key1:=Range("A1"), Order1:=xlAscending, Key2:=Range _
            ("B1"), Order2:=xlAscending, Header:=xlGuess, OrderCustom:=1, _
            MatchCase:=False, Orientation:=xlTopToBottom
' Copy and paste the DNA and Perimeter data to the full database and _
    format the selection
        Range(Cells(1, 4), Cells(I - 1, 5)).Select
        Selection.Copy
        Windows("CASCMP.BLK").Activate
        ActiveSheet.Paste
        Application.CutCopyMode = False
        With Selection.Font
            .Name = "Times New Roman"
            .FontStyle = "Regular"
            .Size = 10
            .Strikethrough = False
            .Superscript = False
            .Subscript = False
            .OutlineFont = False
            .Shadow = False
            .Underline = xlNone
            .ColorIndex = xlAutomatic
        End With
        With Selection
            .HorizontalAlignment = xlCenter
            .VerticalAlignment = xlBottom
            .WrapText = False
            .Orientation = xlHorizontal
        End With
        With Selection.Borders(xlLeft)
            .Weight = xlThin
            .ColorIndex = xlAutomatic
        End With
        With Selection.Borders(xlRight)
            .Weight = xlThin
            .ColorIndex = xlAutomatic
        End With
        With Selection.Borders(xlTop)
            .Weight = xlThin
            .ColorIndex = xlAutomatic
        End With
        With Selection.Borders(xlBottom)
            .Weight = xlThin
            .ColorIndex = xlAutomatic
        End With
        Selection.BorderAround LineStyle:=xlNone
' Enter the column headings for the DNA and Perimeter columns
```

-107-

Macro Source Code

```
        Range("E1").Select
        ActiveCell.FormulaR1C1 = "Pg"
        Range("E2").Select
        ActiveCell.FormulaR1C1 = "DNA"
        Range("F1").Select
        ActiveCell.FormulaR1C1 = "CAS"
        Range("F2").Select
        ActiveCell.FormulaR1C1 = "Perimeter"
        Application.Goto Reference:="Stats"
        Selection.Copy
        Selection.PasteSpecial Paste:=xlValues, Operation:=xlNone, _
            SkipBlanks:=False, Transpose:=False
        Application.CutCopyMode = False
        Columns("F:F").Select
        Selection.Cut
        Columns("AE:AE").Select
        Selection.Insert Shift:=xlToRight
        Selection.NumberFormat = "0.000000"
        Range(Cells(3, 5), Cells(y - 1, 5)).Select
        Selection.NumberFormat = "0.00"
        Sheets("CMP Blank").Select
        Sheets("CMP Blank").Name = CASENUM
' Sort the cell data according to the Cell Number and save the workbook _
    with the same filename as the *.ILM file
        Set CELLDATA = Range(Cells(3, 1), Cells(y - 1, 30))
        CELLDATA.Sort Key1:=Range("A3"), Order1:=xlAscending, Header:=xlGuess, _
            OrderCustom:=1, MatchCase:=False, Orientation:=xlTopToBottom
        Cells(1, 1).Select
        With ActiveWorkbook
            .Title = ""
            .Subject = ""
            .Author = "Craig Miller"
            .Keywords = ""
            .Comments = ""
        End With
        ChDir "F:\USERS\MCM\40X\CMP"
        ActiveWorkbook.SaveAs Filename:=CASENUM, FileFormat:=xlNormal _
            , Password:="", WriteResPassword:="", ReadOnlyRecommended:= _
            False, CreateBackup:=False
' Select the Statistical Calculations, paste them to a blank spreadsheet, _
    and cut and copy all of the values to a single row.
        Range(Cells(y + 2, 1), Cells(y + 6, 30)).Select
        Selection.Cut
        Workbooks.Add Template:="Workbook"
        ActiveSheet.Paste
        Range("A1").Formula = CASENUM
        Range("B2:AD2").Select
        Selection.Cut
        Range("AE1").Select
        ActiveSheet.Paste
        Range("B3:AD3").Select
        Selection.Cut
        Range("BH1").Select
        ActiveSheet.Paste
        Range("B4:AD4").Select
        Selection.Cut
        Range("CK1").Select
        ActiveSheet.Paste
        Range("B5:AD5").Select
        Selection.Cut
        Range("DN1").Select
        ActiveSheet.Paste
        Rows("1:1").Select
        Selection.Copy
' Paste the statistics for the case into the summary file
        Workbooks.Open Filename:="F:\USERS\MCM\40X\SUM-OD.CMP"
        Selection.Insert Shift:=xlDown
        Application.CutCopyMode = False
        ActiveWorkbook.Save
        ActiveWindow.Close
```

-108-

```
        ActiveWorkbook.Saved = TRUE
        ActiveWindow.Close
        ActiveWorkbook.Saved = True
        ActiveWindow.Close
        ActiveWorkbook.Saved = True
        ActiveWindow.Close
        Selection.Delete Shift:=xlUp
        Range("A2").Select
        Application.ScreenUpdating = True
'Continue looping the macro until all of the cases contained in this vector _
   file have been separated and no data is left in the vector file.
        CASENUM = Range("A2").Value
        Wend
'If there is more than one vector file the separate, open the next file
    ActiveWorkbook.Saved = True
    ActiveWindow.Close
    ActiveWorkbook.Saved = True
    ActiveWindow.Close
    GoTo OpenLine
' End the macro and refresh the screen
LastLine:
    ActiveWorkbook.Saved = True
    ActiveWindow.Close
    Application.ScreenUpdating = True
End Sub
```

The following is a flowchart and the source code listing of a computer program for the DNA content information import as set forth in Example II.

Import.40X Flow Diagram
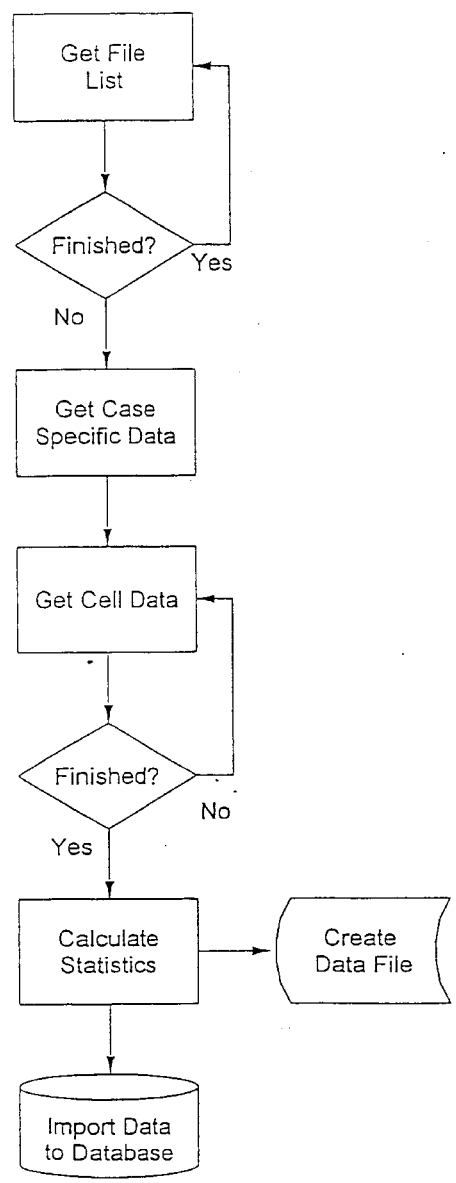

```
UNCTION IMPORT.ILM
  IMPORT.ILM

NOTICE:   --   THIS SOFTWARE IS THE VALUABLE CONFIDENTIAL TRADE SECRET
                   PROPERTY OF ADEPT TECHNOLOGIES, INC.
                   (ADEPT TECH.) OF HOUSTON, TEXAS.  IT MAY NOT BE USED,
                   DISCLOSED, OR REPRODUCED BY ANY MEANS WHATSOEVER WITHOUT
                   THE PRIOR WRITTEN AUTHORIZATION OF ADEPT TECHNOLOGIES.

PROGRAM      : IMPORT.ILM

RETURNS      : INFORMATION - TO DNAILM, CALLING ROUTINE.

DESCRIPTION  : IMPORT CAS DNA *.ILM LISTMODE DATA

TYPE         : PROGRAM

DATE         : 10 MARCH 93

AUTHOR       : Michael P. Bacus

MODS         : 05 MARCH 93 - VERSION 1.00 - FIRST USEABLE VERSION
                 : 15 MARCH 93 - VERSION 1.01 - BUG FIX, OFF BY ONE ON PG HISTOGRAM
                 : 17 JUNE  93 - VERSION 1.02 - MEAN NUCLEAR ROUNDNESS

PLANS        :

DECLARE SUBROUTINE DIRLIST,MSG,PRINT.ILM
DECLARE FUNCTION SEQ
OPEN "CDI.CAS.ILM" TO CDI.ILM.FILE ELSE STOP
OPEN "CDI.CAS" TO CDI.CAS.FILE ELSE STOP
OPEN "CASE" TO C.FILE ELSE STOP
COUNT = 0
PI = 3.1415926535

NEW.PATH = "C:\TEMP\"
INITDIR NEW.PATH:"*.ILM"
RD.NAME = 'RD'
RD.CNT = 0
ANSWER = ''
ANSWER<1> = 0
ANSWER<2> = 0
LOOP
   LIST = DIRLIST()
UNTIL LIST = ''
   COL = 0
   LOOP
      REMOVE FILE.NAME FROM LIST AT COL SETTING FLAG
   UNTIL FLAG = 0 DO
      OLD.FILE.NAME = FILE.NAME
      OLD.FILE.NAME[-3,3] = ''
      OLD.FILE.NAME = OLD.FILE.NAME:'CYT'
      EXTENSION = FILE.NAME[-3,3]
      ILM.ID = ''
      IF EXTENSION = "ILM" THEN

CHECK FOR SIMILAR *.ILM UPLOAD, QUICKLY
```

-112-

```
        OLD.FILE.REC = ''    FILE                     THEN
        OSOPEN NEW.PATH:OLD.    E.NAME TO OLD.ILM.FILE
           OSBREAD OLD.FILE.R    FROM OLD.ILM.FILE AT 0    TH 61000
           OSCLOSE OLD.ILM.FILE                         LENGTH
        END                   REC

COUNT = COUNT + 1
        OSOPEN NEW.PATH:FILE.NAME TO ILM.FILE THEN
           OSBREAD FILE.REC FROM ILM.FILE AT 0 LENGTH 61000
           IF OLD.FILE.REC = FILE.REC THEN
* ACCESSION NUMBER, RECORD KEY
              ILM.REC = ''
              ILM.NUM = 13; REC.POS = 301; REC.LEN = 33
              GOSUB GET.STRING
              ILM.ID = TRIM(ILM.REC<13>)
              ILM.ID = ILM.ID[1,10]
              READ DUMMY FROM CDI.ILM.FILE, ILM.ID THEN
                 PCPERFORM "DEL ":NEW.PATH:FILE.NAME
              END ELSE
                 GOTO MONKEY:
              END
           END ELSE
ONKEY:
              ILM.REC = ''
* ILM.VERSION
              ILM.NUM = 1; REC.POS = 1; REC.LEN = 2
              GOSUB GET.STRING
* SIGNATURE
              ILM.NUM = 2; REC.POS = 3; REC.LEN = 10
              GOSUB GET.STRING
* COMPANY
              ILM.NUM = 3; REC.POS = 13; REC.LEN = 64
              GOSUB GET.STRING
* INSTRUMENT
              ILM.NUM = 4; REC.POS = 77; REC.LEN = 64
              GOSUB GET.STRING
* STAIN
              ILM.NUM = 5; REC.POS = 141; REC.LEN = 64
              GOSUB GET.STRING
* FILTER WAVELENGTH
              ILM.NUM = 6; REC.POS = 205; REC.LEN = 2
              GOSUB GET.INTEGER
* FILTER BANDWIDTH
              ILM.NUM = 7; REC.POS = 207; REC.LEN = 2
              GOSUB GET.INTEGER
* MAGNIFICATION
              ILM.NUM = 8; REC.POS = 209; REC.LEN = 2
              GOSUB GET.INTEGER
* TIME OF CREATION
              ILM.NUM = 9; REC.POS = 211; REC.LEN = 16
              GOSUB GET.STRING
* TIME OF ANALYSIS
              ILM.NUM = 10; REC.POS = 227; REC.LEN = 8
              GOSUB GET.STRING
* OPERATOR ID
              ILM.NUM = 11; REC.POS = 235; REC.LEN = 33
              GOSUB GET.STRING
* PATIENT NAME
              ILM.NUM = 12; REC.POS = 268; REC.LEN = 33
```

-113-

```
        GOSUB GET.STRING
* ACCESSION NUMBER, RECORD KEY
        ILM.NUM = 13; REC.POS = 301; REC.LEN = 33
        GOSUB GET.STRING
        ILM.ID = TRIM(ILM.REC<13>)
        ILM.ID = ILM.ID[1,10]
* SEQUENCE PATH
        ILM.NUM = 13; REC.POS = 334; REC.LEN = 201
        GOSUB GET.STRING
* DNA INDEX
        ILM.NUM = 14; REC.POS = 535; REC.LEN = 8
        GOSUB GET.DOUBLE
* FIELD COUNT
        ILM.NUM = 15; REC.POS = 543; REC.LEN = 2
        GOSUB GET.INTEGER
* CELL COUNT
        ILM.NUM = 16; REC.POS = 545; REC.LEN = 2
        GOSUB GET.INTEGER
* PEAK VALUE
        ILM.NUM = 17; REC.POS = 547; REC.LEN = 2
        GOSUB GET.INTEGER
* CLASS NAME, #1
        ILM.NUM = 18; REC.POS = 549; REC.LEN = 13
        GOSUB GET.STRING
* CLASS NAME, #2
        ILM.NUM = 19; REC.POS = 562; REC.LEN = 13
        GOSUB GET.STRING
* CLASS NAME, #3
        ILM.NUM = 20; REC.POS = 575; REC.LEN = 13
        GOSUB GET.STRING
* CLASS NAME, #4
        ILM.NUM = 21; REC.POS = 588; REC.LEN = 13
        GOSUB GET.STRING
* CLASS NAME, #5
        ILM.NUM = 22; REC.POS = 601; REC.LEN = 13
        GOSUB GET.STRING
* CLASS NAME, #6
        ILM.NUM = 23; REC.POS = 614; REC.LEN = 13
        GOSUB GET.STRING
* CALIBRATION REJECTED CELL ARRAY
*       ILM.NUM = 24; REC.POS = 627; REC.LEN = 128
*       GOSUB GET.CHAR.ARRAY
* CALIBRATION NUCLEAR MASS ARRAY
*       ILM.NUM = 25; REC.POS = 627; REC.LEN = 128
        ILM.NUM = 25; REC.POS = 627; REC.LEN = 128
        GOSUB GET.FLOAT.ARRAY
* CALIBRATION NUCLEAR AREA
*       ILM.NUM = 26; REC.POS = 1267; REC.LEN = 128
        ILM.NUM = 26; REC.POS = 1139; REC.LEN = 128
        GOSUB GET.LONG.ARRAY
* ANALYSIS FIELD COUNT
        ILM.NUM = 51; REC.POS = 1651; REC.LEN = 2
        GOSUB GET.INTEGER
* ANALYSIS CELL COUNT
*       ILM.NUM = 27; REC.POS = 1779; REC.LEN = 2
        ILM.NUM = 27; REC.POS = 1653; REC.LEN = 2
        GOSUB GET.INTEGER
* ANALYSIS CELL TYPE
*       ILM.NUM = 28; REC.POS = 1781; REC.LEN = 512
        ILM.NUM = 28; REC.POS = 1655; REC.LEN = 512
```

```
        GOSUB GET.CHAR.ARRAY
* ANALYSIS NUCLEAR MASS
*       ILM.NUM = 29; REC.POS = 2293; REC.LEN = 512
        ILM.NUM = 29; REC.POS = 2167; REC.LEN = 512
        GOSUB GET.FLOAT.ARRAY
* ANALYSIS NUCLEAR AREA
*       ILM.NUM = 30; REC.POS = 4341; REC.LEN = 512
        ILM.NUM = 30; REC.POS = 4215; REC.LEN = 512
        GOSUB GET.LONG.ARRAY
* 1280 BIN PICOGRAM HISTOGRAM
*       ILM.NUM = 31; REC.POS = 6389; REC.LEN = 1280
        ILM.NUM = 31; REC.POS = 6263; REC.LEN = 1280
        GOSUB GET.INT.ARRAY
        RD.CNT += 1
* FIRST PEAK
        ILM.NUM = 52; REC.POS = 8823; REC.LEN = 2
        GOSUB GET.INTEGER
* INTEGER, SECOND PEAK
        ILM.NUM = 53; REC.POS = 8825; REC.LEN = 2
        GOSUB GET.INTEGER
* FIELD AREA A, FLAG = 1 ON FLAG = ON
        ILM.NUM = 33; REC.POS = 8827; REC.LEN = 2
        GOSUB GET.INTEGER
* MINIMUM BOUNDARY FIELD A
        ILM.NUM = 34; REC.POS = 8829; REC.LEN = 2
        GOSUB GET.INTEGER
* MAXIMUM BOUNDARY FIELD A
        ILM.NUM = 35; REC.POS = 8831; REC.LEN = 2
        GOSUB GET.INTEGER
* FIELD B
        ILM.NUM = 36; REC.POS = 8833; REC.LEN = 2
        GOSUB GET.INTEGER
* MINIMUM BOUNDARY FIELD B
        ILM.NUM = 37; REC.POS = 8835; REC.LEN = 2
        GOSUB GET.INTEGER
* MAXIMUM BOUNDARY FIELD B
        ILM.NUM = 38; REC.POS = 8837; REC.LEN = 2
        GOSUB GET.INTEGER
* FIELD C
        ILM.NUM = 39; REC.POS = 8839; REC.LEN = 2
        GOSUB GET.INTEGER
* MINIMUM BOUNDARY FIELD C
        ILM.NUM = 40; REC.POS = 8841; REC.LEN = 2
        GOSUB GET.INTEGER
* MAXIMUM BOUNDARY FIELD C
        ILM.NUM = 41; REC.POS = 8843; REC.LEN = 2
        GOSUB GET.INTEGER
* FIELD D
        ILM.NUM = 42; REC.POS = 8845; REC.LEN = 2
        GOSUB GET.INTEGER
* MINIMUM BOUNDARY FIELD D
        ILM.NUM = 43; REC.POS = 8847; REC.LEN = 2
        GOSUB GET.INTEGER
* MAXIMUM BOUNDARY FIELD D
        ILM.NUM = 44; REC.POS = 8849; REC.LEN = 2
        GOSUB GET.INTEGER
* FIELD E
        ILM.NUM = 45; REC.POS = 8851; REC.LEN = 2
        GOSUB GET.INTEGER
* MINIMUM BOUNDARY FIELD E
```

-115-

```
                ILM.NUM = 46; REC.POS = 8853; REC.LEN = 2
                GOSUB GET.INTEGER
        * MAXIMUM BOUNDARY FIELD E
                ILM.NUM = 47; REC.POS = 8855; REC.LEN = 2
                GOSUB GET.INTEGER
        * FIELD F
                ILM.NUM = 48; REC.POS = 8857; REC.LEN = 2
                GOSUB GET.INTEGER
        * MINIMUM BOUNDARY FIELD F
                ILM.NUM = 49; REC.POS = 8859; REC.LEN = 2
                GOSUB GET.INTEGER
        * MAXIMUM BOUNDARY FIELD F
                ILM.NUM = 50; REC.POS = 8861; REC.LEN = 2
                GOSUB GET.INTEGER
* CELL REVIEW, DELETED
*               ILM.NUM = 32; REC.POS = 8863; REC.LEN = 2
*               GOSUB GET.INTEGER
*
* READ CELL DATA
*
                ADJUST = 0
                BUF.CNT = 1
                CELL.OFFSET = 0
                TEMP.ILM.REC = ILM.REC
                IF ILM.REC<27> > 512 THEN ILM.REC<27> = 512
                FOR I.CELL = 1 TO ILM.REC<27>
                    IF (8863+CELL.OFFSET+36) > (60000*BUF.CNT) THEN
                       FILE.POS = BUF.CNT*60000
                       OSBREAD FILE.REC FROM ILM.FILE AT FILE.POS-100 LENGTH 61000
                       IF BUF.CNT = 1 THEN
                          ADJUST = ADJUST + 60000-100
                       END ELSE
                          ADJUST = ADJUST + 60000
                       END
                       BUF.CNT += 1
                    END
* CELL XMIN
                ILM.REC<90> = 0
                ILM.NUM = 90; REC.POS = 8863+CELL.OFFSET-ADJUST; REC.LEN = 2
                GOSUB GET.INTEGER
                TEMP.ILM.REC<90,I.CELL> = ILM.REC<90>
* CELL XMAX
                ILM.REC<91> = 0
                ILM.NUM = 91; REC.POS = 8865+CELL.OFFSET-ADJUST; REC.LEN = 2
                GOSUB GET.INTEGER
                TEMP.ILM.REC<91,I.CELL> = ILM.REC<91>
* CELL YMIN
                ILM.REC<92> = 0
                ILM.NUM = 92; REC.POS = 8867+CELL.OFFSET-ADJUST; REC.LEN = 2
                GOSUB GET.INTEGER
                TEMP.ILM.REC<92,I.CELL> = ILM.REC<92>
* CELL YMAX
                ILM.REC<93> = 0
                ILM.NUM = 93; REC.POS = 8869+CELL.OFFSET-ADJUST; REC.LEN = 2
                GOSUB GET.INTEGER
                TEMP.ILM.REC<93,I.CELL> = ILM.REC<93>
* CELL CLASS
                ILM.REC<94> = 0
                ILM.NUM = 94; REC.POS = 8871+CELL.OFFSET-ADJUST; REC.LEN = 2
                GOSUB GET.INTEGER
```

-116-

```
                TEMP.ILM.REC<94,I.CELL> = ILM.REC<94>
* CELL OFFSET
        ILM.REC<95> = 0
        ILM.NUM = 95; REC.POS = 8873+CELL.OFFSET-ADJUST; REC.LEN = 1
        GOSUB GET.LONG
        TEMP.ILM.REC<95,I.CELL> = ILM.REC<95>
* CELL AREA
        ILM.REC<96> = 0
        ILM.NUM = 96; REC.POS = 8877+CELL.OFFSET-ADJUST; REC.LEN = 1
        GOSUB GET.LONG
        TEMP.ILM.REC<96,I.CELL> = ILM.REC<96>
* CELL BUF SIZE
        ILM.REC<97> = 0
        ILM.NUM = 97; REC.POS = 8881+CELL.OFFSET-ADJUST; REC.LEN = 2
        GOSUB GET.INTEGER
        TEMP.ILM.REC<97,I.CELL> = ILM.REC<97>
* CELL MASS
        ILM.REC<98> = 0
        ILM.NUM = 98; REC.POS = 8883+CELL.OFFSET-ADJUST; REC.LEN = 1
        GOSUB GET.FLOAT
        IF LEN(ILM.REC<98>) > 10 THEN
           TEMP.ILM.REC<98,I.CELL> = 0
        END ELSE
           TEMP.ILM.REC<98,I.CELL> = ILM.REC<98>
        END
* CELL SHAPE
        ILM.REC<99> = 0
        ILM.NUM = 99; REC.POS = 8887+CELL.OFFSET-ADJUST; REC.LEN = 1
        GOSUB GET.FLOAT
        TEMP.ILM.REC<99,I.CELL> = ILM.REC<99>
* CELL NAME
        ILM.REC<100> = 0
        ILM.NUM = 100; REC.POS = 8891+CELL.OFFSET-ADJUST; REC.LEN = 8
        GOSUB GET.STRING
        TEMP.ILM.REC<100,I.CELL> = ILM.REC<100>
*
*   Calculate Mean Nuclear Roundness
*
        PERIMETER = SQRT(TEMP.ILM.REC<96,I.CELL>*TEMP.ILM.REC<99,I.CELL>
        TEMP.ILM.REC<101,I.CELL> = ICONV((PERIMETER/(2*PI))/SQRT(TEMP.IL
        TEMP.ILM.REC<101,I.CELL> = ICONV(SQRT(TEMP.ILM.REC<99,I.CELL>/(4
*
        CELL.OFFSET = CELL.OFFSET + ILM.REC<97> + 36
    NEXT I.CELL
    ILM.REC = TEMP.ILM.REC
*
* FIGURE OUT STATISTICS
*
        FOR I = 1 TO 6
          BEGIN CASE
            CASE I = 1
              ON.FLAG = ILM.REC<33>
              MIN = ILM.REC<34>
              MAX = ILM.REC<35>
            CASE I = 2
              ON.FLAG = ILM.REC<36>
              MIN = ILM.REC<37>
              MAX = ILM.REC<38>
            CASE I = 3
              ON.FLAG = ILM.REC<39>
```

-117-

```
            MIN = ILM.REC<40>
            MAX = ILM.REC<41>
         CASE I = 4
            ON.FLAG = ILM.REC<42>
            MIN = ILM.REC<43>
            MAX = ILM.REC<44>
         CASE I = 5
            ON.FLAG = ILM.REC<45>
            MIN = ILM.REC<46>
            MAX = ILM.REC<47>
         CASE I = 6
            ON.FLAG = ILM.REC<48>
            MIN = ILM.REC<49>
            MAX = ILM.REC<50>
      END CASE
      MIN = INT(MIN*ILM.REC<14>*10+.5)/100
      MAX = INT(MAX*ILM.REC<14>*10+.5)/100
      MODAL.DI = 0
      MEAN.DI = 0
      VARIENCE = 0
      STANDARD.DEVIATION = 0
      COEFFICIENT.VARIATION = 0
      PERCENT.CELLS = 0
      CELL.COUNT = 0
      IF ON.FLAG = 1 THEN
         SUM.SQUARED = 0
         SUM.RAW = 0
         MODAL = 0
         FOR J = 1 TO 1280
            IF ILM.REC<31,J> # 0 THEN
               IF ((J-1 >= MIN) AND (J-1 <= MAX)) THEN
                  IF ILM.REC<31,J> > MODAL THEN
                     MODAL = ILM.REC<31,J>
                     MODAL.DI = (J-1)/10/ILM.REC<14>
                  END
                  FOR K = 1 TO ILM.REC<31,J>
                     DI = (J-1)/10/ILM.REC<14>
                     SUM.SQUARED += DI**2
                     SUM.RAW += DI
                     CELL.COUNT += 1
                  NEXT K
               END
            END
         NEXT J
         IF CELL.COUNT # 0 THEN
            MEAN.DI = (SUM.RAW/CELL.COUNT)
         END ELSE
            MEAN.DI = 0
         END
         IF CELL.COUNT > 1 THEN
            VARIENCE = (SUM.SQUARED-((SUM.RAW*SUM.RAW)/CELL.COUNT))/(CELL.
            IF VARIENCE = 0 THEN
               STANDARD.DEVIATION = 0
            END ELSE
               STANDARD.DEVIATION = SQRT(VARIENCE)
            END
            COEFFICIENT.VARIATION = (STANDARD.DEVIATION/MEAN.DI)*100
         END ELSE
            VARIENCE = 0
            STANDARD.DEVIATION = 0
```

-118-

```
              COEFFICIENT.VARIATION = 0
            END
            IF ILM.REC<27> # 0 THEN PERCENT.CELLS = CELL.COUNT/ILM.REC<27>
          END
          ILM.REC<48+I*6> = ICONV(MODAL.DI,'MD2,')
          ILM.REC<49+I*6> = ICONV(MEAN.DI,'MD2,')
          ILM.REC<50+I*6> = ICONV(STANDARD.DEVIATION,'MD2,')
          ILM.REC<51+I*6> = ICONV(COEFFICIENT.VARIATION,'MD2,')
          ILM.REC<52+I*6> = ICONV(PERCENT.CELLS,'MD4,')
          ILM.REC<53+I*6> = CELL.COUNT
        NEXT I
*
* Filter Imported Data
*
        ILM.ID = '93-99999H'
        EXIST.FLAG = 0
        READ DUMMY FROM CDI.ILM.FILE, ILM.ID THEN
          IF ILM.REC = DUMMY THEN EXIST.FLAG = 1
        END
        IF EXIST.FLAG = 0 THEN
*
* CONVERT DATA INTO OLD FORMAT FOR REPORT PRINTING
*
          OFF.SCALE = 0
          Y.SCALE = 0
          CDI.CAS.REC = ''
          FOR I = 1 TO 1280
            IF I > 0 THEN
              BEGIN CASE
                CASE I < 15
                  CDI.CAS.REC<1,1> = CDI.CAS.REC<1,1> + ILM.REC<31,I>
                CASE I < 25
                  CDI.CAS.REC<1,2> = CDI.CAS.REC<1,2> + ILM.REC<31,I>
                CASE I < 35
                  CDI.CAS.REC<1,3> = CDI.CAS.REC<1,3> + ILM.REC<31,I>
                CASE I < 45
                  CDI.CAS.REC<1,4> = CDI.CAS.REC<1,4> + ILM.REC<31,I>
                CASE I < 55
                  CDI.CAS.REC<1,5> = CDI.CAS.REC<1,5> + ILM.REC<31,I>
                CASE I < 65
                  CDI.CAS.REC<1,6> = CDI.CAS.REC<1,6> + ILM.REC<31,I>
                CASE I < 75
                  CDI.CAS.REC<1,7> = CDI.CAS.REC<1,7> + ILM.REC<31,I>
                CASE I < 85
                  CDI.CAS.REC<1,8> = CDI.CAS.REC<1,8> + ILM.REC<31,I>
                CASE I < 95
                  CDI.CAS.REC<1,9> = CDI.CAS.REC<1,9> + ILM.REC<31,I>
                CASE I < 105
                  CDI.CAS.REC<1,10> = CDI.CAS.REC<1,10> + ILM.REC<31,I>
                CASE I < 115
                  CDI.CAS.REC<1,11> = CDI.CAS.REC<1,11> + ILM.REC<31,I>
                CASE I < 125
                  CDI.CAS.REC<1,12> = CDI.CAS.REC<1,12> + ILM.REC<31,I>
                CASE I < 135
                  CDI.CAS.REC<1,13> = CDI.CAS.REC<1,13> + ILM.REC<31,I>
                CASE I < 145
                  CDI.CAS.REC<1,14> = CDI.CAS.REC<1,14> + ILM.REC<31,I>
                CASE I < 155
                  CDI.CAS.REC<1,15> = CDI.CAS.REC<1,15> + ILM.REC<31,I>
                CASE I < 165
```

```
          CDI.CAS.REC<1,16> = CDI.CAS.REC<1,16> + ILM.REC<31,I>
        CASE I < 175
          CDI.CAS.REC<1,17> = CDI.CAS.REC<1,17> + ILM.REC<31,I>
        CASE I < 185
          CDI.CAS.REC<1,18> = CDI.CAS.REC<1,18> + ILM.REC<31,I>
        CASE I < 195
          CDI.CAS.REC<1,19> = CDI.CAS.REC<1,19> + ILM.REC<31,I>
        CASE I < 205
          CDI.CAS.REC<1,20> = CDI.CAS.REC<1,20> + ILM.REC<31,I>
        CASE I < 215
          CDI.CAS.REC<1,21> = CDI.CAS.REC<1,21> + ILM.REC<31,I>
        CASE I < 225
          CDI.CAS.REC<1,22> = CDI.CAS.REC<1,22> + ILM.REC<31,I>
        CASE I < 235
          CDI.CAS.REC<1,23> = CDI.CAS.REC<1,23> + ILM.REC<31,I>
        CASE I < 245
          CDI.CAS.REC<1,24> = CDI.CAS.REC<1,24> + ILM.REC<31,I>
        CASE I < 255
          CDI.CAS.REC<1,25> = CDI.CAS.REC<1,25> + ILM.REC<31,I>
        CASE I < 265
          CDI.CAS.REC<1,26> = CDI.CAS.REC<1,26> + ILM.REC<31,I>
        CASE I < 275
          CDI.CAS.REC<1,27> = CDI.CAS.REC<1,27> + ILM.REC<31,I>
        CASE I < 285
          CDI.CAS.REC<1,28> = CDI.CAS.REC<1,28> + ILM.REC<31,I>
        CASE I < 295
          CDI.CAS.REC<1,29> = CDI.CAS.REC<1,29> + ILM.REC<31,I>
        CASE I < 305
          CDI.CAS.REC<1,30> = CDI.CAS.REC<1,30> + ILM.REC<31,I>
        CASE I < 315
          CDI.CAS.REC<1,31> = CDI.CAS.REC<1,31> + ILM.REC<31,I>
        CASE I < 325
          CDI.CAS.REC<1,32> = CDI.CAS.REC<1,32> + ILM.REC<31,I>
        CASE 1
          OFF.SCALE = OFF.SCALE + ILM.REC<31,I>
      END CASE
    END
  NEXT I
  CDI.CAS.REC<2> = ILM.REC<12>
  IF ILM.REC<52> # 65535 THEN
    IF ILM.REC<14>+.5 < 1 THEN
      CDI.CAS.REC<4> = 0
    END ELSE
      CDI.CAS.REC<4> = (INT(ILM.REC<52>/ILM.REC<14>+.5))/100
    END
  END ELSE
    CDI.CAS.REC<4> = 0
  END
  CDI.CAS.REC<12> = OFF.SCALE
  Y.SCALE = 0
  Y.POS = 0
  FOR I = 1 TO 32
    IF CDI.CAS.REC<1,I> > Y.SCALE THEN
      Y.SCALE = CDI.CAS.REC<1,I>
      Y.POS = I
    END
  NEXT I
  Y.DIV = (Y.SCALE*1.1)/5
  TRANS = 0
  IF Y.POS > 0 THEN
```

-120-

```
        TRANS = 36/CDI.CAS.REC<1,Y.POS>
      END
      FOR I = 1 TO 32
        TEMP = CDI.CAS.REC<1,I>*TRANS
        IF TEMP > 0 AND TEMP < 1 THEN
          CDI.CAS.REC<1,I> = 1
        END ELSE
          CDI.CAS.REC<1,I> = INT(TEMP+.5)
        END
      NEXT I
      FOR I = 1 TO 32
        TEMP = INT(CDI.CAS.REC<1,I>*TRANS+.5)
        IF TEMP > 0 AND TEMP < 1 THEN
          CDI.CAS.REC<1,I> = 1
        END ELSE
          CDI.CAS.REC<1,I> = TEMP
        END
      NEXT I

FOR I = 1 TO 5
        CDI.CAS.REC<23-I> = INT(Y.DIV*I)
      NEXT I
      CDI.CAS.REC<23> = 0
      GOSUB MNR.EXPORT

WRITE CDI.CAS.REC TO CDI.CAS.FILE, ILM.ID
      WRITE ILM.REC TO CDI.ILM.FILE, ILM.ID

PRINT.ILM(ILM.ID)
*
*   PREVIOUS PATIENT HISTORY
*
      PATIENT.NUMBER = XLATE('CASE',ILM.ID,8,'X')
      PCPERFORM "CAPTURE J=JOB12 TI=0 > NUL:"
      IF PATIENT.NUMBER # '' THEN
        OPEN 'LISTS' TO LISTS.FILE ELSE STOP
        LISTS.ID = 'CR':@STATION
        SECOND.ID = 'SR':@STATION
        FIRST.LIST = ''
        FIRST.LIST<1> = ILM.ID
        FIRST.LIST<2> = 0
        SECOND.LIST = ''
        SECOND.LIST<1> = ILM.ID
        SECOND.LIST<2> = 0
        WRITE FIRST.LIST TO LISTS.FILE, LISTS.ID
        WRITE SECOND.LIST TO LISTS.FILE, SECOND.ID
        PERFORM "SELECT CASE WITH PATIENT.NUMBER = "‡PATIENT.NUMBER
        IF @RECCOUNT > 0 THEN
          PERFORM "SELECT CASE WITH DESIGNATOR.CODE = 'C' OR WITH DESIG
          IF @RECCOUNT > 0 THEN
            PERFORM "SELECT CASE WITH RECEIVED.DATE GE '1-1-91' AND WIT
            NEWLIST = ''
            DONE = 0
            LOOP
              READNEXT ID ELSE DONE = 1
            WHILE DONE = 0
              IF ID # ILM.ID[1,9] THEN
                NEWLIST<-1> = ID
              END
            REPEAT
```

-121-

```
                ONE.LIST = ''
                FM.CNT = COUNT(NEWLIST,@FM) + (NEWLIST # '')
                FOR I = 1 TO FM.CNT
                   C.ID = NEWLIST<I>[1,9]
                   READ C.REC FROM C.FILE,C.ID THEN
                      LOCATE 29 IN C.REC<16> USING @VM SETTING POS THEN
                         ONE.LIST<-1> = NEWLIST<I>
                      END ELSE
                         LOCATE 21 IN C.REC<16> USING @VM SETTING POS THEN
                            ONE.LIST<-1> = NEWLIST<I>
                         END
                      END
                   END
                NEXT I
                ABNORMAL.LIST = ''
                FM.CNT = COUNT(ONE.LIST,@FM) + (ONE.LIST # '')
                FOR I = 1 TO FM.CNT
                   ABNORMAL.LIST<I> = ONE.LIST<I>
                NEXT I
                IF FM.CNT > 0 THEN
                   CALL MAKE.LIST(0,ABNORMAL.LIST,'','')
                   PERFORM "MERGE CDI.GREY.ES"
                END
             END
           END
         END
         PCPERFORM "ENDCAP"
         END
       NEW.FILE.NAME = FILE.NAME
       NEW.FILE.NAME[-3,3] = 'CYT'
         PCPERFORM "COPY ":NEW.PATH:FILE.NAME:"   ":NEW.PATH:NEW.FILE.NAME
       END
      END
      OSCLOSE ILM.FILE
    END
    ANSWER<1> = COUNT
    ANSWER<2> = ILM.ID
  REPEAT
 REPEAT
RETURN ANSWER

GET.STRING:
 EOS.FLAG = 1
 I = 1
 LOOP UNTIL (EOS.FLAG = 0 OR I = REC.LEN+1)
    IF SEQ(FILE.REC[REC.POS+I-1,1]) = 0 THEN EOS.FLAG = 0
    IF I = 1 THEN
       ILM.REC<ILM.NUM> = FILE.REC[REC.POS+I-1,1]
    END ELSE
       ILM.REC<ILM.NUM> = ILM.REC<ILM.NUM>:FILE.REC[REC.POS+I-1,1]
    END
    I += 1
 REPEAT
RETURN

GET.DOUBLE:
 EOS.FLAG = 1
 BYTE1 = SEQ(FILE.REC[REC.POS+7,1])
 BYTE1 = FMT(OCONV(BYTE1,"MB"),'R(0)#8')
```

-122-

```
BYTE2 = SEQ(FILE.REC[REC.POS+6,1])
BYTE2 = FMT(OCONV(BYTE2,"MB"),'R(0)#8')

BYTE3 = SEQ(FILE.REC[REC.POS+5,1])
BYTE3 = FMT(OCONV(BYTE3,"MB"),'R(0)#8')

BYTE4 = SEQ(FILE.REC[REC.POS+4,1])
BYTE4 = FMT(OCONV(BYTE4,"MB"),'R(0)#8')

BYTE5 = SEQ(FILE.REC[REC.POS+3,1])
BYTE5 = FMT(OCONV(BYTE5,"MB"),'R(0)#8')

BYTE6 = SEQ(FILE.REC[REC.POS+2,1])
BYTE6 = FMT(OCONV(BYTE6,"MB"),'R(0)#8')

BYTE7 = SEQ(FILE.REC[REC.POS+1,1])
BYTE7 = FMT(OCONV(BYTE7,"MB"),'R(0)#8')

BYTE8 = SEQ(FILE.REC[REC.POS,1])
BYTE8 = FMT(OCONV(BYTE8,"MB"),'R(0)#8')

SIGN = BYTE1[1,1]
BIASED.EXP = ICONV(BYTE1[2,7]:BYTE2[1,4],"MB")-1023
MANTISSA = "1":BYTE2[5,4]:BYTE3:BYTE4:BYTE5:BYTE6:BYTE7:BYTE8
 MANTISSA = BYTE2[5,4]:BYTE3:BYTE4:BYTE5:BYTE6:BYTE7:BYTE8
MAN.SUM = 0
MULTIPLIER = 1.0
FOR I = 1 TO 54
   IF MANTISSA[I,1] = 1 THEN MAN.SUM += MANTISSA[I,1]*MULTIPLIER
   MULTIPLIER = MULTIPLIER/2
NEXT I

ILM.REC<ILM.NUM> = ((-1)**SIGN)*(2**BIASED.EXP)*(MAN.SUM)
:TURN

:T.INTEGER:
EOS.FLAG = 1
I = 1
LOOP UNTIL (I = REC.LEN+1)
   IF I = 1 THEN
      ILM.REC<ILM.NUM> = SEQ(FILE.REC[REC.POS+I-1,1])
   END ELSE
      ILM.REC<ILM.NUM> = ILM.REC<ILM.NUM>+SEQ(FILE.REC[REC.POS+I-1,1])*256
   END
   I += 1
REPEAT
:TURN

:T.CHAR.ARRAY:
FOR I.C = 1 TO REC.LEN
   ILM.REC<ILM.NUM,I.C> = FILE.REC[REC.POS+I.C-1,1]
NEXT I.C
:TURN

:T.FLOAT.ARRAY:
THIS COULD BE MESSED UP, NOT CHECKED
FOR I = 1 TO REC.LEN
   BYTE1 = SEQ(FILE.REC[REC.POS+3,1])
   BYTE1 = FMT(OCONV(BYTE1,"MB"),'R(0)#8')
```

-123-

```
    BYTE2 = SEQ(FILE.REC[REC.POS+2,1])
    BYTE2 = FMT(OCONV(BYTE2,"MB"),'R(0)#8')

BYTE3 = SEQ(FILE.REC[REC.POS+1,1])
    BYTE3 = FMT(OCONV(BYTE3,"MB"),'R(0)#8')

BYTE4 = SEQ(FILE.REC[REC.POS,1])
    BYTE4 = FMT(OCONV(BYTE4,"MB"),'R(0)#8')

REC.POS += 4
    SIGN = BYTE1[1,1]
    BIASED.EXP = ICONV(BYTE1[2,7]:BYTE2[1,1],"MB")-127
    MANTISSA = "1":BYTE2[2,7]:BYTE3:BYTE4
      MANTISSA = BYTE2[2,7]:BYTE3:BYTE4
    MAN.SUM = 0
    MULTIPLIER = 1.0
    FOR J = 1 TO 25
      IF MANTISSA[J,1] = 1 THEN MAN.SUM += MANTISSA[J,1]*MULTIPLIER
      MULTIPLIER = MULTIPLIER/2
    NEXT J
    ILM.REC<ILM.NUM,I> = OCONV(((-1)**SIGN)*(2**BIASED.EXP)*(MAN.SUM)*100,'MD2')
  NEXT I
:TURN

:T.FLOAT:
THIS COULD BE MESSED UP, NOT CHECKED
BYTE1 = SEQ(FILE.REC[REC.POS+3,1])
BYTE1 = FMT(OCONV(BYTE1,"MB"),'R(0)#8')

BYTE2 = SEQ(FILE.REC[REC.POS+2,1])
BYTE2 = FMT(OCONV(BYTE2,"MB"),'R(0)#8')

BYTE3 = SEQ(FILE.REC[REC.POS+1,1])
BYTE3 = FMT(OCONV(BYTE3,"MB"),'R(0)#8')

BYTE4 = SEQ(FILE.REC[REC.POS,1])
BYTE4 = FMT(OCONV(BYTE4,"MB"),'R(0)#8')

REC.POS += 4
SIGN = BYTE1[1,1]
BIASED.EXP = ICONV(BYTE1[2,7]:BYTE2[1,1],"MB")-127
MANTISSA = "1":BYTE2[2,7]:BYTE3:BYTE4
    MANTISSA = BYTE2[2,7]:BYTE3:BYTE4
MAN.SUM = 0
MULTIPLIER = 1.0
FOR J = 1 TO 25
  IF MANTISSA[J,1] = 1 THEN MAN.SUM += MANTISSA[J,1]*MULTIPLIER
  MULTIPLIER = MULTIPLIER/2
NEXT J
ILM.REC<ILM.NUM> = OCONV(((-1)**SIGN)*(2**BIASED.EXP)*(MAN.SUM)*100,'MD2')
:TURN

:T.LONG.ARRAY:
  FOR I = 0 TO REC.LEN-1
    LONG.SUM = SEQ(FILE.REC[REC.POS+I*4,1]) + 256*SEQ(FILE.REC[REC.POS+I*4+1,1])
    LONG.SUM = LONG.SUM + 65536*SEQ(FILE.REC[REC.POS+I*4+2,1]) + 16777216*SEQ(FI
    ILM.REC<ILM.NUM,I+1> = LONG.SUM
  NEXT I
:TURN
```

-124-

```
ET.LONG:
  LONG.SUM = SEQ(FILE.REC[REC.POS,1]) + 256*SEQ(FILE.REC[REC.POS+1,1])
  LONG.SUM = LONG.SUM + 65536*SEQ(FILE.REC[REC.POS+2,1]) + 16777216*SEQ(FILE.RE
  ILM.REC<ILM.NUM> = LONG.SUM
ETURN

ET.INT.ARRAY:
  FOR I.GIA = 0 TO REC.LEN-1
    ILM.REC<ILM.NUM,I.GIA+1> = SEQ(FILE.REC[REC.POS+I.GIA*2,1]) + 256*SEQ(FILE.
  NEXT I.GIA
ETURN

NR.EXPORT:
  OPEN 'DOS' TO D.FILE ELSE STOP
  MNR.PATH = 'F:\USERS\MCM\PFS\'
  MNR.FILE.NAME = ''
  CR = CHAR(13)
  LF = CHAR(10)
  D.REC = ''
  MNR.FILE.NAME = ILM.ID[4,7]".TXT"
  D.REC = ILM.ID:CR:LF
  FOR I = 1 TO ILM.REC<27>
  ? D.REC := FMT(INT(100*ILM.REC<96,I>/5.4704+.5),'MD2'):",  ":FMT(ILM.REC<99,I>
  NEXT I
  WRITE D.REC TO D.FILE,MNR.PATH:MNR.FILE.NAME
ETURN
```

-125-

The following is the Microsoft Excel v5.0 source code for the macro program used to convert the JVB v1.0 database files as set forth in Example III.

JVB Macro Source Code

```
' JVB Macro
' Macro recorded 6/24/94 by Craig Miller
'
' Keyboard Shortcut: Ctrl+j
'
Sub JVB()
OpenLine:
    MsgBox "Open the ILM Morphometry *.CSV file which you wish to separate, or end the macro by selecting the END.CSV file"
    ChDrive "C"
    ChDir "C:\IMAGING.JVB\FILES\STUDY.ILM"
    OpenFile = Application.GetOpenFilename("Text (*.csv), *.csv")
    Workbooks.Open Filename:=OpenFile
    FileLength = Len(OpenFile)
    SearchStr = "M\"
    Period = InStr(OpenFile, SearchStr)
    OpenFile1 = Mid(OpenFile, Period + 2)
    FileLength1 = Len(OpenFile1)
    SearchStr1 = "."
    Period1 = InStr(OpenFile1, SearchStr1)
    OpenFile2 = Left(OpenFile1, Period1 - 1)
    CASENUM = Range("B2").Value
' If there are no values in the file, end the macro. If data is present, proceed
    If CASENUM = "" Then GoTo LastLine Else GoTo FormatLine
FormatLine:
    Application.ScreenUpdating = False
    Cells.Select
    With Selection
        .HorizontalAlignment = xlCenter
        .VerticalAlignment = xlBottom
        .WrapText = False
        .Orientation = xlHorizontal
    End With
    Columns("A:A").Select
    Selection.Delete Shift:=xlToLeft
    Columns("I:I").Select
    Selection.Cut
    Columns("B:B").Select
    Selection.Insert Shift:=xlToRight
    Columns("D:D").Select
    Selection.Cut
    Columns("AL:AL").Select
    Selection.Insert Shift:=xlToRight
    Columns("F:N").Select
    Selection.Cut
    Columns("AL:AL").Select
    Selection.Insert Shift:=xlToRight
    Columns("AH:AH").Select
    Selection.Cut
    Columns("AB:AB").Select
    Selection.Insert Shift:=xlToRight
    Columns("A:A").Select
    Selection.NumberFormat = "@"
    Columns("B:AK").Select
    Selection.NumberFormat = "0.000000"
    Selection.EntireColumn.AutoFit
    Columns("E:E").NumberFormat = "0.00"
    Columns("AB:AB").NumberFormat = "0"
    Columns("AD:AD").NumberFormat = "0.00"
    Columns("AE:AE").NumberFormat = "0.00"
    Range("A2").Select
    Application.ScreenUpdating = True
    ChDrive "F"
    ChDir "F:\USERS\MCM\40X"
        With ActiveWorkbook
            .Title = ""
            .Subject = ""
            .Author = "Craig Miller"
            .Keywords = ""
```

JVB Macro Source Code

```
            .Comments = ""
        End With
    ActiveWorkbook.SaveAs Filename:=OpenFile2, FileFormat:=xlNormal, _
        Password:="", WriteResPassword:="", ReadOnlyRecommended:= _
        False, CreateBackup:=False
    Application.ScreenUpdating = False
    CASENUM = Range("A2").Value
    While CASENUM <> ""
        Application.ScreenUpdating = False
' Select all cells pertaining to this particular case
        y = 3
            While Cells(y, 1) = CASENUM
                y = y + 1
            Wend
' Select the cells for one case, copy them to a blank JVB template, _
  and delete the first and last row (blank rows from template).
        Range(Cells(2, 1), Cells(y - 1, 37)).Select
        Selection.Copy
        Workbooks.Open Filename:="C:\CRAIG\MACROS\JVBCMP.BLK"
        Selection.Insert Shift:=xlDown
            With Selection.Font
                .Name = "Times New Roman"
                .FontStyle = "Regular"
                .Size = 10
                .Strikethrough = False
                .Superscript = False
                .Subscript = False
                .OutlineFont = False
                .Shadow = False
                .Underline = xlNone
                .ColorIndex = xlAutomatic
            End With
            With Selection
                .HorizontalAlignment = xlCenter
                .VerticalAlignment = xlBottom
                .WrapText = False
                .Orientation = xlHorizontal
            End With
            With Selection.Borders(xlLeft)
                .Weight = xlThin
                .ColorIndex = xlAutomatic
            End With
            With Selection.Borders(xlRight)
                .Weight = xlThin
                .ColorIndex = xlAutomatic
            End With
            With Selection.Borders(xlTop)
                .Weight = xlThin
                .ColorIndex = xlAutomatic
            End With
            With Selection.Borders(xlBottom)
                .Weight = xlThin
                .ColorIndex = xlAutomatic
            End With
        Selection.BorderAround LineStyle:=xlNone
        Columns("A:AK").EntireColumn.AutoFit
        Rows("3:3").Select
        Application.CutCopyMode = False
        Selection.Delete Shift:=xlUp
        y = 3
            While Cells(y, 1) = CASENUM
                y = y + 1
            Wend
        Range(Cells(y, 1), Cells(y, 37)).Select
        Selection.Delete Shift:=xlUp
' Make the first column the cell number
        Range("A1").Select
        ActiveCell.FormulaR1C1 = "Cell"
        Range("A3").Select
        ActiveCell.FormulaR1C1 = "1"
```

JVB Macro Source Code

```
        Range("A4").Select
        ActiveCell.FormulaR1C1 = "2"
            Set Source = Range(Cells(3, 1), Cells(4, 1))
            Set FILL = Range(Cells(3, 1), Cells(y - 1, 1))
        Source.AutoFill destination:=FILL
        Sheets("JVBCMP").Select
        CASENUM = Trim(CASENUM)
        Sheets("JVBCMP").Name = CASENUM
        Range("A1").Select
        ChDir "F:\USERS\MCM\40X"
            With ActiveWorkbook
                .Title = ""
                .Subject = ""
                .Author = "Craig Miller"
                .Keywords = ""
                .Comments = ""
            End With
        ActiveWorkbook.SaveAs Filename:=CASENUM, FileFormat:=xlNormal, _
            Password:="", WriteResPassword:="", ReadOnlyRecommended:= _
            False, CreateBackup:=False
' Select the Statistical Calculations, paste them to a blank spreadsheet, _
    and cut and copy all of the values to a single row.
        Range(Cells(y + 2, 1), Cells(y + 6, 37)).Select
        Selection.Copy
        Selection.PasteSpecial Paste:=xlValues, Operation:=xlNone, _
        SkipBlanks:=False, Transpose:=False
        Selection.Cut
        Workbooks.Add Template:="Workbook"
        ActiveSheet.Paste
        Range("A1").Formula = CASENUM
        Range("B2:AK2").Select
        Selection.Cut
        Range("AL1").Select
        ActiveSheet.Paste
        Range("B3:AK3").Select
        Selection.Cut
        Range("BV1").Select
        ActiveSheet.Paste
        Range("B4:AK4").Select
        Selection.Cut
        Range("DF1").Select
        ActiveSheet.Paste
        Range("B5:AK5").Select
        Selection.Cut
        Range("EP1").Select
        ActiveSheet.Paste
        Rows("1:1").Select
        Selection.Copy
' Paste the statistics for the case into the summary file
        Workbooks.Open Filename:="F:\USERS\MCM\40X\LATTIME.JVB"
        Selection.Insert Shift:=xlDown
        Application.CutCopyMode = False
        ActiveWorkbook.Save
        ActiveWindow.Close
        ActiveWorkbook.Saved = True
        ActiveWindow.Close
        ActiveWorkbook.Saved = True
        ActiveWindow.Close
        Selection.Delete Shift:=xlUp
        Range("A2").Select
        Application.ScreenUpdating = True
'Continue looping the macro until all of the cases contained in this vector _
    file have been separated and no data is left in the vector file.
        CASENUM = Range("A2").Value
    Wend
'If there is more than one vector file to separate, open the next file
    ActiveWorkbook.Saved = True
    ActiveWindow.Close
    GoTo OpenLine
' End the macro and refresh the screen
```

JVB Macro Source Code

```
LastLine:
    ActiveWorkbook.Saved = True
    ActiveWindow.Close
    Application.ScreenUpdating = True
End Sub
```

The following is the source code listing of a computer program for the neural network as set forth in Example XII.

```
/*********************************************************************
File:           sigsin.c
Contents:       Back Propagation neural networks with
                sigmoid, sinusoid and gaussian activation
                function. Data normalized by mean and std.
Date:           Dec, 17, 1992

*********************************************************************/ include     <math.h>
include     <stdio.h>
#define      TRUE           1
#define      FALSE          0
#define      EQUAL          0
#define      SAMPLED        1
#define      UNSAMPLED      0
#define      SINUSOID       0
#define      SIGMOID        1
#define      GAUSSIAN       2
#define      LINEAR         3
#define      NEWEXP         1
#define      RESUM          0
#define      SIG(x)         1.0/(1.0 + exp((double)(-x/10.0)))
#define      SIN(f, x)      sin((double)(f*x))
#define      GAUS(x)        exp((double)(-x*x/40.0))
#define      SLOPE(f, x)    cos((double)(f*x))
#define      MaxPtns        1000         /*Max training + test patterns*/
#define      MaxLayerN      2            /*Max LayerN in configuration*/
#define      MaxWtN         40           /*Max weights per nuron*/
#define      MaxStrLen      100          /*Maximum String Length*/
#define      MaxInputN      20           /*Maximum data input lines*/
#define      NxtLn(s, File) fgets((char*)s,MaxStrLen,(FILE*)File)

/*Network configuration
and control parameters*/ int     TrainPtns = 16;                          /*Total training patterns*/
int     TestPtns = 16;                           /*Total test patterns*/
int     InputN = 4;                              /*Total input nurons*/
int     OutputN = 1;                             /*Total output nurons*/
int     LayerN = 2;                              /*Total LayerN*/
int     NeuronInLayer[MaxLayerN] = {8, 1};       /*Total nurons in each layer*/
int     ActInLayer[MaxLayerN] = {1, 1};          /*Action function confige*/
float   LearnRate = 0.5;                         /*Learning rate*/
float   Threshold = 0.01;                        /*Termination condition*/
float   Frequency = 3.0;                         /*Sinusoid frequency*/
float   InitialRange = 2.0;                      /*Initial range for network*/
float   InputScale = 1.0;                        /*Input Normlization Factor*/
int     RptRate = 20;                            /*Reprot rate*/
int     MaxLoops = 2000;                         /*Maximum loops*/
int     RandSeed = 123456789;                    /*Random seed*/
char    TrainFile[20] = "Traing";                /*Traingin data file name*/
char    TestFile[20] = "Ttest";                  /*Test data file name*/
char    ReportFile[20] = "Report";               /*Output download file*/
char    NetworkFile[20] = "Network";             /*Final NN sctructure*/

/*Input data*/
float   *DataIn[MaxPtns];                        /*Normalized training patterns*/
float   *DataOut[MaxPtns];                       /*Normalized training patterns*/
float   mean[MaxInputN];                         /*Input data mean buffer*/
float   std[MaxInputN];                          /*Input data std buffer*/
float   *InputLayer;                             /*Array of input nurons*/
float   *Target;
char    TrainPrefix[MaxStrLen] = "../cdi-data2/";/*Train data file prefix*/
char    TestPrefix[MaxStrLen] = "../cdi-data2/"; /*Test data file prefix*/
```

```c
typedef struct Neuron {
                        float   Wt[MaxWtN];
                        float   Biase;
                        float   Sum;
                        float   Out;
                        float   Error;
                        float   Delta;
                        int     Activation;
                        }NEURON;

NEURON          *Layer[MaxLayerN];

char *HELP = "Usage:    sigsin NewExpFlag.\n";

main(argc, argv)
int     argc;
char    **argv;
{
int             Loops, Pattern;
int             Spool[MaxPtns], RandSample;
float           SumError;
double          drand48();
void            Initialization();
void            Resum();
void            Output();
void            BackPropagation();
void            DumpOutput();

if((argc==1)||(atoi(argv[1])==NEWEXP))
        Initialization();
else if(atoi(argv[1]) == RESUM)
        Resum();
else{
        printf("%s\n", HELP);
        exit(0);
        }

Loops = 0;
SumError = (float)HUGE;
while((Loops++ <= MaxLoops) && (SumError >= Threshold)){
        for(Pattern=0; Pattern < TrainPtns; Pattern++)   /*Mark as unsampled*/
                Spool[Pattern] = UNSAMPLED;

SumError = 0.0;
        for(Pattern = 0; Pattern < TrainPtns; Pattern++){
                RandSample = TrainPtns * drand48();      /*Randomly sample patns*/
                while(Spool[RandSample] == SAMPLED)
                        RandSample = TrainPtns * drand48();/*Sampled? try other*/
                Output(RandSample);
                BackPropagation();
                DumpOutput(Pattern, Loops, RandSample, &SumError);
                Spool[RandSample] = SAMPLED;             /*Marked as sampled*/
                }
        } if(TestPtns){
        SumError = 0.0;
        for(Pattern = TrainPtns; Pattern < TestPtns + TrainPtns; Pattern++){
                Output(Pattern);
                DumpOutput(Pattern, -1, Pattern, &SumError);
                }
        }
exit();
```

-133-

}

/************************************************************

Routine:    Initialization()

Get in arguments, allocate memory.

************************************************************/

```
void    Initialization()
{
void    ReportArg();
void    GetArguments();
void    AllocateMemory();
void    GetData();
void    srand48();
void    InitialNetwork();
void    NormData();

GetArguments();
ReportArg(NEWEXP);
AllocateMemory();
GetData();
NormData();
srand48(RandSeed);
InitialNetwork();
}
```

/************************************************************

Routine:    GetArguments()

Collect control and network
            configuration parameters.

************************************************************/

```
void    GetArguments()
{
int         i, *ip, tmp;
char        TmpC, TmpS[100];
FILE        *ArgFile;
void        ReadInStr();

if((ArgFile = fopen("arg", "r")) == NULL){
        printf("cannot open file arg to read\n");
        exit(1);
        } while((TmpC = getc(ArgFile)) != EOF){
        ungetc(TmpC, ArgFile);
        ReadInStr(TmpS, ArgFile);
        if(strcmp(TmpS, "Training Data File:")==EQUAL)
                ReadInStr(TrainFile, ArgFile);
        else if(strcmp(TmpS, "Test Data File:")==EQUAL)
                ReadInStr(TestFile, ArgFile);
        else if(strcmp(TmpS, "Report Data File:")==EQUAL)
                ReadInStr(ReportFile, ArgFile);
        else if(strcmp(TmpS, "Network Structure File:")==EQUAL)
                ReadInStr(NetworkFile, ArgFile);
        else if(strcmp(TmpS, "Training Patterns:")==EQUAL){
                fscanf(ArgFile, "%d", &TrainPtns);
                NxtLn(TmpS, ArgFile);
                }
```

-134-

```c
            else if(strcmp(TmpS, "Test Patterns:")==EQUAL){
                    fscanf(ArgFile, "%d", &TestPtns);
                    NxtLn(TmpS, ArgFile);
                    }
            else if(strcmp(TmpS, "Input Neurons:")==EQUAL){
                    fscanf(ArgFile, "%d", &InputN);
                    NxtLn(TmpS, ArgFile);
                    }
            else if(strcmp(TmpS, "Output Neurons:")==EQUAL){
                    fscanf(ArgFile, "%d", &OutputN);
                    NxtLn(TmpS, ArgFile);
                    }
            else if(strcmp(TmpS, "Layers:")==EQUAL){
                    fscanf(ArgFile, "%d", &LayerN);
                    NxtLn(TmpS, ArgFile);
                    }
            else if(strcmp(TmpS, "Neurons in Layer:")==EQUAL){
                    for(i=0; i<LayerN; i++)
                            fscanf(ArgFile, "%d", &NeuronInLayer[i]);
                    NxtLn(TmpS, ArgFile);
                    }
            else if(strcmp(TmpS, "Activation in Layer:")==EQUAL){
                    for(i=0; i<LayerN; i++)
                            fscanf(ArgFile, "%d", &ActInLayer[i]);
                    NxtLn(TmpS, ArgFile);
                    }
            else if(strcmp(TmpS, "Learning Rate:")==EQUAL){
                    fscanf(ArgFile, "%f", &LearnRate);
                    NxtLn(TmpS, ArgFile);
                    }
            else if(strcmp(TmpS, "Random Seed:")==EQUAL){
                    fscanf(ArgFile, "%d", &RandSeed);
                    NxtLn(TmpS, ArgFile);
                    }
            else if(strcmp(TmpS, "Input Scaling:")==EQUAL){
                    fscanf(ArgFile, "%f", &InputScale);
                    if(InputScale==0.0){
                            printf("Warning: 0 scaling factor\n");
                            exit(0);
                            }
                    NxtLn(TmpS, ArgFile);
                    }
            else if(strcmp(TmpS, "Ending Threshold:")==EQUAL){
                    fscanf(ArgFile, "%f", &Threshold);
                    NxtLn(TmpS, ArgFile);
                    }
            else if(strcmp(TmpS, "Frequency:")==EQUAL){
                    fscanf(ArgFile, "%f", &Frequency);
                    NxtLn(TmpS, ArgFile);
                    }
            else if(strcmp(TmpS, "Initial Range:")==EQUAL){
                    fscanf(ArgFile, "%f", &InitialRange);
                    NxtLn(TmpS, ArgFile);
                    }
            else if(strcmp(TmpS, "Report Rate:")==EQUAL){
                    fscanf(ArgFile, "%d", &RptRate);
                    NxtLn(TmpS, ArgFile);
                    }
            else if(strcmp(TmpS, "Maximum Loops:")==EQUAL){
                    fscanf(ArgFile, "%d", &MaxLoops);
                    NxtLn(TmpS, ArgFile);
                    }
            } fclose(ArgFile);
}
```

```
ip = ActInLayer;
for(i=0; i<LayerN; i++)
        fprintf(RptFile, "%d\t", *ip++);

fprintf(RptFile, "\n");
fprintf(RptFile,"Learn Rate: %f\n", LearnRate);
fprintf(RptFile,"Random Seed: %d\n", RandSeed);
fprintf(RptFile,"Input Scaling: %f\n", InputScale);
fprintf(RptFile,"Ending Threshold: %f\n", Threshold);
fprintf(RptFile,"Frequency: %f\n", Frequency);
}

/******************************* 
Routine:        ReadInStr

Read into string, disgard newline character

*******************************************************************/ void    ReadInStr(Str, InFile)
char    *Str;
FILE    *InFile;
{
int     Len;

fgets(Str, MaxStrLen, InFile);
*(Str + strlen(Str) - 1) = '\0';        /*Disgard newline and pad null*/
}

/*******************************************************************

Routine:        ReportArg

Reporte the input arguments.

*******************************************************************/ void    ReportArg(NewExpFlag)
int             NewExpFlag;
{
register        i, *ip;
FILE            *RptFile;

if(NewExpFlag){
        if((RptFile=fopen(ReportFile, "w"))==NULL){
                printf("cannot open file %s to write\n", ReportFile);
                exit(1);
                }
        }
else{
        if((RptFile=fopen(ReportFile, "a"))==NULL){
                printf("cannot open file %s to append\n", ReportFile);
                exit(1);
                }
        } if(!NewExpFlag)
        fprintf(RptFile, "\nRESUMED FROM THE PREVIOUSLY STOPED PROCESS\n\n");
fprintf(RptFile, "Training Data File: %s\n", TrainFile);
fprintf(RptFile, "Test Data File: %s\n", TestFile);
fprintf(RptFile, "Report Data File: %s\n", ReportFile);
fprintf(RptFile, "Network Structure File: %s\n", NetworkFile);
fprintf(RptFile, "Training Patterns: %d\n", TrainPtns);
fprintf(RptFile, "Test Patterns: %d\n", TestPtns);
fprintf(RptFile, "Input Neurons: %d\n", InputN);
fprintf(RptFile, "Output Neurons: %d\n", OutputN);
fprintf(RptFile,"Layers: %d\n", LayerN);
fprintf(RptFile, "Neurons in Layer: ");

ip = NeuronInLayer;
for(i=0; i<LayerN; i++)
        fprintf(RptFile, "%d\t", *ip++);

fprintf(RptFile, "\n");
fprintf(RptFile, "Activation in Layer: ");
```

```
ip = ActInLayer;
for(i=0; i<LayerN; i++)
        fprintf(RptFile, "%d\t", *ip++);

fprintf(RptFile, "\n");
fprintf(RptFile,"Learn Rate: %f\n", LearnRate);
fprintf(RptFile,"Random Seed: %d\n", RandSeed);
fprintf(RptFile,"Input Scaling: %f\n", InputScale);
fprintf(RptFile,"Ending Threshold: %f\n", Threshold);
fprintf(RptFile,"Frequency: %f\n", Frequency);
fprintf(RptFile,"Initial Range %f\n", InitialRange);
fprintf(RptFile,"Report Rate %d\n", RptRate);
fprintf(RptFile,"Maximum Loops %d\n", MaxLoops);

fclose(RptFile);
}

/*****************************************************

Routine:        GetData

Read in training and test data from file

*****************************************************/
void    GetData()
{
register        i, j;
float           *fp1, *fp2, ftmp;
char            *TmpStr;
FILE            *DataFile;

/*Get training data*/
TmpStr = (char *)strcat(TrainPrefix, TrainFile);
if((DataFile = fopen(TmpStr, "r")) == NULL){
        printf("cannot open file %s to read\n", TmpStr);
        exit(1);
        } for(i=0; i<TrainPtns; i++){
        fp1 = DataIn[i];
        fp2 = DataOut[i];
        for(j=0; j<InputN; j++){
                fscanf(DataFile, "%f", &ftmp);
                *fp1++ = ftmp/InputScale;
                }
        for(j=0; j<OutputN; j++)
                fscanf(DataFile, "%f", fp2++);
        }

/*Get test data*/
TmpStr = (char *)strcat(TestPrefix, TestFile);
if(TestPtns){
        if((DataFile = fopen(TmpStr, "r")) == NULL){
                printf("cannot open file %s to read\n", TmpStr);
                exit(1);
                } for(i=TrainPtns; i<TrainPtns + TestPtns; i++){
                fp1 = DataIn[i];
                fp2 = DataOut[i];
                for(j=0; j<InputN; j++){
                        fscanf(DataFile, "%f", &ftmp);
                        *fp1++ = ftmp/InputScale;
                        }
                for(j=0; j<OutputN; j++)
```

-137-

```c
                fscanf(DataFile, "%f", fp2++);
        }
    }
}

/*****************************************
Routine:    NormData

Normalize input data
            to range [0,1].

*****************************************/ void    NormData()
{
int     i, j, ptns;
float   ftmp;
FILE    *RptFile;

ptns = TrainPtns;
for(i=0; i<InputN; i++){
        ftmp = 0.0;
        for(j=0; j<ptns; j++)
                ftmp += DataIn[j][i];
        mean[i] = ftmp/ptns;
        } for(i=0; i<InputN; i++){
        ftmp = 0.0;
        for(j=0; j<ptns; j++)
                ftmp += pow((DataIn[j][i] - mean[i]),2.0);
        std[i] = pow((ftmp/ptns),0.5);
        } ptns = TrainPtns + TestPtns;
for(i=0; i<InputN; i++)
        for(j=0; j<ptns; j++)
                DataIn[j][i] = (DataIn[j][i]-mean[i])/std[i];

if((RptFile = fopen(ReportFile, "a"))==NULL){
        printf("cannot open file %s to write\n", ReportFile);
        exit(0);
        } fprintf(RptFile, "Mean\tSTD\n");
for(i=0; i<InputN; i++){
        fprintf(RptFile, "%f\t", mean[i]);
        fprintf(RptFile, "%f\n", std[i]);
        printf("%f\t", mean[i]);
        printf("%f\n", std[i]);
        }
fprintf(RptFile,"\n\n");
fprintf(RptFile, "Loops\tPtns\tNN-Out\tTarget\tSq-Err\n");
fclose(RptFile);
}

/*****************************************
Routine:    AllocateMemory

Allocate memory to nuron
            structure and other arrays

*****************************************/ void    AllocateMemory()
{
```

-138-

```
register        i;

/*Allocate space
for training data*/ for(i=0; i<TrainPtns + TestPtns; i++){
        if((DataIn[i] = (float*)calloc(InputN, sizeof(float)))==NULL){
                printf("cannot allocate memory to DataIn\n");
                exit(1);
                }
        if((DataOut[i] = (float*)calloc(OutputN, sizeof(float)))==NULL){
                printf("cannot allocate memory to DataOut\n");
                exit(1);
                }
        }

/*Allocate space for
input layer nurons*/ if((InputLayer = (float*)calloc(InputN, sizeof(float)))==NULL){
        printf("cannot allocate memory to InputLayer\n");
        exit(1);
        }

/*Allocate space for nurons
in the rest of Layers*/ for(i=0; i<LayerN; i++)
        if((Layer[i]=(NEURON *)calloc(NeuronInLayer[i],sizeof(NEURON)))==NULL){
                printf("cannot allocate memory to Layer[%d]\n", i);
                exit(1);
                }

/*Allocate space for target values*/ if((Target = (float*)calloc(OutputN, sizeof(float)))==NULL){
        printf("cannot allocate memory to Target\n");
        exit(1);
        }
}

/*****************************************************************************

Routine:        InitialNetwork

Initialize the activation function configuration for
                each layer (nuron) and nuron structure in the network.

*****************************************************************************/ void    InitialNetwork()
{
register        i, j, k;
float           *fp;
NEURON          *NeuronP;
double          drand48();

for(i=0; i<LayerN; i++){
        for(NeuronP = Layer[i], j=0; j<NeuronInLayer[i]; NeuronP++, j++){
                NeuronP->Activation = ActInLayer[i];
                NeuronP->Biase = (drand48() - 0.5) * InitialRange;
                NeuronP->Sum = 0.0;
                NeuronP->Out = 0.0;
                NeuronP->Error = 0.0;
                fp = NeuronP->Wt;
```

```
                    if(i==0)
                            for(k=0; k<InputN; k++)
                                    *fp++ = (drand48() - 0.5) * InitialRange;
                    else
                            for(k=0; k<NeuronInLayer[i-1]; k++)
                                    *fp++ = (drand48() - 0.5) * InitialRange;
            }
        }
}

/**********************************************************************************

Routine:        ReadInNetwork

Initialize the activation function configuration for
                each layer (nuron) and read in the network weight
                values from stoped process.

**********************************************************************************/ void    ReadInNetwork()
{
register        i, j, k;
char            Header, Ctmp;
float           *fp;
NEURON          *NeuronP;
FILE            *NetFp;

if((NetFp=fopen(NetworkFile, "r"))==NULL){
        printf("cannot open file file %s to read\n", NetworkFile);
        exit(1);
        }

Header = 7 + InputN;
while(--Header){                                        /*Read off network file header*/
        fscanf(NetFp, "%c", &Ctmp);
        while(Ctmp!='\n')
                fscanf(NetFp, "%c", &Ctmp);
        } for(i=0; i<LayerN; i++){
        for(NeuronP = Layer[i], j=0; j<NeuronInLayer[i]; NeuronP++, j++){
                NeuronP->Activation = ActInLayer[i];
                fscanf(NetFp, "%f", &(NeuronP->Biase));
                fp = NeuronP->Wt;
                if(i==0)
                        for(k=0; k<InputN; k++)
                                fscanf(NetFp, "%f", fp++);
                else
                        for(k=0; k<NeuronInLayer[i-1]; k++)
                                fscanf(NetFp, "%f", fp++);
                }
        } fclose(NetFp);
}

/**********************************************************************************

Routine:        Resum()

Resum a stoped process.

**********************************************************************************/
```

```
void    Resum()
{
void    ReportArg();
void    GetArguments();
void    AllocateMemory();
void    GetData();
void    InitialNetwork();
void    NormData();

GetArguments();
ReportArg(RESUM);
AllocateMemory();
GetData();
NormData();
ReadInNetwork();
}

/*************************************************************************

Routine:        Output

Calculate the output for each nuron.

*************************************************************************/ void    Output(Pattern)
int     Pattern;
{
int             i, j;
float           Tmp, rt;
NEURON          *NeuronP;
void            GetPattern();
float           GetSum();

GetPattern(Pattern);

for(i=0; i<LayerN; i++){
        NeuronP = Layer[i];
        for(j=0; j<NeuronInLayer[i]; j++, NeuronP++){
                rt = GetSum(i, j);
                Tmp = rt + NeuronP->Biase;
                NeuronP->Sum = Tmp;
                switch (NeuronP->Activation){
                        case SIGMOID:
                                NeuronP->Out = SIG(Tmp);
                                break;
                        case SINUSOID:
                                NeuronP->Out = SIN(Frequency, Tmp);
                                break;
                        case GAUSSIAN:
                                NeuronP->Out = GAUS(Tmp);
                                break;
                        case LINEAR:
                                NeuronP->Out = Tmp;
                                break;
                        default:
                                printf("invalide activation function type\n");
                                exit(0);
                }
        }
}
}
/*************************************************************************

Routine:        GetPattern
```

```
            Get input pattern for network

******************************   ************************    **********/ void    GetPattern(Pattern)
int     Pattern;
{
register        i, j;
float           *fp1, *fp2;

fp1 = InputLayer;
fp2 = DataIn[Pattern];
for(i=0; i<InputN; i++)
        *fp1++ = *fp2++;

fp1 = Target;
fp2 = DataOut[Pattern];
for(i=0; i<OutputN; i++)
        *fp1++ = *fp2++;
}

/***************************************************************************

Routine:        GetSum()

Calculate the sum input for each nuron

***************************************************************************/ float   GetSum(LayerIndex, NeuronIndex)
int     LayerIndex, NeuronIndex;
{
register        i, j;
float           Sum, *fp1, *fp2;
NEURON          *NeuronP1, *NeuronP2;

if(LayerIndex == 0){
        NeuronP1 = (NEURON *)(Layer[LayerIndex] + NeuronIndex);
        fp1 = InputLayer;
        fp2 = NeuronP1->Wt;
        for(Sum=0.0, i=0; i<InputN; i++)
                Sum += (*fp1++ * *fp2++);
        }
else{
        NeuronP1 = (NEURON *)(Layer[LayerIndex] + NeuronIndex);
        NeuronP2 = Layer[LayerIndex - 1];
        fp1 = NeuronP1->Wt;
        for(Sum=0.0, i=0; i<NeuronInLayer[LayerIndex-1]; i++, NeuronP2++)
                Sum += (NeuronP2->Out * *fp1++);
        }
return(Sum);
}

/***************************************************************************

Routine:        BackPropgation

Modify network through backpropgation.

***************************************************************************/ void    BackPropagation()
{
void    GetDelta();
void    UpdateWt();
```

-142-

```
GetDelta();
UpdateWt();
}

/*****************************************************************************

Routine:        GetDelta

Calculate delta values for each nuron in the
                network, out layer and internal layer;

*****************************************************************************/ void    GetDelta()
{
register        i;
void            OutLayerDelta();
void            InterLayerDelta();

OutLayerDelta();

for(i=LayerN-2; i>=0; i--)
        InterLayerDelta(i);

}

/*****************************************************************************

Routine:        OutLayerDelta

Calculate output layer delta

*****************************************************************************/ void    OutLayerDelta()
{
register        i;
float           TmpOut;
NEURON          *NeuronP;

for(NeuronP = Layer[LayerN-1], i=0; i<NeuronInLayer[LayerN-1]; NeuronP++, i++){
        TmpOut = NeuronP->Out;
        NeuronP->Error = Target[i] - TmpOut;
        switch (NeuronP->Activation){
                case SIGMOID:
                        NeuronP->Delta = TmpOut * (1 - TmpOut) * NeuronP->Error;
                        break;
                case SINUSOID:
                        NeuronP->Delta =SLOPE(Frequency, NeuronP->Sum) * NeuronP->Error;
                        break;
                case GAUSSIAN:
                        NeuronP->Delta = -NeuronP->Sum * TmpOut * NeuronP->Error/20;
                        break;
                case LINEAR:
                        NeuronP->Delta = NeuronP->Error;
                        break;
                default:
                        printf("invalide activation function type\n");
                        exit(0);
                }
        }
}
```

```
/***********************************************************************
        Routine:        InterLayerDelta Calculate internal layer Delta

***********************************************************************/ void    InterLayerDelta(LayerIndex)
int     LayerIndex;
{
register        i;
float           TmpOut;
NEURON          *NeuronP;
float           NeuronError();

for(NeuronP=Layer[LayerIndex],i=0; i<NeuronInLayer[LayerIndex]; NeuronP++,i++){
        TmpOut = NeuronP->Out;
        NeuronP->Error = NeuronError(LayerIndex, i);
        switch (NeuronP->Activation){
                case SIGMOID:
                        NeuronP->Delta = TmpOut * (1 - TmpOut) * NeuronP->Error;
                        break;
                case SINUSOID:
                        NeuronP->Delta =SLOPE(Frequency, NeuronP->Sum) * NeuronP->Error;
                        break;
                case GAUSSIAN:
                        NeuronP->Delta = -2 * NeuronP->Sum * TmpOut * NeuronP->Error;
                        break;
                case LINEAR:
                        NeuronP->Delta = NeuronP->Error;
                        break;
                default:
                        printf("invalide activation function type\n");
                        exit(0);
        }
    }
}

/***********************************************************************
        Routine:        NeuronError Calculate error for each nuron in the internal LayerN.

***********************************************************************/ float   NeuronError(LayerIndex, NeuronIndex)
int     LayerIndex, NeuronIndex;
{
register        i;
float           Error;
NEURON          *NeuronP;

Error = 0.0;
for(NeuronP=Layer[LayerIndex+1],i=0;i<NeuronInLayer[LayerIndex+1];NeuronP++,i++)
        Error += (NeuronP->Wt[NeuronIndex] * NeuronP->Delta);

return(Error);
}

/***********************************************************************
        Routine:        UpdateWt Modify the weights associated with each nuron.
```

-144-

```
/*****************************************************************************/
void    UpdateWt()
{
register        i;
void            FirstLayerWt();
void            RestLayerWt();

FirstLayerWt();

for(i=1; i<LayerN; i++)
        RestLayerWt(i);
}

/*****************************************************************************

Routine:        FirstLayerWt

Modify the weights related to the first layer nurons.

*****************************************************************************/ void    FirstLayerWt()
{
register        i, j;
float           *fp1, *fp2;
NEURON          *NeuronP;

for(NeuronP = Layer[0], i=0; i<NeuronInLayer[0]; NeuronP++, i++){
        fp1 = InputLayer;
        fp2 = NeuronP->Wt;
        for(j=0; j<InputN; j++)
                *fp2++ += LearnRate * NeuronP->Delta * *fp1++;
        NeuronP->Biase += (LearnRate * NeuronP->Delta);
        }
}

/*****************************************************************************

Routine:        RestLayerWt

Modify the weights related to the nurons of other LayerN.

*****************************************************************************/ void    RestLayerWt(LayerIndex)
{
register        i, j;
float           *fp;
NEURON          *NeuronP1, *NeuronP2;

for(NeuronP1=Layer[LayerIndex],i=0;i<NeuronInLayer[LayerIndex];NeuronP1++,i++){
        fp = NeuronP1->Wt;
        NeuronP2 = Layer[LayerIndex - 1];
        for(j=0; j<NeuronInLayer[LayerIndex - 1]; j++){
                *fp++ += (LearnRate*NeuronP1->Delta*NeuronP2->Out);
                NeuronP2++;
                }
        NeuronP1->Biase += (LearnRate * NeuronP1->Delta);
        }
}

/*****************************************************************************
```

-145-

```
Routine:      DumpOutput

Save output to report file and rturn it to main.
***************************************************************************/ void    DumpOutput(PtnCnt, Loops, PtnSampled, SumError)
float   *SumError;
int     Loops, PtnCnt, PtnSampled;
{
register        i;
float           SqError, OutError, *fp;
NEURON          *NeuronP;
FILE            *RptFile;
void            DumpNetwork();

fp = DataOut[PtnSampled];
NeuronP = Layer[LayerN-1];
SqError = 0.0;
for(i=0;i<OutputN;fp++,NeuronP++,i++){
        OutError = *fp - NeuronP->Out;
        SqError += OutError*OutError;
        }
*SumError += SqError;

if((Loops % RptRate == 0) || (Loops == -1)){
        if((RptFile=fopen(ReportFile, "a"))==NULL){
                printf("cannot open file %s to append.\n", ReportFile);
                exit(1);
                } fprintf(RptFile, "%d\t%d\t", Loops, PtnSampled);
        NeuronP = Layer[LayerN-1];
        for(NeuronP=Layer[LayerN-1],i=0;i<NeuronInLayer[LayerN-1];NeuronP++,i++)
                fprintf(RptFile, "%6.4f\t", NeuronP->Out);

fp = DataOut[PtnSampled];
        for(i=0; i<OutputN; i++)
                fprintf(RptFile, "%6.4f\t", *fp++);

fprintf(RptFile, "%6.4f\t", SqError);

fprintf(RptFile, "\n");
        fclose(RptFile);
        } if(((Loops%RptRate==0)&&(PtnCnt==TrainPtns-1))||(PtnCnt==TrainPtns+TestPtns-1)){
        if((RptFile=fopen(ReportFile, "a"))==NULL){
                printf("cannot open file %s to append.\n", ReportFile);
                exit(1);
                }
        fprintf(RptFile, "SumError %6.4f\n\n\n", *SumError);
        fclose(RptFile);

DumpNetwork();
        }
}

/***************************************************************************

Routine:      DumpNetwork()

Save the final network configuration, including network
              parameters(layers, layer configuration, activation function
              configuration), weights, biases.
```

−146−

```
/*****************************************************************************/
void DumpNetwork()
{
register       i, j, k, WtN;
float          *fp;
NEURON         *NeuronP;
FILE           *NetFile;

if((NetFile=fopen(NetworkFile, "w"))==NULL){
        printf("cannot open file %s to write\n", NetworkFile);
        exit(1);
        } fprintf(NetFile, "%d\t%d\n", InputN, OutputN);
fprintf(NetFile, "%d\n", LayerN);
for(i=0; i<LayerN; i++)
        fprintf(NetFile, "%d\t", NeuronInLayer[i]);
fprintf(NetFile, "\n");
for(i=0; i<LayerN; i++)
        fprintf(NetFile, "%d\t", ActInLayer[i]);
fprintf(NetFile, "\n%6.4f\n", Frequency);
for(i=0; i<InputN; i++){
        fprintf(NetFile, "%f\t", mean[i]);
        fprintf(NetFile, "%f\n", std[i]);
        }
fprintf(NetFile, "\n\n");

for(i=0;i<LayerN;i++){
        WtN = i==0 ? InputN : NeuronInLayer[i-1];
        for(NeuronP=Layer[i],j=0;j<NeuronInLayer[i];NeuronP++,j++){
                fprintf(NetFile, "\n%6.4f\n", NeuronP->Biase);
                for(fp=NeuronP->Wt, k=0; k<WtN; k++){
                        fprintf(NetFile, "%6.4f ", *fp++);
                        if(k%8==7)
                                fprintf(NetFile, "\n");
                        }
                }
        } fclose(NetFile);
}
```

The following is the source code listing of the CellSheet® v.1.0 computer program as set forth in Example XIII.

Cell Sheet v1.0d Source Code

```
' CellSheetD Macro
' Macro recorded 2/5/95 by Craig Miller
'
' Keyboard Shortcut: Ctrl+b
'
Sub CellSheetD()
' Open a Cell Sheet v1.0d Beta1 *.CSV file from the C:\Imaging.JVB\Files\Study.ILM _
    subdirectory only, other wise you must change the SearchStr value so that _
    it equals the last character in the name of the subdirectory.
    Msg = "Have you converted all of the listmode files using the Cell Sheet v1.0d Program and
all of that programs available parameters, and then exported the data to a *.CSV file?"
    Style = vbYesNo
    Title = "Listmode Conversion Status"
    Status = MsgBox(Msg, Style, Title)
    If Status = vbNo Then GoTo EndLine Else
    Msg = "Have you already created the formatted Excel spreadsheet and you just need to create
a stats file?"
    Style = vbYesNo
    Title = "Create Only Stats File from Existing Spreadsheet?"
    Status1 = MsgBox(Msg, Style, Title)
    If Status1 = vbYes Then GoTo BadStart Else
OpenLine:
    MsgBox "Open the *.CSV file which you with to convert:"
    ChDrive "C"
    ChDir "C:\IMAGING.JVB\FILES\STUDY.ILM"
    CSVFile = Application.GetOpenFilename("Text (*.csv), *.csv")
    If CSVFile = False Then GoTo EndLine Else
    Workbooks.Open Filename:=CSVFile
    FileLength = Len(CSVFile)
    SearchStr = "M\"
    Period = InStr(CSVFile, SearchStr)
    CSVFile1 = Mid(CSVFile, Period + 2)
    FileLength1 = Len(CSVFile1)
    SearchStr1 = "."
    Period1 = InStr(CSVFile1, SearchStr1)
    CSVFile2 = Left(CSVFile1, Period1 - 1)
    CaseNum = Range("B2").Value
    If CaseNum = "" Then GoTo LastLine Else
FormatLine:
' This part of the macro cuts and pastes the columns of data into the correct order.
    FileLocation = Application.InputBox("Enter the directory in which you want all of the files
to be stored.  This must be an existing directory.  Example:  I:\AREV\MCM\TEST", "File Directo
ry", "I:\AREV\MCM\SEXTANT")
    DriveLocation = Left(FileLocation, 1)
    StatsFile = Application.InputBox("Enter a name for the Summary Statistics File:  a file whi
ch will contain all of the statistics for each case.  Example:  TESTSTAT", "Summary Statistics
File Name")
    Application.ScreenUpdating = False
    Workbooks.Open Filename:="C:\CRAIG\MACROS\CSV1DSTA.BLK"
    ChDrive DriveLocation
    ChDir FileLocation
        With ActiveWorkbook
            .Title = ""
            .Subject = ""
            .Author = "Craig Miller"
            .Keywords = ""
            .Comments = ""
        End With
    ActiveWorkbook.SaveAs Filename:=StatsFile, FileFormat:=xlNormal, _
        Password:="", WriteResPassword:="", ReadOnlyRecommended:= _
        False, CreateBackup:=False
    ActiveWindow.Close
    Sheets("Sheet1").Select
    Cells.Select
    With Selection
        .HorizontalAlignment = xlCenter
        .VerticalAlignment = xlBottom
        .WrapText = False
        .Orientation = xlHorizontal
```

Cell Sheet v1.0d Source Code

```
    End With
    Columns("A:A").Select
    Selection.Delete Shift:=xlToLeft
    Columns("I:I").Select
    Selection.Cut
    Columns("B:B").Select
    Selection.Insert Shift:=xlToRight
    Columns("D:D").Select
    Selection.Cut
    Columns("AK:AK").Select
    Selection.Insert Shift:=xlToRight
    Columns("F:N").Select
    Selection.Cut
    Columns("AK:AK").Select
    Selection.Insert Shift:=xlToRight
    Columns("AM:AM").Select
    Selection.Cut
    Columns("AA:AA").Select
    Selection.Insert Shift:=xlToRight
    Columns("AH:AH").Select
    Selection.Cut
    Columns("AB:AB").Select
    Selection.Insert Shift:=xlToRight
    Columns("A:A").Select
    Selection.NumberFormat = "@"
' Determines the number of rows in the spreadsheet
    Range("A2").Select
        c = 2
        While Cells(c, 1).Formula <> ""
            c = c + 1
        Wend
' Rounds Columns B (Summed O.D.), E (Pg DNA), AD (DNA Index), and AE _
    (Density) to two significant digits and Column C (Area) to five significant digits.
    f = 3
        Columns(f).Select
        Selection.Insert Shift:=xlToRight
        Cells(1, f).Formula = Cells(1, f - 1).Value
        Cells(2, f).Formula = "=ROUND(RC[-1],2)"
        Cells(2, f).AutoFill Destination:=Range(Cells(2, f), Cells(c - 1, f)), _
            Type:=xlFillDefault
        Columns(f).Select
        Selection.Copy
        Selection.PasteSpecial Paste:=xlValues, Operation:=xlNone, _
            SkipBlanks:=False, Transpose:=False
        Columns(f - 1).Select
        Application.CutCopyMode = False
        Selection.Delete Shift:=xlToLeft
    f = 4
        Columns(f).Select
        Selection.Insert Shift:=xlToRight
        Cells(1, f).Formula = Cells(1, f - 1).Value
        Cells(2, f).Formula = "=TRUNC(RC[-1],4)"
        Cells(2, f).AutoFill Destination:=Range(Cells(2, f), Cells(c - 1, f)), _
            Type:=xlFillDefault
        Columns(f).Select
        Selection.Copy
        Selection.PasteSpecial Paste:=xlValues, Operation:=xlNone, _
            SkipBlanks:=False, Transpose:=False
        Columns(f - 1).Select
        Application.CutCopyMode = False
        Selection.Delete Shift:=xlToLeft
    f = 6
        Columns(f).Select
        Selection.Insert Shift:=xlToRight
        Cells(1, f).Formula = Cells(1, f - 1).Value
        Cells(2, f).Formula = "=ROUND(RC[-1],2)"
        Cells(2, f).AutoFill Destination:=Range(Cells(2, f), Cells(c - 1, f)), _
            Type:=xlFillDefault
        Columns(f).Select
        Selection.Copy
```

Il Sheet v1.0d Source Code

```
        Selection.PasteSpecial Paste:=xlValues, Operation:=xlNone, _
            SkipBlanks:=False, Transpose:=False
        Columns(f - 1).Select
        Application.CutCopyMode = False
        Selection.Delete Shift:=xlToLeft
    f = 31
        Columns(f).Select
        Selection.Insert Shift:=xlToRight
        Cells(1, f).Formula = Cells(1, f - 1).Value
        Cells(2, f).Formula = "=ROUND(RC[-1],2)"
        Cells(2, f).AutoFill Destination:=Range(Cells(2, f), Cells(c - 1, f)), _
            Type:=xlFillDefault
        Columns(f).Select
        Selection.Copy
        Selection.PasteSpecial Paste:=xlValues, Operation:=xlNone, _
            SkipBlanks:=False, Transpose:=False
        Columns(f - 1).Select
        Application.CutCopyMode = False
        Selection.Delete Shift:=xlToLeft
    f = 32
        Columns(f).Select
        Selection.Insert Shift:=xlToRight
        Cells(1, f).Formula = Cells(1, f - 1).Value
        Cells(2, f).Formula = "=ROUND(RC[-1],2)"
        Cells(2, f).AutoFill Destination:=Range(Cells(2, f), Cells(c - 1, f)), _
            Type:=xlFillDefault
        Columns(f).Select
        Selection.Copy
        Selection.PasteSpecial Paste:=xlValues, Operation:=xlNone, _
            SkipBlanks:=False, Transpose:=False
        Columns(f - 1).Select
        Application.CutCopyMode = False
        Selection.Delete Shift:=xlToLeft
' Assigns the correct Cell Classification # to each cell based upon _
    MCM1 filter values (R&D Filter for CAS200).
    Range("AB2").Select
        c = 2
        While Cells(c, 5).Formula <> ""
            If Cells(c, 5).Formula < 5.74 Then
                Cells(c, 28).Formula = 1
            ElseIf Cells(c, 5).Formula >= 5.74 And Cells(c, 5).Formula < 8.63 Then
                Cells(c, 28).Formula = 2
            ElseIf Cells(c, 5).Formula >= 8.63 And Cells(c, 5).Formula < 12.85 Then
                Cells(c, 28).Formula = 3
            ElseIf Cells(c, 5).Formula >= 12.85 And Cells(c, 5).Formula < 17.95 Then
                Cells(c, 28).Formula = 5
            Else Cells(c, 28).Formula = 6
            End If
            c = c + 1
        Wend
' Formats the number display for the spreadsheet and adjusts the column width
    Columns("B:AK").Select
    Selection.NumberFormat = "0.000000"
    Columns("B:B").Select
    Selection.NumberFormat = "0.00"
    Columns("C:C").Select
    Selection.NumberFormat = "0.0000"
    Columns("E:E").Select
    Selection.NumberFormat = "0.00"
    Columns("AD:AD").Select
    Selection.NumberFormat = "0.00"
    Columns("AE:AE").Select
    Selection.NumberFormat = "0.00"
    Columns("A:AM").Select
    Selection.EntireColumn.AutoFit
    Range("A2").Select
    Application.ScreenUpdating = True
' Saves the newly formatted spreadsheet as an Excel file to the drive _
    and directory which you specify.
    ChDrive DriveLocation
```

-151-

Cell Sheet v1.0d Source Code

```
    ChDir FileLocation
        With ActiveWorkbook
            .Title = ""
            .Subject = ""
            .Author = "Craig Miller"
            .Keywords = ""
            .Comments = ""
        End With
    ActiveWorkbook.SaveAs Filename:=CSVFile2, FileFormat:=xlNormal, _
        Password:="", WriteResPassword:="", ReadOnlyRecommended:= _
        False, CreateBackup:=False
    Application.ScreenUpdating = False
    GoTo GoodStart
BadStart:
    FileLocation = Application.InputBox("Enter the directory in which you want all of the files
to be stored.  This must be an existing directory.  Example:  I:\AREV\MCM\TEST", "File Directo
ry", "I:\AREV\MCM\SEXTANT")
    DriveLocation = Left(FileLocation, 1)
    StatsFile = Application.InputBox("Enter a name for the Summary Statistics File: a file whi
ch will contain all of the statistics for each case.  Example:  TESTSTAT", "Summary Statistics
 File Name")
    Application.ScreenUpdating = False
    Workbooks.Open Filename:="C:\CRAIG\MACROS\CSV1DSTA.BLK"
    ChDrive DriveLocation
    ChDir FileLocation
        With ActiveWorkbook
            .Title = ""
            .Subject = ""
            .Author = "Craig Miller"
            .Keywords = ""
            .Comments = ""
        End With
    ActiveWorkbook.SaveAs Filename:=StatsFile, FileFormat:=xlNormal, _
        Password:="", WriteResPassword:="", ReadOnlyRecommended:= _
        False, CreateBackup:=False
    ActiveWindow.Close
    MsgBox "Open the *.XLS file which you with to convert:"
    XLSFile = Application.GetOpenFilename("Excel (*.xls), *.xls")
    If XLSFile = False Then GoTo EndLine Else
    Workbooks.Open Filename:=XLSFile
    GoTo GoodStart
GoodStart:
    CaseNum = Range("A2").Value
    While CaseNum <> ""
        Application.ScreenUpdating = False
' Select all cells pertaining to this particular case
        y = 3
            While Cells(y, 1) = CaseNum
                y = y + 1
            Wend
' Select the cells for one case, copy them to a blank Cell Sheet template, _
    and delete the first and last row (blank rows from template).
        Range(Cells(2, 1), Cells(y - 1, 39)).Select
        Selection.Copy
        Workbooks.Open Filename:="C:\CRAIG\MACROS\CSV1DNMD.BLK"
        Selection.Insert Shift:=xlDown
            With Selection.Font
                .Name = "Times New Roman"
                .FontStyle = "Regular"
                .Size = 10
                .Strikethrough = False
                .Superscript = False
                .Subscript = False
                .OutlineFont = False
                .Shadow = False
                .Underline = xlNone
                .ColorIndex = xlAutomatic
            End With
            With Selection
                .HorizontalAlignment = xlCenter
```

-152-

Cell Sheet v1.0d Source Code

```
            .VerticalAlignment = xlBottom
            .WrapText = False
            .Orientation = xlHorizontal
        End With
        With Selection.Borders(xlLeft)
            .Weight = xlThin
            .ColorIndex = xlAutomatic
        End With
        With Selection.Borders(xlRight)
            .Weight = xlThin
            .ColorIndex = xlAutomatic
        End With
        With Selection.Borders(xlTop)
            .Weight = xlThin
            .ColorIndex = xlAutomatic
        End With
        With Selection.Borders(xlBottom)
            .Weight = xlThin
            .ColorIndex = xlAutomatic
        End With
        Selection.BorderAround LineStyle:=xlNone
        Columns("A:AM").EntireColumn.AutoFit
        Rows("3:3").Select
        Application.CutCopyMode = False
        Selection.Delete Shift:=xlUp
        y = 3
            While Cells(y, 1) = CaseNum
                y = y + 1
            Wend
        Range(Cells(y, 1), Cells(y, 39)).Select
        Selection.Delete Shift:=xlUp
' Makes the first column the cell number and changes the sheet name.
        Range("A1").Select
        ActiveCell.FormulaR1C1 = "Cell"
        Range("A3").Select
        ActiveCell.FormulaR1C1 = "1"
        Range("A4").Select
        ActiveCell.FormulaR1C1 = "2"
            Set Source = Range(Cells(3, 1), Cells(4, 1))
            Set Fill = Range(Cells(3, 1), Cells(y - 1, 1))
        Source.AutoFill Destination:=Fill
        Sheets("CSV1dNMD").Select
        CaseNum = Trim(CaseNum)
        Sheets("CSV1dNMD").Name = CaseNum
        Range("A1").Select
' Saves the separated spreadsheet as an Excel file to the specified directory.
        ChDir FileLocation
        With ActiveWorkbook
            .Title = ""
            .Subject = ""
            .Author = "Craig Miller"
            .Keywords = ""
            .Comments = ""
        End With
        ActiveWorkbook.SaveAs Filename:=CaseNum, FileFormat:=xlNormal, _
            Password:="", WriteResPassword:="", ReadOnlyRecommended:= _
            False, CreateBackup:=False
' Selects the Statistical Calculations, pastes them to a blank spreadsheet, _
    and cuts and copies all of the values to a single row.
        Range(Cells(y + 2, 1), Cells(y + 13, 39)).Select
        Selection.Copy
        Selection.PasteSpecial Paste:=xlValues, Operation:=xlNone, _
        SkipBlanks:=False, Transpose:=False
        Selection.Cut
        Workbooks.Add Template:="Workbook"
        ActiveSheet.Paste
            With Selection.Borders(xlLeft)
                .Weight = xlThin
                .ColorIndex = xlAutomatic
            End With
```

-153-

Call Sheet v1.0d Source Code

```
        With Selection.Borders(xlRight)
            .Weight = xlThin
            .ColorIndex = xlAutomatic
        End With
        With Selection.Borders(xlTop)
            .Weight = xlThin
            .ColorIndex = xlAutomatic
        End With
        With Selection.Borders(xlBottom)
            .Weight = xlThin
            .ColorIndex = xlAutomatic
        End With
        Selection.BorderAround LineStyle:=xlNone
        Range("A1").Formula = CaseNum
        Range("B2:AM2").Select
        Selection.Cut
        Range("AN1").Select
        ActiveSheet.Paste
        Range("B3:AM3").Select
        Selection.Cut
        Range("BZ1").Select
        ActiveSheet.Paste
        Range("B4:AM4").Select
        Selection.Cut
        Range("DL1").Select
        ActiveSheet.Paste
        Range("B5:AM5").Select
        Selection.Cut
        Range("EX1").Select
        ActiveSheet.Paste
        Range("F9").Select
        Selection.Cut
        Range("GJ1").Select
        ActiveSheet.Paste
        Range("F10").Select
        Selection.Cut
        Range("GK1").Select
        ActiveSheet.Paste
        Range("F11").Select
        Selection.Cut
        Range("GL1").Select
        ActiveSheet.Paste
        Rows("1:1").Select
        Selection.Copy
' Pastes the statistics for the case into the specified summary file.
        ChDrive DriveLocation
        ChDir FileLocation
        Workbooks.Open Filename:=StatsFile
        Selection.Insert Shift:=xlDown
        Application.CutCopyMode = False
        ActiveWorkbook.Save
        ActiveWindow.Close
        ActiveWorkbook.Saved = True
        ActiveWindow.Close
        ActiveWorkbook.Saved = True
        ActiveWindow.Close
        Selection.Delete Shift:=xlUp
        Range("A2").Select
        Application.ScreenUpdating = True
'Continues to loop the macro until all of the cases contained in this vector
   file have been separated and no data is left in the vector file.
        CaseNum = Range("A2").Value
    Wend
'If there is more than one vector file to separate, opens the next file
    ActiveWorkbook.Saved = True
    ActiveWindow.Close
    Msg1 = "Do you wish to convert another *.CSV file?"
    Style1 = vbYesNo
    Title1 = "Continue?"
    Response1 = MsgBox(Msg1, Style1, Title1)
```

-154-

Sheet v1.0d Source Code

```
    If Response1 = vbNo Then
            GoTo EndLine
        Else GoTo OpenLine
    End If
' Ends the macro and refreshes the screen
LastLine:
    ActiveWorkbook.Saved = True
    ActiveWindow.Close
    Application.ScreenUpdating = True
EndLine:
End Sub
```

REFERENCES

The following references, to the extent that they provide exemplary procedural or other details supplementary to those set forth herein, are specifically incorporated herein by reference.

1. Ashenayi, K., Vogh, J., Tai, H. M., Sayeh, M. R., Mostafavi, M. T., "Single-Layer Perceptron Capable of Classifying 2N+1 Distinct Patterns," IASTED International Journal of Modelling and Simulation, Vol. 10, No. 4, 1990, pp. 124–128.
2. Ashenayi, K., Singh, S., and Sayeh, M. R., "Pattern Classification Using Associative Memory," paper presented at 31 St. Midwest Symposium on Circuits and Systems, pp. 169–172, Aug. 11–12, 1988.
3. Ashenayi, K., Vogh, J., and Sayeh, M. R., 1992, "Gaussian Perceptron Capable of Classifying " 2N+1"Distinct Classes of Input Patterns," IASTED Journal of Control and Computers, Vol. 20, No. 2, pp. 54–60.
4. Austenfeld, M S, Treatment of Stage Al prostate cancer: The case for observation. Seminars in Urology, XI: 58–63, 1993.
5. Bahnson, R R. Treatment of Stage A1 prostate cancer: The Case for treatment.
Seminars in Urology, XI: 54–57, 1993.
6. Bibbo, M, Kim, D H, di Lareto, C, Galera-Davidson. H, Thompson, D, and Dytch, H E. Architectural morphometric and photometric features and their relationship to the main subjective clues of grading prostate cancer. Anal. Quant. Cytol. Ilistol., 12: 85–90, 1990.
7. Block, H. D., "The Perceptron: a Model for Brain Functioning. I," Reviews of Modern Physics, 34, pp. 123–135, 1962.
8. Bonner, R. B., Hemstreet, G. P., Fradet, Y., Min, K. Y., Hurst, R. E., 1993, "Bladder Cancer Risk Assessment with Quantitative Fluorescence Image Analysis of Tumor Markers in Exfoliated Bladder Cells. Cancer 72: 2461–69.
9. Boone, C W and Kelloff, G J. Intraepithelial neoplasia, surrogate endpoint biomarkers, and cancer chemoprevention. J. Cell. Biochem. (Suppl), 17F: 37–48, 1993.
10. Boring, C. C., Squires, T. S. and Tsong, T. Cancer Statistics, C A, 41:19–36, 1991.
11. Bostwick, D G, Montironi, R, Nagle, R, Pretlow, T, Miller, G, Wheeler, T, Epstein, J I, and Sakr, W. Current and proposed biologic markers in prostate cancer. J. Cell. Biochem. (Suppl.) 16H: 65–67, 1992.
12. Bostwick, D G, Graham, S D, Napalkov, P, Abrahamsson, P-A, di Sant'Agnese, P A, Algaba F, Hoisaeter P A, Lee, F, Littrup, P, Mostofi, F K, Denis, L, Schroeder, F, Murphy, G P. Staging of early prostate cancer: A proposed tumor volume-based prognostic index. Urology, 41: 403–411, 1993.
13. Bostwick, D G, Amin, M B, Dundore, P, Marsh, W, and Schultz, D S. Architectural patterns of high grade prostatic intraepithelial neoplasia. Human Pathology, 24: 298–310, 1993.
14. Brady, M. L., Raghavan, R., and Slawny, J., "Back Propagation Fails to Separate Where Perceptron Succeed," IEEE Transactions on Circuits and Systems, Vol. 36, No. 5, pp. 665–674, May 1989.
15. Cancer Facts and Figures—1993. New York: American Cancer Society, Inc.,
16. Cantrell, B. B., deklerk, D. P., Eggleston, J. C., Boitnott, J. K. and Walsh, P. C. Pathological factors that influence prognosis in stage A prostatic cancer: The influence of extent versus grade. J. Urol., 125:516, 1981.
17. Carpenter, G. A. and Grossberg, S., "The ART of Adaptive Pattern Recognition by Self-Organizing Neural Network," Computer, pp. 77–88, March 1988.
18. Carter, H. B. and Coffey, D. S. Prostate cancer: The magnitude of the problem in the United States. In: A Multidisciplinary Analysis of Controversies in the Management of Prostate Cancer, Coffey, D. S., Resnick, M. I., Dorr, F. A. and Karr, J. P. (eds.), New York: Plenum Publishing Corp., pp. 1–7, 1988.
19. Catalona, W. J. and Bigg, S. W. Nerve-sparing radical prostatectomy: evaluation of results after 250 patients. J. Urol. 143:538–543, 1990.
20. Christen, R, Xiao, J, Minimo, C, Gibbons, G, Fitzpatrick, B T, Galera-Davidson, H, Bartels, P H, and Bibbo, M. Chromatin texture features in hematoxylin and eosin-stained prostate tissue. Analytical Quant. Cytol. Histol., 15: 383–388, 1991.
21. Clark, T. D., Askin, F. B. and Bagnell, C. F. Nuclear roundness factor: A quantitative approach to grading in prostatic carcinoma, reliability of needle biopsy tissue, and the effect of tumor stage on usefulness. Prostate, 10:199, 1987.
22. DARPA Neural Network Study, AFCEA International Pres, Fairfax, Va., November 1988.
23. Dawson, A. E., Cibas, E. S., Bacus, J. W. and Weinberg, D. S. "Chromatin Texture Measurement by Markovian Analysis, Use of Nuclear Models to Define and Select Texture Features," Analytical and Quantitative Cytology and Histology, 15: 227–35, 1993.
24. Diamond D A, Berry S J, Umbricht C, Jewett H J, and Coffey D S. Computerized image analysis of nuclear shape as a prognostic factor for prostatic cancer. The Prostate 1982; 3:321–332.
25. Diamond D A, Berry S J, Jewett H J, Eggleston, and Coffey D S. A new method to assess metastatic potential of human prostate cancer: relative nuclear roundness. J Urol 1982; 128:729–734.
26. Eichenberger, T., Mihatsch, M. J., Oberholzer, M., Gschwind, R. and Rutishauser, G. Prostate Cancer. Part A: Research, Endocrine Treatment; and Histopathology. Alan R. Liss, Inc., New York, pp. 533–537, 1987.
27. Epstein, J. I., Oesterling, J. E. and Walsh, P. C. Tumor volume versus percentage involved by tumor correlated with progression in stage A prostatic cancer. J. Urol. 139:980, 1988.
28. Epstein, J. I., Berry, S. J. and Eggleston, J. C. Nuclear roundness factor: A predictor of prognosis in untreated stage A2 prostate cancer. Cancer 54:1666, 1984.
29. Franks, L M. Latent carcinoma of the prostate. J. Pathol Bacteriol. 68: 603–616, 1954.
30. Freiha, F. S. Selection criteria for radical prostatectomy based on morphometric studies. In: Consensus Development Conference on Management of Clinically Localized Prostate Cancer, Program and Abstracts, p. 73, Jun. 15–17, 1987.
31. Gibbons, R. P., Correa, R. J., Jr., Brannen, G. E. and Mason, J. T. Total prostatectomy for localized prostatic cancer. J. Urol., 131:73, 1984.
32. Gleason D F, The Veterans Administrative Cooperative Urological Research Group. Histological grading and clinical staging of prostatic carcinoma. In: Tannenbaum M, editor. Urologic pathology: the prostate. Philadelphia: Lea and Febiger, 1977:171–98.
33. Gleason, D. F. Histologic grading of prostatic carcinoma. In: Bostwick D G (Ed): Pathology of the Prostate, New York, Churchhill-Livingstone, pp 83–90, 1990.
34. Gleason, D. F., Mellinger, G. T. and the Veterans Administrative Cooperative Urological Research Group. Prediction of prognosis for prostatic adenocarcinoma by combined histological grading and clinical staging. J. Urol., 111:58, 1974.

35. Han, J. Y., Syeh, M. R. and Zhang, J., "Convergence and Limit Points of Neural Network and Its Applications in Pattern Recognition," IEEE Transaction on Systems, Man, and Cybernectics, Vol. 19, No. 5, pp. 1217–1222, 1989.

36. Hopfield, J. J. "Neural Networks and Physical Systems with Emergent Collective Computational Abilities," Proc. Natl. Acad. Science, USA, Vol. 79, pp. 2554–2558, April 1982.

37. Irinopoulou, T., Rigaut J. P., and Benson M. C. Toward Objective Prognostic Grading of Prostatic carcinoma Using Image Analysis. Analytical and Quantitative Cytology and histology, 15: 341–44, 1993.

38. Isaacs, J. T (Ed). Prostate Cancer Cell and Molecular Mechanisms in Diagnosis and Treatment. Cancer Surveys 11: 1–287, 1991.

39. Kohonen, T., Self-Organization and Associative Memory, 2ND Ed., Springer-Verlag, New York, 1987.

40. Lippmann, R. P., "An Introduction to Computing With Neural Nets," IEEE ASSP Magazine, pp. 4–22, April 1987.

41. Lippmann, R. P., and Martin, E. A., "Multi-Style Training for Robust Isolated-Word Speech Recognition," in ICASSP 87, April 1987, 705–708.

42. McNeal, J. E., Kindrachuk, R. A., Freiha, F. S., Bostwick, D. G., et. al. Patterns of progression in prostate cancer. Lancet, 1:60, 1986.

43. Middleton, R. G., Smith, J. A., Jr., Metzer, R. B. and Hamilton, P. E. Patient survival and local recurrence rate following radical prostatectomy for prostatic cancer. J. Urol. 136:422-, 1986.

44. Miller, G. J. and Shikes, J. L. Nuclear roundness as a predictor of response to hormonal therapy of patients with stage D2 prostatic carcinoma. IN: *Prognostic Cytometry and Cytopathology of prostate cancer*. Karr, J. P., Coffey, D. S. and Gardner W. (Eds.), Elsevier Science Publishing Co., Inc., New York, pp. 349–354, 1988.

45. Minsky, M. L. and Papert, S. A., Perceptrons, Expanded Edition, MIT Press, Cambridge, Mass., 1988.

46. Mohler J L, Partin A W, Epstein J I, Lohr W D, and Coffey D S. Nuclear roundness factor measurement for assessment of prognosis of patients with prostatic carcinoma: II. Standardization of methodology for histologic sections. *J Urol* 1988; 139:1085–1090.

47. Mohler J L, Partin A W, Lohr W D, and Coffey D S. Nuclear roundness factor measurement for assessment of prognosis of patients with prostatic carcinoma: I. Testing of a digitization system. *J Urol* 1988; 139:1080–4.

48. Mostofi F K. Grading of prostatic carcinoma. *Cancer Chemother. Rep.* 1975; 59:111–7.

49. Murphy, G. P., Gaeta, J. F., Pickren, J. and Wajsman, Z. Current status of classification and staging of prostate cancer. Cancer, 45:1889, 1980.

50. Myers, R. P. and Fleming, T. R. Course of localized adenocarcinoma of the prostate treated by radical prostatectomy. Prostate, 4: 461, 1983.

51. Narayan, P., Michael, M., Jajodia, P., Stein, R., Gonzalez, J., Ljung, B., Chu, K. and Myall, B. Automated image analysis—a new technique to predict metastatic potential of prostate carcinomas? J. Urol., 141 (4 part 2): 183 (Abstract), 1989.

52. Nowell, P. C. Mechanisms of tumor progression. Cancer Res., 46:2203, 1986.

53. Oesterling, J. E. PSA leads the way for detecting and following prostate cancer. Contemporary Urol. 5:60–81, 1993.

54. Oesterling, J. E. Prostate specific antigen: A critical assessment of the most useful tumor marker for adenocarcinoma of the prostate. J. Urol., 145:907–923, 1991.

55. Pack R and Spitz M A. Epidemiology of prostate cancer, with emphasis on familial clusters. The Cancer Bulletin, 45: 384–388, 1993.

56. Parker, D. B., "Learning-Logic," Innovation Report, 581–64, File 1, Office of Technology Licensing, Stanford University, October, 1982.

57. Partin, A. W., Pound, C. R., Clemens, J. Q., Epstein, J. I. and Walsh, P. C.: Prostate specific antigen after anatomic radical prostatectomy: The Johns Hopkins Experience after ten years. Urol. Clin. North Am., November, 20:713, 1993.

58. Partin, A. W., Yoo, J., Carter, H. B., Pearson, J. D., Chan, D. W., Epstein, J. I. and Walsh P. C. The use of prostate specific antigen, clinical stage and gleason score to predict pathologic stage in men with clinically localized prostate cancer. J. Urol. 150:105–110, 1993.

59. Partin A W, Walsh A C, Pitcock R V, Mohler J L, Epstein J I, and Coffey D S. A comparison of nuclear morphometry and Gleason grade as a predictor of prognosis in stage A2 prostate cancer: A critical analysis. *J Urol* 1989; 142:1254–1258.

60. Partin, A. W. The development of a system for the quantitative analysis of tumor cell motility: Application to prostate cancer. Doctoral Thesis, The Johns Hopkins University, 1988.

61. Partin, A. W., Carter, H. B., Chan, D. W., Epstein, J. I, Oesterling, J. E., Rock, R. C., Weber, J. P. and Walsh, P. C. Prostate specific antigen in the staging of localized prostate cancer: Influence of tumor differentiation, tumor volume and benign hyperplasia. J. Urol., 143:747, 1990.

62. Partin, A. W., Epstein, J. I., Cho, K. R., Gittelsohn, A. M. and Walsh, P. C. Morphometric measurement of tumor volume and percent of gland involvement las predictors of pathologic stage in clinical stage B prostate cancer. J. Urol., 141:341, 1989.

63. Partin A W, Steinberg G D, Pitcock R V, Wu L, Piantadosi S, Coffey D S, and Epstein J I. Use of nuclear morphometry, gleason histologic scoring, clinical stage, and age to predict disease-free survival among patients with prostate cancer. *Cancer* 1992, 70(1): 161–168.

64. Partin, A. W., Steinberg, G. D., Pitcock, R. V., Wu, L., Piantadosi, S., Coffey, D. S. and Epstein, J. I. Use of nuclear morphometry, Gleason histologic scoring, clinical stage and age to predict disease free survival among patients with prostate cancer. Cancer 70:161–168, 1992.

65. Paulson, D. F. Radiotherapy versus surgery for localized prostate cancer. Urol. Clin. North Am., 14:675, 1987.

66. Paulson, D. F., Stone, A. R., Walther, P. J., Tucker, J. A. and Cox, E. B. Radical prostatectomy: Anatomical predictors of success or failure. J. Urol., 136:1041, 1986.

67. Pisters L I. and Babaian R J. Status of early prostate cancer detection. The Cancer Bulletin, 45: 389–396, 1993.

68. Pressman, N. J. "Markovian Analysis of Cervical Images," J Histochemistry and Cytochemistry, 24: 138–44, 1976.

69. Reed, J. A., Manahan, L. J., Park, C. S., and Brigati, D. J. Complete one-hour immunochemistry based on capillary action. BioTechniques 13: 434–442.

70. Reed, T. and Hans Du Buf, J., 1993, "A Review of Recent Texture segmentation and Feature Extraction Techniques," *CVGIP:Image Understanding*, 57, pp. 359–372.

71. Robey, E. L. and Schellhammer, P. F. Local failure after definitive therapy for prostatic cancer. J. Urol., 137:613, 1987.

72. Rosenblatt, R., Principles of Neurodynamics, Spartan Books, New York, 1962.

73. Rumelhart, D. E., McClelland, J. L., and The PDP Research Group, Parallel Distributed Processing Explorations in the Microstructures of Cognition Vol. 1:Foundations, MIT Press, Cambridge, Mass., 1988.
74. Scardino P T. Early detection of prostate cancer. Urol Clin North America 16: 635–655, 1989.
75. Sejnowski, T. J. and Rosenberg, C. M., "Parallel Networks that Learn to Pronounce English Text," Complex Systems, 1, 145–168.
76. Shankey, V T, Kallioniemi, O-P, Koslowski, J M, Leiber, M L, Mayall, B H, Miller, G, and Smith G J. Consensus review of the clinical utility of DNA content cytometry in prostate cancer. Cytometry, 14: 497–500, 1993.
77. Thompson I M, Brawley 0, and Kramer B. Chemoprevention in carcinoma of the prostate. Oncology 7 (Supplement), 49–53, 1993.
78. Van Gool, L., Dewaele, P., and Oosterlinck, A., 1983, "Texture Analysis Anno 1983, " Computer Vision, Graphic, and Image Processing, 29, pp. 336–357.
79. Veltri et al. Quantitative nuclear morphometry, Markovian texture descriptors, and DNA content captured on a CAS-200 image analysis system, combined with PCNA and HER-2/neu immunohistochemistry for prediction of prostate cancer progression. J. Cellular Biochemistry, Supplement, 19:249–258, 1994.
80. Veltri et al. Correlation of nuclear texture and shape descriptors, DNA ploidy, HER-2/neu and PD-41 cellular biomarkers with non-organ confined tumor status in prostate cancer. AUA Ninetieth Annual Meeting, Abstract #249, las Begas, Volume 153, Number 4, April 1995.
81. Veltri et al. Evaluation of DNA content and chromatin complexity as stratification parameters to assess severe urothelial atypias in urinary cytology specimens obtained in a pathology reference laboratory. AUA Ninetieth Annual Meeting, Abstract #912, Las Vegas, Volume 153, Number 4, April 1995.
82. Veltri et al. Correlation of chromatin complexity, DNA content, HER-2/neu, PD-41, and PCNA with prostate cancer organ confined disease status. AACR Eighty-Sixth Annual meeting, Galley Poster #1617, Toronto, Canada, Volume 36, March 1995.
83. Vogh, J. and Ashenayi, K., "A Solution to the Perceptron XOR Problem With a Gaussian Function," in the proceedings of the 1989 Southeastern Simulation Conference, Pensacola, Florida, pp. 7–12, October 16–17, 1989.
84. Walsh, P. C. and Jewett, H. J. Radical surgery for prostatic cancer. Cancer, 45:1906, 1980.
85. Wasserrnan, Phillip D. Neural Computing Theory and Practice, Van Nostrand and Reinhold, New York, 1989.
86. Werbos, P. J., "Beyond Regression: New Tools for Prediction and Analysis in the Behavioral Sciences," Ph.D. Thesis, Harvard University, 1974.

What is claimed is:

1. A method for predicting the loss of organ confinement, comprising:
    (a) obtaining prostate cells from a subject;
    (b) analyzing predictive parameters in the prostate cells, wherein the predictive parameters are univariately or multivariately significant nuclear morphometric descriptors, including Markovian nuclear texture features, and selected biomarkers; and
    (c) predicting the loss of organ confinement by statistical analysis of the predictive parameters.
2. The method according to claim 1, wherein the nuclear morphometric descriptors are selected from the group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.
3. The method according to claim 1, wherein the nuclear morphometric descriptors are selected from the group consisting of object sum optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, and configurable run length.
4. The method according to claim 1, wherein the selected biomarkers include Gleason score.
5. The method according to claim 4, wherein the selected biomarkers further include number of positive sextant core biopsies, sum % area tumor involvement, DNA ploidy, and tumor location.
6. The method according to claim 5, wherein the selected biomarkers further include senrun PSA antigenicity.
7. The method according to claim 6, wherein the biomarkers further include RT-PCR mRNA levels.
8. The method according to claim 1, wherein the statistical analysis is performed by a neural network.
9. The method according to claim 1, wherein the statistical analysis is multivariate analysis.
10. A method for predicting the loss of organ confinement before radical prostatectomy comprising the steps of:
    a) obtaining prostate biopsy cells from a subject;
    b) generating nuclear morphometric descriptors for the prostate cells; and
    c) predicting the probability of loss of organ confinement by statistical analysis of the nuclear morphometric descriptors.
11. The method according to claim 10, wherein the statistical analysis is multivariate statistical analysis.
12. The method according to claim 10, wherein the predictive parameters include nuclear morphonetric descriptors and biomarkers selected from the group consisting of Gleason score, serum PSA, number of positive sextant core biopsies, tumor location, DNA ploidy, and sum % area of tumor involvement.
13. The method according to claim 10, wherein the selected biomarkers further include RT-PCR mRNA levels.
14. The method according to claim 12, wherein nuclear morphometric descriptors are selected from the group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.
15. The method according to claim 12, wherein nuclear morphometric descriptors are selected from the group consisting of object sum optical density object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y, maximum diameter, minimum diameter, elongation, run length, and configurable run length.

16. The method according to claim 14, wherein the nuclear morphometric descriptors are Markovian nuclear texture features.

17. A method of determining the loss of organ confinement comprising:
   a) providing a neural network;
   b) training the neural network using predictive parameters obtained from a set of prostate tumor cells known to lose organ confinement and a set of prostate tumor cells known not to lose organ confinement, wherein said predictive parameters comprise nuclear morphometric descriptors including Markovian nuclear texture features;
   c) analyzing predictive parameters in prostate tumor cells of an individual having an unknown state of organ confinement; and
   d) predicting the loss of organ confinement in cells of the individual having an unknown state of organ confinement using the predictive parameters and the trained neural network.

18. The method according to claim 17, wherein the predictive parameters further include biomarkers selected from the group consisting of serum PSA, tumor location, number of positive sextant core biopsies, sum % area of tumor involvement, quantitative nuclear grade, DNA ploidy, and Gleason score.

19. The method according to claim 17, wherein the nuclear morphometric descriptors are selected from the group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.

20. The method according to claim 17, wherein the nuclear morphometric descriptors are selected from the group consisting of object sum optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6=Hyperploid), perimeter, DNA index, density, average optical density, feret X, feret Y. maximum diameter, minimum diameter, elongation, run length, and configurable run length.

21. The method according to claim 18, wherein the selected biomarkers further include RT-PCR mRNA levels.

22. The method according to claim 17, wherein the neural network is of the back propagation type.

23. The method of claim 17, wherein the neural network is of a hybrid type.

24. A method for predicting the loss of organ confinement in a prostate biopsy sample comprising the steps of:
   (a) obtaining biopsy cells from a subject;
   (b) analyzing predictive parameters from the prostate cells, the predictive parameters including nuclear morphometric descriptors;
   (c) utilizing statistical analysis to determine multivariately significant nuclear morphometric descriptors to calculate a quantitative nuclear grade; and
   (d) predicting the probability of loss of organ confinement status in the patient by statistical analysis of the quantitative nuclear grade.

25. The method of claim 24 further including the steps of analyzing predictive parameters from the prostate cells including utilizing statistical analysis to determine univariately significant patient derived pathology and clinical information variables that contribute to a multivariate model solution and predicting the probability of loss of organ confinement status in the patient by further statistical analysis of the quantitative nuclear grade and univariately significant patient derived pathology and clinical information variables.

26. The method according to claim 24 wherein the statistical analysis is by logistic regression analysis.

27. The method of claim 24 wherein the statistical analysis is by a neural network.

28. The method according to claim 18 or claim 24 wherein the nuclear morphometric descriptors used to calculate quantitative nuclear grade are selected from a group consisting of difference entropy, information measure A, information measure B, maximal correlation coefficient, angular second moment, coefficient of variation, contrast, peak transition probability, correlation, diagonal variance, difference moment, diagonal moment, inverse difference moment, second diagonal moment, sum average, product moment, sum variance, triangular symmetry, sum entropy, blobness, entropy, difference variance, and standard deviation.

29. The method according to claim 18 or claim 24 wherein the nuclear morphometric descriptors used to calculate quantitative nuclear grade are selected from a group consisting of object sum optical density, object size, object shape, picograms of DNA, angular second moment, contrast, correlation, difference moment, inverse difference moment, sum average, sum variance, sum entropy, entropy, difference variance, difference entropy, information measure A, information measure B, maximal correlation coefficient, coefficient of variation, peak transition probability, diagonal variance, diagonal moment, second diagonal moment, product moment, triangular symmetry, standard deviation, cell classification (1=Hypodiploid, 2=Diploid, 3=S-Phase, 5=Tetraploid, 6-Hyperploid), perimeter, DNA index, density, average optical density, feret X, feret Y, maximum diameter, minimum diameter, elongation, run length, and configurable run length.

30. The method of claim 1, wherein the statistical analysis is logistic regression, discriminate analysis, recursive partitioning, classification and regression tree analysis, or neural network.

31. The method of claim 10, wherein the statistical analysis is logistic regression, discriminate analysis, recursive partitioning, classification and regression tree analysis, or neural network.

32. The method according to claim 25, wherein the patient derived pathology and clinical information variables are selected from the group consisting of serum PSA, Gleason score, number of positive sextant core biopsies, tumor location, DNA ploidy, and sum % area of tumor involvement.

33. The method according to claim 32, wherein the patient derived pathology and clinical information variables further include RT-PCR mRNA levels.

* * * * *

UNITED STATES PATENT AND TRADEMARK OFFICE
CERTIFICATE OF CORRECTION

PATENT NO. : 5,989,811

DATED : November 23, 1999

INVENTOR(S) : Robert W. Veltri et al.

It is certified that error appears in the above-identified patent and that said Letters Patent is hereby corrected as shown below:

At column 166, line 31, please delete "senrun" and insert therefor -- serum --.

Signed and Sealed this

First Day of August, 2000

Attest:

Q. TODD DICKINSON

Attesting Officer

Director of Patents and Trademarks